US011478422B2

(12) United States Patent
Kakumanu et al.

(10) Patent No.: US 11,478,422 B2
(45) Date of Patent: *Oct. 25, 2022

(54) FILM FORMULATIONS CONTAINING DEXMEDETOMIDINE AND METHODS OF PRODUCING THEM

(71) Applicants: BioXcel Therapeutics, Inc., New Haven, CT (US); ARx, LLC, Glen Rock, PA (US)

(72) Inventors: Vasukumar Kakumanu, Guntur (IN); David Christian Hanley, Brookfield, CT (US); Frank Yocca, Clinton, CT (US); Chetan Dalpatbhai Lathia, Woodbridge, CT (US); Scott David Barnhart, Glen Rock, PA (US)

(73) Assignees: BioXcel Therapeutics, Inc., New Haven, CT (US); ARx, LLC, Glen Rock, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/931,630

(22) Filed: Jul. 17, 2020

(65) Prior Publication Data

US 2020/0345635 A1 Nov. 5, 2020

Related U.S. Application Data

(63) Continuation of application No. 16/453,679, filed on Jun. 26, 2019, now Pat. No. 10,792,246.

(60) Provisional application No. 62/849,747, filed on May 17, 2019, provisional application No. 62/798,842, filed on Jan. 30, 2019, provisional application No. 62/787,649, filed on Jan. 2, 2019, provisional application No. 62/767,422, filed on Nov. 14, 2018, provisional application No. 62/693,726, filed on Jul. 3, 2018, provisional application No. 62/690,407, filed on Jun. 27, 2018.

(51) Int. Cl.
| | |
|---|---|
| A61K 9/00 | (2006.01) |
| A61K 47/38 | (2006.01) |
| A61K 9/70 | (2006.01) |
| A61K 31/4174 | (2006.01) |
| A61P 25/22 | (2006.01) |
| A61K 47/34 | (2017.01) |

(52) U.S. Cl.
CPC .......... *A61K 9/0056* (2013.01); *A61K 9/7007* (2013.01); *A61K 31/4174* (2013.01); *A61K 47/34* (2013.01); *A61K 47/38* (2013.01); *A61P 25/22* (2018.01)

(58) Field of Classification Search
None
See application file for complete search history.

(56) References Cited

U.S. PATENT DOCUMENTS

| | | |
|---|---|---|
| 4,670,455 A | 6/1987 | Virtanen et al. |
| 4,839,170 A | 6/1989 | Sarnoff et al. |
| 5,395,907 A | 3/1995 | Zajaczkowski et al. |
| 5,508,367 A | 4/1996 | Zajaczkowski et al. |
| 5,565,268 A | 10/1996 | Zajaczkowski et al. |
| 5,605,911 A | 2/1997 | Olney et al. |
| 5,700,873 A | 12/1997 | Zajaczkowski et al. |
| 5,712,301 A | 1/1998 | Jaatinen et al. |
| 5,726,250 A | 3/1998 | Zajaczkowski |
| 5,731,387 A | 3/1998 | Zajaczkowski |
| 5,951,999 A | 9/1999 | Therriault et al. |
| 6,174,546 B1 | 1/2001 | Therriault et al. |
| 6,200,604 B1 | 3/2001 | Panther et al. |
| 6,221,392 B1 | 4/2001 | Khankari et al. |
| 6,239,228 B1 | 5/2001 | Zajaczkowski et al. |
| 6,716,867 B1 | 4/2004 | Aantaa et al. |
| 6,753,782 B2 | 6/2004 | Power |
| 7,001,609 B1 | 2/2006 | Matson et al. |
| 7,357,891 B2 | 4/2008 | Yang et al. |
| 7,425,292 B2 | 9/2008 | Yang et al. |
| 7,470,397 B2 | 12/2008 | Meathrel et al. |
| 7,579,019 B2 | 8/2009 | Tapolsky et al. |
| 7,630,758 B2 | 12/2009 | Lapinlampi et al. |
| 7,666,337 B2 | 2/2010 | Yang et al. |
| 7,727,466 B2 | 6/2010 | Meathrel et al. |
| 7,897,080 B2 | 3/2011 | Yang et al. |
| 7,972,618 B2 | 7/2011 | Fuisz et al. |
| 8,241,661 B1 | 8/2012 | Fuisz et al. |
| 8,242,158 B1 | 8/2012 | Roychowdhury et al. |
| 8,282,954 B2 | 10/2012 | Bogue et al. |

(Continued)

FOREIGN PATENT DOCUMENTS

| | | |
|---|---|---|
| AU | 2007201370 B2 | 9/2009 |
| AU | 2009238370 B2 | 7/2011 |

(Continued)

OTHER PUBLICATIONS

Aantaa, et al., "Intramuscular dexmedetomidine, a novel alpha$_2$-adrenoceptor agonist, as premedication for minor gynaecological surgery." Acta Anaesthesiol Scand. (1991); 35(4): 283-288.

Abdelaziz, et al., "Effect of intranasal dexmedetomidine or intranasal midazolam on prevention of emergence agitation in pediatric strabismus surgery: A randomized controlled study." Egyptian Journal of Anaesthesia (2016) 32: 285-291.

Abdelmageed, et al., "Intramuscular dexmedetomidine for prevention of shivering after general anesthesia in patients undergoing arthroscopic anterior cruciate ligament reconstruction." Ain-Shams Journal of Anesthesiology (2014); 7(2): 156-162.

(Continued)

*Primary Examiner* — Robert T. Crow
*Assistant Examiner* — John P Nguyen
(74) *Attorney, Agent, or Firm* — Cooley LLP

(57) ABSTRACT

Disclosed herein is a self-supporting, dissolvable, film containing dexmedetomidine or a pharmaceutically acceptable salt thereof. The film is administered orally to treat various conditions, particularly agitation, by transmucosal delivery of the active agent.

8 Claims, 22 Drawing Sheets

(56) References Cited

U.S. PATENT DOCUMENTS

| | | |
|---|---|---|
| 8,324,260 B1 | 12/2012 | Garcia da Rocha et al. |
| 8,338,470 B1 | 12/2012 | Roychowdhury et al. |
| 8,364,221 B2 | 1/2013 | Mannheimer et al. |
| 8,414,922 B2 | 4/2013 | Bryson et al. |
| 8,436,033 B1 | 5/2013 | Roychowdhury et al. |
| 8,455,527 B1 | 6/2013 | Roychowdhury et al. |
| 8,568,777 B2 | 10/2013 | Fuisz |
| 8,617,589 B2 | 12/2013 | Fuisz et al. |
| 8,648,106 B2 | 2/2014 | Roychowdhury et al. |
| 8,663,687 B2 | 3/2014 | Myers et al. |
| 8,663,696 B2 | 3/2014 | Myers et al. |
| 8,685,437 B2 | 4/2014 | Yang et al. |
| 8,846,074 B2 | 9/2014 | Bryson et al. |
| 8,882,684 B2 | 11/2014 | Halperin et al. |
| 8,882,703 B2 | 11/2014 | Hickle |
| 8,900,498 B2 | 12/2014 | Yang et al. |
| 8,936,825 B2 | 1/2015 | Myers et al. |
| 9,073,294 B2 | 7/2015 | Kumar et al. |
| 9,248,146 B2 | 2/2016 | Barnhart et al. |
| 9,283,219 B2 | 3/2016 | Bryson et al. |
| 9,303,918 B2 | 4/2016 | Li |
| 9,320,712 B2 | 4/2016 | Roychowdhury et al. |
| 9,346,601 B2 | 5/2016 | Bogue et al. |
| 9,427,412 B2 | 8/2016 | Bryson et al. |
| 9,441,142 B2 | 9/2016 | Malik et al. |
| 9,545,376 B2 | 1/2017 | Musho et al. |
| 9,561,191 B2 | 2/2017 | Myers et al. |
| 9,572,773 B2 | 2/2017 | Dormady et al. |
| 9,585,961 B2 | 3/2017 | Barnhart et al. |
| 9,616,049 B2 | 4/2017 | Roychowdhury et al. |
| 9,649,296 B1 | 5/2017 | Pizza |
| 9,662,297 B2 | 5/2017 | Musho et al. |
| 9,662,301 B2 | 5/2017 | Musho et al. |
| 9,717,796 B1 | 8/2017 | Pizza |
| 9,795,559 B2 | 10/2017 | Henwood et al. |
| 9,814,674 B2 | 11/2017 | Musho et al. |
| 9,855,221 B2 | 1/2018 | Myers et al. |
| 9,901,650 B2 | 2/2018 | Nedergaard et al. |
| 9,931,305 B2 | 4/2018 | Yang et al. |
| 9,937,122 B2 | 4/2018 | Zhu et al. |
| 9,937,123 B2 | 4/2018 | Barnhart et al. |
| 9,993,428 B2 | 6/2018 | Gerard et al. |
| 10,130,684 B2 | 11/2018 | Rubin et al. |
| 10,130,766 B1 | 11/2018 | Bibian et al. |
| 10,137,245 B2 | 11/2018 | Melker et al. |
| 10,285,953 B2 | 5/2019 | Bryson et al. |
| 10,314,503 B2 | 6/2019 | Prerau et al. |
| 10,383,574 B2 | 8/2019 | Purdon et al. |
| 10,602,978 B2 | 3/2020 | Purdon et al. |
| 10,792,246 B2 | 10/2020 | Kakumanu et al. |
| 11,116,723 B2 | 9/2021 | Temtsin-Krayz |
| 2002/0037977 A1 | 3/2002 | Feldstein et al. |
| 2003/0096012 A1 | 5/2003 | Besse et al. |
| 2003/0124191 A1 | 7/2003 | Besse et al. |
| 2003/0145854 A1 | 8/2003 | Hickle |
| 2003/0158242 A1 | 8/2003 | Kugelmann |
| 2004/0138312 A1 | 7/2004 | Wheeler et al. |
| 2005/0037055 A1 | 2/2005 | Yang et al. |
| 2005/0118217 A1 | 6/2005 | Barnhart et al. |
| 2005/0222270 A1 | 10/2005 | Olney et al. |
| 2006/0058590 A1 | 3/2006 | Shaw |
| 2006/0058700 A1 | 3/2006 | Marro et al. |
| 2006/0069086 A1 | 3/2006 | Michalow |
| 2007/0281003 A1* | 12/2007 | Fuisz ............... A61K 9/006 424/443 |
| 2008/0026040 A1 | 1/2008 | Farr et al. |
| 2008/0124381 A1 | 5/2008 | Barnhart et al. |
| 2008/0280947 A1 | 11/2008 | Blondino et al. |
| 2008/0299005 A1 | 12/2008 | Meathrel et al. |
| 2008/0306980 A1 | 12/2008 | Brunner et al. |
| 2009/0076156 A1 | 3/2009 | Husain et al. |
| 2009/0099480 A1 | 4/2009 | Salgo et al. |
| 2009/0142850 A1 | 6/2009 | Meathrel et al. |
| 2009/0275853 A1 | 11/2009 | Sarkela |
| 2010/0130566 A1 | 5/2010 | Purpura et al. |
| 2010/0196286 A1 | 8/2010 | Armer et al. |
| 2011/0021588 A1 | 1/2011 | Henwood et al. |
| 2011/0066004 A1 | 3/2011 | Sullivan et al. |
| 2011/0245633 A1 | 10/2011 | Goldberg et al. |
| 2011/0290694 A1 | 12/2011 | Fuisz et al. |
| 2012/0076921 A1 | 3/2012 | Myers et al. |
| 2012/0100278 A1 | 4/2012 | Nowak et al. |
| 2012/0195955 A1 | 8/2012 | Bryson et al. |
| 2012/0309804 A1 | 12/2012 | Horn |
| 2012/0325209 A1 | 12/2012 | Quintin |
| 2012/0328688 A1 | 12/2012 | Fuisz et al. |
| 2013/0072532 A1 | 3/2013 | Henwood et al. |
| 2013/0095156 A1 | 4/2013 | Barnhart et al. |
| 2013/0096172 A1 | 4/2013 | Garcia da Rocha et al. |
| 2013/0116215 A1 | 5/2013 | Coma et al. |
| 2013/0178465 A1 | 7/2013 | Henwood et al. |
| 2013/0225626 A1 | 8/2013 | Bryson et al. |
| 2014/0010873 A1 | 1/2014 | Tygesen et al. |
| 2014/0163080 A1 | 6/2014 | Horn |
| 2014/0203480 A1 | 7/2014 | Musho et al. |
| 2014/0261990 A1 | 9/2014 | Dadey et al. |
| 2014/0287181 A1 | 9/2014 | Milik et al. |
| 2014/0316217 A1 | 10/2014 | Purdon et al. |
| 2014/0323898 A1 | 10/2014 | Purdon et al. |
| 2014/0377329 A1 | 12/2014 | Bryson et al. |
| 2015/0098980 A1 | 4/2015 | Pongpeerapat et al. |
| 2015/0098981 A1 | 4/2015 | Pongpeerapat et al. |
| 2015/0098982 A1 | 4/2015 | Pongpeerapat et al. |
| 2015/0098983 A1 | 4/2015 | Pongpeerapat et al. |
| 2015/0098997 A1 | 4/2015 | Pongpeerapat et al. |
| 2015/0141772 A1 | 5/2015 | LeBoeuf et al. |
| 2015/0250957 A1 | 9/2015 | Albalat |
| 2015/0258067 A1 | 9/2015 | Kokkonen et al. |
| 2016/0000945 A1 | 1/2016 | Nedergaard et al. |
| 2016/0113885 A1 | 4/2016 | Myers et al. |
| 2016/0151299 A1 | 6/2016 | Bryson et al. |
| 2016/0310441 A1 | 10/2016 | Yamazaki et al. |
| 2016/0324446 A1 | 11/2016 | Prerau et al. |
| 2016/0338972 A1 | 11/2016 | Bryson et al. |
| 2016/0374588 A1 | 12/2016 | Shariff et al. |
| 2017/0087084 A1 | 3/2017 | Musho et al. |
| 2017/0087097 A1 | 3/2017 | Musho et al. |
| 2017/0128358 A1 | 5/2017 | Barnhart et al. |
| 2017/0128421 A1 | 5/2017 | Sura et al. |
| 2017/0165235 A1 | 6/2017 | Roychowdhury et al. |
| 2017/0231556 A1 | 8/2017 | Purdon et al. |
| 2017/0239221 A1 | 8/2017 | Negi et al. |
| 2017/0246108 A1 | 8/2017 | Musho et al. |
| 2017/0252294 A1 | 9/2017 | Musho et al. |
| 2017/0273611 A1 | 9/2017 | Purdon et al. |
| 2017/0274174 A1 | 9/2017 | Purdon et al. |
| 2017/0296482 A1 | 10/2017 | Myers et al. |
| 2018/0055764 A1 | 3/2018 | Henwood et al. |
| 2018/0065767 A1 | 3/2018 | Bogue et al. |
| 2018/0098937 A1 | 4/2018 | Horn |
| 2018/0110897 A1 | 4/2018 | Bush et al. |
| 2018/0147201 A1 | 5/2018 | Toledano |
| 2018/0177797 A1 | 6/2018 | Berdahl et al. |
| 2018/0360736 A1 | 12/2018 | Obeid et al. |
| 2019/0209022 A1 | 7/2019 | Sobol et al. |
| 2019/0216345 A1 | 7/2019 | Scheib |
| 2019/0216389 A1 | 7/2019 | Scheib |
| 2019/0365715 A1 | 12/2019 | Nandabalan et al. |
| 2019/0374158 A1 | 12/2019 | Brown et al. |
| 2020/0000708 A1 | 1/2020 | Barnhart et al. |
| 2020/0000717 A1 | 1/2020 | Kakumanu et al. |
| 2020/0069650 A1 | 3/2020 | Korpivaara et al. |
| 2020/0093800 A1 | 3/2020 | Pongpeerapat et al. |
| 2020/0168340 A1 | 5/2020 | Park et al. |
| 2021/0077388 A1 | 3/2021 | Kakumanu et al. |
| 2021/0267944 A1 | 9/2021 | Yocca et al. |
| 2022/0031663 A1 | 2/2022 | Nandabalan et al. |
| 2022/0110864 A1 | 4/2022 | Kakumanu et al. |

(56) References Cited

U.S. PATENT DOCUMENTS

| | | |
|---|---|---|
| 2022/0142918 A1 | 5/2022 | Kakumanu et al. |
| 2022/0160629 A1 | 5/2022 | Kakumanu et al. |
| 2022/0202373 A1 | 6/2022 | Yocca et al. |

FOREIGN PATENT DOCUMENTS

| | | |
|---|---|---|
| AU | 2014227693 B2 | 6/2018 |
| CA | 2324967 A1 | 5/2002 |
| CN | 101496801 A | 8/2009 |
| CN | 102657635 A | 9/2012 |
| CN | 104784174 A | 7/2015 |
| CN | 105287519 A | 2/2016 |
| CN | 106539778 A | 3/2017 |
| CN | 106727443 A | 5/2017 |
| CN | 106727524 A1 | 5/2017 |
| CN | 107137399 A | 9/2017 |
| CN | 107412204 A | 12/2017 |
| CN | 107693485 A | 2/2018 |
| CN | 109620802 A | 4/2019 |
| CN | 110893186 A | 3/2020 |
| CN | 111481506 A | 8/2020 |
| CN | 112138250 A | 12/2020 |
| EP | 0681601 B1 | 2/1999 |
| EP | 1549305 B1 | 4/2009 |
| EP | 1695094 B1 | 6/2013 |
| EP | 3326612 A1 | 5/2018 |
| JP | 2009-526829 A | 7/2009 |
| KR | 10-1859486 B1 | 6/2018 |
| KR | 10-2019-0109310 A | 9/2019 |
| RU | 2635532 C1 | 11/2017 |
| WO | WO 95/14746 A2 | 6/1995 |
| WO | WO 98/37111 A1 | 8/1998 |
| WO | WO 2004/032913 A1 | 4/2004 |
| WO | WO 2005/032519 A1 | 4/2005 |
| WO | WO 2005/039499 A2 | 5/2005 |
| WO | WO 2006/090371 A2 | 8/2006 |
| WO | WO 2008/079721 A1 | 7/2008 |
| WO | WO 2008/091588 A1 | 7/2008 |
| WO | WO 2009/048606 A1 | 4/2009 |
| WO | WO 2009/076165 A1 | 6/2009 |
| WO | WO 2010/132882 A2 | 11/2010 |
| WO | WO 2012/009144 A2 | 1/2012 |
| WO | WO 2012/075373 A2 | 6/2012 |
| WO | WO 2012/083269 A1 | 6/2012 |
| WO | WO 2012/177326 A1 | 12/2012 |
| WO | WO 2013/090278 A2 | 6/2013 |
| WO | WO 2013/090278 A3 | 6/2013 |
| WO | WO 2013/103378 A1 | 7/2013 |
| WO | WO 2013/130577 A2 | 9/2013 |
| WO | WO 2013/173317 A1 | 11/2013 |
| WO | WO 2014/130777 A1 | 8/2014 |
| WO | WO 2014/153489 A1 | 9/2014 |
| WO | WO 2014/176444 A1 | 10/2014 |
| WO | WO 2015/054058 A1 | 4/2015 |
| WO | WO 2015/054059 A2 | 4/2015 |
| WO | WO 2015/054061 A1 | 4/2015 |
| WO | WO 2015/054063 A1 | 4/2015 |
| WO | WO 2016/061413 A1 | 4/2016 |
| WO | WO 2016/061554 A1 | 4/2016 |
| WO | WO 2016/075365 A1 | 5/2016 |
| WO | WO 2016/089997 A1 | 6/2016 |
| WO | WO 2017/117627 A1 | 7/2017 |
| WO | WO 2018/072015 A1 | 4/2018 |
| WO | WO 2018/086498 A1 | 5/2018 |
| WO | WO 2018/109272 A1 | 6/2018 |
| WO | WO 2018/116202 A1 | 6/2018 |
| WO | WO 2018/126182 A1 | 7/2018 |
| WO | WO 2019/036253 A1 | 2/2019 |
| WO | WO 2019/070929 A1 | 4/2019 |
| WO | WO 2019/158810 A1 | 8/2019 |
| WO | WO 2020/006073 A1 | 1/2020 |
| WO | WO 2020/006092 A1 | 1/2020 |
| WO | WO 2020/006119 A1 | 1/2020 |
| WO | WO 2020/259440 A1 | 12/2020 |
| WO | WO 2021/016112 A2 | 1/2021 |
| WO | WO 2021/055595 A1 | 3/2021 |

OTHER PUBLICATIONS

Adami, et al., "Combinations of dexmedetomidine and alfaxalone with butorphanol in cats: application of an innovative stepwise optimization method to identify optimal clinical doses for intramuscular anaesthesia." J Feline Med Surg. (2016); 18 (10): 846-853.

Ahmad, et al., "Effects of Midazolam or Midazolam-Fentanyl on Sedation and Analgesia Produced by Intramuscular Dexmedetomidine in Dogs." Asian Journal of Animal Sciences (2011); 5 (5): 302-316.

Aho, et al., "Intramuscularly administered dexmedetomidine attenuates hemodynamic and stress hormone responses to gynecologic laparoscopy." Anesth Analg. (1992); 75(6): 932-939.

Aich, et al., "A Comparison of Intranasal Dexmedetomidine and Intranasal Midazolam for Premedication in Children Undergoing Elective Surgeries." International Journal of Science and Research (IJSR) (2016); 5 (7): 1730-1737.

Akin, et al., "Dexmedetomidine vs midazolam for premedication of pediatric patients undergoing anesthesia." Pediatric Anesthesia (2012); 22 (9): 871-876.

Albertson et al., "Is It Prime Time for Alpha2-Adrenocepter Agonists in the Treatment of Withdrawal Syndromes?," J. Med. Toxicol. (2014) 10:369-381.

Ali and Abdellatif, "Prevention of sevoflurane related emergence agitation in children undergoing adenotonsillectomy: A comparison of dexmedetomidine and propofol." Saudi J Anaesth. (2013); 7(3): 296-300, 7 pages.

Ambi, et al., "Intranasal dexmedetomidine for paediatric sedation for diagnostic magnetic resonance imaging studies." Indian J Anaesth. (2012); 56(6): 587-588.

Ansah, et al., "Comparison of three doses of dexmedetomidine with medetomidine in cats following intramuscular administration." Veterinary Pharmacology and Therapeutics (1998); 21(5): 380-387.

Antonino and Junior, "Effectiveness Of Intramuscular Dexmedetomidine And Methadone In Combination To Intratesticular Lidodaine For Orquiectomy In Dogs—Preliminary Study." Investigação (2017); vol. 16, No. 7. Abstract, 2 pages.

Anttila, et al., "Bioavailability of dexmedetomidine after extravascular doses in healthy subjects." British Journal of Clinical Pharmacology (2003); 56(6): 691-693.

Anusua, et al., "Efficacy of Dexmedetomidine in Reducing Emergence Agitation After Sevoflurane Anaesthesia in Indian Paediatric Population." International Journal of Scientific Research (2015); 4(7): ISSN No. 2277-8179, pp. 458-461.

ANZCTR Clinical Trial ID: ACTRN12616001522404, Does ketamine improve the quality of sedation of intranasal dexmedetomidine premedication in children. Fujian Provincial Hospital, Date Registered Nov. 4, 2016, Date Last Updated Jan. 29, 2018, https://www.anzctr.org.au/Trial/Registration/TrialReview.aspx?id=369976, downloaded May 6, 2018, 5 pages.

Assad, et al., "Comparative study between prophylactic single dose of fentanyl and dexmedetomidine in the management of agitation after sevoflurane anesthesia in children." Egyptian Journal of Anaesthesia (2011); 27(1): 31-37.

Aungst, et al., "Comparison of nasal, rectal, buccal, sublingual and intramuscular insulin efficacy and the effects of a bile salt absorption promoter." Journal of Pharmacology and Experimental Therapeutics (1988); 244(1): 23-27.

Ayeko and Mohamed, "Prevention and treatment of sevoflurane emergence agitation and delirium in children with dexmedetomidine." Saudi J Anaesth. (2014); 8(4): 570-571.

Baddigam et al., "Dexmedetomidine in the Treatment of Withdrawal Syndromes in Cardiothoracic Surgery Patients," J. Intensive Care Med., 2005;20(2):118-123.

Bajwa et al., "Dexmedetomidine: An Adjuvant Making Large Inroads into Clinical Practice," Annals of Medical and Health Sciences Research, Oct.-Dec. 2013, vol. 3, Issue 4, pp. 475-483.

Bakri, et al., "Comparison of dexmedetomidine or ondansetron with haloperidol for treatment of postoperative delirium in trauma patients

(56) References Cited

OTHER PUBLICATIONS admitted to intensive care unit: randomized controlled trial." Anaesth Pain & Intensive Care (2015); 19(2): 118-123.

Behrle, et al., "Intranasal Dexmedetomidine as a Sedative for Pediatric Procedural Sedation." J Pediatr Pharmacol Ther (2017); 22 (1): 4-8.

Belgrade et al., "Dexmedetomidine Infusion for the Management of Opioid-Induced Hyperalgesia," Pain Med., 2010;11:1819-1826.

Belkin et al., "Alpha-2 receptor agonists for the treatment of posttraumatic stress disorder," Drugs in Context 2015; 4: 212286, 5 pages.

Bergese et al., "A Phase IIIb, Randomized, Double-blind, Placebo-controlled, Multicenter Study Evaluating the Safety and Efficacy of Dexmedetomidine for Sedation During Awake Fiberoptic Intubation," American Journal of Therapeutics (2010) 17, 586-595.

Bhardwaj, et al., "Abstract PR227: Comparison of Nasal Dexmedetomidine with Oral Midazolam for Premedication in Children Effect on Psychomotor Recovery." Anesthesia & Analgesia (2016); 123 (3S_Suppl): p. 288.

Bhat, et al., "Comparison of intranasal dexmedetomidine and dexmedetomidine-ketamine for premedication in pediatrics patients: A randomized double-blind study." Anesth Essays Res. (2016); 10 (2): 349-355.

Biermann, et al., "Sedative, cardiovascular, haematologic and biochemical effects of four different drug combinations administered intramuscularly in cats." Veterinary Anaesthesia and Analgesia (2012); 39 (2): 137-150.

BioXcel Therapeutics, Inc., "BioXcel Therapeutics, Inc. (BTAI) CEO Vimal Mehta on Q2 2018 Results—Earnings Call Transcript," Seeking Alpha, Aug. 12, 2018, 13 pages, retrieved from: https://seekingalpha.com/article/4198129-bioxcel-therapeutics-inc-btai-ceo-vimal-mehta-q2-2018-results-earnings-call-transcript?part=single.

BioXcel Therapeutics, Inc., "BioXcel Therapeutics Provides Update on the Clinical Advancement of BXCL501 for the Acute Treatment of Agitation," Globe Newswire, Oct. 30, 2018, 2 pages, retrieved from: https://www.globenewswire.com/news-release/2018/10/30/1638858/0/en/BioXcel-Therapeutics-Provides-Update-on-the-Clinical-Advancement-of-BXCL501-for-the-Acute-Treatment-of-Agitation.html.

BioXcel Therapeutics, Inc., "BioXcel Therapeutics Reports Positive Results from Study in Agitated Schizophrenia Patients Supporting BXCL501 Clinical Development," Globe Newswire, Nov. 14, 2018, 3 pages, retrieved from: https://www.globenewswire.com/news-release/2018/11/14/1651151/0/en/BioXcel-Therapeutics-Reports-Positive-Results-from-Study-in-Agitated-Schizophrenia-Patients-Supporting-BXCL501-Clinical-Development.html.

BioXcel Therapeutics, Inc., "BioXcel Therapeutics Reports Second Quarter 2018 Financial Results and Provides Business Update," Globe Newswire, Aug. 8, 2018, 3 pages, retrieved from: https://ir.bioxceltherapeutics.com/press-releases/detail/49/bioxcel-therapeutics-reports-second-quarter-2018-financial.

BioXcel Therapeutics, Inc., "BioXcel Therapeutics Reports Third Quarter 2018 Quarterly Results and Provides Business Update," Globe Newswire, Nov. 9, 2018, 3 pages, retrieved from: https://ir.bioxceltherapeutics.com/press-releases/detail/61/bioxcel-therapeutics-reports-third-quarter-2018-quarterly.

BioXcel Therapeutics, Inc., "BioXcel Therapeutics to Host Second Quarter 2018 Financial Results and Business Update," Globe Newswire, Aug. 2, 2018, 2 pages, retrieved from: https://ir.bioxceltherapeutics.com/press-releases/detail/47/bioxcel-therapeutics-to-host-second-quarter-2018-financial.

Bonanno, et al., "Effectiveness of preoperative intranasal dexmedetomidine compared with oral midazolam for the prevention of emergence delirium in pediatric patients undergoing general anesthesia: a systematic review protocol." JBI Database of Systematic Reviews and Implementation Reports: 2016; 14 (8): 70-79.

Bond, et al., "Dexmedetomidine Nasal Sedation Produces More Oculocardiac Reflex During Strabismus Surgery." Journal of Pediatric Ophthalmology and Strabismus (2016); 53 (5): 318.

Boriosi et al., "Safety and Efficacy of Buccal Dexmedetomidine for MRI Sedation in School-Aged Children," Hospital Pediatrics, May 2019, vol. 9, Issue 5, pp. 348-354.

Boyer, Jeanne, "Calming patient agitation with dexmedetomidine." Nursing Critical Care (2010); 5 (1): 30-34.

Bryson, et al., "Treatment-resistant postictal agitation after electroconvulsive therapy (ECT) controlled with dexmedetomidine." The Journal of ECT (2013); 29(2): e18.

Candiotti et al., "Monitored Anesthesia Care with Dexmedetomidine: A Prospective, Randomized, Double-Blind, Multicenter Trial," Anesth Analg 2010;110(1):47-56.

Canfrán, et al., "Comparison of sedation scores and propofol induction doses in dogs after intramuscular administration of dexmedetomidine alone or in combination with methadone, midazolam, or methadone plus midazolam." The Veterinary Journal (2016); 210: 56-60.

Carrasco et al., "Dexmedetomidine for the Treatment of Hyperactive Delirium Refractory to Haloperidol in Nonintubated ICU Patients: A Nonrandomized Controlled Trial," Critical Care Medicine, 2016, 44:1295-1306, 12 pages.

Carter, et al., "Onset and quality of sedation after intramuscular administration of dexmedetomidine and hydromorphone in various muscle groups in dogs." Journal of the American Veterinary Medical Association (2013); 243(11): 1569-1572.

Center for Drug Evaluation and Research, Application No. 21-038, Medical Review(s), Drug Name: Precedex (dexmedetomidine hcl injection), Dec. 18, 1998, 183 pages.

Center for Drug Evaluation and Research, Application No. 21-038, Pharmacology Review(s), Drug Name: Precedex (dexmedetomidine hcl injection), Dec. 18, 1998, 184 pages.

Chao and Zhong, "Effects of preoperative intranasal Dexmedetomidine for the bispectral index and median effective concentration of Sevoflurane in children with abdominal surgery by inhalation anesthesia of Sevoflurane." China Medical Herald Magazine (2017); 14 (34): 66-69, 73 (with English Abstract).

Chen, et al., "Effect of dexmedetomidine on emergence agitation after oral and maxillofacial surgery." Shanghai Journal of Stomatology (2013); 22(6): 698-701 [with English Abstract/Summary].

Chen et al., "Dexmedetomidine alleviated isoflurane-induced neurotoxicity in aged rats," Int J Clin Exp Med 2018;11(4):3686-3692.

Chen et al., "Protective role of dexmedetomidine in unmethylated CpG-induced inflammation responses in BV2 microglia cells," Folia Neuropathol 2016; 54 (4): 382-391.

Cheon and Tkachenko, "Use of dexmedetomidine for prevention of post-operative agitation in a 14 year-old male with Angelman's Syndrome." University of Chicago, Chicago, IL (2014); 1 page.

Cheung, et al., "Analgesic and sedative effects of intranasal dexmedetomidine in third molar surgery under local anaesthesia." British Journal of Anaesthesia (2011); 107 (3): 430-437.

Cheung, et al., "Evaluation of the Analgesic Efficacy of Local Dexmedetomidine Application," Clin J Pain, Jun. 2011, vol. 27, No. 5, pp. 337-382.

Cheung, et al., "Intranasal dexmedetomidine in combination with patient-controlled sedation during upper gastrointestinal endoscopy: a randomised trial." Acta Anestheologica Scandinavica (2015); 59 (2): 215-223.

Chowdhury et al., "General intensive care for patients with traumatic brain injury: An update," Saudi Journal of Anaesthesia, 2014, vol. 8, Issue 2, pp. 256-263.

Christiansen, et al., "Sedation of red porgy (*Pagrus pagrus*) and black sea bass (*Centropristis striata*) using ketamine (K), dexmedetomidine (D) and midazolam (M) delivered via intramuscular injection." Journal of Zoo and Aquarium Research (2014); 2 (3): 62-68.

Cimen, et al., "Comparison of buccal and nasal dexmedetomidine premedication for pediatric patients." Paediatr Anaesth. (2013); 23(2): 134-138.

Citalopram/opiate alkaloids Serotonin syndrome, treated with dexmedetomidine: case report, Reactions Weekly, Nov. 2015, vol. 1579, Issue 1, p. 117.

Clinical Trial Registration No. ChiCTR-IOR-17012415, "Effect of nasal dexmedetomidine on the prevention of emergence agitation in children undergoing day surgery with desoflurane anesthesia."

(56) References Cited

OTHER PUBLICATIONS

Guangzhou Women and Children Medical Center, Date of Registration: Aug. 18, 2017, Estimated Trial End Date: Mar. 31, 2018, http://www.chictr.org.cn/showprojen.aspx?proj=21174, downloaded May 5, 2018, 3 pages.
ClinicalTrials.gov Identifier: NCT00095251, MENDS Study: Trial in Ventilated ICU Patients Comparing an Alpha2 Agonist Versus a Gamma Aminobutyric Acid (GABA)-Agonist to Determine Delirium Rates, Efficacy of Sedation, Analgesia and Discharge Cognitive Status, First Posted—Nov. 2, 2004, Last Update Posted—Sep. 11, 2018, retrieved from https://clinicaltrials.gov/ct2/show/NCT00095251, 8 pages.
ClinicalTrials.gov Identifier: NCT00351299, Randomized Controlled Trial of Dexmedetomidine for the Treatment of Intensive Care Unit (ICU) Delirium, Jul. 12, 2006, Last Update Posted—Jun. 9, 2017, retrieved from https://clinicaltrials.gov/ct2/show/NCT00351299, 15 pages.
ClinicalTrials.gov Identifier: NCT00417664, Is Dexmedetomidine Associated With a Lower Incidence of Postoperative Delirium When Compared to Propofol or Midazolam in Cardiac Surgery Patients, First Posted—Jan. 4, 2007, Last Update Posted—Jan. 4, 2007, retrieved from https://clinicaltrials.gov/ct2/show/NCT00417664, 5 pages.
ClinicalTrials.gov Identifier: NCT00455143, Cognitive Protection—Dexmedetomidine and Cognitive Reserve, First Posted—Apr. 3, 2007, Last Update Posted—Jul. 17, 2019, retrieved from https://clinicaltrials.gov/ct2/show/NCT00455143, 20 pages.
ClinicalTrials.gov Identifier: NCT00460473, A Research Study to Evaluate the Effectiveness of Dexmedetomidine in Preventing Delirium After Hip Fracture Repair Surgery, First Posted—Apr. 16, 2007, Last Update Posted—Jul. 24, 2015, retrieved from https://clinicaltrials.gov/ct2/show/NCT00460473, 7 pages.
ClinicalTrials.gov Identifier: NCT00464763, A Research Study to Evaluate the Effectiveness of Dexmedetomidine in Preventing Delirium After Heart Surgery, First Posted—Apr. 24, 2007, Last Update Posted—Mar. 21, 2017, retrieved from https://clinicaltrials.gov/ct2/show/NCT00460473, 7 pages.
ClinicalTrials.gov Identifier: NCT00468052, Decrease Emergence Agitation and Provide Pain Relief for Children Undergoing Tonsillectomy & Adenoidectomy, First Posted—May 1, 2007, Last Update Posted—Dec. 5, 2016, retrieved from https://clinicaltrials.gov/ct2/show/NCT00468052, 24 pages.
ClinicalTrials.gov Identifier: NCT00505804, A Comparison of Dexmedetomidine and Haloperidol in Patients With Intensive Care Unit (ICU)-Associated Agitation and Delirium (Dex), First Posted—Jul. 25, 2007, Last Update Posted—Jan. 24, 2013, retrieved from https://clinicaltrials.gov/ct2/show/NCT00505804, 6 pages.
ClinicalTrials.gov Identifier: NCT00561678, Perioperative Cognitive Function—Dexmedetomidine and Cognitive Reserve, First Posted—Nov. 21, 2007, Last Update Posted—Apr. 23, 2018, retrieved from https://clinicaltrials.gov/ct2/show/NCT00561678, 23 pages.
ClinicalTrials.gov Identifier: NCT00654329, Dexmedetomidine vs Fentanyl for BMT (DexBMT). Children's Research Institute, First Posted Apr. 8, 2018, Results First Posted Apr. 25, 2011, Last Update Posted Apr. 25, 2011, Study Start Date Aug. 2005, https://clinicaltrials.gov/ct2/show/NCT00654329, downloaded May 5, 2018, 6 pages.
ClinicalTrials.gov Identifier: NCT00778063, Study Using Dexmedetomidine to Decreases Emergence Delirium in Pediatric Patients (PED-DEX). Ochsner Health System, First Posted Oct. 23, 2008, Last Update Posted Mar. 15, 2013, Study Start Date Mar. 2009, https://clinicaltrials.gov/ct2/show/NCT00778063, downloaded May 6, 2018, 8 pages.
ClinicalTrials.gov Identifier: NCT00837187, Bioavailability of Dexmedetomidine After Intranasal Administration (INDEX). University of Turku, First Posted Feb. 5, 2009, Last Update Posted Jan. 13, 2010, Study Start Date Mar. 2009, https://clinicaltrials.gov/ct2/show/NCT00837187, downloaded May 6, 2018, 6 pages.
ClinicalTrials.gov Identifier: NCT00857727, Use of Dexmedetomidine to Reduce Emergence Delirium Incident in Children (DexPeds), First Posted—Mar. 9, 2009, Last Update Posted—Nov. 27, 2018, retrieved from https://clinicaltrials.gov/ct2/show/NCT00857727, 18 pages.
ClinicalTrials.gov Identifier: NCT01065701, Comparison of Two Doses of Intranasal Dexmedetomidine as Premedication in Children. The University of Hong Kong, First Posted Feb. 9, 2010, Last Update Posted Oct. 26, 2017, Study Start Date Jul. 2009, https://clinicaltrials.gov/ct2/show/NCT01065701, downloaded May 6, 2018, 5 pages.
ClinicalTrials.gov Identifier: NCT01132794, A Study to Assess the Analgesia and Sedation Using Intranasal Dexmedetomidine in Third Molar Surgery Under Local Anaesthesia. The University of Hong Kong, First Posted May 28, 2010, Last Update Posted Jun. 16, 2010, https://clinicaltrials.gov/ct2/show/NCT01132794, downloaded May 5, 2018, 6 pages.
ClinicalTrials.gov Identifier: NCT01140529, Dexmedetomidine for the Treatment of Delirium After Heart Surgery (DexinDelir), First Posted—Jun. 9, 2010, Last Update Posted—Nov. 1, 2016, retrieved from https://clinicaltrials.gov/ct2/show/NCT01140529, 5 pages.
ClinicalTrials.gov Identifier: NCT01151865, Dexmedetomidine to Lessen Intensive Care Unit (ICU) Agitation (DahLIA), First Posted—Jun. 29, 2010, Last Update Posted—Jan. 21, 2015, retrieved from https://clinicaltrials.gov/ct2/show/NCT01151865, 9 pages.
ClinicalTrials.gov Identifier: NCT01188551, Dexmedetomidine Versus Fentanyl Following Pressure Equalization Tube Placement. Nationwide Children's Hospital, First Posted Aug. 25, 2010, Last Update Posted Apr. 1, 2014, Study Start Date Jan. 2011, https://clinicaltrials.gov/ct2/show/NCT01188551, downloaded May 5, 2018, 6 pages.
ClinicalTrials.gov Identifier: NCT01255904, A Trial Of Oral Chloral Hydrate Versus Intranasal Dexmedetomidine For Sedated Abr Exams. Baylor College of Medicine, First Posted Dec. 8, 2010, Last Update Posted May 16, 2016, Study Start Date Aug. 2011, https://clinicaltrials.gov/ct2/show/NCT01255904, downloaded May 6, 2018, 5 pages.
ClinicalTrials.gov Identifier: NCT01283412, Dexmedetomidine on Postoperative Delirium and Quality of Recovery in Geriatric Patients, First Posted—Jan. 26, 2011, Last Update Posted—Nov. 20, 2013, retrieved from https://clinicaltrials.gov/ct2/show/NCT01283412, 4 pages.
ClinicalTrials.gov Identifier: NCT01353378, Use of Dexmedetomidine in Children Undergoing Oral Maxillofacial Surgery to Decrease Emergence Delirium, First Posted—May 13, 2011, Last Update Posted—May 5, 2017, retrieved from https://clinicaltrials.gov/ct2/show/NCT01353378, 5 pages.
ClinicalTrials.gov Identifier: NCT01362205, Dexmedetomidine (Precedex®) for Severe Alcohol Withdrawal Syndrome (AWS) and Alcohol Withdrawal Delirium (AWD), First Posted—May 30, 2011, Last Update Posted—Nov. 6, 2017, retrieved from https://clinicaltrials.gov/ct2/show/NCT01362205, 36 pages.
ClinicalTrials.gov Identifier: NCT01374737, ED50 of Dexmedetomidine to Prevent Emergence Agitation in Children, First Posted—Jun. 16, 2011, Last Update Posted—Jun. 16, 2011, downloaded Feb. 11, 2018 https://clinicaltrials.gov/ct2/show/NCT01374737, 5 pages.
ClinicalTrials.gov Identifier: NCT01378741, Reducing Delirium After Cardiac Surgery: A Multifaceted Approach Of Perioperative Care, First Posted—Jun. 22, 2011, Last Update Posted—Apr. 21, 2015, retrieved from https://clinicaltrials.gov/ct2/show/NCT01378741, 5 pages.
ClinicalTrials.gov Identifier: NCT01512355, The Effect of Dexmedetomidine on Decreasing Emergence Agitation and Delirium in Pediatric Patients Undergoing Strabismus Surgery, First Posted—Jan. 19, 2012, Last Update Posted—Jul. 16, 2015, retrieved from https://clinicaltrials.gov/ct2/show/NCT01512355, 5 pages.
ClinicalTrials.gov Identifier: NCT01513772, The Effect of Dexmedetomidine on the Emergence Agitation in Nasal Surgery, First Posted—Jan. 20, 2012, Last Update Posted—Aug. 9, 2012, retrieved from https://clinicaltrials.gov/ct2/show/NCT01513772, 4 pages.
ClinicalTrials.gov Identifier: NCT01517438, Effects of Serotonin Inhibitors on Patient-controlled Analgesia Related Nausea and

(56) References Cited

OTHER PUBLICATIONS

Vomiting, First Posted—Jan. 25, 2012, Last Update Posted—Jan. 25, 2012, retrieved from https://clinicaltrials.gov/ct2/show/NCT01517438, 4 pages.
ClinicalTrials.gov Identifier: NCT01517932, Effects of Dexmedetomidine on Stress Response and Postoperative Analgesia, First Posted—Jan. 25, 2012, Last Update Posted—Mar. 20, 2013, retrieved from https://clinicaltrials.gov/ct2/show/NCT01517932, 6 pages.
ClinicalTrials.gov Identifier: NCT01524367, Effect of Single-dose Dexmedetomidine on Emergence Excitement in Adults With Nasotracheal Intubation After Orthognathic Surgery, First Posted—Feb. 2, 2012, Last Update Posted—Feb. 6, 2015, retrieved from https://clinicaltrials.gov/ct2/show/NCT01524367, 6 pages.
ClinicalTrials.gov Identifier: NCT01528891, Dexmedetomidine as a Rapid Bolus in Children for Emergence Agitation, First Posted—Feb. 8, 2012, Last Update Posted—Jan. 20, 2016, downloaded Feb. 11, 2018 https://clinicaltrials.gov/ct2/show/results/NCT01528891, 6 pages.
ClinicalTrials.gov Identifier: NCT01528891, Dexmedetomidine as a Rapid Bolus in Children for Emergence Agitation, First Posted—Feb. 8, 2012, Last Update Posted—Mar. 8, 2018, retrieved from https://clinicaltrials.gov/ct2/show/results/NCT01528891, 15 pages.
ClinicalTrials.gov Identifier: NCT01535287, The Effect of Intramuscular Dexmedetomidine on Emergence Agitation in Children Undergoing With or Without Tube Insertion Under General Anesthesia. First Posted—Feb. 17, 2012, Last Update Posted—Feb. 17, 2012, Study Start Date—Jun. 2010, Estimated Study Completion Date—Jan. 2013, 9 pages.
ClinicalTrials.gov Identifier: NCT01535287, The Effect of Intramuscular Dexmedetomidine on Emergence Agitation in Children Undergoing With or Without Tube Insertion Under General Anesthesia. First Posted—Feb. 17, 2012, Last Update Posted—Jul. 9, 2018, retrieved from https://clinicaltrials.gov/ct2/show/NCT01535287, 24 pages.
ClinicalTrials.gov Identifier: NCT01578161, The Effect of Dexmedetomidine on Emergence Agitation in Children Undergoing a Surgery Under Desflurane Anesthesia, First Posted—Apr. 16, 2012, Last Update Posted—Apr. 16, 2012, downloaded Feb. 11, 2018 https://clinicaltrials.gov/ct2/show/NCT01578161, 6 pages.
ClinicalTrials.gov Identifier: NCT01691001, Effect of Dexmedetomidine on Sevoflurane Requirements and Emergence Agitation in Children Undergoing Ambulatory Surgery, First Posted—Sep. 24, 2012, Last Update Posted—Sep. 24, 2012, retrieved from https://clinicaltrials.gov/ct2/show/NCT01691001, 4 pages.
ClinicalTrials.gov Identifier: NCT01739933, The MENDS2 Study, Maximizing the Efficacy of Sedation and Reducing Neurological Dysfunction and Mortality in Septic Patients With Acute Respiratory Failure (MENDS2), First Posted—Dec. 4, 2012, Last Update Posted—Apr. 5, 2019, retrieved from https://clinicaltrials.gov/ct2/show/NCT01739933, 11 pages.
ClinicalTrials.gov Identifier: NCT01791296, Does Nightly Dexmedetomidine Improve Sleep and Reduce Delirium in ICU Patients? (SKY-DEX), First Posted—Feb. 13, 2013, Last Update Posted—Mar. 17, 2017, retrieved from https://clinicaltrials.gov/ct2/show/NCT01791296, 8 pages.
ClinicalTrials.gov Identifier: NCT01887184, Sedation Using Intranasal Dexmedetomidine in Upper Gastrointestinal Endoscopy. The University of Hong Kong, First Posted Jun. 26, 2013, Last Update Posted Oct. 28, 2014, Study Start Date Jan. 2009, https://clinicaltrials.gov/ct2/show/NCT01887184, downloaded May 5, 2018, 7 pages.
ClinicalTrials.gov Identifier: NCT01895023, Effects of Dexmedetomidine Premedication on Emergence Agitation After Strabismus Surgery in Children. Yao Yusheng, First Posted Jul. 10, 2013, Last Update Posted Jan. 6, 2015, Study Start Date Sep. 2013, https://clinicaltrials.gov/ct2/show/NCT01895023, downloaded May 5, 2018, 7 pages.
ClinicalTrials.gov Identifier: NCT01900405, Intranasal Dexmedetomidine Sedation for Pediatric CT Imaging. University of Sao Paulo, First Posted Jul. 16, 2013, Last Update Posted Jul. 16, 2013, Study Start Date Apr. 2013, downloaded https://clinicaltrials.gov/ct2/show/NCT01900405, downloaded May 6, 2018, 7 pages.
ClinicalTrials.gov Identifier: NCT01901588, Efficacy of Single-Shot Dexmedetomidine Versus Placebo in Preventing Pediatric Emergence Delirium in Strabismus Surgery, First Posted—Mar. 8, 2016, Last Update Posted—Last Update Posted—Jul. 11, 2016, retrieved from https://clinicaltrials.gov/ct2/show/NCT01901588, 5 pages.
ClinicalTrials.gov Identifier: NCT01904760, Dexmedetomidine to Prevent Agitation After Free Flap Surgery, First Posted—Jul. 22, 2013, Last Update Posted—Nov. 13, 2014, retrieved from https://clinicaltrials.gov/ct2/show/NCT01904760, 6 pages.
ClinicalTrials.gov Identifier: NCT01934049, Postoperative Recovery in Elderly Patients Undergoing Hip Hemi-arthroplasty, First Posted—Sep. 4, 2013, Last Update Posted—Sep. 10, 2013, retrieved from https://clinicaltrials.gov/ct2/show/NCT01934049, 7 pages.
ClinicalTrials.gov Identifier: NCT01937611, Intramuscular Dexmedetomidine as Premedication. First Posted—Sep. 9, 2013, Last Update Posted—Sep. 9, 2013, Study Start Date—Mar. 2013, Estimated Study Completion Date—Oct. 2013, 8 pages.
ClinicalTrials.gov Identifier: NCT01966315, The Comparison of Dexmedetomidine and Midazolam for the Sleep in Intensive Care Unit, First Posted—Oct. 21, 2013, Last Update Posted—Apr. 23, 2019, retrieved from https://clinicaltrials.gov/ct2/show/NCT01966315, 5 pages.
ClinicalTrials.gov Identifier: NCT02007798, Small-dose Dexmedetomidine Effects on Recovery Profiles of Supratentorial Tumors Patients From General Anesthesia, First Posted—Dec. 11, 2013, Last Update Posted—Jan. 14, 2014, retrieved from https://clinicaltrials.gov/ct2/show/NCT02007798, 8 pages.
ClinicalTrials.gov Identifier: NCT02072083, Intranasal Dexmedetomidine vs Midazolam-ketamine Combination for Premedication of Pediatric Patients. TC Erciyes University, First Posted Feb. 26, 2014, Last Update Posted Apr. 14, 2015, Study Start Date Feb. 2014, https://clinicaltrials.gov/ct2/show/NCT02072083, downloaded May 5, 2018, 6 pages.
ClinicalTrials.gov Identifier: NCT02077712, Intranasal Dexmedetomidine Sedation for Ophthalmic Examinations in Children (DEX-EYE). Sun Yat-sen University, First Posted Mar. 4, 2014, Last Update Posted May 3, 2016, Study Start Date Feb. 2014, https://clinicaltrials.gov/ct2/show/NCT02077712, downloaded May 5, 2018, 7 pages.
ClinicalTrials.gov Identifier: NCT02080169, Safety and Efficacy of Combined Sedation With Midazolam and Dexmedetomidine in ICU Patients, First Posted—Mar. 6, 2014, Last Update Posted—Mar. 6, 2014, retrieved from https://clinicaltrials.gov/ct2/show/NCT02080169, 8 pages.
ClinicalTrials.gov Identifier: NCT02096068, Neuroprotection With Dexmedetomidine in Patients Undergoing Elective Cardiac or Abdominal Surgery (Neuprodex), First Posted—Mar. 26, 2014, Last Update Posted—Aug. 22, 2018, retrieved from https://clinicaltrials.gov/ct2/show/NCT02096068, 9 pages.
ClinicalTrials.gov Identifier: NCT02104297, Effect of Deksmedetomidine and Remifentanil in Extubation Agitation (EA), First Posted—Apr. 4, 2014, Last Update Posted—Apr. 4, 2014, retrieved from https://clinicaltrials.gov/ct2/show/NCT02104297, 5 pages.
ClinicalTrials.gov Identifier: NCT02108171, Intranasal Dexmedetomidine Premedication. Guangzhou First People's Hospital, First Posted Apr. 9, 2014, Last Update Posted Mar. 14, 2016, Study Start Date Mar. 2014, https://clinicaltrials.gov/ct2/show/NCT02108171, downloaded May 5, 2018, 24 pages.
ClinicalTrials.gov Identifier: NCT02117726, Impact of Various Sedation Regimens on the Incidence of Delirium, First Posted—Apr. 21, 2014, Last Update Posted—Jul. 16, 2014, retrieved from https://clinicaltrials.gov/ct2/show/NCT02117726, 7 pages.
ClinicalTrials.gov Identifier: NCT02168439, Intranasal Dexmedetomidine vs Intranasal Midazolam as Anxiolysis Prior to Pediatric Laceration Repair. University of Pittsburgh, Results First Posted Mar. 10, 2017, Last Update Posted Mar. 10, 2017, Study Start Date Jun. 2014, https://clinicaltrials.gov/ct2/show/NCT02168439, downloaded May 6, 2018, 6 pages.

(56) References Cited

OTHER PUBLICATIONS

ClinicalTrials.gov Identifier: NCT02169336, Placebo-Controlled Evaluation of Intranasal Dexmedetomidine for Postoperative Analgesia Following Bunionectomy. Recro Pharma, Inc., First Posted Jun. 23, 2014, Last Update Posted Dec. 10, 2015, Study Start Date Jun. 2014, https://clinicaltrials.gov/ct2/show/NCT02169336, downloaded May 6, 2018, 7 pages.

ClinicalTrials.gov Identifier: NCT02169843, Minimizing ICU Neurological Dysfunction With Dexmedetomidine-induced Sleep (MINDDS), First Posted—Jun. 23, 2014, Last Update Posted—Jun. 23, 2014, retrieved from https://clinicaltrials.gov/ct2/show/NCT02169843, 6 pages.

ClinicalTrials.gov Identifier: NCT02211118, Sedation and Physiological Effects of Intranasal Dexmedetomidine in Severe COPD. Dayton VA Medical Center, First Posted Aug. 7, 2014, Last Update Posted Feb. 8, 2017, Study Start Date Oct. 2014, https://clinicaltrials.gov/ct2/show/NCT02211118, 6 pages.

ClinicalTrials.gov Identifier: NCT02222636, The Clinical Research of Intranasal Dexmedetomidine Used in Plastic Surgery of Children. Xijing Hospital, First Posted Aug. 21, 2014, Last Update Posted Aug. 21, 2014, Study Start Date Sep. 2014, https://clinicaltrials.gov/ct2/show/NCT02222636, downloaded May 6, 2018, 6 pages.

ClinicalTrials.gov Identifier: NCT02225210, Effects of Dexmedetomidine Sedation on Delirium and Haemodynamic in Mechanical Ventilated Elderly Patients, First Posted—Aug. 26, 2014, Last Update Posted—Aug. 26, 2014, retrieved from https://clinicaltrials.gov/ct2/show/NCT02225210, 6 pages.

ClinicalTrials.gov Identifier: NCT02267538, Dexmedetomidine and Delirium in Patients After Cardiac Surgery, First Posted—Feb. 2, 2018, Last Update Posted—Mar. 5, 2018, retrieved from https://clinicaltrials.gov/ct2/show/NCT02267538, 12 pages.

ClinicalTrials.gov Identifier: NCT02366299, Comparison of Dexmedetomidine and Propofol on the Delirium and Neuroinflammation in Patients With SIRS, First Posted—Feb. 19, 2015, Last Update Posted—Feb. 19, 2015, retrieved from https://clinicaltrials.gov/ct2/show/NCT02366299, 4 pages.

ClinicalTrials.gov Identifier: NCT02239445, Intranasal Dexmedetomidine VS Oral Chloral Hydrate for Rescue Sedation During Magnetic Resonance Imaging. Guangzhou Women and Children's Medical Center, First Posted Sep. 12, 2014, Last Update Posted May 12, 2015, Study Start Date Sep. 2014, https://clinicaltrials.gov/ct2/show/NCT02239445, downloaded May 6, 2018, 7 pages.

ClinicalTrials.gov Identifier: NCT02245256, Efficacy of Low-dose Dexmedetomidine to Prevent Delirium in Liver Transplant Patients, First Posted—Sep. 19, 2014, Last Update Posted—Jan. 25, 2018, retrieved from https://clinicaltrials.gov/ct2/show/NCT02245256, 5 pages.

ClinicalTrials.gov Identifier: NCT02250703, Intranasal Dexmedetomidine Premedication in Children. Results First Posted Jul. 7, 2017, Last Update Posted Jul. 7, 2017, Study Start Date Sep. 2014, downloaded https://clinicaltrials.gov/ct2/show/NCT02250703, downloaded May 6, 2018, 8 pages.

ClinicalTrials.gov Identifier: NCT02253199, The Effect of Age on the Median Effective Dose (ED50) of Intranasal Dexmedetomidine for Rescue Sedation Following Failed Sedation With Oral Chloral Hydrate During Magnetic Resonance Imaging. Guangzhou Women and Children's Medical Center, First Posted Oct. 1, 2014, Last Update Posted Mar. 29, 2016, Study Start Date Oct. 2014, https://clinicaltrials.gov/ct2/show/NCT02253199, downloaded May 5, 2018, 7 pages.

ClinicalTrials.gov Identifier: NCT02275182, Impact of Dexmedetomidine on the Post-Operative Cognition Dysfunction(POCD) in Geriatric Patients, First Posted—Oct. 27, 2014, Last Update Posted—Apr. 25, 2018, retrieved from https://clinicaltrials.gov/ct2/show/NCT02275182, 8 pages.

ClinicalTrials.gov Identifier: NCT02284243, Placebo-Controlled Evaluation of Intranasal Dexmedetomidine for Postoperative Analgesia Following Bunionectomy Surgery. Recro Pharma, Inc., First Posted Nov. 5, 2014, Last Update Posted May 2, 2017, Study Start Date Oct. 2014, https://clinicaltrials.gov/ct2/show/NCT02284243, downloaded May 6, 2018, 8 pages.

ClinicalTrials.gov Identifier: NCT02299232, Dexmedetomidine in Children for Magnetic Resonance Imaging (MRI) Sedation (DEX). Sisli Hamidiye Etfal Training and Research Hospital, First Posted Nov. 24, 2014, Last Update Posted Oct. 25, 2017, Study Start Date Feb. 2014, https://clinicaltrials.gov/ct2/show/NCT02299232, downloaded May 6, 2018, 6 pages.

ClinicalTrials.gov Identifier: NCT02394418, Effect of Sevoflurane, Propofol and Dexmedetomidine on Delirium & Neuroinflammation in Mechanically Ventilated Patients, First Posted—Mar. 20, 2015, Last Update Posted—Jul. 5, 2017, retrieved from https://clinicaltrials.gov/ct2/show/NCT02394418, 5 pages.

ClinicalTrials.gov Identifier: NCT02412150, Effect of Dexmedetomidine After Thyroidectomy, First Posted—Apr. 9, 2015, Last Update Posted—Mar. 6, 2019, retrieved from https://clinicaltrials.gov/ct2/show/NCT02412150, 4 pages.

ClinicalTrials.gov Identifier: NCT02459509, A Comparison of Two Doses of Intranasal Dexmedetomidine for Premedication in Children. The University of Hong Kong, First Posted Jun. 2, 2015, Last Update Posted Apr. 18, 2016, Study Start Date Jun. 2015, https://clinicaltrials.gov/ct2/show/NCT02459509, downloaded May 6, 2018, 8 pages.

ClinicalTrials.gov Identifier: NCT02509949, Effects of Dexmedetomidine on Delirium After Living Donor Renal Transplantation in Adult Patients, First Posted—Jul. 28, 2015, Last Update Posted—Jun. 12, 2018, retrieved from https://clinicaltrials.gov/ct2/show/NCT02509949, 4 pages.

ClinicalTrials.gov Identifier: NCT02528513, Midazolam Used Alone or Sequential Use of Midazolam and Propofol/Dexmedetomidine in Mechanically Ventilated Patients, First Posted—Aug. 19, 2015, Last Update Posted—Apr. 28, 2016, retrieved from https://clinicaltrials.gov/ct2/show/NCT02528513, 9 pages.

ClinicalTrials.gov Identifier: NCT02544906, Propofol Versus Dexmedetomidine for Prevention of Sevoflurane Agitation in Recipients of Living Donor Liver Transplantation (Agitation), First Posted—Sep. 9, 2015, Last Update Posted—Sep. 9, 2015, retrieved from https://clinicaltrials.gov/ct2/show/NCT02544906, 4 pages.

ClinicalTrials.gov Identifier: NCT02546765, Dexmedetomidine and IV Acetaminophen for the Prevention of Postoperative Delirium Following Cardiac Surgery (DEXACET), First Posted—Sep. 11, 2015, Last Update Posted—Aug. 1, 2018, retrieved from https://clinicaltrials.gov/ct2/show/NCT02546765, 9 pages.

ClinicalTrials.gov Identifier: NCT02548923, Dexmedetomidine Versus Propofol for Prolonged Sedation in Critically III Trauma and Surgical Patients, First Posted—Sep. 14, 2015, Last Update Posted—Sep. 14, 2015, retrieved from https://clinicaltrials.gov/ct2/show/NCT02548923, 5 pages.

ClinicalTrials.gov Identifier: NCT02573558, Intraoperative Sedation and Postoperative Delirium, First Posted—Oct. 12, 2015, Last Update Posted—Apr. 6, 2016, retrieved from https://clinicaltrials.gov/ct2/show/NCT02573558, 5 pages.

ClinicalTrials.gov Identifier: NCT02675049, Efficacy and Optimal Dose Selection of Intranasal Dexmedetomidine During Breast Lumpectomy Under Local Anaesthesia. Tianjin Medical University Cancer Institute and Hospital, First Posted Feb. 5, 2016, Last Update Posted Mar. 1, 2016, Study Start Date Jan. 2016, https://clinicaltrials.gov/ct2/show/NCT02675049, downloaded May 5, 2018, 6 pages.

ClinicalTrials.gov Identifier: NCT02699801, Dexmedetomidine Use in ICU Sedation and Postoperative Recovery in Elderly Patients and Post-cardiac Surgery (DIRECT), First Posted—Mar. 4, 2016, Last Update Posted—Nov. 3, 2016, retrieved from https://clinicaltrials.gov/ct2/show/NCT02699801, 8 pages.

ClinicalTrials.gov Identifier: NCT02720705, Transbucal Dexmedetomidine for Prevention of Sevoflurane Emergence Agitation in Pre-school Children, First Posted—Mar. 28, 2016, Last Update Posted—Dec. 27, 2017, downloaded Feb. 11, 2018 https://clinicaltrials.gov/ct2/show/NCT02720705, 7 pages.

ClinicalTrials.gov Identifier: NCT02720705, Transbucal Dexmedetomidine for Prevention of Sevoflurane Emergence Agitation in Pre-school Children, First Posted—Mar. 28, 2016, Last

(56) References Cited

OTHER PUBLICATIONS

Update Posted—Nov. 1, 2018, retrieved from https://clinicaltrials.gov/ct2/show/NCT02720705, 6 pages.

ClinicalTrials.gov Identifier: NCT02757495, Can Caudal Dexmedetomidine Prevents Sevoflurane Induced Emergence Agitation in Children, First Posted—May 2, 2016, Last Update Posted—Feb. 27, 2019, retrieved from https://clinicaltrials.gov/ct2/show/NCT02757495, 6 pages.

ClinicalTrials.gov Identifier: NCT02773797, Placebo Controlled Evaluation of Sedation and Physiological Response to Intranasal Dexmedetomidine in Severe COPD. Dayton VA Medical Center, First PostedMay 16, 2016, Last Update Posted May 16, 2016, Study Start Date Aug. 2016, https://clinicaltrials.gov/ct2/show/NCT02773797, 7 pages.

ClinicalTrials.gov Identifier: NCT02780427, ED50 and ED95 of Intranasal Dexmedetomidine in Pediatric Patients Undergoing Transthoracic Echocardiography Study. Guangzhou Women and Children's Medical Center, First Posted May 23, 2016, Last Update Posted Nov. 21, 2017, Study Start Date Jun. 2016, https://clinicaltrials.gov/ct2/show/NCT02780427, downloaded May 6, 2018, 8 pages.

ClinicalTrials.gov Identifier: NCT02793986, Dexmedetomidine vs Propofol Sedation Reduces Postoperative Delirium in Patients Receiving Hip Arthroplasty, First Posted—Jun. 8, 2016, Last Update Posted—Jun. 29, 2017, retrieved from https://clinicaltrials.gov/ct2/show/NCT02793986, 6 pages.

ClinicalTrials.gov Identifier: NCT02809937, Dexmedetomidine and Long-term Outcome in Elderly Patients After Surgery, First Posted—Jun. 22, 2016, Last Update Posted—Jun. 16, 2017, retrieved from https://clinicaltrials.gov/ct2/show/NCT02809937, 10 pages.

ClinicalTrials.gov Identifier: NCT02818569, Repurposing Dexmedetomidine as an Orally Administered Sleep Therapeutic, First Posted—Jun. 29, 2016, Last Update Posted—Aug. 17, 2018, retrieved from https://clinicaltrials.gov/ct2/show/NCT02818569, 5 pages.

ClinicalTrials.gov Identifier: NCT02836431, Pharmacokinetic Study of Dexmedetomidine After Intra-nasal Dosing in Children. Children's Hospital Medical Center, First Posted Jul. 19, 2016, Last Update Posted Aug. 1, 2017, Study Start Date Jan. 2016, https://clinicaltrials.gov/ct2/show/NCT02836431, downloaded May 6, 2018, 8 pages.

ClinicalTrials.gov Identifier: NCT02856594, Minimizing ICU Neurological Dysfunction With Dexmedetomidine-induced Sleep (MINDDS), First Posted—Aug. 5, 2016, Last Update Posted—Jan. 8, 2019, retrieved from https://clinicaltrials.gov/ct2/show/NCT02856594, 6 pages.

ClinicalTrials.gov Identifier: NCT02903407, Pain, Agitation and Delirium (PAD) Protocol in the Duke CICU, First Posted—Sep. 16, 2016, Last Update Posted—Oct. 18, 2018, retrieved from https://clinicaltrials.gov/ct2/show/NCT02903407, 9 pages.

ClinicalTrials.gov Identifier: NCT02917018, Effect of Dexmedetomidine on Stress Response and Emergence Agitation During Laparoscopic Surgery, First Posted—Sep. 28, 2016, Last Update Posted—Jan. 4, 2017, downloaded Feb. 11, 2018 https://clinicaltrials.gov/ct2/show/NCT02917018, 6 pages.

ClinicalTrials.gov Identifier: NCT02923128, Whether Dexmedetomidine Can Improve the Prognosis of Elderly Patients With Postoperative Cognitive Dysfunction, First Posted—Oct. 4, 2016, Last Update Posted—Oct. 11, 2016, retrieved from https://clinicaltrials.gov/ct2/show/NCT02923128, 7 pages.

ClinicalTrials.gov Identifier: NCT02951793, Abuse and Addiction in ICU, First Posted—Nov. 1, 2016, Last Update Posted—May 19, 2017, retrieved from https://clinicaltrials.gov/ct2/show/NCT02951793, 7 pages.

ClinicalTrials.gov Identifier: NCT02955732, Pharmacological Characteristics of Intranasally Given Dexmedetomidine in Paediatric Patients (PINDEX). Turku University Hospital, First Posted Nov. 4, 2016, Last Update Posted Dec. 14, 2017, Study Start Date Jan. 1, 2017, https://clinicaltrials.gov/ct2/show/NCT02955732, downloaded May 6, 2018, 6 pages.

ClinicalTrials.gov Identifier: NCT02985697, Safety and Efficacy of Intranasal Dexmedetomidine. Bon Secours Pediatric Dental Associates, First Posted Dec. 7, 2016, Last Update Posted Dec. 7, 2016, Study Start Date Jan. 2017, https://clinicaltrials.gov/ct2/show/NCT02985697, downloaded May 6, 2018, 8 pages.

ClinicalTrials.gov Identifier: NCT03012984, Dexmedetomidine Supplemented Analgesia and Incidence of Postoperative Delirium, First Posted—Jan. 6, 2017, Last Update Posted—Jul. 31, 2018, retrieved from https://clinicaltrials.gov/ct2/show/NCT03012984, 13 pages.

ClinicalTrials.gov Identifier: NCT03069638, Intranasal Dexmedetomidine Sedation During Intraarticular Joint Injections in Pediatric Population. University of Oulu, First Posted Mar. 3, 2017, Last Update Posted Mar. 15, 2018, Actual Study Start Date Feb. 1, 2017, https://clinicaltrials.gov/ct2/show/NCT03069638, downloaded May 6, 2018, 7 pages.

ClinicalTrials.gov Identifier: NCT03078946, Dexmedetomidine Versus Morphine and Midazolam in Prevention and Treatment of Delirium After Adult Cardiac Surgery, First Posted—Mar. 14, 2017, Last Update Posted—Mar. 14, 2017, retrieved from https://clinicaltrials.gov/ct2/show/NCT03078946, 6 pages.

ClinicalTrials.gov Identifier: NCT03120247, Pharmacokinetics and Pharmacodynamics of Oral Transmucosal Dexmedetomidine. (OTM/DEX/PK), First Posted—Apr. 19, 2017, Last Update Posted—Apr. 19, 2017, downloaded Feb. 11, 2018 https://clinicaltrials.gov/ct2/show/NCT03120247, 7 pages.

ClinicalTrials.gov Identifier: NCT03120247, Pharmacokinetics and Pharmacodynamics of Oral Transmucosal Dexmedetomidine. (OTM/DEX/PK), First Posted—Apr. 19, 2017, Last Update Posted—Oct. 2, 2018, retrieved from https://clinicaltrials.gov/ct2/show/NCT03120247, 6 pages.

ClinicalTrials.gov Identifier: NCT03120442, Postoperative Delirium After Total Knee Arthroplasty Under Regional Anesthesia, First Posted—Apr. 19, 2017, Last Update Posted—Mar. 26, 2019, retrieved from https://clinicaltrials.gov/ct2/show/NCT03120442, 12 pages.

ClinicalTrials.gov Identifier: NCT03131375, Dexmedetomidine Reduces Emergence Delirium in Children Undergoing Tonsillectomy With Propofol Anesthesia, First Posted—Apr. 27, 2017, Last Update Posted—Jul. 9, 2018, retrieved from https://clinicaltrials.gov/ct2/show/NCT03131375, 7 pages.

ClinicalTrials.gov Identifier: NCT03151863, Intranasal Dexmedetomidine for Procedural Pain Management in Elderly Adults in Palliative Care (INDEX). Walid HABRE, First Posted May 12, 2017, Last Update Posted May 16, 2017, Estimated Study Start Date Jul. 1, 2017, https://clinicaltrials.gov/ct2/show/NCT03151863, downloaded May 5, 2018, 9 pages.

ClinicalTrials.gov Identifier: NCT03171740, Premedication With Intranasal Dexmedetomidine or Midazolam for Prevention of Emergence Agitation in Children. Brasilia University Hospital, First Posted May 31, 2017, Last Update Posted Sep. 13, 2017, Study Start Date Jun. 1, 2017, https://clinicaltrials.gov/ct2/show/NCT03171740, downloaded May 5, 2018, 8 pages.

ClinicalTrials.gov Identifier: NCT03171740, Premedication With Intranasal Dexmedetomidine or Midazolam for Prevention of Emergence Agitation in Children, First Posted—May 31, 2017, Last Update Posted—Jul. 13, 2018, retrieved from https://clinicaltrials.gov/ct2/show/NCT03171740, 7 pages.

ClinicalTrials.gov Identifier: NCT03172897, Low-dose Dexmedetomidine in Mechanically Ventilated ICU Patients, First Posted—Jun. 1, 2017, Last Update Posted—Jun. 21, 2019, retrieved from https://clinicaltrials.gov/ct2/show/NCT03172897, 10 pages.

ClinicalTrials.gov Identifier: NCT03174678, Dexmedetomidine Premedication in Children, First Posted—Jun. 2, 2017, Last Update Posted—Jun. 2, 2017, retrieved from https://clinicaltrials.gov/ct2/show/NCT03174678, 6 pages.

ClinicalTrials.gov Identifier: NCT03220880, Intranasal Dexmedetomidine Sedation in Children for Nonpainful Procedures. Columbia University, First Posted Jul. 18, 2017, Last Update Posted Apr. 10, 2018, Study Start Date Nov. 1, 2018, https://clinicaltrials.gov/ct2/show/NCT03220880, downloaded May 5, 2018, 9 pages.

ClinicalTrials.gov Identifier: NCT03251222, Intranasal Sedation With Dexmedetomidine. University Medical Centre Ljubljana, First Posted Aug. 16, 2017, Last Update Posted Aug. 16, 2017, Actual

(56) References Cited

OTHER PUBLICATIONS

Study Start Date Jan. 1, 2017, https://clinicaltrials.gov/ct2/show/NCT03251222, downloaded May 6, 2018, 8 pages.
ClinicalTrials.gov Identifier: NCT03251651, Intraoperative Sedatives and Postoperative Deilirium, First Posted—Aug. 16, 2017, Last Update Posted—Apr. 24, 2018, retrieved from https://clinicaltrials.gov/ct2/show/NCT03251651, 6 pages.
ClinicalTrials.gov Identifier: NCT03262090, Effect of Dexmedetomidine on the Prevention of Emergence Agitation in Children Undergoing Day Surgery, First Posted—Aug. 25, 2017, Last Update Posted—Jun. 25, 2019, retrieved from https://clinicaltrials.gov/ct2/show/NCT03262090, 6 pages.
ClinicalTrials.gov Identifier: NCT03290625, Intranasal Sedation With Dexmedetomidine and Ketamine in Pediatric Dentistry (NASO II). Universidade Federal de Goias, First Posted Sep. 25, 2017, Last Update Posted Feb. 20, 2018, Actual Study Start Date Nov. 9, 2017, https://clinicaltrials.gov/ct2/show/NCT03290625, downloaded May 6, 2018, 10 pages.
ClinicalTrials.gov Identifier: NCT03293277, Safety, Pharmacokinetics and Pharmacodynamics of Intranasal Dexmedetomidine in Healthy Subjects. Jiangsu HengRui Medicine Co., Ltd., First Posted Sep. 26, 2017, Last Update Posted Jan. 23, 2018, Study Start Date Jul. 26, 2017, https://clinicaltrials.gov/ct2/show/NCT03293277, downloaded May 5, 2018, 7 pages.
ClinicalTrials.gov Identifier: NCT03293927, Polypharmacy-related Adverse Events in Critically Ill Children, First Posted—Sep. 26, 2017, Last Update Posted—Jul. 18, 2019, retrieved from https://clinicaltrials.gov/ct2/show/NCT03293927, 5 pages.
ClinicalTrials.gov Identifier: NCT03317067, Effects of Dexmedetomidine on Delirium Duration of Nonintubated ICU Patients (4D Trial) (4D), First Posted—Oct. 23, 2017, Last Update Posted—Feb. 4, 2019, retrieved from https://clinicaltrials.gov/ct2/show/NCT03317067, 7 pages.
ClinicalTrials.gov Identifier: NCT03323593, Pharmacokinetics of Different Mode Administration of Intranasal Dexmedetomidine. The University of Hong Kong, First Posted Oct. 27, 2017, Last Update Posted Oct. 27, 2017, Study Start Date May 2013, https://clinicaltrials.gov/ct2/show/NCT03323593, downloaded May 6, 2018, 5 pages.
ClinicalTrials.gov Identifier: NCT03337672, Comparison of Dexmedetomidine and Midazolam for Prevention of Emergence Delirium in Children, First Posted—Nov. 9, 2017, Last Update Posted—Jan. 9, 2019, retrieved from https://clinicaltrials.gov/ct2/show/NCT03337672, 6 pages.
ClinicalTrials.gov Identifier: NCT03346226, How Different Sedatives Affect Hip Fracture Patient's Postoperative Delirium, First Posted—Nov. 17, 2017, Last Update Posted—Dec. 13, 2017, retrieved from https://clinicaltrials.gov/ct2/show/NCT03346226, 9 pages.
ClinicalTrials.gov Identifier: NCT03394430, Comparison of Midazolam or Dexmedetomidine on Epileptiform EEG During Sevoflurane Mask Induction. First Posted Jan. 9, 2018, Last Update Posted Feb. 13, 2018, Estimated Study Start Date Apr. 1, 2018, https://clinicaltrials.gov/ct2/show/NCT03394430, downloaded May 5, 2018, 8 pages.
ClinicalTrials.gov Identifier: NCT03399838, Comparing in Dexmedetomidine With po/pr Midazolam for Procedural Sedation in the Pediatric Emergency Department (PedINDEX). University Hospital Inselspital, Berne, First Posted Jan. 16, 2018, Last Update Posted Jan. 16, 2018, https://clinicaltrials.gov/ct2/show/NCT03399838, downloaded May 6, 2018, 6 pages.
ClinicalTrials.gov Identifier: NCT03417999, Pharmacokinetic Study of Intranasal Dexmedetomidine in Pediatric Patients With Congenital Heart Disease. Children's Hospital of Philadelphia, First Posted Jan. 31, 2018, Last Update Posted Apr. 12, 2018, Estimated Study Start Date May 2018, https://clinicaltrials.gov/ct2/show/NCT03417999, downloaded May 6, 2018, 7 pages.
ClinicalTrials.gov Identifier: NCT03477994, Efficacy of Dexmedetomidine Versus Clonidine to Control Delirium in Patients Undergoing CABG, First Posted—Mar. 27, 2018, Last Update Posted—Jul. 11, 2019, retrieved from https://clinicaltrials.gov/ct2/show/NCT03477994, 6 pages.
ClinicalTrials.gov Identifier: NCT03596775, Effect of Dexmedetomidine on Emergence Agitation and Postoperative Behavior Changes in Children, First Posted—Jul. 24, 2018, Last Update Posted—Sep. 7, 2018, retrieved from https://clinicaltrials.gov/ct2/show/NCT03596775?cond=Dexmedetomidine&sfpd_s=07%2F14%2F2018&sfpd_e=11%2F20%2F2018&rank=29, 7 pages.
ClinicalTrials.gov Identifier: NCT03600727, Propofol and Dexmedetomidine on Inflammation, First Posted—Jul. 26, 2018, Last Update Posted—Jul. 26, 2018, retrieved from https://clinicaltrials.gov/ct2/show/NCT03600727?cond=Dexmedetomidine&sfpd_s=07%2F14%2F2018&sfpd_e=11%2F20%2F2018&rank=21, 6 pages.
ClinicalTrials.gov Identifier: NCT03624595, Low-dose Dexmedetomidine and Postoperative Delirium After Cardiac Surgery, First Posted—Aug. 10, 2018, Last Update Posted—Apr. 24, 2019, retrieved from https://clinicaltrials.gov/ct2/show/NCT03624595?cond=Dexmedetomidine&sfpd_s=07%2F14%2F2018&sfpd_e=11%2F20%2F2018&rank=2, 12 pages.
ClinicalTrials.gov Identifier: NCT03629262, Dexmedetomidine Supplemented Intravenous Analgesia in Elderly After Orthopedic Surgery, First Posted—Aug. 14, 2018, Last Update Posted—Dec. 11, 2018, retrieved from https://clinicaltrials.gov/ct2/show/NCT03629262?cond=Dexmedetomidine&sfpd_s=07%2F14%2F2018&sfpd_e=11%2F20%2F2018&rank=3, 11 pages.
ClinicalTrials.gov Identifier: NCT03629483, Dexmedetomidine Combined With Ropivacaine for Postoperative Continuous Femoral Nerve Block, First Posted—Aug. 14, 2018, Last Update Posted—Dec. 11, 2018, retrieved from https://clinicaltrials.gov/ct2/show/NCT03629483?cond=Dexmedetomidine&sfpd_s=07%2F14%2F2018&sfpd_e=11%2F20%2F2018&rank=4, 10 pages.
ClinicalTrials.gov Identifier: NCT03655847, Acceptable Hemodynamic Changes in Dexmedetomidine for Single Intravenous Bolus Injection, First Posted—Aug. 31, 2018, Last Update Posted—Feb. 15, 2019, retrieved from https://clinicaltrials.gov/ct2/show/NCT03655847?cond=Dexmedetomidine&sfpd_s=07%2F14%2F2018&sfpd_e=11%2F20%2F2018&rank=9, 7 pages.
ClinicalTrials.gov Identifier: NCT03668951, Pharmacokinetic Study of Dexmedetomidine After Intra-Nasal and Buccal Dosing in Children (DexPK), First Posted—Sep. 13, 2018, Last Update Posted—Sep. 13, 2018, retrieved from https://clinicaltrials.gov/ct2/show/NCT03668951?term=buccal&cond=dexmedetomidine&sfpd_s=07%2F01%2F2018&rank=1, 7 pages.
ClinicalTrials.gov Identifier: NCT03708315, Precedex for Schizophrenia (DEX), First Posted—Oct. 17, 2018, Last Update Posted—Oct. 17, 2018, retrieved from https://clinicaltrials.gov/ct2/show/NCT03708315?cond=Dexmedetomidine&sfpd_s=07%2F14%2F2018&sfpd_e=11%2F20%2F2018&rank=33, 6 pages.
ClinicalTrials.gov Identifier: NCT03742180, Sublingual Ketorolac Compared to Intranasal Dexmedetomidine for Postoperative Analgesia in Pediatric Patients Undergoing Bilateral Myringotomy, First Posted—Nov. 15, 2018, Last Update Posted—Nov. 15, 2018, retrieved from https://clinicaltrials.gov/ct2/show/NCT03742180?term=sublingual&cond=dexmedetomidine&sfpd_s=07%2F01%2F2018&rank=1, 6 pages.
ClinicalTrials.gov Identifier: NCT03779282, KETODEX for Emergence Delirium in Children Undergoing Outpatient Strabismus Surgery, First Posted—Dec. 18, 2018, Last Update Posted—Dec. 18, 2018, retrieved from https://clinicaltrials.gov/ct2/show/NCT03779282?term=dexmedetomidine&cond=Agitation%2C+Emergence, 5 pages.
ClinicalTrials.gov Identifier: NCT03877120, Treatment Of Alcohol Withdrawal Syndrome: Dexmedetomidine Vs Diazepam In A Hospital O'horan, First Posted—Mar. 15, 2019, Last Update Posted—Mar. 15, 2019, retrieved from https://clinicaltrials.gov/ct2/show/NCT03877120, 6 pages.
ClinicalTrials.gov Identifier: NCT03938831, Dexmedetomidine and Delirium in Elderly Patients, First Posted—May 6, 2019, Last Update Posted—May 6, 2019, retrieved from https://clinicaltrials.gov/ct2/show/NCT03938831, 5 pages.
Chokroverty, S., "Overview of sleep & sleep disorders," Indian J Med Res 131, Feb. 2010, pp. 126-140.
Cohen, et al., "Intranasal Dexmedetomidine for Sedation for noncontrast CT Scans in Children." Anesthesiology 2008; 109, A998, 1 page.

(56) References Cited

OTHER PUBLICATIONS

Cohen et al., "Oral transmucosal administration of dexmedetomidine for sedation in 4 dogs," Can Vet J. Nov. 2015; 56(11): 1144-1148.
Cohen, et al., "Treatment of post-electroconvulsive therapy agitation with dexmedetomidine." The Journal of ECT (2013); 29(2): e23-e24.
Congdon, et al., "Evaluation of the sedative and cardiovascular effects of intramuscular administration of dexmedetomidine with and without concurrent atropine administration in dogs." Journal of the American Veterinary Medical Association (2011); 239(1): 81-89.
Cozzi, et al., "Intranasal Dexmedetomidine Sedation as Adjuvant Therapy in Acute Asthma Exacerbation With Marked Anxiety and Agitation." Ann Emerg Med. (2016); 69(1): 125-127.
Czinn, et al., "Effectiveness of Intramuscular Dexmedetomidine for Sedation in Young Children Undergoing Diagnostic Testing." The Anesthiology Annual Meeting, American Society of Anestheologists (2011); Abstract A578, 2 pages.
Diaper et al., "Pharmacological strategies for detoxification," Br J Clin Pharmacol (2013), 77(2):302-314.
Dewhirst, et al., "Pain management following myringotomy and tube placement: Intranasal dexmedetomidine versus intranasal fentanyl." Int J Pediatr Otorhinolaryngol. (2014); 78 (7): 1090-1094.
Djaiani et al., "Dexmedetomidine versus Propofol Sedation Reduces Delirium after Cardiac Surgery," Anesthesiology 2016; 124:362-368.
Dogru, et al., "The Effectiveness of Intramuscular Dexmedetomidine on Hemodynamic Responses During Tracheal Intubation and Anesthesia Induction of Hypertensive Patients: A Randomized, Double-Blind, Placebo-Controlled Study." Current Therapeutic Research (2007); 68(5): 292-302.
Dua, et al., "Comparative evaluation of dexmedetomidine as a premedication given intranasally vs orally in children between 1 to 8 years of age undergoing minor surgical procedures." Pediatric Anesthesia and Critical Care Journal (2016); 4(1): 13-17.
Dyck, et al., "The pharmacokinetics and hemodynamic effects of intravenous and intramuscular dexmedetomidine hydrochloride in adult human volunteers." Anesthesiology (1993); 78(5): 813-820.
Ebert et al., "The Effects of Increasing Plasma Concentrations of Dexmedetomidine in Humans," Anesthesiology 2000; 93:382-394.
El-Gohary and Rizk, "Dexmedetomidine for Emergence Agitation after Sevoflurane Anesthesia in Preschool Children Undergoing Day Case Surgery: Comparative Dose-Ranging Study." The Medical Journal of Cairo University (2011); 79(2): 17-23.
El-Hamid and Yassin, "Effect of intranasal dexmedetomidine on emergence agitation after sevoflurane anesthesia in children undergoing tonsillectomy and/or adenoidectomy." Saudi Journal of Anesthesia (2017); 11 (2): 137-143.
Emerick, D., "Automatic pain pathways," Dr. Darren R. Emerick, Apr. 2019, 1 page.
Emerick, D., "SUMO Pharma Version 1.4," Dr. Darren R. Emerick, Apr. 2019, 3 pages.
Emerick, D., "SUMO Pharma Version 1.4a," Dr. Darren R. Emerick, Apr. 2019, 1 page.
Emerick, D., "SUMO Pharma Version 1.5," Dr. Darren R. Emerick, Apr. 2019, 2 pages.
Emerick, D., "SUMO Pharma Version 1.6," Dr. Darren R. Emerick, Apr. 2019, 1 page.
Emery, et al., "Sedative Effects of Intranasal Midazolam and Dexmedetomidine in 2 Species of Tortoises (Chelonoidis carbonaria and Geochelone platynota)." Journal of Exotic Pet Medicine (2014); 23 (4): 380-383.
Erkola, et al., "Comparison of intramuscular dexmedetomidine and midazolam premedication for elective abdominal hysterectomy." Anesth Analg. (1994); 79(4): 646-653.
EudraCT Clinical Trial No. 2016-001567-37, Efficacy of single dose intranasal dexmedetomidine for conscious sedation in dental practice in dentophobic uncooperative patients with intellectual disability. University Medical Center Groningen, Date of record first entered Jul. 20, 2016, https://www.clinicaltrialsregister.eu/ctr-search/trial/2016-001567-37/NL, downloaded May 6, 2018, 5 pages.

Extended European Search Report for European Patent Application No. 15850725.1, dated May 24, 2018, 11 pages.
Ezz, "Preoperative intranasal dexmedetomidine versus intranasal ketamine for prevention of emergence agitation after sevoflurane in myringotomy patients: A randomized clinical trial." Egyptian Journal of Anaesthesia (2017); 33 (2): 141-146.
Farag et al., "Using Dexmedetomidine to Manage Patients with Cocaine and Opioid Withdrawal, Who Are Undergoing Cerebral Angioplasty for Cerebral Vasospasm," Anesthesia & Analgesia, Dec. 2006, vol. 103, No. 6, pp. 1618-1620.
Finkel et al., "The use of dexmedetomidine to facilitate acute discontinuation of opioids after cardiac transplantation in children," Critical Care Medicine, Sep. 2005, 33(9):2110-2112.
Finkel et al., "The Use of Dexmedetomidine to Facilitate Opioid and Benzodiazepine Detoxification in an Infant," Anesthesia & Analgesia, 2004, 98:1658-9.
Garg et al., "Use of dexmedetomidine with Propofol in modified electroconvulsive therapy: stable hemodynamics, optimum seizure duration and early recovery," Anaesthesia and Anaesthetics, 2018, 2(1): 1-5.
Garrity et al., "Dexmedetomidine-Induced Sedation Does Not Mimic the Neurobehavioral Phenotypes of Sleep in Sprague Dawley Rat," Sleep 2015;38(1):73-84.
Gaudio, et al., "Alfaxalone anaesthesia in Lemur catta following dexmedetomidine-butorphanol-midazolam sedation." Veterinary Anaesthesia and Analgesia (2018); 45(3): 351-356.
Ghai, et al., "Effect of Low Dose Dexmedetomidine on Emergence Delirium and Recovery Profile following Sevoflurane Induction in Pediatric Cataract Surgeries." Journal of Anesthesiology (2015); vol. 2015, Article ID 617074, 7 pages.
Ghali, et al., "Preanesthetic medication in children: A comparison of intranasal dexmedetomidine versus oral midazolam." Saudi J Anaesth. (2011); 5 (4): 387-391.
Gilsbach et al., "Are the pharmacology and physiology of α2adrenoceptors determined by α2-heteroreceptors and autoreceptors respectively?," British Journal of Pharmacology (2012) 165 90-102.
Gioeni et al., "Evaluation of an oral transmucosal administration of dexmedetomidine-butorphanol and dexmedetomidine-methadone in dogs," International Journal of Health and Animal Science Food Safety, vol. IV, No. 1s, Proceeding of Veterinary and Animal Science Days 2017, Jun. 6-8, Milan, Italy, 2 pages.
Giovannitti et al., "Alpha-2 Adrenergic Receptor Agonists: A Review of Current Clinical Applications," Anesth Prog, 2015, 62:31-38.
Granholm, et al., "Evaluation of the clinical efficacy and safety of intramuscular and intravenous doses of dexmedetomidine and medetomidine in dogs and their reversal with atipamezole." Veterinary Anaesthesia and Analgesia (2006); 33(4): 214-223.
Grubb, et al., "Cardiovascular and respiratory effects, and quality of anesthesia produced by alfaxalone administered intramuscularly to cats sedated with dexmedetomidine and hydromorphone." Journal of Feline Medicine and Surgery (2013); 15 (10): 858-865.
Guler, et al., "Single-dose dexmedetomidine reduces agitation and provides smooth extubation after pediatric adenotonsillectomy." Pediatric Anesthesia (2005); 15(9): 762-766.
Gumus et al., "Comparison of Effects of Different Dexmedetomidine and Chloral Hydrate Doses Used in Sedation on Electroencephalography in Pediatric Patients," Journal of Child Neurology 2015, vol. 30(8) 983-988.
Gupta, et al., "Comparison between intranasal dexmedetomidine and intranasal midazolam as premedication for brain magnetic resonance imaging in pediatric patients: A prospective randomized double blind trial." J Anaesthesiol Clin Pharmacol. (2017); 33 (2): 236-240.
Gutiérrez, R.E.P., "Clinical case of rapid opiate detoxification under anesthesia," Anestesia Pediatrica e Neonatale, vol. 9, No. 1, Sep.-Oct. 2011, 10 pages.
Gyanesh, et al., "Comparison between intranasal dexmedetomidine and intranasal ketamine as premedication for procedural sedation in children undergoing MRI: a double-blind, randomized, placebo-controlled trial." J Anesth. (2014); 28 (1): 12-18.

(56) References Cited

OTHER PUBLICATIONS

Haenecour et al., "Prolonged Dexmedetomidine Infusion and Drug Withdrawal In Critically Ill Children," J Pediatr Pharmacol Ther 2017;22(6):453-460.
Han, et al., "A randomized study of intranasal vs. intravenous infusion of dexmedetomidine in gastroscopy." Int J Clin Pharmacol Ther. (2014); 52 (9): 756-761.
Hauber, et al., "Dexmedetomidine as a Rapid Bolus for Treatment and Prophylactic Prevention of Emergence Agitation in Anesthetized Children." Anesthesia & Analgesia (2015); 121(5): 1308-1315.
Hitt, et al., "An Evaluation of Intranasal Sufentanil and Dexmedetomidine for Pediatric Dental Sedation." Pharmaceutics (2014); 6 (1): 175-184.
Honey et al., "α2-Receptor Agonists for Treatment and Prevention of Iatrogenic Opioid Abstinence Syndrome in Critically Ill Patients," Ann Pharmacother., 2009;43:1506-1511.
Hospira Safety Data Sheet, Precedex (dexmedetomidine hydrochloride) Injection, Solution, Jun. 2, 2014, pp. 1-7.
Hossein, et al., "Comparing the effect of premedication with intra-nasal dexmedetomidine and intra-nasal midazolam on sedation and anxiety level in children undergoing elective surgery." Journal of Anaesthesiology and Pain (2016); 6 (3): 1-10. Abstract.
Hrishi, et al., "A Novel Use of a Novel Drug: Preoperative Nasal Preparation with Dexmedetomidine for Transnasal Transsphenoidal Neurosurgery Approach in Skull Base Neurosurgery." Indian Journal of Neurosurgery (2017); 06 (03): 170-175.
Hsu et al., "Selection of medications for pediatric procedural sedation outside of the operating room," UpToDate, Oct. 10, 2017, 15 pages, retrieved from https://www.uptodate.com/contents/selection-of-medications-for-pediatric-procedural-sedation-outside-of-the-operating-room.
Huang et al., "Dexmedetomidine Directly Increases Tau Phosphorylation," Journal of Alzheimer's Disease (2015) 44:839-850.
Ibacache, et al., "Single-Dose Dexmedetomidine Reduces Agitation After Sevoflurane Anesthesia in Children." Anesthesia & Analgesia (2004); 98(1): 60-63.
Ibrahim, "A prospective, randomized, double blinded comparison of intranasal dexmedetomodine vs intranasal ketamine in combination with intravenous midazolam for procedural sedation in school aged children undergoing MRI." Anesthesia Essays and Researches (2014); 8 (2): 179-186.
Iirola, et al., "Bioavailability of dexmedetomidine after intranasal administration." European Journal of Clinical Pharmacology (2011); 67 (8): 825-831.
Iirola, et al., "Population pharmacokinetics of dexmedetomidine during long-term sedation in intensive care patients," British Journal of Anaesthesia 108 (3): 460-8 (2012).
International Preliminary Report on Patentability in International Application No. PCT/US2015/055828 dated Apr. 18, 2017, 8 pages.
International Search Report and Written Opinion, for International Application No. PCT/US2017/069030, dated Feb. 28, 2018, 8 pages.
International Search Report, PCT appl. no. PCT/US2015/055828, 4 pages (dated Mar. 1, 2016).
International Search Report and Written Opinion of the International Searching Authority for International Application No. PCT/US2019/039268, dated Sep. 13, 2019, 20 pages.
IRCT Registration No. IRCT2015103011398N9, Effect of intranasal adminstration of dexmedetomidine in providing moderate sedation for patients undergoing ERCP ; a randomized control trial. Iran University of Medical Sciences, Registration date Nov. 4, 2015, http://en.irct.ir/trial/11663, downloaded May 5, 2018, 12 pages.
Isik, et al., "Dexmedetomidine decreases emergence agitation in pediatric patients after sevoflurane anesthesia without surgery." Pediatric Anesthesia (2006); 16(7): 748-753.
Jaakola, et al., "Intramuscular dexmedetomidine premedication—an alternative to midazolam-fentanyl-combination in elective hysterectomy?" Acta Anaesthesiol Scand. (1994); 38(3): 238-243.
Jayaram, et al., "A comparative study to evaluate the effect of intranasal dexmedetomidine versus oral alprazolam as a premedication agent in morbidly obese patients undergoing bariatric surgery." J Anaesthesiol Clin Pharmacol. (2013); 29(2): 179-182.
Jia, et al., "A randomised study of intranasal dexmedetomidine and oral ketamine for premedication in children." Anaesthesia (2013); 68 (9): 944-949.
Jiří, "Intramuscular Dexmedetomidine In Burns Victims—Preliminary Results." Anaesthesiology and Intensive Care Medicine (2008); 2: 82-86 (with English Abstract).
Jung et al., "1877: Dexmedetomidine for Treatment of Refractory Opioid Withdrawal," Critical Care Medicine: Dec. 2016, vol. 44, No. 12 (Suppl.), p. 544.
Jung et al., "Dexmedetomidine for Treatment of Refractory Heroin Withdrawal," Journal of Emergency Nursing, 2017, 43(2): 182-184.
Jung, et al., "Effect of dexmedetomidine on emergence agitation in male patients undergoing closed reduction of a nasal bone fracture." RMJ (2015); 40(2): 191-196.
Kambow, et al., "Randomized Double Blind Clinical Trial Of Intramuscular Dexmedetomidine V/S Midazolam As Premedication In Paediatric Surgical Patients." J. Evolution Med. Dent. Sci. (2016); 5(42): 2566-2570.
Karaaslan, et al., "Comparison of buccal and intramuscular dexmedetomidine premedication for arthroscopic knee surgery." Journal of Clinical Anesthesia (2006); 18(8): 589-593.
Kästner, et al., "Clinical comparison of preanaesthetic intramuscular medetomidine and dexmedetomidine in domestic sheep." DTW. Deutsche Tierärztliche Wochenschrift (2001); 108 (10): 409-413.
Kaya, et al., "The Effects of Intramuscular Dexmedetomidine Premedication on Hemodynamics, Plasma Norepinephrine, Cortisol and Glucose Concentrations." O.M.Ü. T>p Dergisi (2006); 23(1): 9-16.
Keating, G., "Dexmedetomidine: A Review of Its Use for Sedation in the Intensive Care Setting," Drugs (2015) 75:1119-1130.
Keles et al., "The Effect of Oral Dexmedetomidine Premedication on Preoperative Cooperation and Emergence Delirium in Children Undergoing Dental Procedures," Hindawi BioMed Research International, 2017, vol. 2017, Article ID 6742183, 7 pages.
Kelley, et al., "Intramuscular Dexmedetomidine & Midazolam for Preoperative Sedation: A Case Series." Pediatric Anasthesia (Winter 2013), University of Pittsburgh, Poster Board, 1 page http://www2.pedsanesthesia.org/meetings/2013winter/posters/uploads/373--NM-293.pdf.
Khenissi, et al., "Comparison of intramuscular alfaxalone and ketamine combined with dexmedetomidine and butorphanol for castration in cats." Journal of Feline Medicine and Surgery (2016); 19(8): 791-797.
Kim, et al., "Appropriate dose of dexmedetomidine for the prevention of emergence agitation after desflurane anesthesia for tonsillectomy or adenoidectomy in children: up and down sequential allocation." BMC Anesthesiology (2015); 15: 79, 6 pages.
Kim, et al., "Dexmedetomidine for sedation in pediatric patients who received more than 20 sessions of radiation therapy—two cases report." Korean Journal of Anesthesiology (2016); 69 (6): 627-631.
Kim et al., "Risk Factors of Emergence Agitation in Adults Undergoing General Anesthesia for Nasal Surgery," Clinical and Experimental Otorhinolaryngology vol. 8, No. 1, 46-51, Mar. 2015.
Kobayashi, et al., "Efficacy of Dexmedetomidine for Controlling Delirium in Intensive Care Unit Patients." Japanese Journal of Anesthesiology [Masui] (2007); 56(10): 1155-1160.
Kobayashi, et al., "Mechanism of the Inhibitory Effect of Surfactants on Intramuscular Absorption of Drugs." Chemical and Pharmaceutical Bulletin (1977); 25(7): 1547-1554.
Konia, M., "Oral dexmedetomidine for preoperative sedation in an adult uncooperative autistic patient," Journal of Clinical Anesthesia (2016) 34, 29-31.
Korpivaara et al., "Dexmedetomidine oromucosal gel for noise-associated acute anxiety and fear in dogs—a randomised, double-blind, placebo-controlled clinical study," Veterinary Record (2017) 180, 356, 7 pages.

(56) References Cited

OTHER PUBLICATIONS

Korpivaara et al., "Effect of dexmedetomidine oromucosal gel for alleviation of canine acute fear and anxiety associated with noise at sub-sedative doses—A pilot study," BSAVA Congress 2014, Poster, 1 page.

Kostoglou, et al., "Effect of β-carotene on health status and performance of sows and their litters." Jornal of Animal Physiology and Animal Nutrition (2000); 83 (3): 150-157.

Krimins, et al., "Hemodynamic effects in dogs after intramuscular administration of a combination of dexmedetomidine-butorphanol-tiletamine-zolazepam or dexmedetomidine-butorphanol-ketamine." American Journal of Veterinary Research (2012); 73(9): 1363-1370. Abstract only.

Kumar, et al., "Efficacy of intranasal dexmedetomidine versus oral midazolam for paediatric premedication." Indian J Anaesth (2017); 61: 125-130.

Kumar et al., "Role of dexmedetomidine for sedation in a patient with schizophrenia for strabismus surgery," Indian J Anaesth. Nov. 2016; 60(11): 856-857.

Kumari, et al., "Clinico-anesthetic and Hemodynamic Effects of Midazolam and Dexmedetomidine-Midazolam with Propofol in Dogs During Ovariohysterectomy." The Philippine Journal of Veterinary Medicine (2017); 54(1): 46-53.

Kundra et al., "Oral ketamine and dexmedetomidine in adults' burns wound dressing—A randomized double blind cross over study," Burns 39 (2013) 1150-1156.

Kurlansky, et al., "Role of the carrier solution in cyclosporine pharmacokinetics in the baboon." The Journal of Heart Transplantion (1986); 5(4): 312-316.

Lami et al., "Transmucosal dexmedetomidine for computed tomography sedation," Paediatr Anaesth., 2008, 18:349-350.

Lehman et al., "Practice Guideline for the Treatment of Patients With Schizophrenia," American Psychiatric Association Practice Guidelines, Second Edition, 2010, 184 pages.

Levänen, et al., "Dexmedetomidine Premedication Attenuates Ketamine-induced Cardiostimulatory Effects and Postanesthetic Delirium." Anesthesiology (1995); 82: 1117-1125.

Li, et al., "A comparison of intranasal dexmedetomidine for sedation in children administered either by atomiser or by drops." Anaesthesia (2016); 71: 522-528.

Li et al., "Dexmedetomidine inhibits inflammation in microglia cells under stimulation of LPS and ATP by c-Fos/NLRP3/caspase-1 cascades," EXCLI Journal 2018;17:302-311.

Li et al., "Impact of dexmedetomidine on the incidence of delirium in elderly patients after cardiac surgery: A randomized controlled trial," PLoS ONE (2017) 12(2): e0170757, 15 pages.

Li, et al., "Intranasal dexmedetomidine for sedation in children undergoing transthoracic echocardiography study—a prospective observational study." Pediatric Anesthesia (2015); 25 (9): 891-896.

Li, et al., "Intranasal dexmedetomidine with and without buccal midazolam for procedural sedation in autistic children: a double-blind randomised controlled trial." The Lancet (2017); 390 (4): S26.

Lili, et al., "The application of dexmedetomidine in children undergoing vitreoretinal surgery." Journal of Anesthesia (2012); 26(4): 556-561.

Lin, et al., "Efficacy of premedication with intranasal dexmedetomidine on inhalational induction and postoperative emergence agitation in pediatric undergoing cataract surgery with sevoflurane." Journal of Clinical Anesthesia (2016); 33: 289-295.

Louis et al., "Effects of dexmedetomidine on delirium duration of non-intubated ICU patients (4D trial): study protocol for a randomized trial," Trials (2018) 19:307, 11 pages.

Lu, et al., "Intranasal Dexmedetomidine as a Sedative Premedication for Patients Undergoing Suspension Laryngoscopy: A Randomized Double-Blind Study." PLoS ONE (2016); 11(5): e0154192.

Malhotra, et al., "Comparative evaluation of dexmedetomidine and midazolam-ketamine combination as sedative agents in pediatric dentistry: A double-blinded randomized controlled trial." Contemp Clin Dent (2016); 7: 186-192.

Manaa, et al., "Fentanyl versus dexmedetomidine effect on agitation after sevoflurane anaesthesia." Saudi J Anaesth. (2007); 1(2): 57-61, 10 pages.

Martin et al., "The Role of the α2-Adrenoceptor Agonist Dexmedetomidine in Postsurgical Sedation in the Intensive Care Unit," J Intensive Care Med 2003;18:29-41.

Mason, et al., "Intramuscular dexmedetomidine for pediatric electroencephalogram (EEG) sedation: 10AP3-7." European Journal of Anaesthesiology (EJA) (2012); 29: p. 161.

Mason, et al., "Intramuscular Dexmedetomidine Sedation for Pediatric MRI and CT." American Journal of Roentgenology (2011); 197: 720-725.

Mason, et al., "Intramuscular dexmedetomidine: an effective route of sedation preserves background activity for pediatric electroencephalograms." J Pediatr. (2012); 161(5): 927-932.

Mazy et al., "Spinal anesthesia for lengthy lower limb orthopedic surgeries: dexmedetomidine plus fentanyl versus dexmedetomidine," Ain-Shams Journal of Anesthesiology (2019) 11:10, 8 pages.

Micieli, et al., "Sedative and cardiovascular effects of intranasal or intramuscular dexmedetomidine in healthy dogs." Vet Anaesth Analg. (2017); 44(4): 703-709.

Miller, et al., "Dosing and efficacy of intranasal dexmedetomidine sedation for pediatric transthoracic echocardiography: a retrospective study." Canadian Journal of Anesthesia (2016); 63 (7): 834-841.

Mizrak, et al., "Dexmedetomidine Use during Strabismus Surgery in Agitated Children." Med Princ Pract (2011); 20(5): 427-432.

Mizrak, et al., "Premedication with dexmedetomidine and midazolam attenuates agitation after electroconvulsive therapy." J Anesth. (2009); 23(1): 6-10.

Mohite et al., "Role of dexmedetomidine in pediatric dental sedation," J Dent Anesth Pain Med., Apr. 2019;19(2):83-90.

Moshiri et al., "Premedication effect of dexmedetomidine and alfentanil on seizure time, recovery duration, and hemodynamic responses in electroconvulsive therapy," Annals of Cardiac Anaesthesia, Apr.-Jun. 2016, vol. 19, Issue 2, pp. 263-268.

Mostafa, et al., "Effect of Different Doses of Dexmedetomidine on Stress Response and Emergence Agitation after Laparoscopic Cholecystectomy: Randomized Controlled Double-Blind Study." J Anesth Clin Res (2017); 8: 707, 6 pages.

Mountain et al., "Dexmedetomidine as a Pediatric Anesthetic Premedication to Reduce Anxiety and to Deter Emergence Delirium," AANA Journal, Jun. 2011, vol. 79, No. 3, pp. 219-224.

Mukherjee, et al., "Emergence agitation prevention in paediatric ambulatory surgery: A comparison between intranasal Dexmedetomidine and Clonidine." J Res Pharm Pract. (2015); 4(1): 24-30.

Mult, A., "Prolonged Dexmedetomidine Infusion as an Adjunct in Treating Sedation-Induced Withdrawal," Anesth Analg 2003;96:1054-1055.

Na, et al., "Randomized controlled trial on influence of nasal administration of dexmedetomidine after induction of anesthesia on agitation of children in ophthalmologic surgery." Adverse Drug Reactions Journal (2016); 18 (2): 95-98. Abstract only.

Naples, et al., "Comparison of the Anesthetic Effects of Oral Transmucosal Versus Injectable Medetomidine in Combination with Tiletamine-Zolazepam for Immobilization of Chimpanzees (*Pan troglodytes*)." Journal of Zoo and Wildlife Medicine (2010); 41 (1): 50-62.

Nasr et al., "Ultra-rapid opiate detoxification using dexmedetomidine under general anesthesia," J Opioid Manag., 2011;7(5):337-344.

Neville, et al., "Double-blind Randomized Controlled Trial of Intranasal Dexmedetomidine Versus Intranasal Midazolam as Anxiolysis Prior to Pediatric Laceration Repair in the Emergency Department." Acad Emerg Med. (2016); 23 (8): 910-917.

Ni, et al., "Effect of Dexmedetomidine on Preventing Postoperative Agitation in Children: A Meta-Analysis." PLoS ONE (2015); 10 (5): eQ128450.

Nizari et al., "Non-amyloidogenic effects of α2 adrenergic agonists: implications for brimonidine-mediated neuroprotection," Cell Death Dis., 2016; 7(12): e2514, 13 pages.

Nooh, et al., "Intranasal atomized dexmedetomidine for sedation during third molar extraction." Int J Oral Maxillofac Surg. (2013); 42 (7): 857-862.

(56) References Cited

OTHER PUBLICATIONS

O'Brien, et al., "Dexmedetomidine and the successful management of electroconvulsive therapy postictal agitation: a case report." The Journal of ECT (2010); 26(2): 131-133.
Oschman et al., "Dexmedetomidine for opioid and benzodiazepine withdrawal in pediatric patients," Am J Health-Syst Pharm. 2011; 68:1233-8.
Ouchi et al., "Dexmedetomidine Dose Dependently Enhances the Local Anesthetic Action of Lidocaine in Inferior Alveolar Nerve Block A Randomized Double-Blind Study," Reg Anesth Pain Med 2016;41: 348-355.
Özcengiz et al., "Oral melatonin, dexmedetomidine, and midazolam for prevention of postoperative agitation in children," J Anesth (2011) 25:184-188.
Pant et al., "Comparison of sublingual midazolam and dexmedetomidine for premedication in children," Minerva Anestesiologica, 2014, 80(2):167-175.
Park et al., "Dexmedetomidine Oral Mucosa Patch for Sedation Suppresses Apoptosis in Hippocampus of Normal Rats," Int Neurourol J 2017;21 Suppl 1:S39-47.
Patel, et al., "Vasovagal syncope and severe bradycardia following intranasal dexmedetomidine for pediatric procedural sedation." Paediatr Anaesth. (2014); 24 (4): 446-448.
Pavithra, et al., "Comparison of two doses of intranasal dexmedetomidine as premedication in children." Pediatric Anesthesia and Critical Care Journal (2017); 5(2): 86-94.
Peker, et al., "Buccal versus intramuscular dexmedetomidine premedication for arthroscopic knee surgery under spinal anesthesia: A-600." European Journal of Anaesthesiology (EJA) (2006); 23: p. 156.
Peng, et al., "Premedication with dexmedetomidine in pediatric patients: a systematic review and meta-analysis." Clinics (2014); 69(11): 777-786.
Penttilä et al., "Cardiovascular and parasympathetic effects of dexmedetomidine in healthy subjects," Canadian Journal of Physiology and Pharmacology, 2004, 82(5): 359-362.
Pestieau, et al., "The effect of dexmedetomidine during myringotomy and pressure-equalizing tube placement in children." Pediatric Anesthesia (2011); 21 (11): 1128-1135.
Phan et al., "Clinical Uses of Dexmedetomidine in Pediatric Patients," Pediatr Drugs, 2008;10(1):49-69.
Pinelas, et al., "Effects of different doses of dexmedetomidine on anaesthetic induction with alfaxalone—a clinical trial." Veterinary Anaesthesia and Analgesia (2013); 41(4): 378-385.
Pons, et al., "Effects of dexmedetomidine administered at acupuncture point GV20 compared to intramuscular route in dogs." J Small Anim Pract. (2016); 58(1): 23-28.
Porters, et al., "Pharmacokinetics of oral transmucosal and intramuscular dexmedetomidine combined with buprenorphine in cats." Journal of Veterinary Pharmacology and Therapeutics (2014); 38 (2): 203-208.
Porters, et al., "Sedative and antinociceptive effects of dexmedetomidine and buprenorphine after oral transmucosal or intramuscular administration in cats." Veterinary Anaesthesia and Analgesia (2014); 41 (1): 90-96.
Prabhu and Mehandale, "Comparison of oral dexmedetomidine versus oral midazolam as premedication to prevent emergence agitation after sevoflurane anaesthesia in paediatric patients." Indian J Anaesth. (2017); 61(2): 131-136.
Precedex Label, Highlights of Prescribing Information, Mar. 2016, 23 pages.
Proctor et al., "Oral Dexmedetomidine Attenuates Hemodynamic Responses during Emergence from General Anesthesia in Chronically Instrumented Dogs," Anesthesiology, 1991, 74:108-114.
Proctor et al., "Premedication with Oral Dexmedetomidine Alters Hemodynamic Actions of Intravenous Anesthetic Agents in Chronically Instrumented Dogs," Anesthesiology, 1992, 77:554-562.
Qi, et al., "The observation of the sedation effects of intranasal methods of dexmedetomidine for magnetic resonance imaging in children." BIO Web of Conferences 8, 01043 (2017), 4 pages.

Qiao, et al., "Intranasal atomised dexmedetomidine optimises surgical field visualisation with decreased blood loss during endoscopic sinus surgery: a randomized study." Rhinology (2016); 54: 38-44.
Rajalakshmi, et al., "A Comparative Study Between Intranasal Dexmedetomidine and Intranasal Ketamine As A Premedication in Paediatric Surgeries." Indian Journal of Applied Research (2014); 4 (12): 379-381.
Raszplewicz, et al., "Comparison of sedation scores and propofol induction doses in dogs after intramuscular premedication with butorphanol and either dexmedetomidine or medetomidine." Veterinary Anaesthesia and Analgesia (2013); 40(6): 584-589.
Ravipati, et al., "Dexmedetomidine decreases the requirement of ketamine and propofol during burns debridement and dressings." Clinical Investigation (2014); 58(2): 138-142.
Ray et al., "Dexmedetomidine for sedation during electroencephalographic analysis in children with autism, pervasive developmental disorders, and seizure disorders," Journal of Clinical Anesthesia (2008) 20, 364-368.
Riker et al., "Dexmedetomidine vs Midazolam for Sedation of Critically Ill Patients A Randomized Trial," JAMA, 2009;301(5):489-499.
Roberts et al., "Characterizing the experience of agitation in patients with bipolar disorder and schizophrenia," BMC Psychiatry (2018) 18:104.
Rojas-Gomez and Nystrom, "Sedation and Physiological Response to Intranasal Dexmedetomidine (IN-DEX) in Patients with Severe Chronic Obstructive Pulmonary Disease (COPD)." ATS Journals 2016: Abstract A3548; American Journal of Respiratory and Critical Care Medicine (2016); 193: 1.
Ryu et al., "Sedation Protocol Using Dexmedetomidine for Third Molar Extraction," J Oral Maxillofac Surg, 2016 74:926.e1-926.e7, 7 pages.
Sakurai et al., "Buccal administration of dexmedetomidine as a preanesthetic in children," Journal of Anesthesia, 2010, 24:49-53.
Santana and Mills, "Retrospective study of intranasal dexmedetomidine as a prophylactic against emergence delirium in pediatric patients undergoing ear tube surgery." International Journal of Pediatric Otorhinolaryngology (2017); 100: 39-43.
Santangelo, et al., "Transnasal administration of a combination of dexmedetomidine, midazolam and butorphanol produces deep sedation in New Zealand White rabbits." Veterinary Anaesthesia and Analgesia (2016); 43 (2): 209-214.
Santos, et al., "Effects of intramuscular dexmedetomidine in combination with ketamine or alfaxalone in swine." Veterinary Anaesthesia and Analgesia (2016); 43 (1): 81-85.
Santos, et al., "Sedative and cardiorespiratory effects of dexmedetomidine and buprenorphine administered to cats via oral transmucosal or intramuscular routes." Veterinary Anaesthesia and Analgesia (2010); 37 (5): 417-424.
Sato, et al., "Effect of single-dose dexmedetomidine on emergence agitation and recovery profiles after sevoflurane anesthesia in pediatric ambulatory surgery." Journal of Anesthesia (2010); 24(5): 675-682.
Saito et al., "Usefulness of dexmedetomidine to prevent emergence agitation in a patient with Krabbe disease: a case report," JA Clinical Reports (2018) 4:34, 4 pages.
Savla, et al., "Effect of intranasal dexmedetomidine or oral midazolam premedication on sevoflurane EC50 for successful laryngeal mask airway placement in children: a randomized, double-blind, placebo-controlled trial." Pediatric Research (2014); 24 (4): 433-439.
Scheinin, et al., "Intramuscular Dexmedetomidine as Premedication for General Anesthesia: A Comparative Multicenter Study." Anesthesiology (1993); 78: 1065-1075.
Scheinin, et al., "Pharmacodynamics and pharmacokinetics of intramuscular dexmedetomidine." Clinical Pharmacology & Therapeutics (1992); 52(5): 537-546.
Schmidt, et al., "Effects of preanesthetic administration of midazolam, clonidine, or dexmedetomidine on postoperative pain and anxiety in children." Pediatric Anesthesia (2007); 17(7): 667-674.

(56) References Cited

OTHER PUBLICATIONS

Schnellbacher, et al., "The Efficacy of Intranasal Administration of Dexmedetomidine and Ketamine to Yellow-Bellied Sliders (*Trachemys scripta scripta*)." Journal of Herpetological Medicine and Surgery (2012); 22 (3-4): 91-98.
Segovia, et al., "Pre-anaesthetic medication with intranasal dexmedetomidine and oral midazolam as an anxiolytic. A clinical trial." Analesdepediatria (2013); 81 (4): 226-231.
Sethi, et al., "Conscious sedation in a psychiatric patient: A challenge." J Anaesthesiol Clin Pharmacol. (2017); 33(3): 416-417.
Shah, et al., "Physiologic and biochemical effects of electroacupuncture combined with intramuscular administration of dexmedetomidine to provide analgesia in goats." American Journal of Veterinary Research (2016); 77 (3): 252-259.
Shams and El-Masry, "Ketofol-Dexmedetomidine combination in ECT: A punch for depression and agitation." Indian Journal of Anaesthesia (2014); 58(3): 275-280.
Sharan et al., "A comparison of dexmedetomidine with propofol versus esmolol with propofol to attenuate the hemodynamic stress responses after electroconvulsive therapy," Indian J Psychiatry, Jul.-Sep. 2017; 59(3): 366-369.
Shehabi, et al., "The effect of dexmedetomidine on agitation during weaning of mechanical ventilation in critically ill patients." Anaesthesia and Intensive Care (2010); 38 (1): 82-90.
Sheta, et al., "Intranasal dexmedetomidine vs midazolam for premedication in children undergoing complete dental rehabilitation: a double-blinded randomized controlled trial." Pediatric Anesthesia (2014); 24 (2): 181-189.
Shetty and Aggarwal, "Efficacy of Intranasal Dexmedetomidine for Conscious Sedation in Patients Undergoing Surgical Removal of Impacted Third Molar: A Double-Blind Split Mouth Study." Journal of Maxillofacial and Oral Surgery (2016); 15 (4): 512-516.
Shi, et al., "Intranasal Dexmedetomidine in Termination of First Trimester Pregnancy of Suction Evacuation." J Anesth Clin Res (2017); 8 (11): 1000781, 7 pages.
Singh et al., "A comparative evaluation of analgo-sedative effects of oral dexmedetomidine and ketamine: a triple-blind, randomized study," Anesthesia 24 (2014) 1252-1259.
Singla, et al., "Comparison of dexmedetomidine versus midazolam for intranasal premedication in children posted for elective surgery: a doubleblind, randomised study." Southern African Journal of Anaesthesia and Analgesia (2015); 21 (6):154-157.
Sivrikaya, et al., "Intranasal Dexmedetomidine Versus Midazolam Premedication in Paediatric Patients: A Prospective Study." Ecronicon Anaesthesia (2015); 2 (3): 139-147.
Slingsby, et al., "Thermal antinociception after dexmedetomidine administration in cats: a comparison between intramuscular and oral transmucosal administration." J Feline Med Surg. (2009); 11(10): 829-834.
Sobel, et al., "Intramuscular administration of human tissue-type plasminogen activator in rabbits and dogs and its implications for coronary thrombolysis." Circulation (1987); 75 (6): 1261-1272.
Song, et al., "Dexmedetomidine Injection during Strabismus Surgery Reduces Emergence Agitation without Increasing the Oculocardiac Reflex in Children: A Randomized Controlled Trial." PLoS ONE (2016); 11(9): e0162785, 12 pages.
Spalink, et al., "Intranasal dexmedetomidine for adrenergic crisis in familial dysautonomia." Clinical Autonomic Research (2017); 27 (4): 279-282.
Srinivasa, et al., "Study of Dexmedetomidine as intramuscular premedication in outpatient cataract surgery: A placebo-controlled study." IAIM (2016); 3(2): 60-68.
Sulton, et al., "The Use of Intranasal Dexmedetomidine and Midazolam for Sedated Magnetic Resonance Imaging in Children: A Report From the Pediatric Sedation Research Consortium." Pediatric Emergency Care (2017); 00: 00-00, 5 pages, Published Ahead of Print.
Su et al., "Dexmedetomidine for prevention of delirium in elderly patients after non-cardiac surgery: a randomised, double-blind, placebo-controlled trial," Lancet 2016; 388: 1893-1902.

Sun et al., "Dexmedetomidine inhibits astrocyte pyroptosis and subsequently protects the brain in in vitro and in vivo models of sepsis," Cell Death and Disease (2019) 10:167, 13 pages.
Sun, et al., "Low-Dose Intramuscular Dexmedetomidine as Premedication: A Randomized Controlled Trial." Med Sci Monit (2014); 20: 2714-2719.
Sundaram and Mathian, "A Comparative Evaluation of Intranasal Dexmedetomidine and Intranasal Midazolam for Premedication in Children: A Double Blind Randomised Controlled Trial." JIDA (2011); 5 (7): 777-781.
Surendar, et al., "A comparative evaluation of intranasal dexmedetomidine, midazolam and ketamine for their sedative and analgesic properties: a triple blind randomized study." J Clin Pediatr Dent. (2014); 38 (3): 255-261.
Sutcliffe, et al., "Efficacy of Selective PDE4D Negative Allosteric Modulators in the Object Retrieval Task in Female Cynomolgus Monkeys (*Macaca fascicularis*)." PLoS ONE (2014); 9 (7): e102449, pp. 1-16.
Talon, et al., "Intranasal Dexmedetomidine Premedication is Comparable With Midazolam in Burn Children Undergoing Reconstructive Surgery." Journal of Burn Care & Research (2009); 30 (4): 599-605.
Tammam and Wahba, "Quality of MRI pediatric sedation: Comparison between intramuscular and intravenous dexmedetomidine." Egyptian Journal of Anaesthesia (2013); 29: 47-52.
Tammam, "Comparison of the efficacy of dexmedetomidine, ketamine, and a mixture of both for pediatric MRI sedation." Egyptian Journal of Anaesthesia (2013); 29(3): 241-246.
Tang et al., "Dexmedetomidine Controls Agitation and Facilitates Reliable, Serial Neurological Examinations in a Non-Intubated Patient with Traumatic Brain Injury," Neurocrit Care., 2011;15(1):175-181 (Published online: Mar. 3, 2010).
Tang, et al., "Intranasal Dexmedetomidine on Stress Hormones, Inflammatory Markers, and Postoperative Analgesia after Functional Endoscopic Sinus Surgery." Mediators of Inflammation (2015); Article ID 939431, 9 pages.
Tayari, et al., "Methadone and Dexmedetomidine Combination as Premedicant Agents for Ovariectomy in Cats." American Journal of Animal and Veterinary Sciences (2015); 10 (2): 101-111.
Tazeroualti, et al., "Oral clonidine vs midazolam in the prevention of sevoflurane-induced agitation in children. A prospective, randomized, controlled trial." British Journal of Anaesthesia (2007); 98 (5): 667-671.
Tetef, S., "Effectiveness of Transmucosal Sedation for Special Needs Populations in the Ambulatory Care Setting," AORN Journal, Dec. 2014, 100(6):651-669.
Tobi et al., "Emergence Delirium in a Schizophrenic Patient who Underwent Craniotomy for Elevation of Depressed Skull Fracture under General Anaesthesia: A Case Report," International Journal for Case Reports, 2018, vol. 2, No. 2:8, 3 pages.
Tobias, J.D., "Dexmedetomidine to Control Agitation and Delirium from Toxic Ingestions in Adolescents." J Pediatr Pharmacol Ther. (2010); 15(1): 43-48.
Tobias, J.D., "Dexmedetomidine to treat opioid withdrawal in infants following prolonged sedation in the pediatric ICU," J Opioid Manag., 2006;2(4):201-205.
Tobias, J.D., "Subcutaneous dexmedetomidine infusions to treat or prevent drug withdrawal in infants and children," Journal of Opioid Management, 2008, 4(4):187-191.
Tug, et al., "Comparison of Two Different Intranasal Doses of Dexmedetomidine in Children for Magnetic Resonance Imaging Sedation." Paediatr Drugs (2015); 17 (6): 479-485.
UK Competent Authority, Chemicals Regulation Directorate, Health and Safety Executive, United Kingdom "CLH report, Proposal for Harmonised Classification and Labelling Based on Regulation (EC) No. 1272/2008 (CLP Regulation), Annex VI, Part 2, Substance Name: Medetomidine," CLH Report for Medetomidine, Version No. 1, Oct. 2014, pp. 1-64.
UMIN-CTR Clinical Trial Identifier: UMIN000020446, Intranasal Premedication with Dexmedetomidine and midazolam in ophthalmic surgery for pediatrics, are they really equally effective? Mansoura Faculty of Medicine, mansoura university, Date of disclosure of study Feb. 1, 2016, Last modified Jan. 5, 2016, Registered Jan. 5,

(56) References Cited

OTHER PUBLICATIONS 2016, https://upload.umin.ac.jp/cgi-open-bin/ctr_e/ctr_view.cgi?recptno=R000023623, downloaded May 5, 2018, 5 pages.
Upadhyay et al., "Dexmedetomidine Infusion to Facilitate Opioid Detoxification and Withdrawal in a Patient with Chronic Opioid Abuse," Indian Journal of Palliative Care, Sep.-Dec. 2011, vol. 17, Issue 3, p. 251-254.
Upadhyay et al., "Prolonged dexmedetomidine infusion to facilitate drug detoxification and withdrawal in patients with multiple drugs addiction," Crit Care & Shock (2011) 14:84-88.
Vega et al., "Prevention of Opioid Withdrawal Syndrome After Pediatric Heart Transplantation: Usefulness of Dexmedetomidine," Scientific Letters/Rev Esp Cardiol, 2013;66(7):593-595.
Virkkilä, et al., "Dexmedetomidine as intramuscular premedication for day-case cataract surgery." Anaesthesia (1994); 49(10): 853-858.
Virkkilä, et al., "Dexmedetomidine as intramuscular premedication in outpatient cataract surgery." Anaesthesia (1993); 48(6): 482-487.
Walsh, et al., "Use of intranasal dexmedetomidine for preoperative sedation in the pediatric population: a case series." Anesthesiology 2008; 109, A1378, 1 page.
Wang, et al., "The sedative effects and the attenuation of cardiovascular and arousal responses during anesthesia induction and intubation in pediatric patients: a randomized comparison between two different doses of preoperative intranasal dexmedetomidine." Paediatr Anaesth (2014); 24 (3): 275-281.
Whittington et al., "Dexmedetomidine induces tau hyperphosphorylation in the mouse hippocampus," Alzheimer's & Dementia, Jul. 2012, vol. 8, Issue 4, Supplement, pp. P461-P462.
Wilson et al., "The Psychopharmacology of Agitation: Consensus Statement of the American Association for Emergency Psychiatry Project BETA Psychopharmacology Workgroup," West J Emerg Med. 2012;13(1):26-34.
Winstock et al., "'Should I stay or should I go?' Coming off methadone and buprenorphine treatment," International Journal of Drug Policy (2011) 22:77-81.
Wong and Freeman, "Cutaneous allergic reaction to intramuscular vitamin K1." Australian Journal of Dermatology (1999); 40 (3): 147-152.
Written Opinion of the International Searching Authority, PCT appl. No. PCT/US2015/055828, 7 pages (dated Mar. 1, 2016).
Wu, et al., "Intranasally Administered Adjunctive Dexmedetomidine Reduces Perioperative Anesthetic Requirements in General Anesthesia." Yonsei Med J (2016); 57 (4): 998-1005.
Wu et al., "Neuroprotective effect of dexmedetomidine in a murine model of traumatic brain injury," Scientific Reports, (2018) 8:4935, 10 pages.
Xu, et al., "Effects of dexmedetomidine on the recovery profiles from general anesthesia in patients undergoing endoscopic sinus surgery." Int J Clin Exp Med (2016); 9(5): 8405-8410.
Yamane et al., "Effect of Dexmedetomidine Injected Into the Oral Mucosa in Combination With Lidocaine on Local Anesthetic Potency in Humans: A Crossover Double-Blind Study," J Oral Maxillofac Surg, 2015 73:616-621.
Yang et al., "Effect of dexmedetomidine on postoperative cognitive dysfunction and inflammation in patients after general anaesthesia, A PRISMA-compliant systematic review and meta-analysis," Medicine (2019) 98:18(e15383), 10 pages.
Yao, et al., "Intranasal dexmedetomidine premedication reduces minimum alveolar concentration of sevoflurane for laryngeal mask airway insertion and emergence delirium in children: a prospective, randomized, double-blind, placebo-controlled trial." Pediatric Anesthesia (2015); 25 (5): 492-498.
Yingyi, et al., "ED50 of dexmedetomidine nasal drip in induction of hypnosis in children during computed tomography." Zhonghua Yi Xue Za Zhi (2014); 94(24): 1886-1888 (with English Abstract).
Yuen, et al., "A Comparison of Intranasal Dexmedetomidine and Oral Midazolam for Premedication in Pediatric Anesthesia: A Double-Blinded Randomized Controlled Trial." Anesthesia & Analgesia (2008); 106 (6): 1715-1721.
Yuen, et al., "A Double-Blind, Crossover Assessment of the Sedative and Analgesic Effects of Intranasal Dexmedetomidine." Anesthesia & Analgesia (2007); 105 (2): 374-380.
Yuen, et al., "A randomised comparison of two intranasal dexmedetomidine doses for premedication in children." Anaesthesia (2012); 67 (11): 1210-1216.
Yuen, et al., "Optimal timing for the administration of intranasal dexmedetomidine for premedication in children." Anaesthesia (2010); 65 (9): 922-939.
Yun, et al., "Effects of intranasal dexmedetomidine for children undergoing cleft lip and palate repair surgery." International Journal of Somatology (2016); 43 (4): 401-405 (with English Abstract).
Zhang, et al., "Median Effective Dose of Intranasal Dexmedetomidine for Rescue Sedation in Pediatric Patients Undergoing Magnetic Resonance Imaging." Anesthesiology (2016); 125 (6): 1130-1135.
Zhang et al., "The Effect of Dexmedetomidine on Cognitive Function and Protein Expression of Aβ, p-Tau, and PSD95 after Extracorporeal Circulation Operation in Aged Rats," Hindawi BioMed Research International, Jan. 2018, vol. 2018, Article ID 4014021, 8 pages.
Zhang et al., "The Safety and Efficacy of Intranasal Dexmedetomidine During Electrochemotherapy for Facial Vascular Malformation: A Double-Blind, Randomized Clinical Trial," J Oral Maxillofac Surg, 2013 71:1835-1842.
Zheng et al., "Administration of Dexmedetomidine inhibited NLRP3 inflammasome and microglial cell activities in hippocampus of traumatic brain injury rats," Bioscience Reports, Accepted Manuscript, Sep. 19, 2018, 29 pages.
Zornow, et al., "Dexmedetomidine Decreases Cerebral Blood Flow Velocity in Humans." Journal of Cerebral Blood Flow & Metabolism (1993); 13(2): 350-353.
Zub et al., "Preliminary experience with oral dexmedetomidine for procedural and anesthetic premedication," Pediatric Anesthesia 2005 15: 932-938.
Aravindhanthan et al., "Sublingual spray: a new technology oriented formulation with multiple benefits," Int. J. Res. Pharm. Sci., 2019, 10(4), 2875-2885.
Bartlett et al., "Understanding the Oral Mucosal Absorption and Resulting Clinical Pharmacokinetics of Asenapine," AAPS PharmSciTech, Dec. 2012, vol. 13, No. 4, pp. 1110-1115.
Guthrie et. al., "Pharmacologic interventions for the treatment of opioid dependence and withdrawal," DICP Jul.-Aug. 1990; 24(7-8): 721-734.
International Search Report and Written Opinion of the International Searching Authority for International Application No. PCT/US2021/017857, dated Apr. 26, 2021, 9 pages.
Kawaai et al., "Dexmedetomidine decreases the oral mucosal blood flow," British Journal of Oral and Maxillofacial Surgery (2013) 51: 928-931.
Parikh et al., "Single-Dose Pharmacokinetics of Fentanyl Sublingual Spray and Oral Transmucosal Fentanyl Citrate in Healthy Volunteers: A Randomized Crossover Study," Clinical Therapeutics, 2013, vol. 35, No. 3, pp. 236-243.
Parmar et al., "A Review On Sublingual Spray: Novel Drug Delivery System," IJPSR, 2017; vol. 8(11): 4533-4539.
Sazuka et al., "Dexmedetomidine dose dependently decreases oral tissue blood flow during sevoflurane and propofol anesthesia in rabbits," Journal of Oral and Maxillofacial Surgery, 2012, 70(8): 1808-1814.
Tomita et al., "The Effect of Dexmedetomidine on Oral Mucosal Blood Flow and the Absorption of Lidocaine," Anesth Prog 2018, 65: 168-176.
International Search Report and Written Opinion of the International Searching Authority for International Application No. PCT/US2019/039308, dated Sep. 13, 2019, 15 pages.
International Search Report and Written Opinion of the International Searching Authority for International Application No. PCT/US2020/051256, dated Dec. 10, 2020, 18 pages.
International Search Report and Written Opinion of the International Searching Authority for International Application No. PCT/US2020/0426186, dated Mar. 1, 2021, 18 pages.
Montoya et al., "Validation of the Excited Component of the Positive and Negative Syndrome Scale (PANSS-EC) in a natural-

(56) References Cited

OTHER PUBLICATIONS istic sample of 278 patients with acute psychosis and agitation in a psychiatric emergency room," Health and Quality of Life Outcomes, 2011, 9:18, 11 pages.

Nuamah et al., "The past, present and future of opioid withdrawal assessment: a scoping review of scales and technologies," BMC Medical Informatics and Decision Making (2019) 19:113, 11 pages.

Wikipedia, Bipolar I disorder, Mar. 30, 2018, 5 pages, retrieved from https://en.wikipedia.org/w/index.php?title=Bipolar_I_disorder&oldid=833316388.

Abdel-Ghaffar et al., "Oral trans-mucosal dexmedetomidine for controlling of emergence agitation in children undergoing tonsillectomy: a randomized controlled trial," Rev Bras Anestesiol. 2019;69(5):469-476 with English abstract.

Barends et al., "Intranasal dexmedetomidine in elderly subjects with or without beta blockade: a randomised double-blind single-ascending-dose cohort study," British Journal of Anaesthesia, (2020) 124 (4): 411-419.

Bienvenu et al., "Treatment of four psychiatric emergencies in the intensive care unit," Critical Care Medicine (2012) 40(9):2662-2670.

BioXcel Therapeutics, Inc., "BioXcel Therapeutics Announces BXCL501 Program Initiative for Prevention and Treatment of Acute Agitation using Wearable Digital Devices," Sep. 18, 2019, 3 pages, retrieved from: https://www.globenewswire.com/en/news-release/2019/09/18/1917334/0/en/BioXcel-Therapeutics-Announces-BXCL501-Program-lnitiative-for-Prevention-and-Treatment-of-Acute-Agitation-using-Wearable-Digital-Devices.html.

BioXcel Therapeutics, Inc., "BioXcel Therapeutics Announces First Patient Enrolled in Phase 1 b/2 Study of BXCL501 for Acute Treatment of Agitation Associated with Dementia," Jan. 7, 2020, 3 pages, retrieved from https://www.globenewswire.com/news-release/2020/01/07/1967125/0/en/BioXcel-Therapeutics-Announces-First-Patient-Enrolled-in-Phase-1b-2-Study-of-BXCL501-for-Acute-Treatment-of-Agitation-Associated-with-Dementia.html.

BioXcel Therapeutics, Inc., "Next Wave of Medicines Utilizing AI," Jun. 2020, 30 pages, retrieved from https://d1io3yog0oux5.cloudfront.net/_ec77451 d0911d660fb193909a0a1ba0e/bioxceltherapeutics/db/445/3421 /pdf/BioXcel+Therapeutics+Presentation_June+11 .pdf.

BioXcel Therapeutics, Inc., United States Securities and Exchange Commission, Form 10-K, Annual Report Pursuant to Section 13 or 15(d) of the Securities Exchange Act of 1934, For the year ended Dec. 31, 2019, 135 pages.

Changlu et al., "Determination of Effective Dosage in Intranasal Dexmedetomidine Sedation for MRI Scanning with Modified Dixon's Up-and-Down Method in Children," China Pharmaceuticals, (2015), 24(22), 22-24, with English abstract.

ClinicalTrials.gov Identifier: NCT02836431, Pharmacokinetic Study of Dexmedetomidine After Intra-nasal Dosing in Children, First Posted—Jul. 19, 2016, Last Update Posted—Jul. 30, 2018, retrieved from https://clinicaltrials.gov/ct2/show/NCT02836431, 8 pages.

ClinicalTrials.gov Identifier: NCT02955732, Pharmacological Characteristics of Intranasally Given Dexmedetomidine in Paediatric Patients (PINDEX), First Posted Nov. 4, 2016, Last Update Posted—Sep. 12, 2018, retrieved from https://clinicaltrials.gov/ct2/show/NCT02955732, 6 pages.

ClinicalTrials.gov Identifier: NCT03069638, Intranasal Dexmedetomidine Sedation During Intra-articular Joint Injections in Pediatric Population, First Posted—Mar. 3, 2017, Last Update Posted—May 12, 2021, retrieved from https://clinicaltrials.gov/ct2/show/NCT03069638, 8 pages.

ClinicalTrials.gov Identifier: NCT03668951, Pharmacokinetic Study of Dexmedetomidine After IntraNasal and Buccal Dosing in Children (DexPK), First Posted—Sep. 13, 2018, Last Update Posted—May 18, 2021, retrieved from https://clinicaltrials.gov/ct2/show/study/NCT03668951, 7 pages.

ClinicalTrials.gov Identifier: NCT03806777, Intra-nasal Dexmedetomidine for Children Undergoing MRI Imaging (DexmedMRI), First Posted—Jan. 16, 2019, Last Update Posted—Jan. 25, 2019, retrieved from https://clinicaltrials.gov/ct2/show/NCT03806777, 7 pages.

ClinicalTrials.gov Identifier: NCT03926663, Intranasal Injection of Dexmedetomidine and Bupivacaine in Septoplasty Surgeries, First Posted—Apr. 24, 2019, Last Update Posted—Aug. 1, 2019, retrieved from https://clinicaltrials.gov/ct2/show/NCT03926663, 7 pages.

ClinicalTrials.gov Identifier: NCT03957304, Intranasal Dexmedetomidine Dose-finding Study, First Posted—May 21, 2019, Last Update Posted—May 7, 2021, retrieved from https://clinicaltrials.gov/ct2/show/NCT03957304, 9 pages.

ClinicalTrials.gov Identifier: NCT04200235, A Trial of Dexmedetomidine Hydrochloride Nasal Spray in Preoperative Sedation of Children, First Posted—Dec. 16, 2019, Last Update Posted—Sep. 9, 2020, retrieved from https://clinicaltrials.gov/ct2/show/NCT04200235, 8 pages.

ClinicalTrials.gov Identifier: NCT04270708, Intranasal Dexmedetomidine vs Oral Triclofos Sodium for EEG in Children With Autism, First Posted—Feb. 17, 2020, Last Update Posted—Feb. 17, 2020, retrieved from https://clinicaltrials.gov/ct2/show/NCT04270708, 8 pages.

ClinicalTrials.gov Identifier: NCT04383418, A Trial of Dexmedetomidine Hydrochloride Nasal Spray in Preoperative Sedation of Adults, First Posted—May 12, 2020, Last Update Posted—Jul. 15, 2021, retrieved from https://clinicaltrials.gov/ct2/show/NCT04383418, 7 pages.

ClinicalTrials.gov Identifier: NCT04509414, Intranasal Dexmedetomidine for Deep-sedated Pediatric Dental Patients, First Posted—Aug. 12, 2020, Last Update Posted—Aug. 12, 2020, retrieved from https://clinicaltrials.gov/ct2/show/NCT04509414, 8 pages.

ClinicalTrials.gov Identifier: NCT04665453, Dexmedetomidine and Melatonin for Sleep Induction for EEG in Children (MeloDex), First Posted—Dec. 11, 2020, Last Update Posted—Dec. 16, 2020, retrieved from https://clinicaltrials.gov/ct2/show/NCT04665453, 9 pages.

ClinicalTrials.gov Identifier: NCT04669457, Pediatric Delirium, First Posted—Dec. 16, 2020, Last Update Posted—May 11, 2021, retrieved from https://clinicaltrials.gov/ct2/show/NCT04669457, 8 pages.

ClinicalTrials.gov Identifier: NCT04859283, Premedication With Intranasal Dexmedetomidine in Sedation of Patients Undergoing Total Knee Arthroplasty (TKADEX), First Posted—Apr. 26, 2021, Last Update Posted—Sep. 10, 2021, retrieved from https://clinicaltrials.gov/ct2/show/NCT04859283, 7 pages.

ClinicalTrials.gov Identifier: NCT05065775, Bioavailability of Intranasal Dexmedetomidine (INDEX), First Posted—Oct. 4, 2021, Last Update Posted—Oct. 12, 2021, retrieved from https://clinicaltrials.gov/ct2/show/NCT05065775, 7 pages.

ClinicalTrials.gov Identifier: NCT05111431, A Trial of Dexmedetomidine Hydrochloride Nasal Spray in Preoperative Sedation of Children, First Posted—Nov. 8, 2021, Last Update Posted—Dec. 16, 2021, retrieved from https://clinicaltrials.gov/ct2/show/NCT05111431, 7 pages.

Darrouj et al. "Dexmedetomidine infusion as adjunctive therapy to benzodiazepines for acute alcohol withdrawal," Annals of Pharmacotherapy (2008), 42(11), 1703-1705.

Dundar et al., "Pharmacological treatment of acute agitation associated with psychotic and bipolar disorder: a systematic review and meta-analysis," Hum. Psychopharmacol Clin Exp 2016, 31: 268-285.

Economopoulos, O., "BioXcel Therapeutics CEO Says Wearable Devices Are Another Tool To Combat Alzheimer's Agitation," Benzinga, Apr. 15, 2020, xx pages, retrieved from: https://www.benzinga.com/general/biotech/20/04/15808398/bioxcel-therapeutics-ceo-says-wearable-devices-are-another-tool-to-combat-alzheimers-agitation.

Extended European Search Report for European Patent Application No. 19824839.5, dated Feb. 28, 2022, 14 pages.

Extended European Search Report for European Patent Application No. 19826778.3, dated May 10, 2022, 6 pages.

(56) References Cited

OTHER PUBLICATIONS

Ferguson et al., "Intranasal dexmedetomidine: Procedural sedation in palliative care: A case report," Palliat Med. 2021, 35(8): 1625-1628.
Garg et al., "Efficacy of dexmedetomidine for prevention of emergence agitation in patients posted for nasal surgery under desflurane anaesthesia: A prospective double-blinded randomised controlled trial," Indian J Anaesth 2018;62:524-30.
Gu et al., "ED50 of Intranasal Dexmedetomidine Sedation for Transthoracic Echocardiography in Children with or without a History of Cardiac Surgery for Cyanotic Congenital Heart Disease," Hindawi BioMed Research International, 2020, vol. 2020, Article ID 1349432, 7 pages.
Hong et al., "Dexmedetomidine alleviates smoke-induced bronchial and alveolar epithelial cell injury," Gen Physiol Biophys., May 2020;39(3):293-300.
Hong et al., "Dexmedetomidine preconditioning ameliorates lung injury induced by pulmonary ischemia/reperfusion by upregulating promoter histone H3K4me3 modification of KGF-2," Experimental Cell Research, Sep. 2021, 406, 112762, 11 pages.
Jia et al., "Application of intranasal dexmedetomidine hydrochloride combined sevoflurane inhalation anesthesia in pediatric lingual frenoplasty," Journal of Xinxiang Medical University (2015), 32(8), 732-734, English Abstract only.
Jun et al., "The effects of intranasal dexmedetomidine premedication in children: a systematic review and meta-analysis," Can J Anesth/J Can Anesth (2017) 64:947-961.
Kang et al., "The correlation of heart rate between natural sleep and dexmedetomidine sedation," Korean J Anesthesiol. Apr. 2019; 72(2): 164-168.
Lei et al., "Incidence and risk factors of bradycardia in pediatric patients undergoing intranasal dexmedetomidine sedation," Acta Anaesthesiologica Scandinavica (2020), 64: 464-471.
Li et al., "Comparison of preoperative application of different doses of dexmedetomidine intranasal in children undergoing outpatient surgery," Sichuan Yixue (2015), 36(09), 1209-1211. DOI:10.16252/j.cnki.issn1004-0501-2015.09.002.
Li et al., "Pharmacokinetic and pharmacodynamic study of intranasal and intravenous dexmedetomidine," British Journal of Anaesthesia (2018), 120(5), 960-968.
Li et al., "The 95% effective dose of intranasal dexmedetomidine sedation for pulmonary function testing in children aged 1-3 years: A biased coin design up-and-down sequential method," Journal of Clinical Anesthesia (2020), 63, 109746, 5 pages.
Liu et al., "Comparison of sedative effects of two methods of intranasal dexmedetomidine in cardiac ultrasonography in infants with congenital heart disease," Practical Medicine and Clinic . 2015,18(12), 1452-1454, English Abstract only.
Liu et al., "Determination of the 90% effective dose of intranasal dexmedetomidine for sedation during electroencephalography in children," Acta Anaesthesiologica Scandinavica (2019), 63, 847-852.
Liu et al., "Safety and sedative effect of intranasal dexmedetomidine in mandibular third molar surgery: a systematic review and meta-analysis," Drug Design, Development and Therapy (2019), 13:1301-1310.
Liyan, Chu et al., "Effect of dexmedetomidine on minimum alveolar concentration of sevoflurane in children undergoing inhalation anesthesia," Beijing Yixue / Beijing Medical Journal, 2017, vol. 39, Issue 6, pp. 581-584 (English abstract only).
MacCioli et al., "Dexmedetomidine to Facilitate Drug Withdrawal," Anesthesiology, Feb. 2003, V 98, No. 2, pp. 575-575.
Madhav et al., "Orotransmucosal drug delivery systems: A review," Journal of Controlled Release (2009) 140: 2-11.
Mahmoud et al., "Dexmedetomidine: review, update, and future considerations of paediatric perioperative and periprocedural applications and limitations," British Journal of Anaesthesia 2015, 171-82, doi: 10.1093/bja/aev226.
Miller et al., "Comparison of Intranasal Dexmedetomidine and Oral Pentobarbital Sedation for Transthoracic Echocardiography in Infants and Toddlers: A Prospective, Randomized, Double-Blind Trial," Anesthesia & Analgesia, Jun. 2018, vol. 126, No. 6, pp. 2009-2016.
Miller et al., "Does intranasal dexmedetomidine provide adequate plasma concentrations for sedation in children: a pharmacokinetic study," British Journal of Anaesthesia (2018), 120(5), 1056-1065.
Misra et al., "Effect of preoperative dexmedetomidine nebulization on the hemodynamic response to laryngoscopy and intubation: a randomized control trial," Korean Journal of Anesthesiology 2021; 74(2): 150-157.
Mohr et al., "Treatment of acute agitation in psychotic disorders," Neuroendocrinology Letters, 2005, vol. 26, No. 4, pp. 327-335.
Muszkat et al., "Alpha2-Adrenergic Receptor—Induced Vascular Constriction in Blacks and Whites," Hypertension, 2004; 43:31-35.
Nawrat, A., "Triple combo: calming Alzheimer's agitation with AI, wearables and a novel drug," Medical Device Network, Jan. 28, 2020, 4 pages, retrieved from https://www.medicaldevice-network.com/analysis/wearable-ai-device-for-agitation/#:~:text=.
Nitturi et al., "A Comparative Evaluation of Intranasal Dexmedetomidine and Intranasal Midazolam for Premedication in Pediatric Surgery," IAIM, 2018; 5(1): 82-94.
Niyogi et al., "Attenuation of haemodynamic responses to laryngoscopy and endotracheal intubation with dexmedetomidine: A comparison between intravenous and intranasal route," Indian J Anaesth 2019;63:915-923.
Posner, "Measuring Alertness," Ann. N.Y. Acad. Sci. (2008) 1129:193-199.
Purushotham et al., "Intranasal Dexmedetomidine Versus Oral Midazolam As Premedication In Anaesthesia In Children," RJPBCS, July-Aug. 2017, 8(4), pp. 1219-1241.
Qiao et al., "Pediatric premedication: a double-blind randomized trial of dexmedetomidine or ketamine alone versus a combination of dexmedetomidine and ketamine," BMC Anesthesiology (2017) 17:158, 7 pages.
Qiu et al., "Sedative effects of different doses of intranasal dexmedetomidine in different age groups of children," Journal of Medical Postgraduates 2014;(4):394-397, English abstract only.
Rahman et al., "The use of dexmedetomidine for refractory agitation in substance abuse patient," Crit Care & Shock (2010) 13:59-60.
Rathbone et al., "Mechanisms, barriers and pathways of oral mucosal drug permeation," Advanced Drug Delivery Reviews, (1993) 12: 41-60.
Reade and Finfer, "Sedation and delirium in the intensive care unit," N Engl J Med 2014; 370: 444-54.
Roosens et al., "The use of dexmedetomidine in extreme agitation," Tijdschrift Voor Psychiatrie (2017) 59:9, 554-558, with English abstract.
Rosen et al., "The Pittsburgh Agitation Scale," American Journal of Geriatric Psychiatry, 1994, 1 page.
Saad et al., "Intranasal dexmedetomidine versus intranasal midazolam as pre-anesthetic medication in pediatric age group undergoing adenotonsillectomy," Ain-Shams Journal of Anesthesiology (2020) 12:40, 10 pages.
Staines, R., "BioXcel to trial Apple Watch-drug combination to prevent Alzheimer's agitation episodes," PharmaPhorum, Sep. 19, 2019, 2 pages, retrieved from: https://pharmaphorum.com/news/bioxcel-to-trial-apple-watch-drug-combination-to-prevent-alzheimers-agitation-episodes/.
Tang et al., "The effect of intranasal administration of dexmedetomidine to assist local anesthesia in patients with endoscopic nasal surgery," Chinese Journal of Anesthesiology, 2016, 36(2), English abstract only, 4 pages.
Trevisan et al., "Intranasal dexmedetomidine and intravenous ketamine for procedural sedation in a child with alpha-mannosidosis: a magic bullet?" Italian Journal of Pediatrics (2019) 45:119, 6 pages.
Uusalo et al., "Feasibility of Intranasal Dexmedetomidine in Treatment of Postoperative Restlessness, Agitation, and Pain in Geriatric Orthopedic Patients," Drugs & Aging (2021) vol. 38, pp. 441-450.
Uusalo et al., "Pharmacokinetics and Sedative Effects of Intranasal Dexmedetomidine in Ambulatory Pediatric Patients," Anesth Analg. Apr. 2020; 130(4):949-957.
Wang et al., "Comparison of Intranasal Dexmedetomidine and Oral Midazolam for Premedication in Pediatric Dental Patients under

(56) References Cited

OTHER PUBLICATIONS

General Anesthesia: A Randomised Clinical Trial," BioMed Research International, 2020, vol. 2020, Article ID 5142913, 7 pages.

Wang et al., "Effects of dexmedetomidine nasal spray on preoperative sedation and analgesia and postoperative agitation in children with ventricular septal defect closure," Chinese Journal of Experimental Surgery, 2016, 33(3), English abstract only, 4 pages.

Wang et al., "Pharmacokinetics of Intranasally Administered Dexmedetomidine in Chinese Children," Front. Pharmacol., Jul. 2019, 10:756, 9 pages.

Whittington et al., "Dexmedetomidine increases tau phosphorylation under normothermic conditions in vivo and in vitro," Neurobiology of Aging (2015) 36: 2414-2428.

Wu et al., "Efficacy and safety of intravenous dexmedetomidine in adjuvant general anesthesia," Chinese Journal of Anesthesiology, 2007, Issue 9, 773-776, English abstract only, 4 pages.

Xu et al., "Effects of Two Intranasal Dexmedetomidine Doses as Premedication on Sevoflurane EC 50 for Successful Laryngeal Mask Airway Placement in Children," Zhongguo Yi Xue Ke Xue Yuan Xue Bao. Dec. 2, 2016;38(6):627-631, English abstract only.

Xu et al., "Efficacy and Safety of Intranasal Dexmedetomidine During Recovery From Sevoflurane Anesthesia in Children: A Systematic Review and Meta-analysis," Clin Neuropharmacol, 2021; 44:157-168.

Xu et al., "ED50 of dexmedetomidine nasal drip in induction of hypnosis in children during computed tomography," Zhonghua Yi Xue Za Zhi. Jun. 2, 2014;94(24): 1886-8, English abstract only.

Yang et al., "Analysis of 17 948 pediatric patients undergoing procedural sedation with a combination of intranasal dexmedetomidine and ketamine," Paediatr Anaesth., 2019; 29(1):85-91.

Yang et al., "Fifty Percent Effective Dose of Intranasal Dexmedetomidine Sedation for Transthoracic Echocardiography in Children With Cyanotic and Acyanotic Congenital Heart Disease," Journal of Cardiothoracic and Vascular Anesthesia (2020), 34, 966-971.

\* cited by examiner

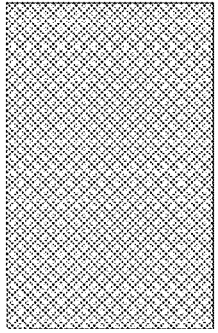
FIG. 1: cross-sectional (side) view and area (top) view of an exemplary monolithic matrix film

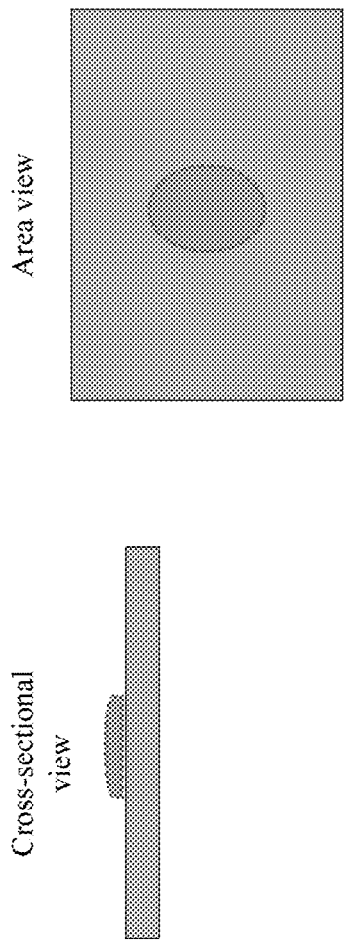
FIG. 2: cross-sectional (side) view and area (top) view of an exemplary micro-deposited matrix film

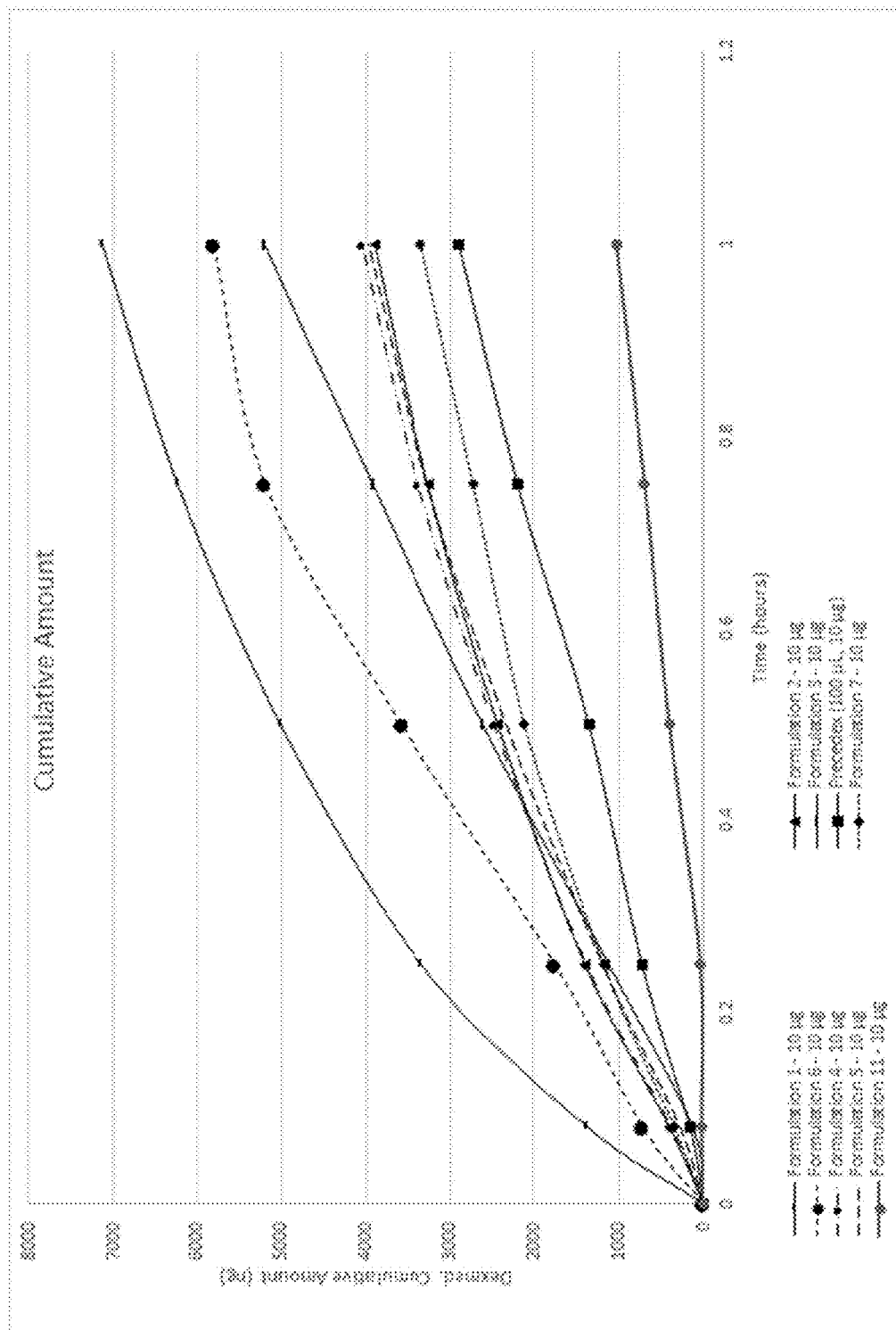
FIG. 3: Diffusion of Dexmedetomidine in Formulations 1 to 7 and Formulation 11 and Precedex® through oral cell culture membrane

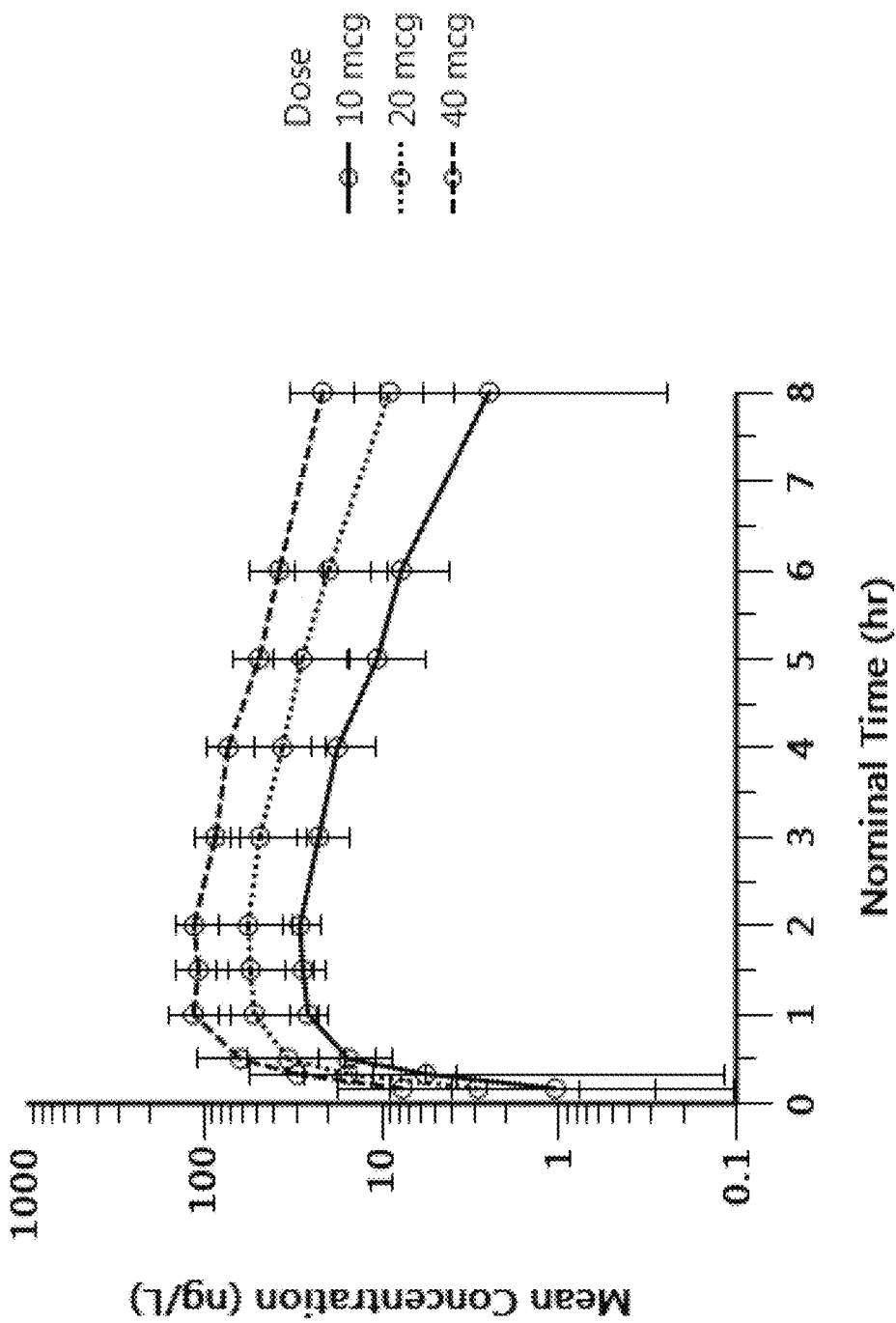
FIG. 4: Mean Dexmedetomidine Plasma Log Concentration vs. Time for Dose Levels 10, 20 and 40 mcg Dexmedetomidine Sublingual Film– Semi-log Scale

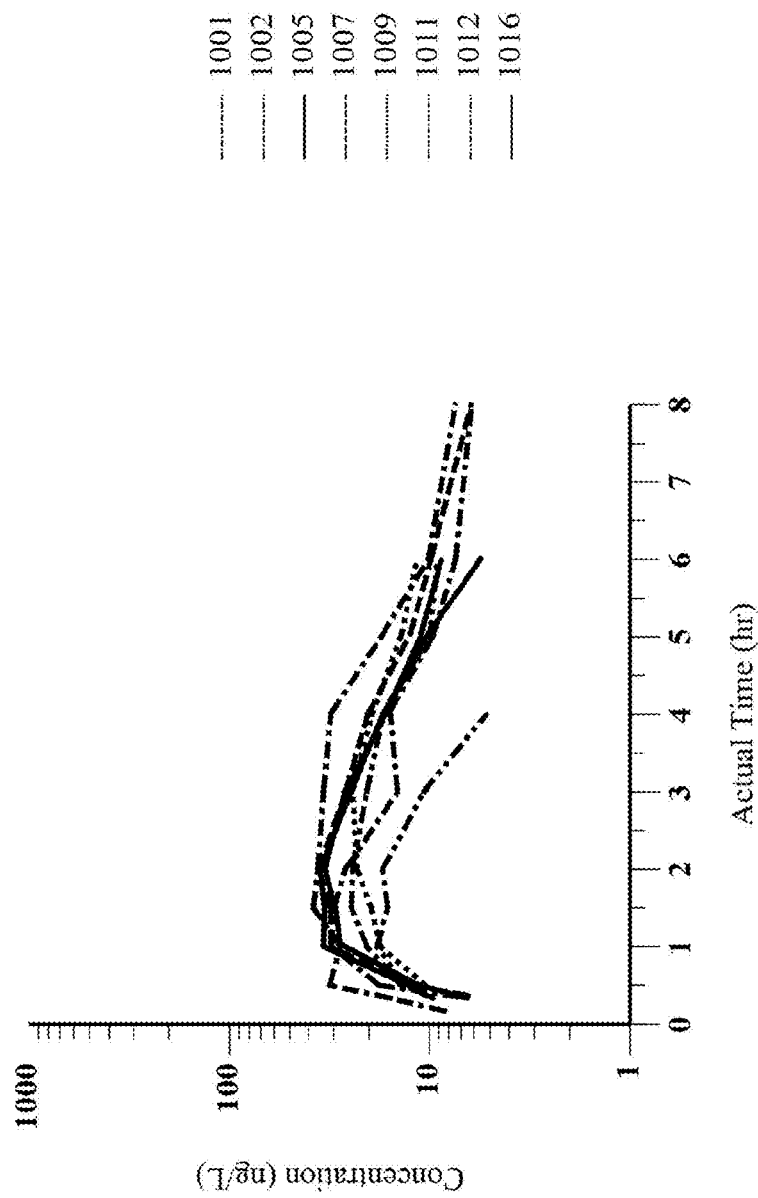
FIG 5A: Individual Dexmedetomidine Concentration-time Profiles for all Subjects by dose after administration of Dexmedetomidine sublingual film (10 mcg) Semi-log Scale

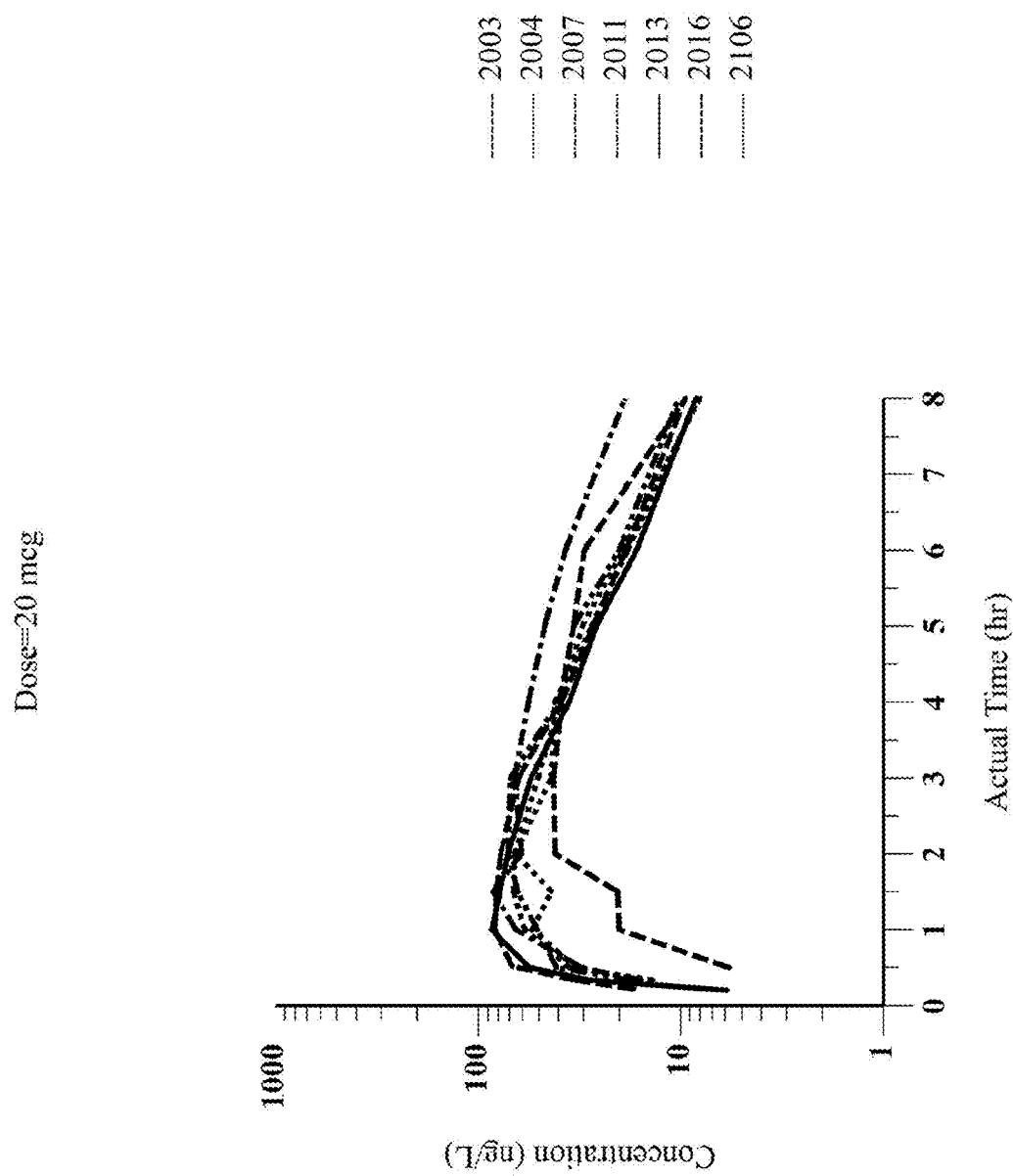
FIG 5B: Individual Dexmedetomidine Concentration-time Profiles for all Subjects by dose after administration of Dexmedetomidine sublingual film (20 mcg) Semi-log Scale

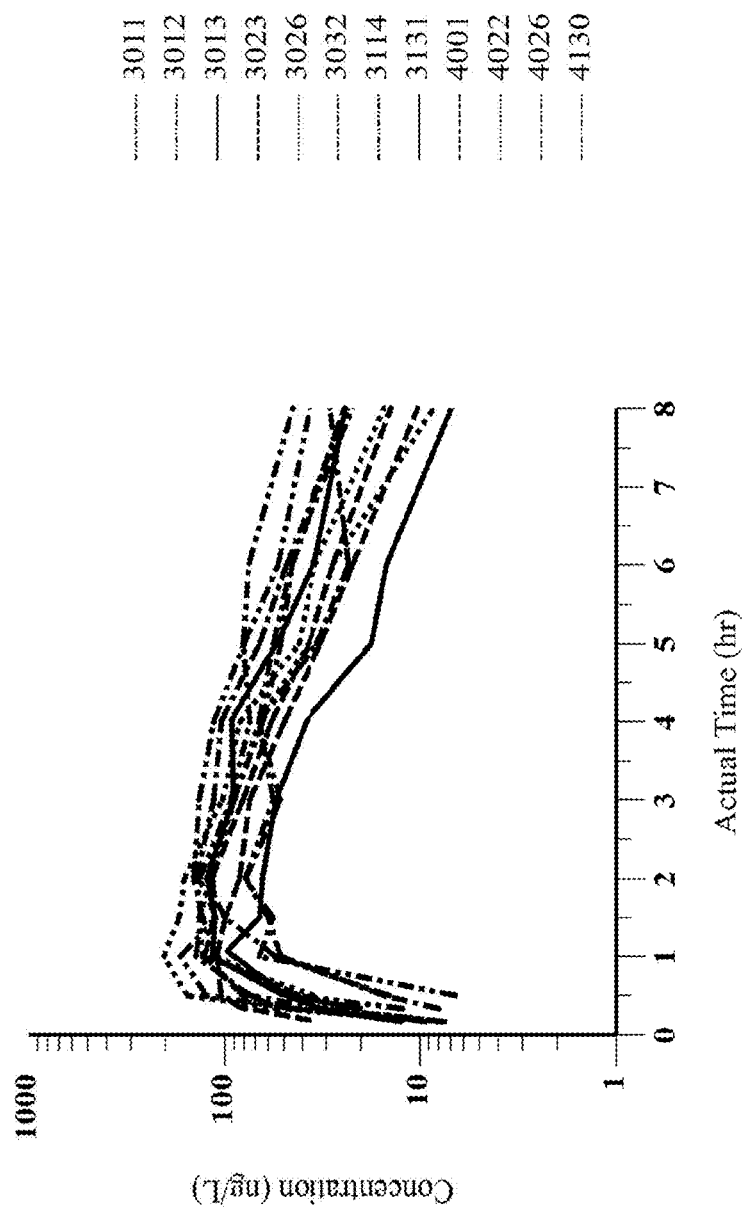
FIG 5C: Individual Dexmedetomidine Concentration-time Profiles for all Subjects by dose after administration of Dexmedetomidine sublingual film (40 mcg) Semi-log Scale

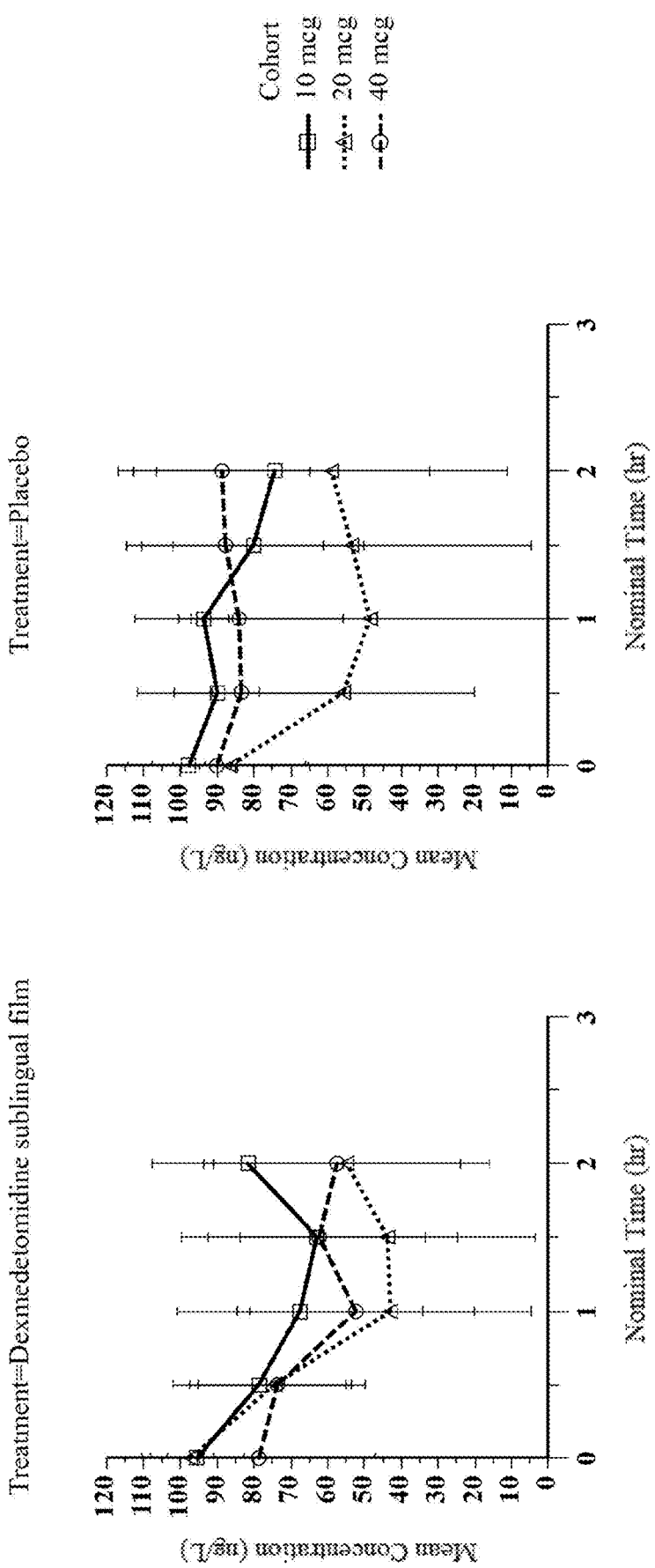
FIG 6: Mean VAS/S score vs. Nominal Time after administration of Dexmedetomidine sublingual film (10, 20, 40 mcg) and Placebo

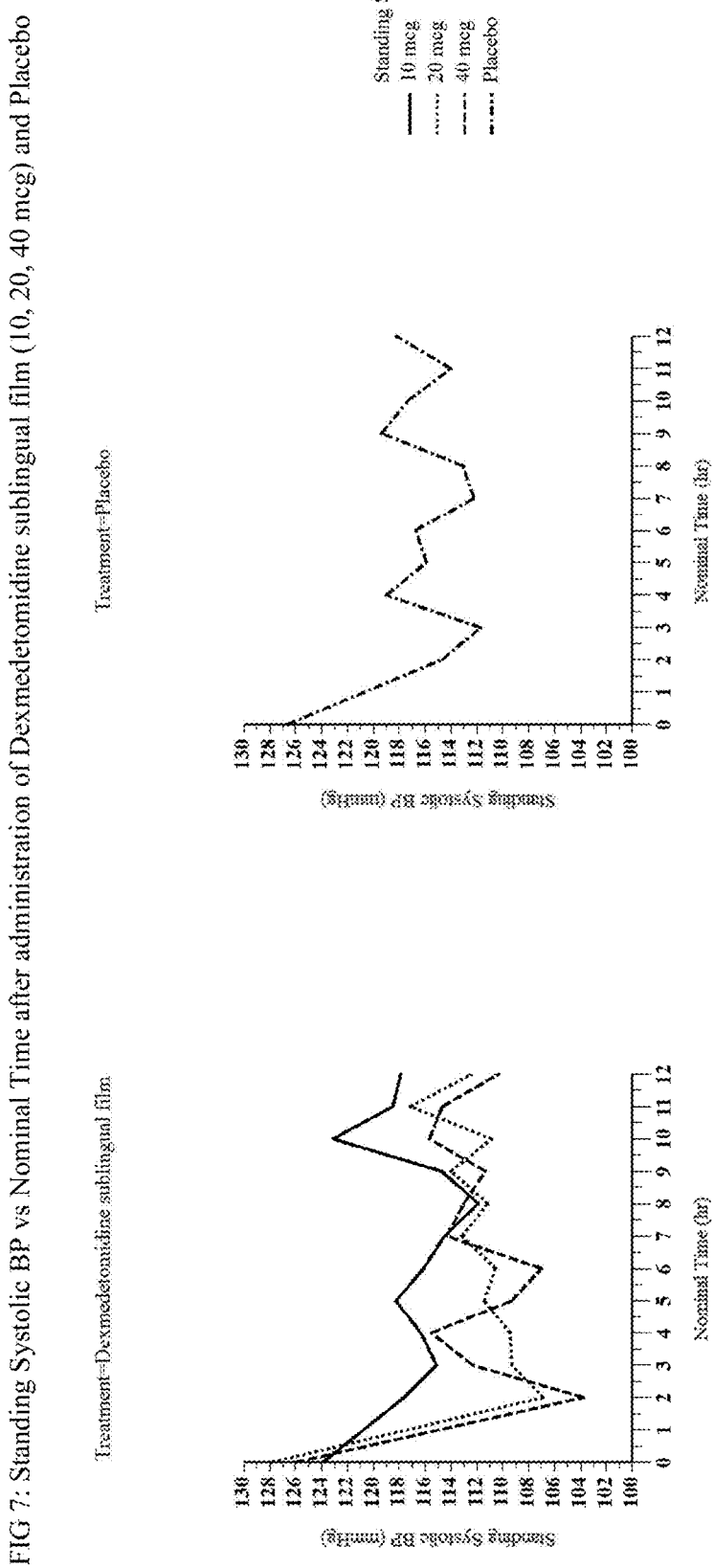
FIG 7: Standing Systolic BP vs Nominal Time after administration of Dexmedetomidine sublingual film (10, 20, 40 mcg) and Placebo

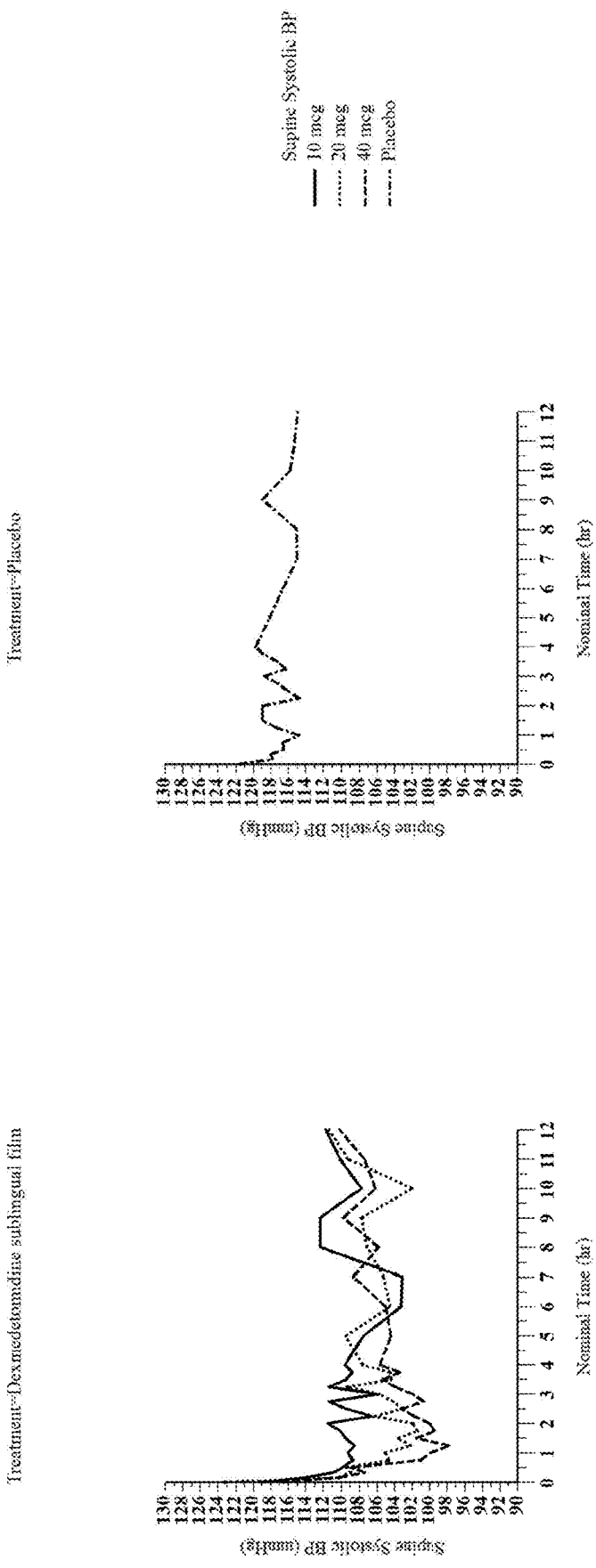
FIG 8: Supine Systolic BP. vs Nominal Time after administration of Dexmedetomidine sublingual film 10 mcg, 20 mcg and 40 mcg and Placebo

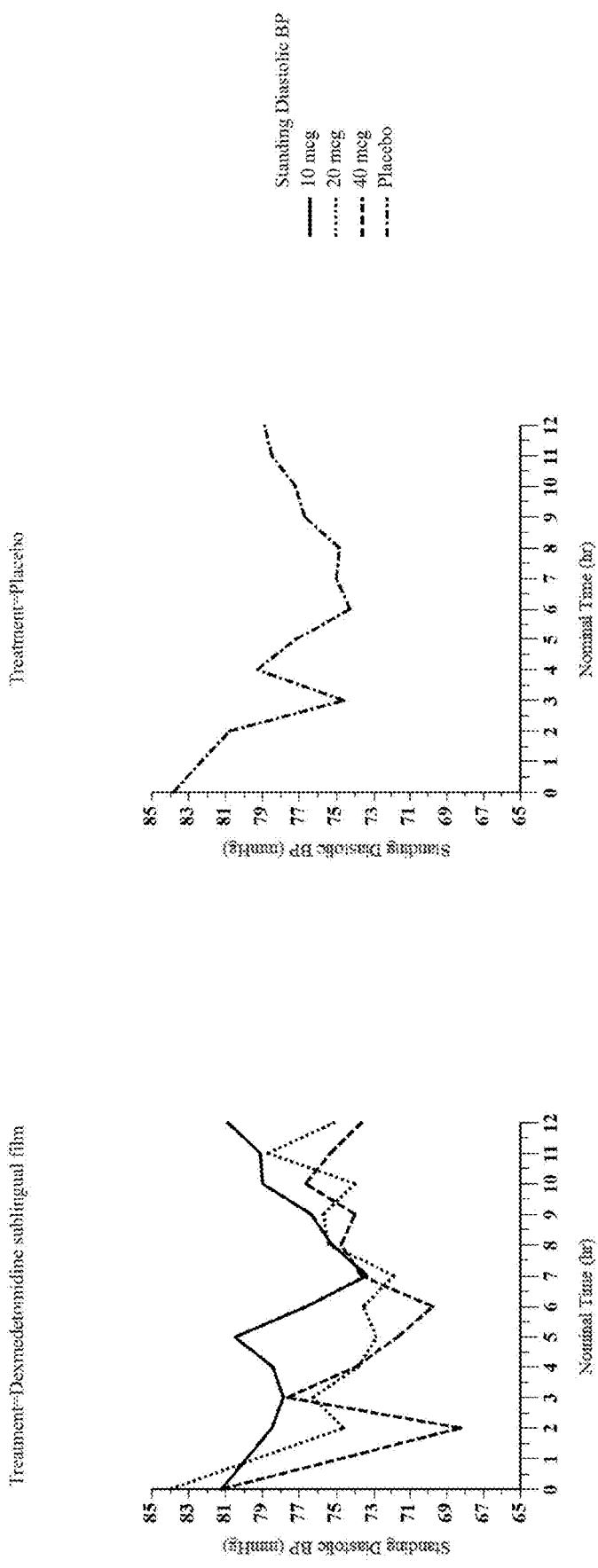
FIG 9: Standing Diastolic BP vs Nominal Time after administration of Dexmedetomidine sublingual film 10 mcg, 20 mcg and 40 mcg and Placebo

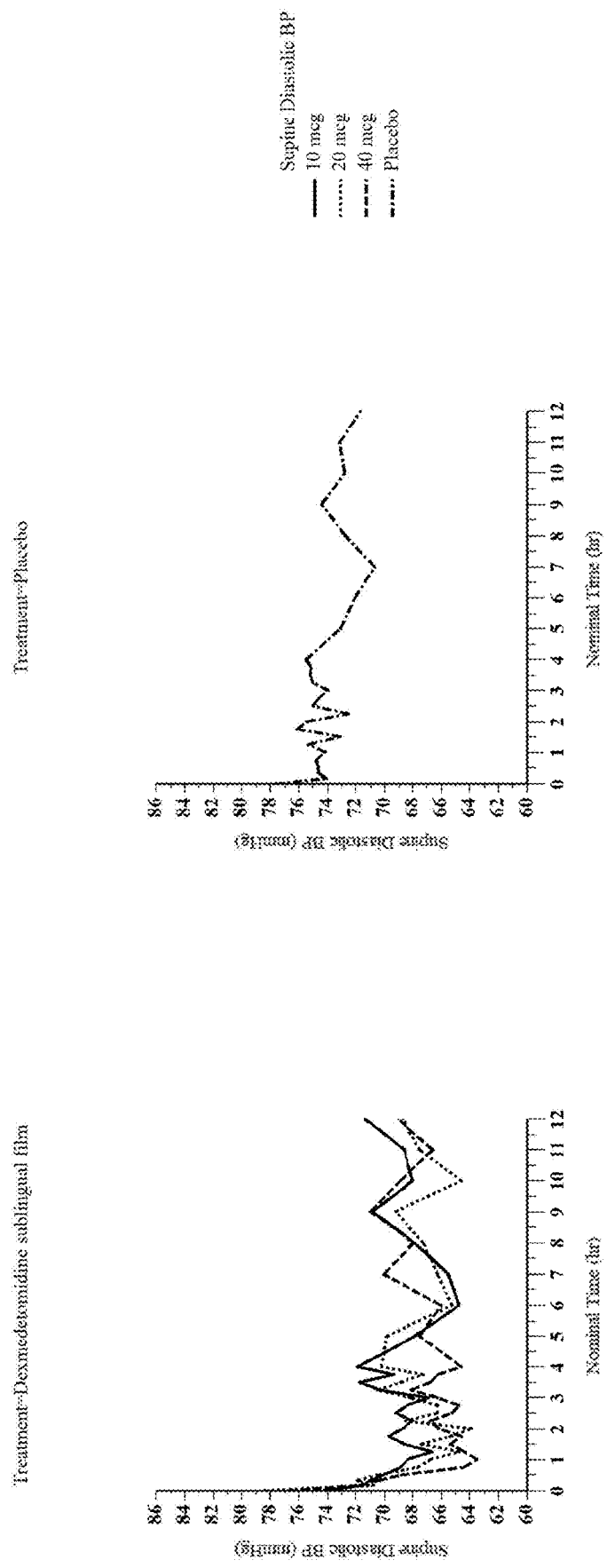
FIG 10: Supine Diastolic BP vs Nominal Time after administration of Dexmedetomidine sublingual film 10 mcg, 20 mcg and 40 mcg and Placebo

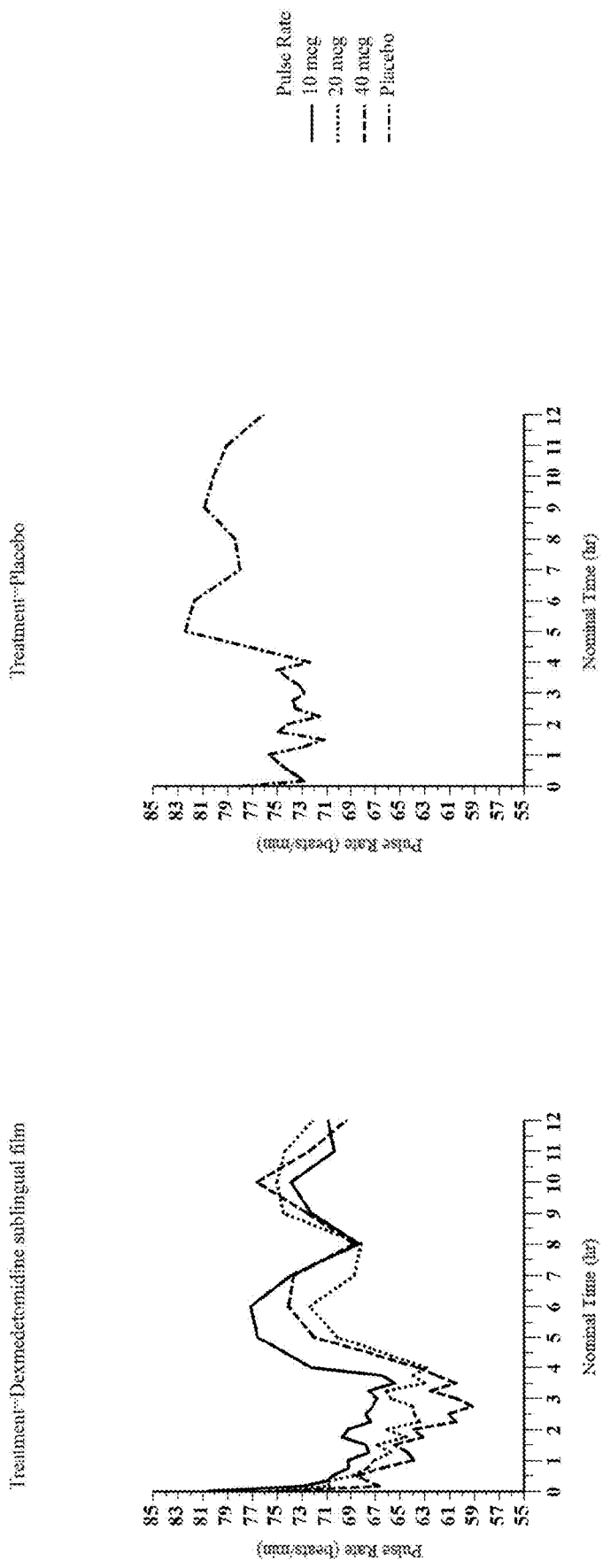
FIG 11: Pulse Rate vs Nominal Time after administration of Dexmedetomidine sublingual film 10 mcg, 20 mcg and 40 mcg and Placebo

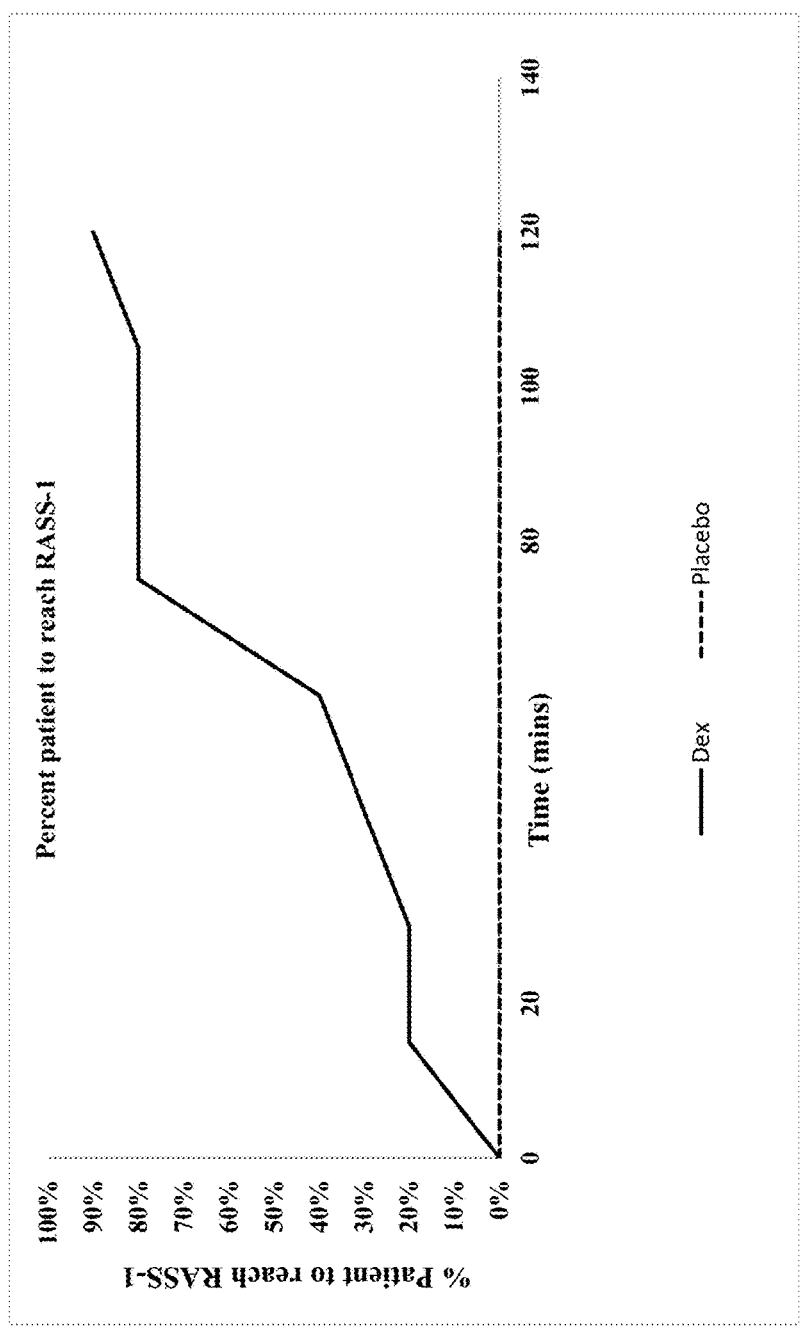
FIG. 12: Percentage of schizophrenic patients achieving RASS -1 in the treatment arm (IV dexmedetomidine hydrochloride treated group) versus placebo group

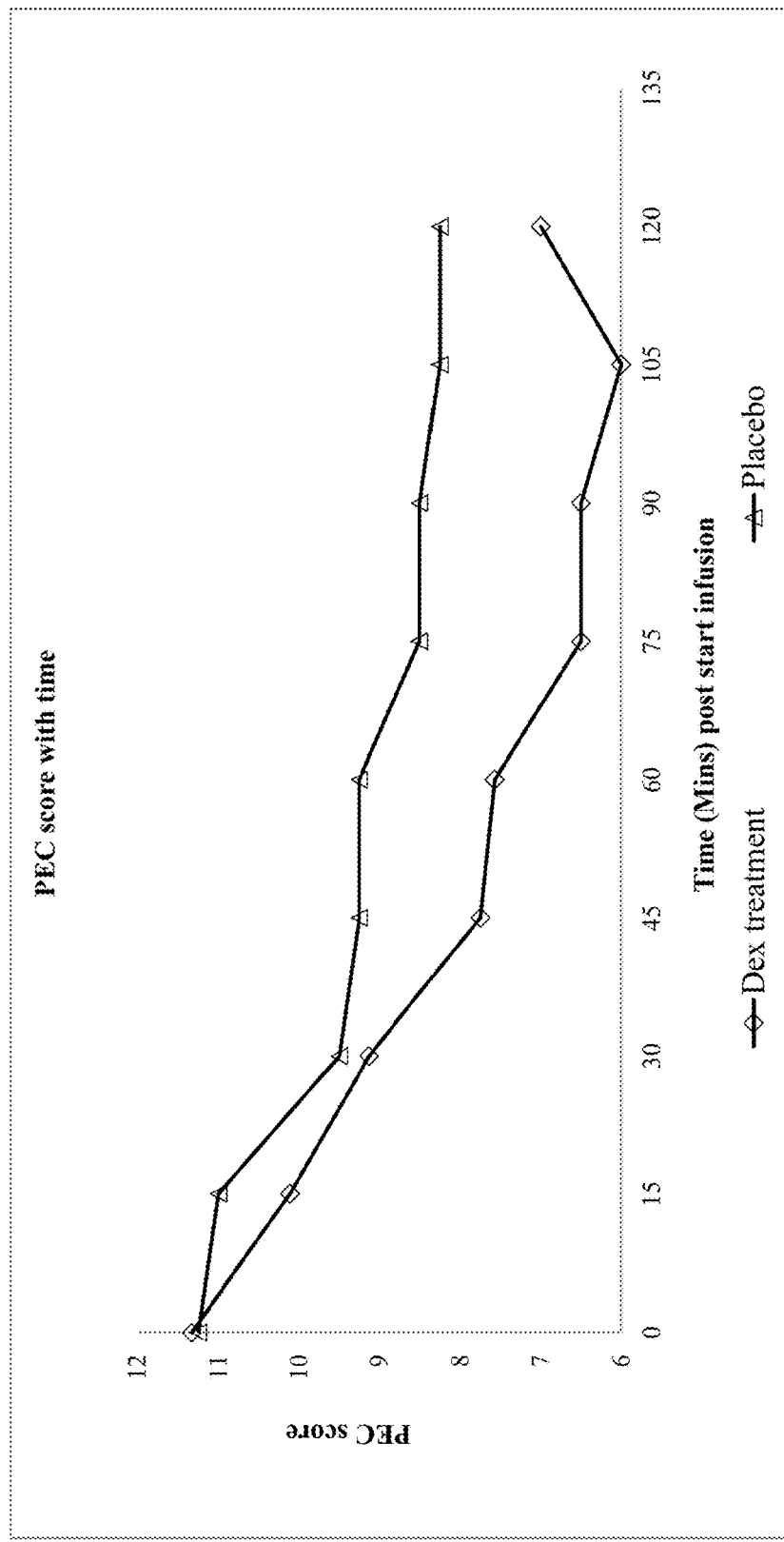
FIG. 13: Mean drop in PEC score in schizophrenic patients in the treatment arm (IV dexmedetomidine hydrochloride treated group) versus placebo group

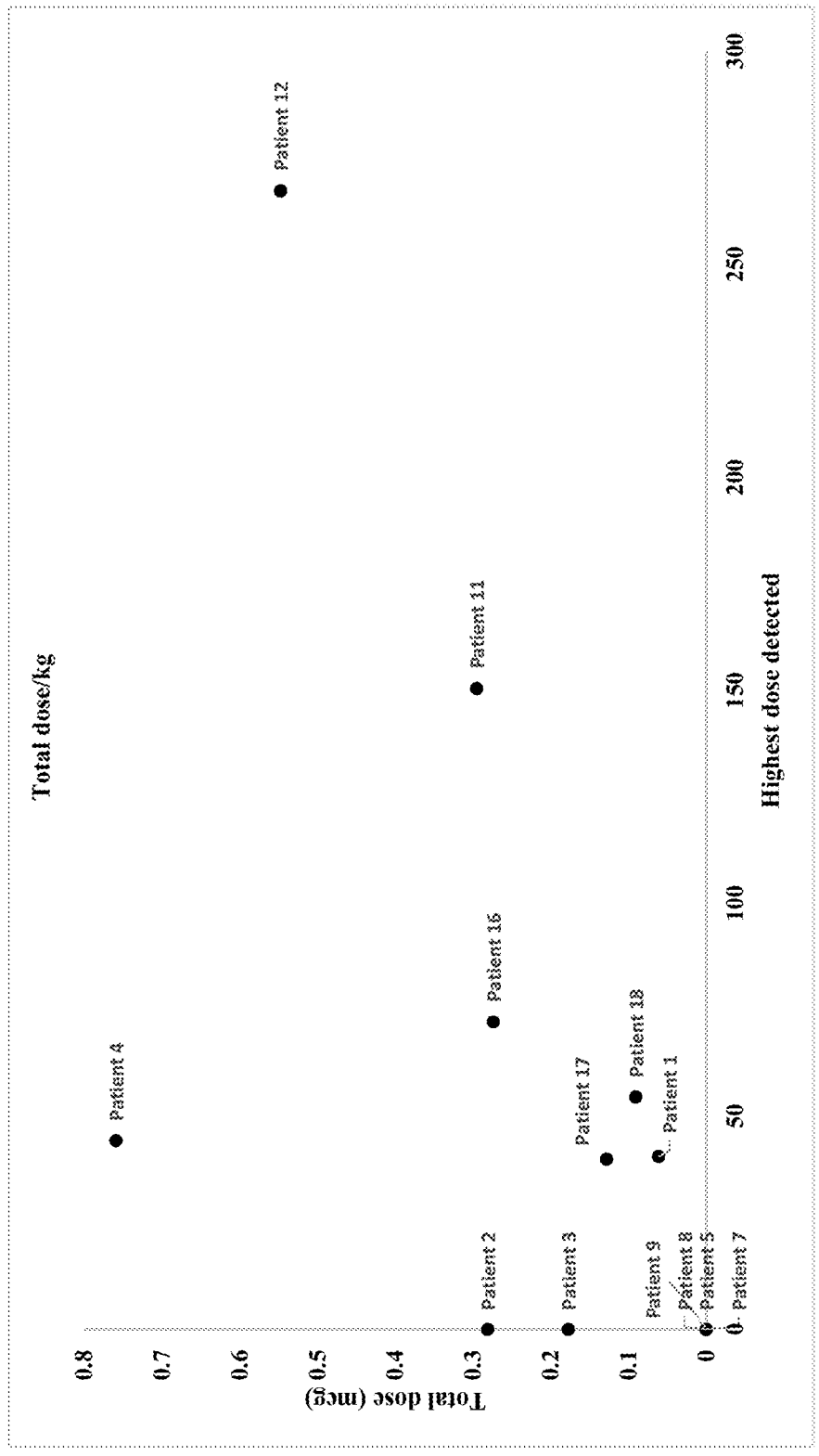
FIG. 14: Maximum doses of IV dexmedetomidine hydrochloride received by schizophrenic patients for the treatment of agitation

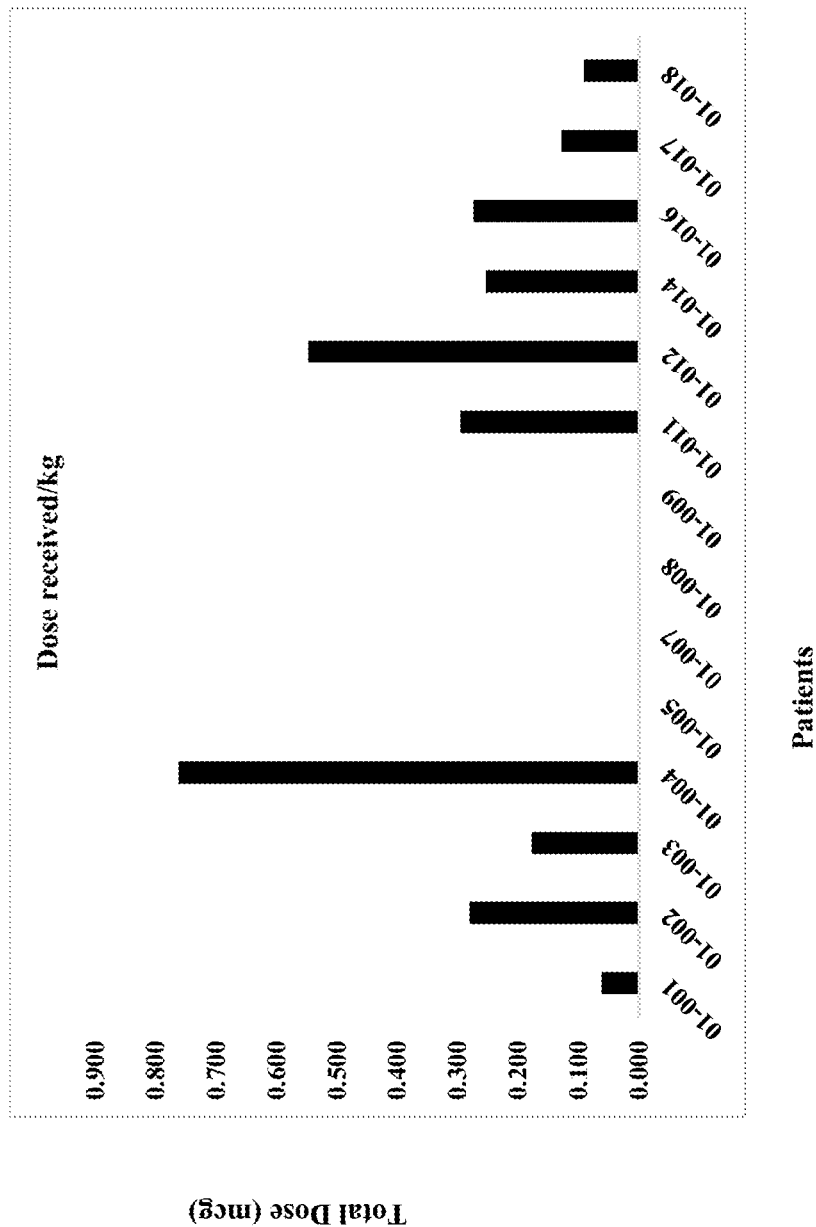
FIG. 15: Total intravenous dose of IV dexmedetomidine hydrochloride received by schizophrenic patients for the treatment of agitation

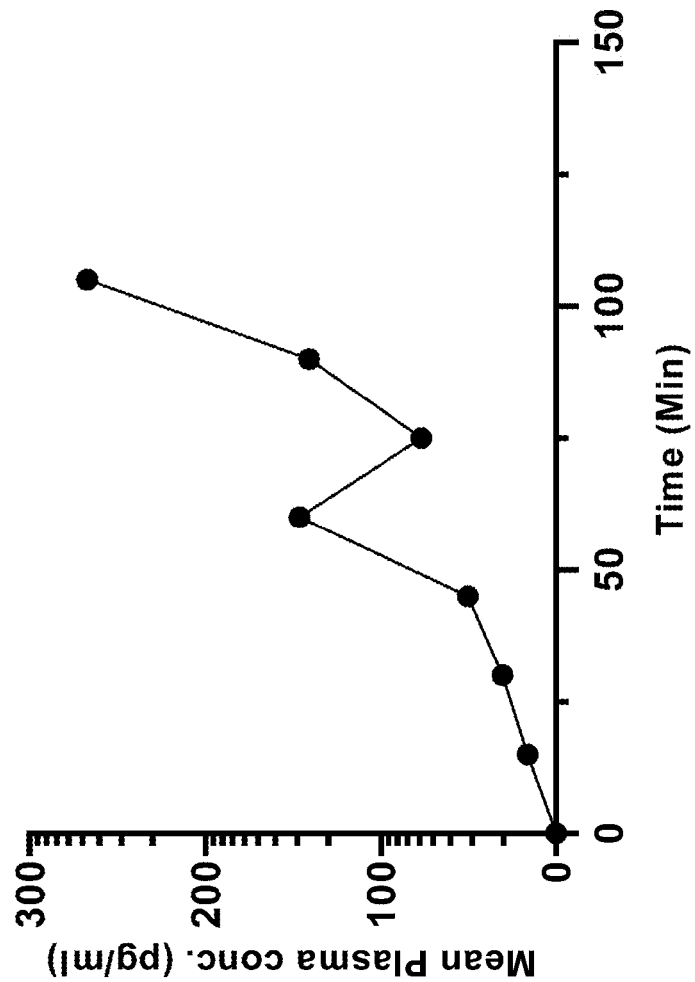
FIG 16: Mean Plasma concentration (pg/ml) vs actual time. Plasma concentration mean values in schizophrenic patients treated with IV dexmedetomidine hydrochloride - Semi-log scale

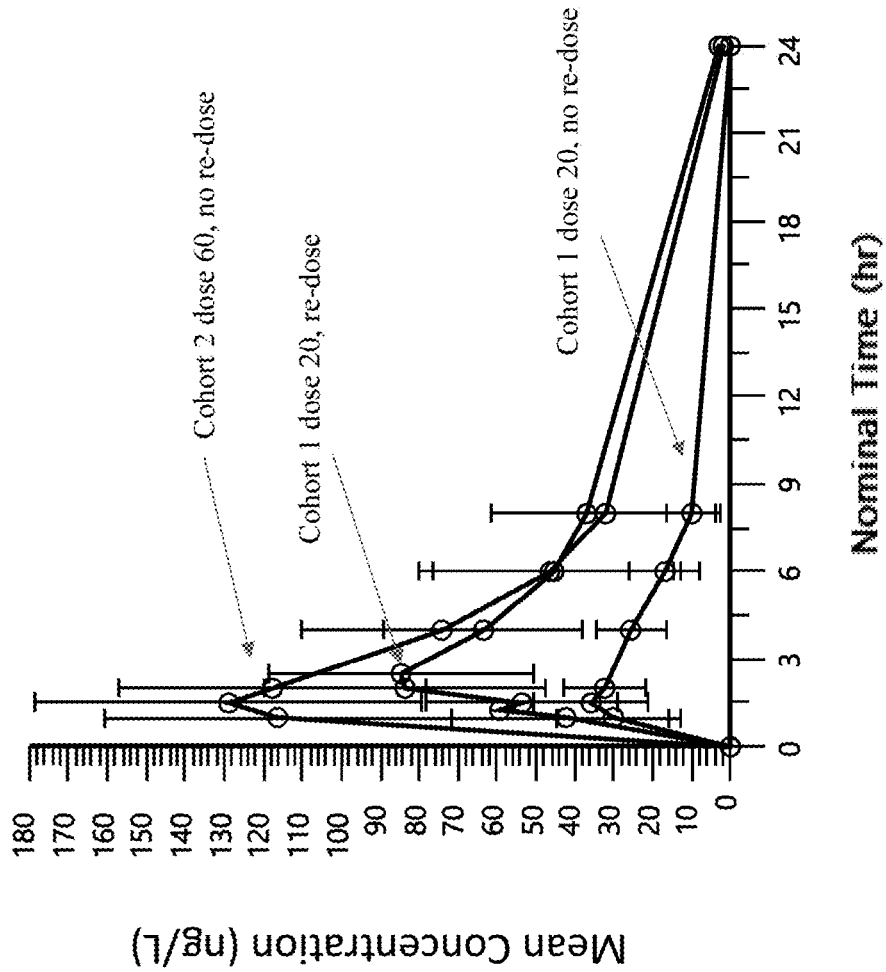
FIG. 17. Mean (±SD) Dexmedetomidine Plasma Concentration-Time, sorted by Dose Level (Linear Scale)

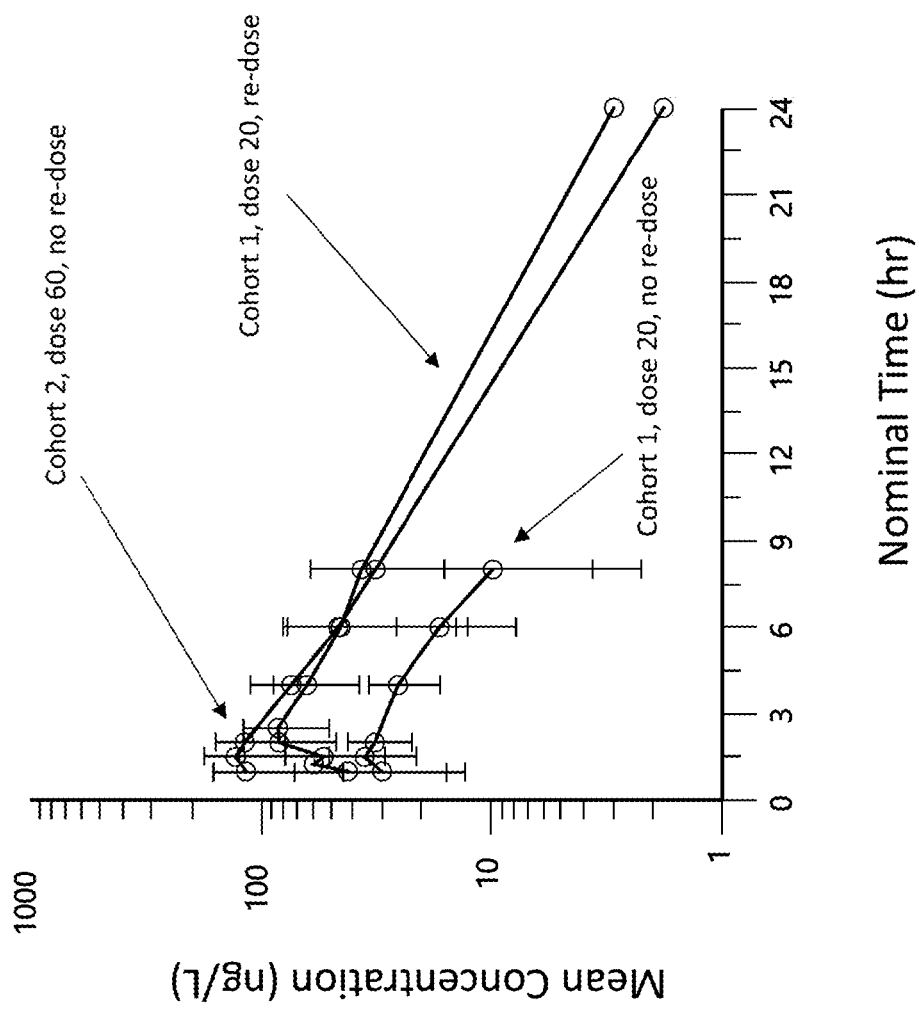
FIG. 18. Mean (±SD) Dexmedetomidine Plasma Concentration-Time, sorted by Dose Level (Semi-log Scale)

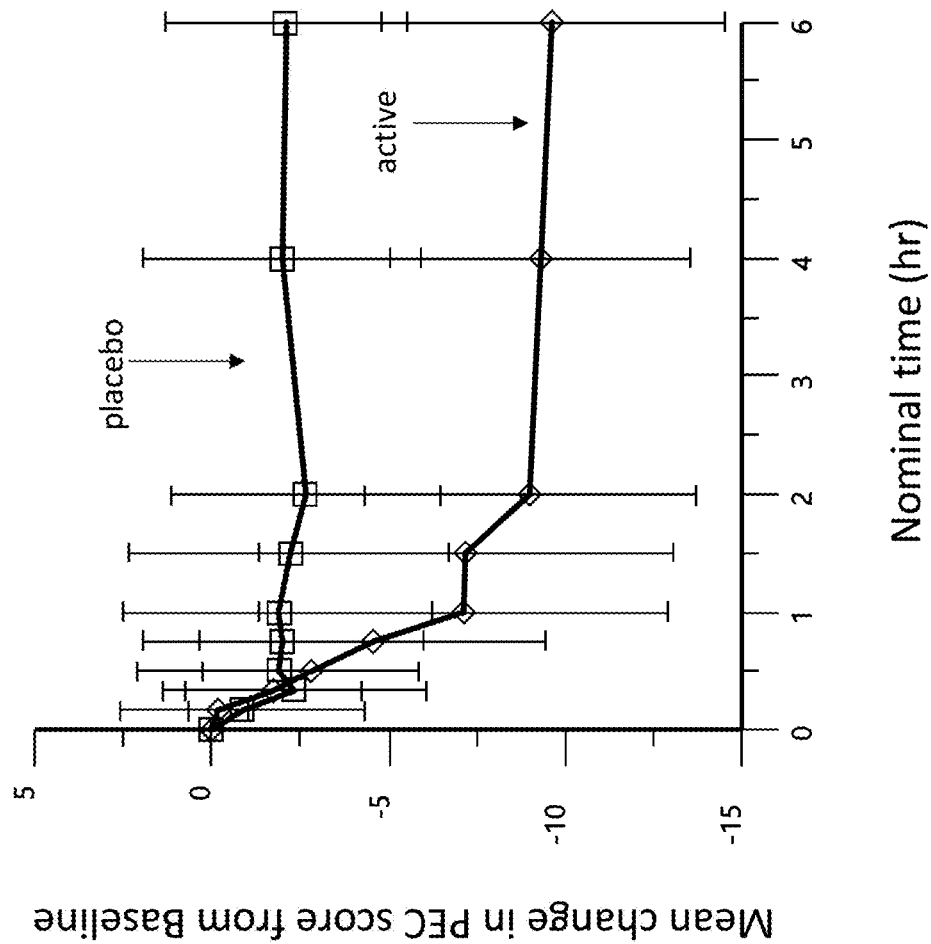
FIG 19: Mean (± SD) Change in PEC Score from Baseline (Cohort 3, dose 120, no redose)

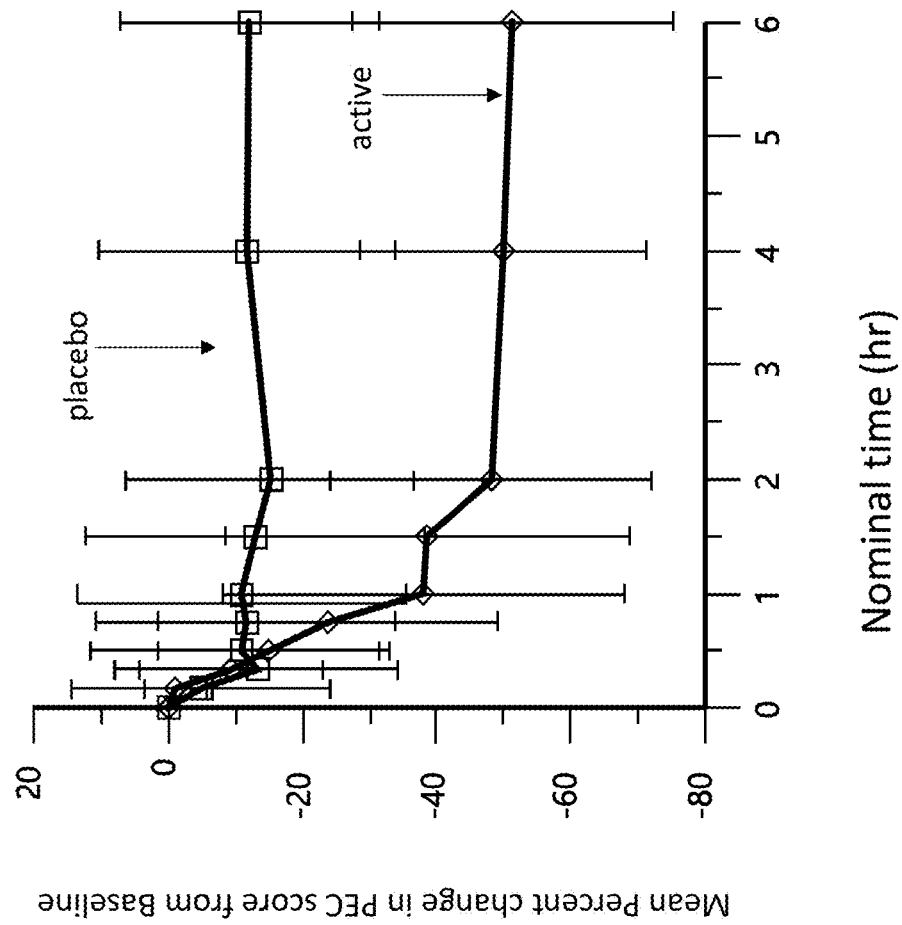
FIG 20: Mean (± SD) Percent Change in PEC Score from Baseline, (Cohort 3, dose 120, no redose)

FILM FORMULATIONS CONTAINING DEXMEDETOMIDINE AND METHODS OF PRODUCING THEM

CROSS-REFERENCE TO RELATED APPLICATIONS

This application is a continuation of U.S. patent application Ser. No. 16/453,679, filed Jun. 26, 2019, now U.S. Pat. No. 10,792,246 and claims the benefit of priority to U.S. Provisional Application Nos. 62/690,407, filed Jun. 27, 2018; 62/693,726, filed Jul. 3, 2018; 62/767,422, filed Nov. 14, 2018; 62/787,649, filed Jan. 2, 2019; 62/798,842, filed Jan. 30, 2019; and 62/849,747, filed May 17, 2019; each of which is herein incorporated by reference in its entirety for all purposes.

FIELD OF THE INVENTION

Disclosed herein is a self-supporting, dissolvable, film containing dexmedetomidine or a pharmaceutically acceptable salt thereof. The film is administered orally to treat various conditions, particularly agitation, by transmucosal delivery of the active agent. The film is formulated to produce a rapid onset of action without the significant sedation normally associated with the administration of dexmedetomidine.

BACKGROUND OF THE INVENTION

On Dec. 17, 1999, the U.S. Food and Drug Administration approved a dexmedetomidine product, PRECEDEX®, formulated as an intravenous solution for continuous infusion, and indicated as a sedative agent for initially intubated and mechanically ventilated patients during treatment in an intensive care setting. PRECEDEX® was later approved as a sedative agent for non-intubated patients prior to and/or during surgical and other procedures.

In addition to its use as a sedative, dexmedetomidine also has analgesic and anti-agitation properties. However, to date, it has not been possible to develop a formulation comprising dexmedetomidine for use as an anti-agitation agent. For example, PRECEDEX® is not a suitable anti-agitation agent for the following reasons: it can presently only be administered in an enrolled healthcare facility to patients; the ability to titrate the dose to suit individual patient requirements is challenging; self-administration is generally impractical since PRECEDEX® is administered as an injection; and its significant sedative properties can be undesirable in many settings to treat agitated subjects.

A continuing, unmet need exists for non-addictive anti-agitation medicines. A dexmedetomidine-based medicine that could be self-administered, e.g. orally, to produce rapid relief from agitation without significant sedation would be highly valuable addition to agitation treatment options. However, administering dexmedetomidine orally to provide fast relief from agitation is challenging. For example, sublingual tablets have a tendency to be swallowed before complete dissolution and trans-mucosal delivery, leading to wastage of active substance due to hepatic first pass metabolism. As a result, sublingual tablets may not achieve therapeutic levels of dexmedetomidine in the blood plasma. Oral sprays, especially for sublingual delivery, also have deficiencies, such as dose inaccuracy, swallowing of drug, the need for frequent dosing, patient non-compliance, and cost of goods. In addition, significant cardiovascular side-effects have been shown to occur in human subjects treated with dexmedetomidine hydrochloride when administered as a sublingual spray (see International Patent Application Publication No. WO 2010/132882). WO 2010/132882 teaches than, when dexmedetomidine hydrochloride was administered sublingually or administered by IV, a significant number of subjects experienced hypotension post-administration together with an undesirably high level of sedation. Hypotension was observed at a sublingual dose of 100 micrograms dexmedetomidine and, to a lesser extent, at 50 micrograms. These, and other, limitations taught by existing dexmedetomidine formulations have disincentivized the development of an oral dexmedetomidine formulation to treat agitation. However, the inventors of this application have now surprisingly discovered a new oral film formulation which can be administered to treat agitation without the aforementioned limitations.

SUMMARY OF THE INVENTION

The disclosure provides a self-supporting, dissolvable, film comprising dexmedetomidine or a pharmaceutically acceptable salt thereof, one or more water-soluble polymers, and, optionally, one or more pharmaceutically acceptable carriers. The film is formulated to release dexmedetomidine rapidly, enabling dexmedetomidine to be absorbed transmucosally to provide effective anti-agitation relief for patients within minutes, without concomitant significant sedation.

In one embodiment, the disclosure provides a pharmaceutical film composition suitable for sublingual administration, comprising, or consisting essentially of, a therapeutically effective amount of dexmedetomidine or a pharmaceutically acceptable salt thereof, a polymer component consisting of one or more water-soluble polymers; and, optionally, one or more pharmaceutically acceptable carriers.

In one embodiment, the disclosure provides film formulations comprising a polymer-based film substrate (e.g. a drug-free polymer matrix film) containing on the surface of the substrate dexmedetomidine or a pharmaceutically acceptable salt thereof. Dexmedetomidine or a pharmaceutically acceptable salt thereof may be conveniently applied to the surface of the film substrate as part of a composition also comprising a liquid carrier, and optionally a polymer component and/or one or more additional pharmaceutically acceptable carriers (hereinafter referred to as the "dexmedetomidine composition").

The dexmedetomidine composition may, in one aspect of this disclosure, be applied to the film substrate as a single droplet or multiple droplets at one or more specific substrate locations, or alternatively through discrete deposition (e.g. micro-deposition) of the dexmedetomidine composition at isolated locations on a common placebo film.

In another aspect, the disclosure provides film formulations comprising a polymer-based film substrate (e.g. a drug-free polymer matrix film) onto the surface of which is stenciled the dexmedetomidine composition at one or more discrete locations.

In another aspect, the dexmedetomidine composition may be present on the surface of the film substrate, after drying, as one or more discrete lines. The line(s) may be applied using either a direct deposition or stenciling method.

In some embodiments, the substrate is formed as a continuous web of film, which may be cut into smaller individual films following deposition of the individual units of the dexmedetomidine composition and drying.

One advantage of such films is the ability to deposit a high concentration of dexmedetomidine onto the surface of the "placebo" substrate for rapid trans-mucosal delivery of dexmedetomidine. Another advantage is that the use of individually formed doses limits variation of the active ingredient between dosage units. Particularly in the case when the surface of the film substrate is stenciled with the dexmedetomidine composition, advantages include the ability to deliver readily an appropriate thickness of dexmedetomidine composition onto the surface of the film. Still another advantage of the deposition method includes the ability to incorporate a combination of dexmedetomidine or a pharmaceutically acceptable salt thereof and one or more additional actives into a single unit dose, even if the active ingredients would otherwise be incompatible with one another, through discrete deposition of those active ingredients at separate locations on the substrate. Yet another advantage is the avoidance of yield losses associated with conventional dissolvable film production processes. Because the formulations used to create the film generally contain relatively expensive pharmaceuticals, these yield losses represent a significant cost.

In a further embodiment, the disclosure provides film formulations comprising dexmedetomidine or a pharmaceutically acceptable salt thereof disposed within a polymer matrix, e.g. wherein dexmedetomidine or a pharmaceutically acceptable salt thereof is substantially uniformally distributed throughout the film.

The disclosure also provides processes for preparing films of the present disclosure. In one process, a film is produced in which dexmedetomidine or a pharmaceutically acceptable salt thereof is disposed (e.g. substantially uniformally distributed) within a polymer-based film. In another process, a film is produced in which dexmedetomidine or a pharmaceutically acceptable salt thereof is present on the surface of a polymer-based film substrate.

Also disclosed herein, as embodiments of the disclosure, are solutions or suspensions containing dexmedetomidine or a pharmaceutically acceptable salt thereof suitable for depositing onto the surface of the polymer-based film substrate (i.e. the "dexmedetomidine compositions").

The disclosure also provides methods of treating agitation in a human by administering the films disclosed herein. Various conditions requiring anti-agitation therapy may be treated by sublingual administration of a film disclosed herein, including agitation associated with neurodegenerative and neuropsychiatric diseases, particularly in non-institutionalized patients. The treatment provides effective non-coercive anti-agitation therapy with adequate safety profile, and favorable tolerability, thus mitigating the risk of high blood pressure/respiratory depression.

The administration of a film composition of the present disclosure to a patient suffering from agitation substantially reduces the risk of violence and injury to the patient and others by preventing the condition from worsening and/or limiting the duration and severity of the agitation outburst. The film compositions of the present disclosure are especially useful in managing acute agitation events. They can also be safely administered either in a clinical facility or outside of a clinical facility.

These and other features, advantages and objects of the various embodiments will be better understood with reference to the following description of the invention.

BRIEF DESCRIPTION OF THE DRAWINGS

FIG. 1: shows a cross-sectional (side) view and area (top) view of an exemplary monolithic drug-containing matrix film disclosed herein.

FIG. 2: shows a cross-sectional (side) view and area (top) view of an exemplary micro-deposited matrix film disclosed herein.

FIG. 3 compares the diffusion of dexmedetomidine film formulations disclosed herein (represented by Formulations 1 to 7 and Formulation 11 of Example 1 hereinafter) through an oral cell culture membrane versus the diffusion of PRECEDEX®.

FIG. 4 shows the mean dexmedetomidine plasma log concentration vs. time for dose levels 10, 20 and 40 mcg of dexmedetomdine sublingual film (Semi-log scale). Error bars represent 1 standard deviation.

FIG. 5A: depicts individual dexmedetomidine concentration-time profiles for all subjects by dose after administration of dexmedetomidine sublingual film (10 mcg) Semi-log Scale. Dexmedetomidine sublingual film is exemplified in Example 1, Formulation 12.

FIG. 5B: depicts individual dexmedetomidine concentration-time profiles for all subjects by dose after administration of dexmedetomidine sublingual film (20 mcg) Semi-log Scale. Dexmedetomidine sublingual film is exemplified in Example 1, Formulation 12.

FIG. 5C: depicts individual dexmedetomidine concentration-time profiles for all subjects by dose after administration of dexmedetomidine sublingual film (40 mcg) Semi-log Scale. Dexmedetomidine sublingual film is exemplified in Example 1, Formulation 12.

FIG. 6: depicts mean VAS/S score vs. Nominal Time after administration of dexmedetomidine sublingual film (10, 20, 40 mcg) and Placebo. Dexmedetomidine sublingual film is exemplified in Example 1, Formulation 12.

FIG. 7: depicts standing Systolic BP vs Nominal Time after administration of dexmedetomidine sublingual film (10, 20, 40 mcg) and Placebo. Dexmedetomidine sublingual film is exemplified in Example 1, Formulation 12.

FIG. 8: depicts supine Systolic BP. vs Nominal Time after administration of dexmedetomidine sublingual film 10 mcg, 20 mcg and 40 mcg and Placebo. Dexmedetomidine sublingual film is exemplified in Example 1, Formulation 12.

FIG. 9: depicts standing Diastolic BP vs Nominal Time after administration of dexmedetomidine sublingual film 10 mcg, 20 mcg and 40 mcg and Placebo. Dexmedetomidine sublingual film is exemplified in Example 1, Formulation 12.

FIG. 10: depicts supine Diastolic BP vs Nominal Time after administration of dexmedetomidine sublingual film 10 mcg, 20 mcg and 40 mcg and Placebo. Dexmedetomidine sublingual film is exemplified in Example 1, Formulation 12.

FIG. 11: depicts pulse Rate vs Nominal Time after administration of dexmedetomidine sublingual film 10 mcg, 20 mcg and 40 mcg and Placebo. Dexmedetomidine sublingual film is exemplified in Example 1, Formulation 12.

FIG. 12: depicts the percentage of schizophrenic patients achieving RASS −1 in the treatment arm (IV dexmedetomidine hydrochloride treated group) versus placebo group.

FIG. 13: depicts the reduction in PEC score with time in schizophrenic patients in the treatment arm (IV dexmedetomidine hydrochloride treated group) versus placebo group.

FIG. 14: depicts the maximum doses of IV dexmedetomidine hydrochloride received by schizophrenic patients for the treatment of agitation.

FIG. 15: depicts the total intravenous dose of dexmedetomidine hydrochloride received by schizophrenic patients for the treatment of agitation.

FIG. 16: depicts the mean Plasma concentration (pg/ml) vs actual time in schizophrenic patients treated with dexmedetomidine hydrochloride.

FIG. 17: depicts the mean (±SD) dexmedetomidine plasma concentration-time, sorted by dose level (Linear Scale)

FIG. 18: depicts the mean (±SD) dexmedetomidine plasma concentration-time, sorted by dose level (Semi-log Scale)

FIG. 19: depicts the mean (±SD) change in PEC Score from baseline in schizophrenic patients treated with dexmedetomidine hydrochloride (120 mcg) versus pooled placebo group FIG. 20: depicts the mean (±SD) percent change in PEC Score from baseline in schizophrenic patients treated with dexmedetomidine hydrochloride (120 mcg) versus pooled placebo group

DETAILED DESCRIPTION

Abbreviations

AD: Alzheimer disease;
AUC: Area under the curve;
$AUC_{last}$: area under the curve, calculated to the last observable time point;
$C_{max}$: maximum plasma concentration;
CT: Computed tomography;
DPBS: Dulbeccos phosphate-buffered saline;
DLB: Dementia with Lewy bodies;
FTD: Fronto temporal disease;
HPC: Hydroxypropyl cellulose;
IPD: In-patient Departments;
MW: Molecular weight;
$MRT_{last}$: Mean residence time, calculated to the last observable time point;
MRI: Magnetic resonance imaging;
mm: Millimeter;
OPD: Out-Patient Department;
PANSS: Positive and Negative Syndrome Scale
PEC: PANSS Excitement Component
PEO: Polyethylene oxide;
PD: Parkinson disease;
PTSD: Post-traumatic stress disorder
RASS: Richmond Agitation Sedation Scale
TEER: Transepitheleal electrical resistance;
$T_{max}$: Time of maximum plasma concentration
Wt %: Weight percentage

Definitions

It will be understood that the term "film" herein includes thin films, sheets and wafers, in any shape, including rectangular, square, or other desired shape. The film may be of any desired thickness and size, such that it can be conveniently placed sub-lingually in the patient. For example, the film may be a relatively thin film having a thickness of from about 20 micrometers to about 200 micrometers, or may be a somewhat thicker film having a thickness of from about 20 micrometers to about 1000 micrometers. In certain embodiments, the film may be even thicker, e.g., having a thickness greater than about 30 millimeters.

As used herein, the phrase "water-soluble polymer" refers to (i) a polymer that is at least partially soluble in water, and desirably fully or predominantly soluble in water, and/or (ii) a polymer that absorbs water. Polymers that absorb water are referred to herein as water-swellable polymers. Suitable polymers include polymers that are water-soluble at room temperature and other temperatures, such as temperatures exceeding room temperature. Moreover, suitable polymers include polymers that are water-soluble at pressures less than atmospheric pressure. Desirably, water-swellable polymers have at least a 20 percent by weight water uptake, e.g. a 25 or greater percent by weight water uptake. In one embodiment, film formulations comprise one or more water-soluble polymers that promote the dissolution of the film upon contact with oral mucosal fluids.

The terms "formulation" and "composition" are used interchangeably, except where otherwise clearly intended to have different meanings.

The term "pharmaceutically acceptable carrier" refers to a pharmacologically inert substance to be used as a carrier. As used herein, the phrase "carrier" and "excipients" are used interchangeably, except where otherwise clearly intended to have different meanings.

As used herein, the term "monolithic" in the context of a film composition, refers to a single layer polymer film as a "placebo" film matrix or a drug-containing film matrix. In some aspects, a monolithic film is used as a drug-free film matrix intermediate product in the preparation of a drug micro-deposited matrix film composition.

As used here, the term "dosage form" refers to a film composition in a portion that delivers a single dose, in a single administration, to a subject.

The term "self-supporting" means the films herein maintain structural integrity upon handling without the need for a backing layer. Some flexibility in the film is contemplated and may be desirable.

The term "dissolvable" means the films herein are readily disintegrated, e.g. at least within about 20 minutes, following administration to the oral mucosa. Disintegration is achieved by saliva and/or other aqueous materials on the mucosal surface.

The term "without significant sedation" and the like means that the patient experiences a level of sedation not greater than Level 3 on the Ramsay Sedation Scale. Level 3 means sedated, but responds to commands. In certain aspects, the dexmedetomidine may be dosed to achieve a Richmond Agitation Sedation Scale (RASS) of −1 ("light sedation").

As used herein, "about" means plus or minus 10% of the indicated numerical value.

As used herein, the phrase "disposed within a polymer matrix" means that dexmedetomidine or a pharmaceutically acceptable salt thereof is incorporated directly into the polymer solution prior to the formation of the solid polymer matrix film composition.

As used herein, the phrase "deposited on the surface of a polymer matrix" means that dexmedetomidine or a pharmaceutically acceptable salt thereof is formulated as liquid composition separate from the preparation of the solid polymer matrix, and deposited onto the solid polymer, e.g. as one or more micro-deposits, where it dries. The dried product is sometimes referred to herein as the "micro-deposited matrix film". The drug liquid formulation may be in any form, including as a solution, emulsion, suspension, or dispersion.

Film Compositions:

The present disclosure provides pharmaceutical film compositions comprising, or consisting essentially of, dexmedetomidine or a pharmaceutically acceptable salt thereof, as an active agent, a polymer component, and optionally one or more pharmaceutically acceptable carriers. The disclosed film compositions have desirably functional attributes for sublingual administration. In particular, the disintegration time of the film compositions is such that the oromucosal delivery of dexmedetomidine or a pharmaceutically acceptable salt thereof is effective to rapidly treat agitation in a subject. For example, the film compositions may conveniently disintegrate completely sublingually in about 15 seconds to about 180 seconds, for example, about 30 seconds to about 180 seconds, including about 120 seconds. Disintegration times in about this time-frame assist in optimal sub-lingual delivery of the drug and in optimal onset of drug effect.

Active Agent

Dexmedetomidine has the IUPAC name (+) 4-(S)-[1-(2, 3-dimethylphenyl)ethyl]-1H-imidazole. As the monohydrochloride salt, it is predominantly used as a medication for the sedation of patients during treatment in an intensive care setting or to sedate patients prior to and/or during surgical and other procedures. Such medication is currently sold under the registered trade name "PRECEDEX".

Pharmaceutically acceptable salts of dexmedetomidine that may be used in the film compositions disclosed herein include generally any suitable salt that has been or may be approved by the US FDA or other appropriate foreign or domestic agency for administration to a human. Non-limiting examples of suitable pharmaceutically acceptable salts include salts of inorganic acids such as hydrochloric, hydrobromic, nitric, carbonic, monohydrocarbonic, phosphoric, monohydrogen phosphoric, dihydrogen phosphoric, sulfuric, hydrogen sulfuric, and hydroiodic acid. Other examples include salts derived from non-toxic organic acids, including acetic, propionic, isobutyric, maleic, malonic, benzoic, succinic, suberic, fumaric, lactic, mandelic, phthalic, benzenesulfonic, p-toluenesulfonic, citric, tartaric, and methanesulfonic acids, or combinations of these acid salts. Exemplary salts include dexmedetomidine hydrochloride, dexmedetomidine hydrobromide, dexmedetomidine sulfate, dexmedetomidine sulfonate, dexmedetomidine phosphate, dexmedetomidine nitrate, dexmedetomidine formate, dexmedetomidine citrate, dexmedetomidine tartrate, dexmedetomidine malate, dexmedetomidine benzoate, dexmedetomidine salicylate, dexmedetomidine ascorbate or the like. In other embodiments, deuterated forms of dexmedetomidine or a pharmaceutically acceptable salt thereof may be included in the film composition.

Dexmedetomidine or a pharmaceutically acceptable salt thereof may conveniently comprise about 0.01% to about 50%, e.g. about 0.05% to about 30%, e.g. about 0.05% to about 20%, e.g. about 0.05% to about 3% weight/weight (w/w) based on the total weight of a film composition on a dry weight basis. However, it will be appreciated that, when the film composition is a micro-deposited matrix film, the w/w % of dexmedetomidine or a pharmaceutically acceptable salt may vary from the afore-mentioned percentages depending on the total dimensions (and therefore total weight) of each unit dose of film.

In one aspect, dexmedetomidine or a pharmaceutically acceptable salt thereof may be present at about 0.05 mcg to about 3 mcg for each 100 mcg of unit dose total weight of film composition.

The film formulations disclosed herein comprise dexmedetomidine or a pharmaceutically acceptable salt thereof either (i) disposed within a polymer matrix or (ii) deposited on the surface of a polymer matrix, e.g., on the surface of a "placebo" film.

Further, dexmedetomidine or a pharmaceutically acceptable salt thereof may be incorporated as part of a film composition in a taste-masked form. In this embodiment, particles of drug may be coated or granulated with a taste-masking agent, for example a polymer, oil, or wax.

Polymer Component

The polymer component consists of one or more water-soluble polymers. The polymer component is present in the film composition in a sufficient amount to ensure disintegration of the subsequently formed film matrix is achieved in the oral mucosa within a suitable timeframe, for example, allowing the film matrix to disintegrate completely sublingually in about 15 seconds to about 180 seconds, for example, about 30 seconds to about 180 seconds, including about 120 seconds. The present disclosure provides film compositions comprising at least one water-soluble polymer that yield films of sufficient film strength (i.e. self-supporting) and rapid disintegration profiles. In one aspect of the disclosure, the polymer component consists of a single water-soluble polymer. In another aspect, the polymer component consists of two or more water-soluble polymers, including two or more of the same water-soluble polymers having different molecular weights.

When present in one or more droplets of the dexmedetomidine composition which is deposited onto the surface of the polymer substrate, the polymer component may, for example, consist of the water-soluble polymer hydroxypropyl cellulose, although different water-soluble polymers are also contemplated as described hereinafter under the definition "first water-soluble polymer" and "second water soluble polymer". For example, the polymer component may consist of one, two or three hydroxypropyl celluloses having different molecular weights. The molecular weights of the different hydroxypropyl celluloses may conveniently range from (i) less than about 60,000 daltons (e.g. about 5,000 daltons to about 49,000 daltons) (ii) about 90,000 daltons to about 200,000 daltons and (iii) about 200,000 daltons to about 500,000 daltons. The two or more hydroxypropyl celluloses may be mixed in any suitable ratio to achieve the desired droplet viscosity. The viscosity of the dexmedetomidine composition solution or suspension can be measured using a Brookfield viscometer with a small sample adapter at a temperature of 25° C. and may range from about 5 cps to about 3700 cps. For example, it may range from about 5 cps to about 500 cps, about 6 cps to about 200 cps, about 6 cps to about 100 cps or about 6 cps to about 50 cps. In one aspect of the present disclosure, the viscosity of the dexmedetomidine composition solution or suspension is from about 6 cps to about 20 cps at 25° C. and a shear rate of about 7 (1/s).

When present in a monolithic (i.e. placebo or drug-containing) film, the polymer component may, for example, consist of one water soluble polymer or two different water-soluble polymers. When two different water-soluble polymers are present, one of the water-soluble polymers may include the same polymer but present in the polymer component as a combination of different molecular weights. For example, the polymer component may consist of one, two or three hydroxypropyl celluloses having different molecular weights, although different water-soluble polymers are also contemplated as described hereinafter under the definition "first water-soluble polymer" and "second water soluble polymer" such as polyethylene oxide. The molecular weights of the different hydroxypropyl celluloses may conveniently range from (i) about 5000 daltons to about 49000 daltons (ii) about 90000 daltons to about 200000 daltons and (iii) about 200,000 daltons to about 500,000 daltons (e.g. about 300000 daltons to about 450000 daltons). The two or more hydroxypropyl celluloses (e.g. low and high molecular weight hydroxypropyl celluloses) may be mixed in any suitable ratio to achieve the desired film properties.

When present in a monolithic (i.e. placebo or drug-containing) film or micro-deposited film matrix composition, the polymer component may conveniently consist of one or more water-soluble polymers having a molecular weight less than about 60,000 daltons (e.g. about 5,000 daltons to about 49,000 daltons), and/or from about 90000 daltons to about 200,000 daltons and/or about 200,000 daltons to about 500,000 daltons (e.g. about 300000 daltons to about 450000 daltons). When a structurally different water-soluble polymer is also present, it may conveniently have a higher molecular weight, for example a molecular weight greater than about 500,000 daltons.

In a related aspect, the disclosure provides pharmaceutical film compositions, comprising: (i) dexmedetomidine or a pharmaceutically acceptable salt thereof; (ii) a polymer component consisting of a first water-soluble polymer having a molecular weight less than about 60,000 daltons (e.g. about 5,000 daltons to about 49,000 daltons), and one or more second-water soluble polymers having a molecular weight greater than about 60,000 daltons; and, optionally, (iii) one or more pharmaceutically acceptable carriers.

In another related aspect, the disclosure provides pharmaceutical film compositions consisting essentially of: (i) dexmedetomidine or a pharmaceutically acceptable salt thereof, (ii) a polymer component consisting of a first water-soluble polymer having a molecular weight less than about 60,000 daltons (e.g. about 5,000 daltons to about 49,000 daltons), and one or more second-water soluble polymers having a molecular weight greater than about 60,000 daltons; and, optionally, (iii) one or more pharmaceutically acceptable carriers.

In yet another aspect, the disclosure provides pharmaceutical film compositions consisting of: (i) dexmedetomidine or a pharmaceutically acceptable salt thereof; (ii) a polymer component consisting of a first water-soluble polymer having a molecular weight less than about 60,000 daltons (e.g. about 5,000 daltons to about 49,000 daltons), and one or more second water-soluble polymers having a molecular weight greater than about 60,000 daltons; and, optionally, (iii) one or more pharmaceutically acceptable carriers.

Examples of one or more first water-soluble polymers are selected from the group consisting of hydroxypropyl cellulose (HPC), hydroxyethyl cellulose, hydroxypropyl methylcellulose (HPMC), carboxymethyl cellulose, methyl cellulose and mixtures thereof, including mixtures of the same polymer having different molecular weights.

Examples of one or more second water-soluble polymers are selected from the group consisting of hydroxypropyl cellulose, hydroxypropyl methylcellulose, hydroxyethyl cellulose, carboxy methylcellulose, methylcellulose and mixtures thereof, including mixtures of the same polymer having different molecular weights. Polyethylene oxide (PEO) may also be present herein as a second water-soluble polymer or may be described separately hereinafter in the pharmaceutical film compositions as an example of a pharmaceutically acceptable carrier, or more particularly, as a mucoadhesive agent.

In one embodiment, the weight ratio of said first water-soluble polymer to said second water-soluble polymer(s) (including PEO when present in the film) in the entire film composition is from about 2:1 to about 1:50, for example about 1:1 to about 1:40, including about 1:1, 1:2, 1:3, 1:5, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40.

In a further embodiment, the weight ratio of said first water-soluble polymer to said second water-soluble polymer (s) (including PEO when present in the film) in the entire film composition is from about 1:10 to about 1:30, about 1:15 to about 1:25 or about 1:15 to about 1:20. In certain aspects, a ratio of about 1:15 to about 1:20 provides beneficial functional effects.

Examples of other water-soluble polymers which may be included in the film with the first water-soluble polymer/second water-soluble polymer or replace such polymer(s) include povidone (polyvinylpyrrolidone), copovidone (co-polymers of N-vinyl-2-pyrrolidone and vinyl acetate), polyvinyl alcohol, polyethylene glycol, polyacrylic acid, methylmethacrylate copolymer, carboxyvinyl copolymers, polydextrose, pullulan, carboxymethyl cellulose, sodium alginate, chitosan, xanthan gum, tragancanth gum, guar gum, acacia gum, arabic gum, starch, carrageenan, gelatin and mixtures thereof.

The water-soluble polymer component, including water-soluble polymer carriers when present, may conveniently comprise about 40% to about 99.8%, about 50% to about 99.7%, about 60% to about 99.6% of the film composition, based on the weight of the film on a dry weight basis.

In one aspect, the polymer component for the film composition comprises a first water-soluble polymer present in an amount of from about 2% to about 15% on a dry weight basis of the polymer component (e.g. at about 3% to about 8% w/w of the total film weight). This water-soluble polymer may conveniently have a molecular weight from about 5,000 daltons to about 49,000 daltons. Examples of suitable such water-soluble polymers include those selected from the group consisting of hydroxypropyl cellulose, hydroxyethyl cellulose, hydroxypropyl methylcellulose, carboxymethyl cellulose, methyl cellulose, and mixtures thereof.

In a further aspect, low molecular weight hydroxypropyl cellulose may be present in the film at about 3% to about 8% w/w of the total film weight.

In a further aspect, the one or more second water-soluble polymers (including water-soluble polymer carriers such as polyethylene oxide) may, for example, be present in an amount of from about 50 to about 98 weight percent on dry weight basis of the polymer component. The one or more second water-soluble polymers each has a molecular weight greater than 60,000 daltons; for example, from about 90,000 daltons to about 1,500,000 daltons, especially when the polymer is selected from the group consisting of polyethylene oxide, hydroxypropyl cellulose, hydroxypropyl methylcellulose, hydroxyethyl cellulose, carboxy methylcellulose, methylcellulose, and mixtures thereof.

In one aspect, the one or more second water-soluble polymers may together be present in the film at about 25% to about 40% w/w of the total film weight when the one or more second water-soluble polymers each has a molecular weight from about 90,000 daltons to about 200,000 daltons and/or from about 200,000 daltons to about 500,000 daltons, and the polymer is selected from the group consisting of hydroxypropyl cellulose, hydroxypropyl methylcellulose, hydroxyethyl cellulose, carboxy methylcellulose, methylcellulose, and mixtures thereof.

In another aspect, a polyethylene oxide may be present in the film at about 50% to about 60% w/w of the total film weight.

In one embodiment, the polymer component for the film composition consists of a low molecular weight, water-soluble polymer (e.g., having a molecular weight less than about 60,000 daltons) and one or more high molecular weight polymers (e.g., having a molecular weight greater about 60,000, up to about 1,500,000 daltons when a polyethylene oxide is included in the polymer mixture or up to about 500,000 daltons when a polyethylene oxide is not included in the polymer mixture). This polymer combination, especially when the polymers are a combination of hydroxypropyl cellulose and polyethylene oxide, lends certain advantages to the tensile strength and pharmacokinetics of the film composition.

In one aspect, the present disclosure provides a thin film composition comprising, e.g. consisting essentially of:
(i) a therapeutically effective amount of dexmedetomidine or a pharmaceutically acceptable salt thereof,
(ii) a polymer component consisting of one or more water-soluble polymers: and
(iii) one or more pharmaceutically acceptable carriers.

In one embodiment, the present disclosure provides a thin film composition comprising, e.g. consisting essentially of:
(i) a therapeutically effective amount of dexmedetomidine or a pharmaceutically acceptable salt thereof,
(ii) a polymer component consisting of: (a) one or more first water-soluble polymer (e.g. hydroxypropyl cellulose, hydroxypropyl methylcellulose, hydroxyethyl cellulose, carboxy methylcellulose, methylcellulose, and mixtures thereof) having a molecular weight from about 5,000 daltons to about 49,000 daltons, for example, in about 2 to about 15 weight percent on dry weight basis of the total polymer component; and (b) one or more second water-soluble polymers (e.g. polyethylene oxide, hydroxypropyl cellulose, hydroxypropyl methylcellulose, hydroxyethyl cellulose, carboxy methylcellulose, methylcellulose, and mixtures thereof) having a molecular weight greater than 60,000 daltons, such as greater than 100000 daltons, for example in about 50 to about 98 weight percent on dry weight basis of the total polymer component; and
(iii) one or more pharmaceutically acceptable carriers.

The molecular weight of hydroxypropyl cellulose, when present in the film of the present disclosure, may be varied, and may be present as both a low molecular weight, water-soluble polymer and as one or more high molecular weight, water-soluble polymers. In some embodiments, the molecular weight may be less than about 60,000 daltons (e.g. about 5,000 daltons to about 49,000 daltons). In other embodiments the molecular weight may be in the range from about 90,000 daltons to about 200,000 daltons. In yet other embodiments, the molecular weight may be in the range from about 200,000 daltons to about 500,000 daltons.

Hydroxypropyl cellulose, when part of the film composition including polyethylene oxide, may conveniently be present in the range from about 10% to about 90% by weight on a dry weight basis of the polymer component, e.g. about 20% to about 80% by weight on dry weight basis of the polymer component, e.g. about 20% to about 50% by weight on dry weight basis of the polymer component, e.g. about 25% to about 45% by weight on dry weight basis of the polymer component.

The molecular weight of polyethylene oxide, when present in the film of the present disclosure, may also be varied. In some embodiments, a water-soluble, high molecular weight polyethylene oxide may be used, for example, to increase muco-adhesivity of the film. In certain embodiments, the molecular weight may range from about 100,000 daltons to about 1,500,000 daltons, including about 100,000, 200,000, 300,000, 600,000, 900,000 or 1,000,000 daltons. In some embodiments, it may be desirable to use a combination of polyethylene oxide having a molecular weight of about 600,000 daltons to about 900,000 daltons with polyethylene oxide having a molecular weight of about 100,000 daltons to about 300,000 daltons in the polymer component.

Polyethylene oxide, when part of the film composition, may conveniently be present range from about 30% to about 90% by weight on a dry weight basis of the total polymer component, e.g. about 40% to about 85% by weight on a dry weight basis of the polymer component, e.g. about 55% to about 80% by weight on a dry weight basis of the polymer component.

Such film compositions may contain the drug dispersed within the film, or micro-deposited onto a surface of the film. When micro-deposited on the surface of a "placebo" film, the drug may conveniently be added as part of a dexmedetomidine composition as one or more droplets in a liquid carrier, such as a solvent (e.g. an alcohol such as ethanol), optionally together with one or more (e.g. two) water-soluble polymers and/or pharmaceutically acceptable carriers. Suitable water-soluble polymers include (1) a low molecular weight, water-soluble polymer, for example a low molecular weight, water-soluble polymer having a molecular weight of less than about 60,000 daltons (e.g. a molecular weight of about 5,000 daltons to about 49,000 daltons and optionally (2) one or more (e.g. one or two) high molecular weight, water-soluble polymers, for example a high molecular weight, water-soluble polymer having a molecular weight of greater than about 60,000 daltons (e.g. a molecular weight of from about 60,000 daltons to about 150,000 daltons such as hydroxypropyl cellulose (77,000 MW), hydroxypropyl cellulose (80,000 MW), hydroxypropyl cellulose (90,000 MW), or hydroxypropyl cellulose (140,000 MW)) and/or a high molecular weight, water-soluble polymer having a molecular weight of greater than about 60,000 daltons (e.g. a molecular weight of from about 200,000 daltons to about 900,000 daltons such as hydroxypropyl cellulose (340,000 MW), hydroxypropyl cellulose (370,000 MW), polyethylene oxide (200,000 MW) or polyethylene oxide (600,000 MW)). Each water-soluble polymer may independently be selected from the group consisting of hydroxypropyl cellulose, hydroxypropyl methylcellulose, hydroxyethyl cellulose, carboxymethyl cellulose, polyethylene oxide and methyl cellulose, e.g. hydroxypropyl cellulose and/or polyethylene oxide.

In one aspect, the dexmedetomidine composition comprises dexmedetomidine hydrochloride, a low molecular weight polymer which is hydroxypropyl cellulose and one or two high molecular weight polymers which are each hydroxypropyl cellulose in an ethanol solvent.

In one aspect, the dexmedetomidine composition comprises hydroxypropyl cellulose (40,000 MW) and one or both of hydroxypropyl cellulose (140,000 MW) and hydroxypropyl cellulose (370,000 MW).

In one aspect, the dexmedetomidine composition comprises only two hydroxypropyl celluloses, namely hydroxypropyl cellulose (40,000 MW) and hydroxypropyl cellulose (140,000 MW).

In other aspects, the dexmedetomidine composition may be added as one or more droplets in an ethanol-based solution, optionally containing a pH-neutralizing agent such as sodium hydroxide.

The viscosity of deposition solution/suspension may range from about 6 cps to about 3700 cps as measured at 25° C. using a Brookfield viscometer with a small sample adapter. As an example, it may range from about 5 cps to about 500 cps, about 6 cps to about 200 cps, about 6 cps to about 100 cps or about 6 cps to about 50 cps. In one aspect of the present disclosure, the viscosity of the dexmedetomidine composition is from about 6 cps to about 20 cps at 25° C. and a shear rate of about 7 (1/s). The deposition composition may be in any form, including as a solution, emulsion, suspension or dispersion.

Following drying to remove the solvent, the film comprises a film substrate (e.g. a placebo) with the dexmedetomidine composition as previously described but absent solvent deposited (e.g. micro-deposited) on the surface of the film substrate. The dried composition may cover the whole of the film substrate surface or only part of the film substrate surface. In one aspect, the composition appears as one or more discrete drug-containing droplets on the film substrate surface. Alternatively, stenciling may be used to achieve a one or more defined and discrete regions of drug-containing composition on the surface of the film substrate.

In one aspect, the disclosure provides a dry film product comprising a film substrate with one or more discrete drug-containing droplets on the film substrate surface, wherein each such drug-containing droplet comprises dexmedetomidine or a pharmaceutically acceptable salt thereof, and hydroxypropyl cellulose of two molecular weights: hydroxypropyl cellulose (40,000 MW) available as HPC-SSL, and hydroxypropyl cellulose (140,000 MW) marketed under the tradename of Klucel™ Type JF NF, and wherein the film substrate comprises hydroxypropyl cellulose of three molecular weights: hydroxypropyl cellulose (40,000 MW), hydroxypropyl cellulose (140,000 MW), and hydroxypropyl cellulose (370,000 MW) marketed under the tradename of Klucel™ Type GF NF. In one aspect, the film substrate also comprises polyethylene oxide (600,000 MW) available under the name of Sentry Polyox WSR 205 LEO NF.

In one aspect, the film comprises a deposition composition (also referred to herein as a "dexmedetomidine composition") comprising: (i) dexmedetomidine hydrochloride, present at about 9% to about 50% w/w of the deposition composition, e.g. about 15% to about 25% w/w of the deposition composition; (ii) hydroxypropyl cellulose (40,000 MW), present at about 5% to about 85% w/w of the deposition composition; (iii) hydroxypropyl cellulose (140,000 MW) present at about 5% to about 85% w/w of the deposition composition; and (iv) hydroxypropyl cellulose (370,000 MW) present at about 0% to about 65% w/w of the deposition composition. The film also comprises a polymer matrix, wherein the polymer matrix comprises: (i) hydroxypropyl cellulose (40,000 MW) present at about 3% to about 40% w/w of the polymer matrix; (ii) hydroxypropyl cellulose (140,000 MW) present at about 3% to about 40% w/w of the polymer matrix; (iii) hydroxypropyl cellulose (370,000 MW) present at about 0% to about 30% w/w of the polymer matrix, and (iv) polyethylene oxide (600,000 MW) present at about 55% to about 75% w/w of the polymer matrix.

The disclosure also provides a monolithic film formulation for sublingual administration. The film comprises a deposition composition comprising: (i) dexmedetomidine hydrochloride, present at about 1% to about 50% w/w of the total composition; (ii) hydroxypropyl cellulose (40,000 MW), present at about 2% to about 30% w/w of the total composition; (iii) hydroxypropyl cellulose (140,000 MW) present at about 2% to about 30% w/w of the total composition; (iv) hydroxypropyl cellulose (370,000 MW) present at about 10% to about 50% w/w of the total composition, (v) polyethylene oxide (600,000 MW) present at about 40% to about 75% w/w of the total composition and (vi) optionally other pharmaceutically acceptable carriers.

In certain aspects, the films disclosed herein combine several types of hydroxypropyl cellulose (HPC) to provide a film with advantageous properties. For example, the film composition may contain two or three of hydroxypropyl cellulose (40,000 MW), hydroxypropyl cellulose (140,000 MW) and hydroxypropyl cellulose (370,000 MW) in combination. In certain embodiments, polyethylene oxide (600,000 MW) is included with these types of HPC when part of a monolithic film.

In certain film compositions, a low molecular weight hydroxypropyl cellulose (e.g. 40,000 MW) is present at about 3% to about 8% (e.g. about 5%) w/w of the total film weight, a high molecular weight hydroxypropyl cellulose (e.g. 140,000 MW) is present at about 3% to about 8% (e.g. about 5%) w/w of the total film weight, a high molecular weight hydroxypropyl cellulose (e.g. 370,000 MW) is present at about 20% to about 40% w/w of the total film weight, and a polyethylene oxide (e.g. 600,000 MW) is present at about 40% to about 70%, (e.g. about 50% to about 60%) w/w of the total film weight. In one aspect, the two high molecular weight, water-soluble polymers are together present at about 25% to about 40% w/w of the total film weight.

The selection and ratio of water-soluble polymers can be made to effect complete dissolution of the film composition in oral mucosal fluids within seconds to minutes, e.g. in about 0.25 minutes to about 15 minutes, thus ensuring delivery of a therapeutically effective amount of dexmedetomidine or a pharmaceutically acceptable salt thereof via the oral mucosa. For example, the film compositions may reside in the sublingual region of the mouth up to about 15 minutes, up to about 10 minutes, or up to about 5 minutes, including for a period of from about 30 seconds to about 15 minutes, about 1 minute to about 10 minutes, or about 1 minute to about 5 minutes.

The standard basket or paddle apparatus described in any pharmacopoeia can be used for in vitro dissolution testing. The selection of dissolution medium will essentially depend as per the sink conditions and highest dose of drug. The temperature of dissolution medium should be maintained at 37±0.5° C. and rpm at 50 (see Bala et al., in Int J Pharm Investigation, vol. 3(2), pages 67-76).

Films disclosed herein have several functional advantages to promote rapid onset of drug effect. In certain aspects, thin films compositions of the disclosure have a disintegration time (DT) of about 15 seconds to about 180 seconds, about 15 seconds to about 160 seconds, about 25 seconds to about 150 seconds, about 15 seconds to about 140 seconds, about 15 seconds to about 120 seconds, about 40 seconds to about 120 seconds, about 50 seconds to about 120 seconds, for example about 120 seconds, when applied sublingually. A disintegration time in this time-frame provides optimal onset of drug effects.

In other certain aspects, thin film compositions of the invention have mucoadhesion properties that provide practical benefits of localizing the film to the sublingual location and reducing, or preventing, effective removal prior to dissolution. This quality is particularly advantageous in a clinical setting with an agitated subject. Thus, in certain aspects, thin film compositions have a mucoadhesion force (the mucoadhesion strength or shear strength) of about 50 g or above, about 100 g or above, about 200 g or above, about 300 g or above, about 400 g or above, about 500 g or above, about 600 g or above, about 700 g or above, about 800 g or above, about 900 g or above, about 1000 g or above. In certain aspects, the mucoadhesion force is in a range of about 300 g to about 4000 g, about 500 g to about 3000 g, or about 1000 g to about 2000 g.

Burst strength of the film also contributes to drug delivery. Certain thin film compositions of the invention have a burst strength at or above 50 g, 100 g, 200 g, 300 g, 400 g, 500 g, 600 g, 700 g, 800 g, 900 g, 1000 g, 1100 g, 1200 g, 1300 g, 1400 g, 1500 g, 1600 g, 1700 g, 1800 g, 1900 g, 2,000 g, 2,500 g, 3,000 g, 3500 g, 4,000 g, 4,500 g, 5,000 g, 5,500 g, 6,000 g, 6,500 g, 7,000 g, 7,500 g, 8,000 g, 8,500 g, 9,000 g, 9,500 g, 10,000 g or 15,000 g. For example, the burst strength may be in a range of about 200 g to about 15000 g, about 300 g to about 10,000 g, or 400 g to about 5000 g.

Pharmaceutically Acceptable Carriers

The film compositions may further comprise one or more pharmaceutically acceptable carriers that includes, but is not limited to, liquid carriers, flavours, sweeteners, refreshing agents, antioxidants, pH adjusting agents, permeation enhancers, mucoadhesive agents, plasticizers, bulking agents, surfactants/non-ionic solubilizers, stabilizers, antifoam agents, colors or the like. In certain embodiments, the film compositions are substantially free of acidic buffer or other acidic agents.

Liquid Carriers

According to one aspect, the pharmaceutically acceptable carrier includes a liquid carrier. The liquid carrier comprises one or more solvents useful in the preparation of the polymer matrix (drug containing or placebo) and deposition composition in the film composition. In some embodiments, the solvent may be water. In some embodiments, the solvent may a polar organic solvent including, but not limited to, ethanol, isopropanol, acetone, butanol, benzyl alcohol and mixtures thereof. In some embodiments, the solvent may be a non-polar organic solvent, such as methylene chloride, toluene, ethyl acetate and mixtures thereof. Certain solvents are alcohols, especially ethanol, water and mixtures thereof.

Desirably, the solvent content in the wet polymer matrix is at least about 30% by weight of the total wet weight of the total film composition prior to drying. The subsequent dried film composition will desirably contain less than about 10% by weight of solvent, more desirably less than about 8% by weight of solvent, even more desirably less than about 6% by weight of solvent and most desirably less than about 2% by weight of solvent.

Flavors/Sweeteners/Refreshing Agents

It may be beneficial to add a sweetener, flavoring agent, refreshing agent, taste-masking agent or a combination thereof to the film compositions to improve the film composition taste.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Certain flavors or flavoring agents include natural and artificial flavors. These flavorings may be chosen from synthetic flavor oils and flavoring aromatics, and/or oils, oleo resins and extracts derived from plants, leaves, flowers, fruits and so forth, and combinations thereof. Non-limiting flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit, and fruit essences including apple, pear, peach, strawberry, raspberry, cherry, plum, pineapple, apricot or the like. These flavorings can be used individually or in combination. Commonly used flavors include mints such as peppermint, artificial vanilla, cinnamon derivatives, and various fruit flavors, whether employed individually or in combination. Flavorings such as aldehydes and esters including cinnamylacetate, cinnamaldehyde, citral, diethylacetal, dihydrocarvyl acetate, eugenyl formate, p-methylanisole, or the like may also be used. Further examples of aldehyde flavorings include, but are not limited to acetaldehyde (apple); benzaldehyde (cherry, almond); cinnamaldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 12,6-dimethyl-5-heptenal, i.e. melonal (melon); 2 dimethyloctanal (greenfruit); and 2-dodecenal (citrus, mandarin); cherry; grape and mixtures thereof. In one embodiment, the flavor is a peppermint oil flavour available as peppermint oil, NF.

The amount of flavoring agent employed is normally a matter of preference, subject to such factors as flavor type, individual flavor, and strength desired. The amount may be varied in order to obtain the result desired in the final product. Such variations are within the capabilities of those skilled in the art without the need for undue experimentation. In general, amounts of about 0.1% to about 30 wt % may be used in the films to supply flavoring.

Suitable sweeteners include both natural and artificial sweeteners. Non-limiting examples of suitable sweeteners include, e.g.: water-soluble sweetening agents such as monosaccharides, disaccharides and polysaccharides such as xylose, ribose, glucose (dextrose), mannose, galactose, fructose (levulose), sucrose (sugar), high fructose corn syrup, maltose, invert sugar (a mixture of fructose and glucose derived from sucrose), partially hydrolyzed starch, corn syrup solids, and dihydrochalcones; water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin or the like; dipeptide based sweeteners, such as L-aspartic acid derived sweeteners, such as L-aspartyl-L-phenylalanine methyl ester (aspartame), L-alpha-aspartyl-N-(2,2,4,4-tetramethyl-3-thietanyl)-D-alaninamide hydrate, methyl esters of L-aspartyl-L-phenylglycerin and L-aspartyl-L-2,5, dihydrophenylglycine, L-aspartyl-2,5-dihydro-L-phenylalanine, L-aspartyl-L-(1-cyclohexyen)-alanine or the like; water-soluble sweeteners derived from naturally occurring water-soluble sweeteners, such as a chlorinated derivatives of ordinary sugar (sucrose), known, for example, as sucralose; and protein based sweeteners such as thaurnatoccous danielli (Thaurnatin I and II), naturally occurring high intensity sweeteners, such as Lo Han Kuo, *stevia*, steviosides, monellin, and glycyrrhizin. In one embodiment, the sweetener is sucralose.

Refreshing agents, also called cooling agents, are chemicals that trigger the cold sensitive receptors creating a cold sensation. Refreshing agents that can be added to the film compositions include menthol, thymol, camphor and eucalyptol. In one embodiment, the refreshing agent is menthol.

Flavoring agents, sweeteners and refreshing agents can be added in conventional quantities, generally up to a total amount of about 0.01% to about 10% of the weight of the film on a dry weight basis, e.g. from about 0.1% to about 7% of the weight of the film on a dry weight basis, e.g. about 0.1% to about 5% based on the weight of the film on a dry weight basis.

Other taste-masking agents include, for example polymers, oils, or waxes. In one embodiment, dexmedetomidine or a pharmaceutically acceptable salt thereof is coated with a taste-masking agent prior to formulation of the film compositions.

In some embodiments, if a taste-masking agent is used to coat the active ingredient, it may be present in an amount of from about 5% to about 80% by weight of the particle or granule containing the active ingredient. In another embodiment, the taste-masking agent is present in an amount from about 25% to about 35% by weight of the particle or granule containing the active ingredient. The precise loading of the active ingredient in the taste-mask coated particle or granule is a function of many parameters, including the specific form of the active ingredient used (i.e. free base or salt thereof), the coating, and any flavors present in the particle or granule or in the film-forming polymer matrix.

Dexmedetomidine or a pharmaceutically acceptable salt thereof may be taste-masked with the above-described taste-masking agents by a variety of techniques. Useful coating techniques include, but are not limited to, fluidized bed coating, spray congealing coating, agglomeration or granulation coating, entrapment coating, coacervation coating, infusion coating, spin coating, ion exchange coating or the like.

Antioxidants

The film compositions may advantageously employ an antioxidant or oxygen scavenger to prevent or reduce oxidative degradation of dexmedetomidine or a pharmaceutically acceptable salt thereof prior to use. Examples of oxygen scavengers or antioxidants that substantially improve long-term stability of the film composition against oxidative degradation include sulfite salts, such as sodium sulfite, sodium bisulfite, sodium metabisulfite and analogous salts of potassium and calcium.

A suitable amount of the sulfite salt (e.g., sodium sulfite) is up to about 5%, e.g. about 0.001% to about 2% based on the weight of the film composition on a dry weight basis.

pH-Adjusting Agents/pH-Neutralizing Agents

The absorption of dexmedetomidine or a pharmaceutical acceptable salt thereof through the oral mucosa may increase when in an alkaline microenvironment. As an example, this may be achieved when the film compositions are maintained at a pH of above 6, from about 6 to about 9, or about 6.5 to about 8. In some embodiments, the film may include an alkaline substance that increases the pH of the film product. Non-limiting examples of pH-adjusting/pH-neutralizing agents include bicarbonates (e.g., sodium bicarbonate), citrates (e.g., potassium citrate), carbonates (e.g., calcium carbonate), lactates (e.g., sodium lactate), acetates (e.g., calcium acetate), alkaline buffer (e.g. glycine), sodium hydroxide, sodium chloride or the like.

An alkaline buffer, such as glycine, is one example of a pH-neutralizing agent.

The pH-adjusting agents/pH-neutralizing agents can be added into the film composition of in amounts effective to stabilize the pH within the desired pH range. A suitable amount of pH-adjusting/pH-neutralizing agent present in the film composition includes, for example, up to about 10%, e.g. about 1% to about 5% based on the weight of the film composition on a dry weight basis.

Conversely, it has been shown (Table 24 in Example 2 hereinafter; comparative formulation 11) that the addition of an acidic buffer (for example lactate buffer) and/or acidic agent (for example, lactic acid) to the film composition has a detrimental effect on the permeability/diffusion of the active ingredient across the oral mucosa.

Permeation Enhancer Agents

To further promote absorption of dexmedetomidine or a pharmaceutical acceptable salt thereof through the oral mucosa and reduce the amount of dexmedetomidine that is introduced into the gastrointestinal tract, it may be advantageous to add a permeation enhancer agent (i.e. a penetration enhancer) to a film composition. Certain effective penetration enhancers that promote absorption of dexmedetomidine or a pharmaceutically acceptable salt thereof across the oral mucosa include alcohols. An alcohol penetration enhancer, such as butanol, can conveniently be added to the film composition in an amount of up to about 10%, e.g. about 0.1% to about 5%, e.g. about 1% to about 3% based on the weight of the film composition on a dry weight basis.

Mucoadhesive Agents

In order to promote adhesion of the film composition to the oral mucosa, it may be advantageous to add a mucoadhesive agent to a film formulation. Examples of mucoadhesive agents that can be added to the film composition include, but are not limited to, sodium alginate, sodium carboxymethyl cellulose, guar gum, polyethylene oxide, hydroxyethyl cellulose, hydroxypropyl cellulose, hydroxypropylmethyl cellulose, karya gum, methylcellulose, retene, tragacanth and the like. One mucoadhesive agent is polyethylene oxide, which may conveniently be added to the film composition in an amount of from about 20% to about 90%, e.g. about 40% to about 70% based on the total weight of the film composition on a dry weight basis. It will be understood that water-soluble mucoadhesive agents that are polymers, such as polyethylene oxide, are also within the definition of a second water-soluble polymer as previously described under the term "polymer component".

Plasticizers

Plasticizers can be advantageously employed in the film compositions, as needed, to suitably modify the flexibility of the film to facilitate processing and allow the film to easily conform to the shape of the part of the oral cavity to which the film is applied. Plasticizers that can be effectively employed herein include polyethylene glycol, propylene glycol, tributyl citrate, triethyl citrate and glycerol. Depending on the selected film-forming polymer(s) and other components of the film formulation, a suitable amount of plasticizer included in the film composition may typically be up to about 10%, e.g. about 0.1% to about 5%, e.g. about 0.5% to about 5% based on the weight of the film on a dry weight basis. For certain applications, higher molecular weight polyethylene glycols may be utilized, including polyethylene oxide.

Bulking Agents

Bulking agents (i.e. fillers) may be added as desired to increase the size of the finished film product to facilitate processing and manufacturing, or to modify properties (e.g., increase or decrease residence time or increase stiffness) of the film formulation. Suitable fillers that can be added to a film composition of include starch, calcium salts, such as calcium carbonate, and sugars, such as lactose, glucose, sucrose, mannose, sorbitol, mannitol, galactitol, sucralose, trehalose and combinations thereof. The amount of filler that can conveniently be added to the film formulation is typically up to about 25%, e.g. about 0.5% to about 20%, e.g. about 1% to about 15%, e.g. about 2% to about 10%, based on the weight of the film composition on a dry weight basis.

Surfactants/Non-Ionic Solubilizers

The film typically incorporates at least one surfactant/non-ionic solubilizer including, for example, but not limited to, a poloxamer, polyoxyl hydrogenated castor oil, glyceryl polyethylene glycol oxystearates, fatty acid glyceryl polyglyceryl esters, polyglyceryl esters, and combinations thereof. The amount of surfactant(s) that can be added to the film composition is typically up to about 5%, e.g. about 0.5% to about 3%, e.g. about 1% to about 3% based on the weight of the film composition on a dry weight basis.

Anti-Foaming Components

Anti-foaming and/or de-foaming components may also be used in a film composition. These components aid in the removal of air, such as entrapped air, from the film compositions. Such entrapped air may lead to non-uniform films. Simethicone is an example of a useful anti-foaming and/or de-foaming agent, although other anti-foaming and/or de-foaming agents may suitable be used. An anti-foaming and/or de-foaming agent such as simethicone may be added to the film composition in an amount from about 0.01% to about 5.0%, more desirably from about 0.05% to about 2.5%, and most desirably from about 0.1% to about 1.0% based on the weight of the film composition on a dry weight basis.

Colorants

Color additives that may be included in a film composition include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminium hydroxide. Other examples of color additives include known azo dyes, organic or inorganic pigments, or coloring agents of natural origin. Certain examples of color additives are inorganic pigments, such as oxides of iron or titanium, added in concentrations ranging from about 0.001% to about 10%, e.g. about 0.01% to about 3%, based on the weight of the film composition on a dry weigh basis. In one embodiment, the color used for the dexmedetomidine composition (i.e. the deposit composition) is different from the color used for the film substrate (e.g. the placebo film).

One color of the monolithic film and the film substrate of the micro-deposited film is emerald green, and available as Fast Emerald Green Shade (06507). One color of the dexmedetomidine composition (i.e. the deposit composition) is a different color from the color of the film substrate, e.g. blue (available as FD&C Blue No. 1).

Manufacture of Film Compositions:

The film compositions may be prepared as disclosed herein.

In general, one of the methods of preparing monolithic thin film formulations involves casting the liquid formulation as a continuous web in the form of wide and long rolls on a continuous substrate (e.g. paper or polyester liners which may or may not have release coatings) to form what is sometimes referred to as a master roll. The manufacturing process includes drying the liquid formulation to remove solvents (aqueous and/or non-aqueous) to yield the thin film on the substrate. The master rolls thus formed are then converted into smaller unit doses through roll slitting and individual unit dose die-cutting. The unit doses are then transferred from the manufacturing substrate for primary product packaging.

As an example, solvent casting may conveniently be used to prepare the polymer film matrix. If the active ingredient is part of the polymer film matrix, the active ingredient, polymer(s) and other ingredients (e.g. carriers) are mixed in a solvent prior to preparing the polymer film matrix. Generally a low shear agitator can be used for bulk mixing and efficient heat transfer while an inline homogenizer can be used for high shear dispersion. The mixer is capable of applying vacuum during processing to eliminate entrapment of air bubbles in the mixture, which manifest as film defects during the subsequent coating process. The ingredients can be added to the mixer in any order and therefore the process is not limited by the order of addition of each ingredient.

During the coating process the mixture is transported to the coating head via a controlled metering pump to assure consistent delivery of the fluid. Coating may utilize a knife-over-roll coating head, reverse roll coating head, or a slot-die coating head based on which technique is most appropriate for the fluid rheology and the substrate to be coated. Those skilled in the art of coating processes appreciate the various techniques and be able to determine the appropriate coating technique based upon the required film parameters. During the coating process, the fluid is deposited onto a release liner and then conveyed through a "drying tunnel."

During the drying process, forced hot air is applied to the top side of the coating, to the bottom side of the coating, or to any combination of top and bottom sides of the coating to achieve a film that contains less than or equal to the specified residual solvent level. Drying ovens can be of any length but are typically between 2-10 meters in length. Multiple drying ovens can be sequentially staged so that the wet coating passes through multiple drying ovens, each of which can be set to different drying temperatures of air pressures. During the drying process the coater may run at line speeds between 0.25-5 meters/minute and the line speed is dictated by the efficiency of the drying process and the specified residual solvent level required for a particular film product. After the film coating has exited the oven, it is wound up onto a core.

In addition to solvent casting, other examples for preparing a polymer film matrix include a semi-solid casting method, solid dispersion extrusion method, rolling method, hot melt extrusion method and the combination thereof.

"Casting" refers to the method in which polymers and additional ingredients (including the active agent) may be dissolved or slurried in a suitable solvent, any entrapped air is removed, the resulting mixture cast onto a suitable substrate, and dried to remove solvent to form a film (e.g. a thin film). The film is then cut into any desired shape and size.

In one embodiment of the solvent casting method, a solution comprising one or more polymers (and optionally one or more suitable pharmaceutically acceptable carriers) is mixed with a solution of the active ingredient (and any other pharmaceutically acceptable carriers), any entrapped air is removed (e.g. under vacuum), and the resulting mixture cast onto a suitable substrate and dried to remove solvent to form a film (e.g. a thin film).

In another embodiment of the solvent casting method, all the film composition ingredients are mixed together in a solvent to produce a solution or slurry, any entrapped air is removed (e.g. under vacuum) and the resulting mixture cast onto a suitable substrate and dried to remove solvent to form a film (e.g. a thin film).

In a further embodiment, when the active ingredient is dispersed within the film polymer matrix (as opposed to deposition on the surface of the "placebo" polymer matrix), the active ingredient may be substantially uniformly distributed throughout the polymer matrix.

If, alternatively, the active ingredient is present on the surface of polymer film matrix, a "placebo" polymer film matrix (i.e. containing no drug) is initially prepared as a continuous polymer film matrix, and the active ingredient as part of a suitable composition (the dexmedetomidine composition) is directly deposited onto the surface of the dried continuous polymer film matrix. In another embodiment, a "placebo" polymer matrix is formed as a continuous web that is cut into individual units prior to depositing the dexmedetomidine composition to the surface of "placebo" polymer matrix. One advantage of micro-deposited matrix compositions and the method used to prepare them is that the final unit doses are less susceptible to variation in the amount of dexmedetomidine present than can occur during the preparation of conventional drug-containing monolithic films. Micro-deposition helps to ensure that a relatively more precise and consistent volume of formulation and dexmedetomidine is deposited. Another advantage of micro-deposited matrix compositions and the method used to prepare them is that different doses can be produced from the same roll of film substrate. The dose either depends on the number of droplets that are applied to a certain area of the substrate or the way the film is cut after application of the droplets is a consistent pattern. Conversely, in drug-containing monolithic films, the process only allows for the preparation of units containing the same dose of drug.

In a detailed embodiment of the solvent casting method, a solution comprising one or more polymers (and optionally any suitable pharmaceutically acceptable carriers) is prepared, any entrapped is air removed (e.g. under vacuum), and the resulting mixture cast onto a suitable substrate and dried to remove solvent to form a film (e.g. a thin film). Separately, the active ingredient and any other necessary ingredients, e.g. pharmaceutically acceptable carrier(s) and/or polymer component, are dissolved/dispersed in a liquid carrier to form an active agent-containing solution or slurry. The resultant active agent solution or slurry is then deposited onto the previously prepared film (i.e. "placebo" polymer matrix) surface.

According to certain exemplary embodiments, the method of depositing the active agent solution or slurry onto a "placebo" polymer matrix is accomplished by direct dispensing as described in more detail below. In certain alternate exemplary embodiments, direct dispensing may also be performed with a needle or array of needles.

Broadly methods of depositing an active ingredient onto a "placebo" polymer matrix, in accordance with exemplary embodiments, employ dispensing a small volume of the active ingredient, typically between 1 µL to about 5000 µL, 1 µL to about 100 µL, 1 µL to about 500 µL, 250 µL to about 750 µL, alternatively between 500 µL to about 1000 µL, alternatively between 1 µL to about 1000 µL, alternatively between 500 µL to about 1500 µL, alternatively between 1000 µL to about 2000 µL alternatively between 1500 µL to about 2500 µL, alternatively between 2000 µL to about 3000 µL directly, alternatively between 2500 µL to about 3500 µL, alternatively between 3000 µL to about 4000 µL, alternatively between 3500 µL to about 4500 µL, alternatively between 4000 µL to about 5000 µL directly on to a surface of the "placebo" polymer matrix. In some embodiments, the entire volume is dispensed in a single step, although for total volumes higher than 10 microliters, it may be desirable to serially dispense multiple iterations of smaller volumes adjacent and/or overlying one another (e.g. in a linear fashion) to form the micro-deposited matrix composition.

Dexmedetomidine may be dispensed from a dispenser head by a force that moves the liquid from reservoir in, or connected to, the dispenser head to the surface of the "placebo" polymer matrix. This may be achieved by positive displacement pumping through the dispensing head positioned over the surface of "placebo" polymer matrix. The "placebo" polymer matrix may be a continuous polymer film sheet or single unit polymer. The dispenser head is typically, not necessarily, a needle like tip of the type used in the aforementioned micro-deposition processes.

The geometry of dexmedetomidine deposition formed by direct dispensing in accordance with exemplary embodiments may be of any type. In some embodiments, the active formulation may be dispensed in a circular shape, as will occur by expressing the formulation from a cylindrical tip in which the surface energy of the substrate surface is uniform. In accordance with other embodiments, square, rectangle, or even more complex polygon shapes may be employed. This may be achieved by providing a dispenser head in which dexmedetomidine solution or slurry exits the head and is pinned between the head and target surface to establish the desired shape. Thus, if the geometry of the dispenser's head surface closest to "placebo" polymer matrix is rectangular, then rectangular deposit is generated.

Alternatively, a single unit dose may be formed by repeated smaller dispensing cycles from one or more dispensing units. Each dispenser head may be attached to a robotic arm that controls where dexmedetomidine liquid formulation is deposited on the "placebo" polymer matrix. Alternatively, the platform on which "placebo" polymer matrix is mounted may be motorized to move the "placebo" polymer matrix as the deposition liquid formulation is being dispensed from a fixed dispenser head. These configurations afford the ability to vary the size and shape of the dose as needed.

It will be appreciated that other ways may also be employed to dispense dexmedetomidine liquid formulation of various geometries. For example, the surface energy of the "placebo" polymer matrix may be modified to result in better wetting by the dexmedetomidine liquid formulation. In one embodiment, a corona or plasma treatment using a mask with openings of the geometry to be obtained provides a well-defined region on the surface of "placebo" polymer matrix of increased surface energy that promotes fluid migration to cover the treated area. In another embodiment, the surface energy of the formulation being dispensed may be modified or tailored to achieve a desired flow characteristic during and after dispensing. In yet another embodiment, a dam or frame in the desired geometry is provided on the "placebo" polymer matrix, followed by dispensing the liquid dexmedetomidine from the dispensing head into the defined area to generate a deposit with a specific geometry and uniformity. The dexmedetomidine composition is deposited on the surface of the "placebo" polymer matrix within the framed area in sufficient volume to fill the framed area at the required depth. This stenciling technique allows the "placebo" polymer matrix to provide a peripheral seal around the active layer when the film is applied to mucosa. This can prevent leakage of the active ingredient from the periphery of the active layer into the oral cavity and further helps to ensure that all of the drug is delivered via the desired mucosal pathway.

It will be appreciated that the fluid characteristics of the dexmedetomidine liquid formulation (the dexmedetomidine composition) being dispensed may impact the ability to consistently obtain uniform film dispensing. For dispensing by a positive displacement pump, the fluid viscosity of the dexmedetomidine formulation is, for example, in the range of 1 to 5000 cps as measured at 25° C. using a Brookfield viscometer using a small sample adapter. However, the particular viscosity of the dexmedetomidine formulation within this range may vary depending upon a variety of factors depending on the characteristics of the deposition to be created, including how the liquid formulation is desired to behave after it is dispensed onto the substrate, which itself may be a function of how a particular film geometry is to be obtained. For example, pinning the liquid film formulation so that it does not spread beyond the intended area may be influenced by the fluid's viscosity, as well as its surface tension and the "placebo" polymer matrix surface energy.

Typically, the solvent casting method produces a film having a thickness of from about 20 micrometers to about 1200 micrometers, e.g. about 50 micrometers to about 1000 micrometers, e.g. about 70 micrometers to about 200 micrometers. The dry film can be cut in appropriate sizes, typically an area of from about 1 square centimeter to about 15 square centimeters (e.g. about 1 cm$^2$ to about 3 cm$^2$), to provide an appropriate dose of dexmedetomidine or a pharmaceutically acceptable salt thereof, e.g. in the size of length of from about 5 mm to about 15 mm (e.g. 8.8 mm±0.5 mm) and width of from about 10 mm to about 30 mm (e.g. 22 mm±1.5 mm).

In one embodiment, the film composition is prepared by a deposition method that results in a "placebo" film having, on the surface thereof, a substantially non-uniform distribution of dexmedetomidine or a pharmaceutically acceptable salt thereof. In certain aspects, where the deposition process requires or benefits from drying following deposition, drying ovens and/or forced hot air may be used. Drying temperature may vary from about 40° C. to about 80° C. Drying temperature is adjusted in such a manner that moisture content of film is about ≤5%. Drying time may vary from about 5 minutes to about 180 minutes, e.g. about 5 minutes to about 60 minutes. In some embodiments, drying time may be about at least 30 minutes. Optionally, gentle air flow and low temperatures (~40-50° C.) in the drying ovens may be used. The fluid rheology of a particular deposition formulation will dictate the particular drying parameters required. In some embodiments, drying conditions may include heating at 70° C. for 5-10 minutes. Each unit contains at least one spot of micro-deposition composition. The viscosity of the micro-deposition solution/suspension (the dexmedetomidine composition) may range from about 6 cps to about 3700 cps, when measured at 25° C. using a Brookfield viscometer with a small sample adapter. For example, the viscosity is from about 6 cps to about 500 cps, about 6 cps to about 200 cps, about 6 cps to about 100 cps, about 6 cps to about 50 cps, or about 6 cps to about 20 cps at 25° C. and a shear rate of about 7 (l/s).

If deposition does not require a drying step, then the process can continue after initial substrate drying and during slitting of master rolls. Since the film is wide web, it is possible that multiple lanes of deposition can occur at the same time. It is also contemplated that the deposition process can be accomplished using a single lane.

Additionally, if the deposition does not require drying following deposition, the packaging machine can be equipped with a slitting station to control the width of the film being processed. This is a standalone station that can function in-line during the processing of finished units. Formulation can be deposited onto the surface of a placebo slit roll by applying a single deposition apparatus in-line at the slitting station. An air-knife and IR heater placed in-line to gently blow air over the film after deposition would provide slight drying of the deposition, despite the application not requiring drying. This reduces the amount of solvent remaining in the deposition if necessary. Following deposition, the film is die-cut and packaged as a unit dose.

In other embodiments, any suitable drying process may be applied such as thermal drying process. Other methods include gas forced air drying in which hot air is blown down on the deposit at high velocity to minimize the boundary layer and facilitate mass transfer, drying in a box oven and IR drying, all by the way of example.

The packed films must be stored at a controlled temperature, e.g. from about 15-30° C.

Another benefit of direct dispensing individual unit doses is an ability to vacuum dry the dispensed dexmedetomidine composition onto the polymer matrix film. The use of vacuum drying provides faster drying times at lower temperatures that, in turn, affords improved productivity, low energy consumption (less heat) and improved film and drug stability as a result of the lower temperatures. Vacuum drying may also yield a better content uniformity and patient dosing by reduced potential for entrapped air or bubble defects. Improved productivity may be achieved by drying more quickly at lower pressures as well as affording integration of other product conversion steps as part of an overall, in-line process sequence.

One example of a deposition method comprises the following steps:
 (i) preparing a first composition comprising a polymer component and one or more pharmaceutically acceptable carriers, including a liquid carrier, and optionally other pharmaceutically acceptable carriers;
 (ii) solvent casting the product of step (i) to produce a polymer matrix ("placebo" polymer matrix);
 (iii) conveying said polymer matrix through a drying apparatus to form a dried polymer matrix;
 (iv) preparing a second composition comprising dexmedetomidine or a pharmaceutically acceptable salt thereof, one or more pharmaceutically acceptable carriers, including a liquid carrier, and optionally other pharmaceutically acceptable carrier(s) and a polymer component;
 (v) depositing the dexmedetomidine composition onto the dried polymer matrix of step (iii) as one or more droplets; and
 (vi) drying, including allowing to dry without using a drying method, to remove at least a portion of the liquid carrier from the product of step (v) to produce the final product.

Additional ingredients can also be applied to the dried film by, for example, printing, spraying, dusting, or vapor adsorption processes, among others.

The film product can be processed into unit doses by any suitable technique, including, for example, die-cutting or cutting across the width of a singular narrow roll to prepare unit doses of any desired geometric size or shape. The unit doses may then conveniently be packaged with various suitable materials known in the art to prevent degradation and protect the active ingredient from adulteration.

Desirably, a series of such unit doses are packaged together in accordance with the prescribed regimen or treatment, e.g., a 10-90 day supply, depending on the particular therapy. Individual films may also comprise a backing material, which can be peeled off prior to use.

The present disclosure also provides film compositions of dexmedetomidine or a pharmaceutically acceptable thereof, wherein the film has the thickness about 0.02 millimeters (20 micrometers) to about 0.2 millimeters (200 micrometers), resulting in weight in the range of about 0.5 milligrams to about 200 milligrams. Thus, in some aspects, the film compositions comprise a polymer matrix monolayer having a limited thickness allowing them to rapidly disintegrate in the oral environment and release dexmedetomidine or a pharmaceutically acceptable salt thereof without undue discomfort to the oral mucosa. Such a composition may be a "placebo" layer with drug deposited on a surface or may contain the active ingredient in the polymer matrix itself.

In a further embodiment, we provide the co-administration of a film of this disclosure together with a long-acting dexmedetomidine formulation. Examples of long-acting dexmedetomidine formulations include transdermal patches and depot products such as depot injections (e.g. IV or IM) or implantable devices. Examples of transdermal patches include patches disclosed in published US patent/patent applications nos. US 2015/0098980, US 2015/0098997, US 2015/0098983, US 2015/0098982, US 2015/0098981, US 2018/0117012, US 20140328898, US 20130072532, U.S. Pat. Nos. 5,817,332, 5,217,718, 5,820,875, and 9,974,754 and related patents/patent applications.

A specific embodiment provides a method of treating agitation in a subject comprising administering to a subject a film of the present disclosure and concurrently or subsequently administering a long-acting transdermal patch formulation of dexmedetomidine, optionally followed by the further administration of a film of the present disclosure.

A further specific embodiment provides a method of treating agitation in a subject comprising administering to a subject a film of the present disclosure and concurrently or subsequently administering a long-acting depot injectable formulation of dexmedetomidine, optionally followed by administration of a film of the present disclosure.

Therapeutic Use of Film Compositions:

The film compositions disclosed herein may be used for the treatment of various disorders/conditions including:

Agitation associated with neurodegenerative conditions selected from the group consisting of: Alzheimer disease, frontotemporal dementia (FTD), dementia, dementia with Lewy bodies (DLB), post-traumatic stress disorder, Parkinson's disease, vascular dementia, vascular cognitive impairment, Huntington's disease, multiple sclerosis, Creutzfeldt-Jakob disease, multiple system atrophy, and progressive supranuclear palsy; senile dementia of the Alzheimer type (SDAT)

Agitation associated with neuropsychiatric conditions selected from the group consisting of: schizophrenia, bipolar disorder, bipolar mania, delirium, and depression, including dementia or mood disorders in subjects with major depression (e.g. stress-related major depression);

Agitation associated with other conditions such as OPD/IPD procedures (e.g. MRI, CT or CAT scan, lumbar puncture, bone marrow aspiration/biopsy, tooth extraction and other dental procedures);

Agitation associated with alcohol, opioid use disorder, opioid withdrawal and substance abuse withdrawal;

Delirium;

Traumatic brain injury (TBI), including TBI subjects with alcohol or substance use disorder (ASUD);

Post-Traumatic Stress Disorder (PTSD), including PTSD subjects with alcohol or substance use disorder (ASUD);

Tardive dyskinesia;

The film compositions disclosed herein find particular use in the treatment of acute agitation associated with the disorders/conditions described above.

The film compositions disclosed herein also find particular use in the treatment of hyper-arousal associated with acute agitation in patients with schizophrenia, bipolar disorder, and dementia.

The film compositions disclosed herein also find particular use in the treatment of acute agitation without causing significant sedation.

The film compositions disclosed herein also find particular use in the treatment of chronic agitation without causing significant sedation.

The film compositions disclosed herein may also be used as adjunct therapeutics to exposure therapy for the treatment of post-traumatic stress disorder (PTSD).

The film compositions disclosed herein may also be used for the treatment of PTSD with or without standard treatment of PTSD.

The film compositions disclosed herein also find particular use in the treatment of post-traumatic stress disorder (PTSD) associated with alcohol or substance use disorder (ASUD).

The film compositions disclosed herein may also be used as an adjunct therapeutic before, during or after Exposure Therapy (ET) for patients undergoing ASUD treatment co-morbid with PTSD or traumatic brain injury.

In one aspect, the film compositions disclosed herein may be used for the treatment of patients with PTSD that suffer from alcohol and/or substance abuse, for example in treating PTSD patients who are seeking to overcome alcohol and/or substance dependence and are susceptible to alcohol and/or substance abuse withdrawal symptoms.

In another aspect, the film compositions disclosed herein may be used for the treatment of patients with TBI that suffer from alcohol and/or substance abuse, for example in treating TBI patients who are seeking to overcome alcohol and/or substance dependence and are susceptible to alcohol and/or substance abuse withdrawal symptoms.

The patients, also referred to as subjects, are typically human subjects. In aspects, the human is at least 55, at least 60, at least 65 or at least 75. The methods and formulations disclosed herein thus have use, for example, in humans aged 55 to 75.

In one aspect, the present disclosure provides methods for treating or ameliorating agitation associated with neurodegenerative conditions by administering to such patients in need of treatment a dexmedetomidine film formulation as described herein.

In another aspect, the present disclosure provides methods for treating or ameliorating agitation associated with neuropsychiatric conditions by administering to such patients in need of treatment a dexmedetomidine film formulation as described herein.

In a further aspect, the present disclosure provides methods for treating or ameliorating agitation associated with other conditions such as OPD/IPD procedures (e.g. MRI, CT or CAT scan, lumbar puncture, bone marrow aspiration/biopsy, tooth extraction or other dental procedures) by administering to such patients in need of treatment a dexmedetomidine film composition as described herein.

In a yet further aspect, the present disclosure provides methods for treating or ameliorating agitation associated with alcohol and substance abuse withdrawal by administering to such patients in need of treatment a dexmedetomidine film formulation as described herein.

The dosage forms disclosed herein dissolve or disintegrate rapidly in the patient's mouth without chewing or the need for water. Because of their ease of administration, such compositions are particularly useful for the specific needs of patients with compromised motor skills.

Typical per unit dose of dexmedetomidine or a pharmaceutically acceptable salt thereof include from about 0.5 micrograms to about 200 micrograms, about 0.5 micrograms to about 150 micrograms, from about 1 microgram to about 100 micrograms, from about 3 micrograms to about 90 micrograms, from about 3 micrograms to about 80 micrograms, from about 3 micrograms to 70 micrograms, from about 3 micrograms to about 60 micrograms, from about 3 micrograms to 50 micrograms, from about 3 micrograms to about 40 micrograms, from about 3 micrograms to about 35 micrograms, from about 5 micrograms to about 35 micrograms, about 10 micrograms to about 50 micrograms, about 10 micrograms to about 40 micrograms, about 10 micrograms to about 35 micrograms, about 15 micrograms to about 35 micrograms or about 15 micrograms to 35 micrograms of dexmedetomidine or a pharmaceutically acceptable salt thereof. In certain embodiments, the per unit dose is about 10 micrograms, about 15 micrograms, about 20 micrograms, about 25 micrograms, about 30 micrograms, about 35 micrograms, about 40 micrograms, about 45 micrograms, about 50 micrograms, about 55 micrograms, about 60 micrograms, about 65 micrograms, about 70 micrograms, about 75 micrograms, about 80 micrograms, about 85 micrograms, about 90 micrograms, about 95 micrograms, about 100 micrograms, about 110 micrograms, about 120 micrograms, about 130 micrograms, about 140 micrograms or about 150 micrograms. Each unit may be administered to the subject multiple times per day, including twice, three times, four times, five times or six times per day.

The exemplary dosage of dexmedetomidine or a pharmaceutically acceptable salt thereof to be administered to a particular patient, will depend on the type and extent of the condition, the overall health status of the particular patient, the particular form of dexmedetomidine or a pharmaceutically acceptable salt thereof being administered, and the particular film formulation used to treat the patient.

Combination Therapy

In one embodiment, the present disclosure provides a film as disclosed herein, wherein the film comprises dexmedetomidine or a pharmaceutically acceptable salt thereof together with one or more additional therapeutic agents. Such combination therapy may be particularly useful in the treatment of agitation in conditions caused or exacerbated by alcohol or other substance abuse, including post-traumatic stress disorder and traumatic brain injury (TBI).

Examples of suitable additional therapeutic agents include opioid antagonists (e.g. naltrexone or naloxone), opioid partial agonists (e.g. buprenorphine, butorphanol, pentazocine or tramadol), and anti-depressants such as serotonin-norepinephrine reuptake inhibitors (e.g. amitriptyline, atomoxetine, desipramine, duloxetine, maprotiline, mefazodone, milnacipran, nefazodone, protripyline, trimipramine, reboxetine, venlafaxine, or viloxazine), or selective serotonin reuptake inhibitors (e.g. citalopram, fluoxetine, paroxetine, sertraline, fluvoxamine, citalopram, or escitalopram). For example, a film as disclosed herein comprising dexmedetomidine or a pharmaceutically acceptable salt thereof can improve the response to currently used treatment in subjects with PTSD, such as serotonin-norepinephrine reuptake inhibitors and selective serotonin reuptake inhibitors, for example by achieving a more rapid response or an augmented response prior to the initial use and after the discontinuation of the serotonin-norepinephrine reuptake inhibitor or selective serotonin reuptake inhibitor, Dexmedetomidine or a pharmaceutically acceptable salt thereof may also be used in combination with a NMDA receptor antagonist such as ketamine to treat major depression, for example agitation in subjects with dementia or mood disorders associated with stress-related major depression.

In one embodiment, the present disclosure provides a. film as disclosed herein, wherein the film comprises dexmedetomidine or a pharmaceutically acceptable salt thereof together with an opioid antagonist or a pharmaceutically acceptable salt thereof.

In a further embodiment, the present disclosure provides a film as disclosed herein, wherein the film comprises dexmedetomidine or a pharmaceutically acceptable salt thereof together with an effective amount of an opioid antagonist or a pharmaceutically acceptable salt thereof for the treatment of agitation, without causing excessive sedation.

In a further embodiment, the present disclosure provides a film as disclosed herein, wherein the film comprises dexmedetomidine or a pharmaceutically acceptable salt thereof together with an effective amount of an opioid antagonist or a pharmaceutically acceptable salt thereof for the treatment of agitation associated with opioid or substance withdrawal.

In a specific embodiment, the present disclosure provides a film as disclosed herein, wherein the film comprises dexmedetomidine or a pharmaceutically acceptable salt thereof together with naltrexone or a pharmaceutically acceptable salt thereof.

In another embodiment, the present disclosure provides a film as disclosed herein, wherein the film comprises dexmedetomidine or a pharmaceutically acceptable salt thereof together with an opioid partial agonist or a pharmaceutically acceptable salt thereof.

In a further embodiment, the present disclosure provides a film as disclosed herein, wherein the film comprises dexmedetomidine or a pharmaceutically acceptable salt thereof together with an effective amount of a partial agonist or a pharmaceutically acceptable salt thereof for the treatment of agitation without causing excessive sedation.

In further embodiment, the present disclosure provides a film as disclosed herein, wherein the film comprises dexmedetomidine or a pharmaceutically acceptable salt thereof together with an effective amount of a partial agonist or a pharmaceutically acceptable salt thereof for the treatment of agitation associated with opioid withdrawal.

In specific embodiment, the present disclosure provides a film as disclosed herein, wherein the film comprises dexmedetomidine or a pharmaceutically acceptable salt thereof together with buprenorphine or a pharmaceutically acceptable salt thereof An effective amount of dexmedetomidine or a pharmaceutically acceptable salt thereof and opioid antagonist or partial agonist may be included in the film of the present disclosure, so as to provide the desired effect.

In one embodiment, the film comprises about 5 micrograms to 150 micrograms of dexmedetomidine or a pharmaceutically acceptable salt thereof and about 2 mg to about 16 mg of the partial agonist per unit. More desirably, the film comprises about 5 micrograms to 150 micrograms of dexmedetomidine or a pharmaceutically acceptable salt thereof and about 4 mg to about 12 mg of partial agonist per unit.

In another embodiment, the film comprises about 5 micrograms to 150 micrograms of dexmedetomidine or a pharmaceutically acceptable salt thereof and about 0.5 mg to about 5 mg of the opioid antagonist per unit. More desirably, the film comprises about 5 micrograms to 150 micrograms of dexmedetomidine or a pharmaceutically acceptable salt thereof and about 1 mg to about 3 mg of opioid antagonist per unit.

In one specific embodiment, the film comprises about 10 micrograms to 60 micrograms of dexmedetomidine or a pharmaceutically acceptable salt thereof and about 0.5 mg naltrexone, or about 10 micrograms to 60 micrograms of dexmedetomidine or a pharmaceutically acceptable salt thereof and about 1 mg naltrexone, or about 10 micrograms to 60 micrograms of dexmedetomidine or a pharmaceutically acceptable salt thereof and about 2 mg naltrexone, or about 10 micrograms to 60 micrograms of dexmedetomidine or a pharmaceutically acceptable salt thereof and about 3 mg naltrexone, or about 10 micrograms to 60 micrograms of dexmedetomidine or a pharmaceutically acceptable salt thereof and about 4 mg naltrexone, or any similar amounts.

In another specific embodiment, the film comprises about 10 micrograms to 60 micrograms of dexmedetomidine or a pharmaceutically acceptable salt thereof and about 2 mg buprenorphine, or about 10 micrograms to 60 micrograms of dexmedetomidine or a pharmaceutically acceptable salt thereof and about 4 ng buprenorphine, or about 10 micrograms to 60 micrograms of dexmedetomidine or a pharmaceutically acceptable salt thereof and about 6 mg buprenorphine, or about 10 micrograms to 60 micrograms of dexmedetomidine or a pharmaceutically acceptable salt thereof and about 8 mg buprenorphine, or about 10 micrograms to 60 micrograms of dexmedetomidine or a pharmaceutically acceptable salt thereof and about 10 mg buprenorphine, or about 10 micrograms to 60 micrograms of dexmedetomidine or a pharmaceutically acceptable salt thereof and about 12 mg buprenorphine, or about 10 micrograms to 60 micrograms of dexmedetomidine or a pharmaceutically acceptable salt thereof and about 16 mg buprenorphine or any similar amounts.

The drug combinations hereinabove may be included in a monolithic film of the present disclosure or a micro-deposition film of the present disclosure. If in a monolithic film, the present disclosure provides for the presence of all drugs in a single matrix film layer. The drugs may also be present in separate monolithic films which are then combined to provide a multi-layer film.

In one embodiment, and more conveniently, the drugs are included in a micro-deposition film of this disclosure. Thus, for example, individual drug compositions may be added as discrete droplets to the surface of the film substrate (i.e. placebo film) according to the general process used and described herein to add the dexmedetomidine composition to a film substrate. The droplets may be added in any pattern to suit the desired unit dose requirements. The droplets may each include a colorant which may be the same or different for each drug composition. It may be convenient to use different colors to distinguish the different drugs on the surface of the film substrate.

In one embodiment, we provide a method of treating agitation in a subject comprising administering to the subject a film of the present disclosure with concomitant exposure therapy.

In another embodiment, examples of suitable therapeutic agents to be combined with dexmedetomidine in the film composition include selective serotonin reuptake inhibitors (SSRIs) such as paroxetine, sertraline, serotonin and norepinephrine reuptake inhibitors (SNRIs) such as desipramine. In one embodiment, the present disclosure provides a film as disclosed herein, wherein the film comprises dexmedetomidine or a pharmaceutically acceptable salt thereof together with a selective serotonin reuptake inhibitor or a pharmaceutically acceptable salt thereof. In another embodiment, the present disclosure provides a film as disclosed herein, wherein the film comprises dexmedetomidine or a pharmaceutically acceptable salt thereof together with a serotonin and norepinephrine reuptake inhibitor or a pharmaceutically acceptable salt thereof.

In specific embodiment, the present disclosure provides a film as disclosed herein, wherein the film comprises dexmedetomidine or a pharmaceutically acceptable salt thereof together with desipramine or a pharmaceutically acceptable salt thereof An effective amount of dexmedetomidine or a pharmaceutically acceptable salt thereof and ketamine or a pharmaceutically acceptable salt thereof may be included in the film of the present disclosure, so as to provide the desired effect,

SPECIFIC EMBODIMENTS

Embodiment 1

A pharmaceutical film composition suitable for sublingual administration, comprising:
(i) a therapeutically effective amount of dexmedetomidine or a pharmaceutically acceptable salt thereof;
(ii) a polymer component consisting of one or more water-soluble polymers; and
(iii) one or more pharmaceutically acceptable carriers.

Embodiment 2

A pharmaceutical film composition suitable for sublingual administration, consisting essentially of:
(i) a therapeutically effective amount of dexmedetomidine or a pharmaceutically acceptable salt thereof;
(ii) a polymer component consisting of one or more water-soluble polymers; and
(iii) one or more pharmaceutically acceptable carriers.

Embodiment 3

The pharmaceutical film composition according to Embodiment 1 or Embodiment 2, wherein said the polymer component consisting of at least two different water-soluble polymers.

Embodiment 4

The pharmaceutical film composition according to Embodiment 3, wherein the first water-soluble polymer has a molecular weight from about 5,000 daltons to about 49,000 daltons and one or more second water-soluble polymers each have a molecular weight greater than about 60,000 daltons.

Embodiment 5

The pharmaceutical film composition according to Embodiment 3 or Embodiment 4, wherein the ratio of first water-soluble polymer to second water-soluble polymer(s) (including PEO when present in the film) in the entire film composition is from about 1:10 to about 1:30, about 1:15 to about 1:25 or about 1:15 to about 1:20.

Embodiment 6

The pharmaceutical film composition according to Embodiment 4, wherein the first water-soluble polymer is selected from the group consisting of hydroxypropyl cellulose, hydroxypropyl methylcellulose, hydroxyethyl cellulose, carboxymethyl cellulose, methyl cellulose, and mixtures thereof.

Embodiment 7

The pharmaceutical film composition according to Embodiment 6, wherein the first water-soluble polymer consisting of hydroxypropyl cellulose and/or hydroxyethyl cellulose.

Embodiment 8

The pharmaceutical film composition according to Embodiment 4, wherein the one or more second water-soluble polymers is/are selected from the group consisting of polyethylene oxide, hydroxypropyl cellulose, hydroxypropyl methylcellulose, hydroxyethyl cellulose, carboxy methylcellulose, methylcellulose and mixtures thereof.

Embodiment 9

The pharmaceutical film composition according to Embodiment 7, wherein the second water-soluble polymer(s) is/are selected from hydroxypropyl cellulose, hydroxyethyl cellulose, polyethylene oxide and mixtures thereof.

Embodiment 10

The pharmaceutical film composition according to any of Embodiments 1 to 9, wherein the dexmedetomidine or a pharmaceutically acceptable salt thereof is dexmedetomidine hydrochloride.

Embodiment 11

The pharmaceutical film composition according to any of Embodiments 1 to 10 in the form of a dosage unit, wherein the amount of dexmedetomidine or a pharmaceutically acceptable salt thereof present per unit is from about 0.5 micrograms to about 150 micrograms, from about 1 microgram to about 100 micrograms, from about 3 micrograms to about 90 micrograms, from about 3 micrograms to about 80 micrograms, from about 3 micrograms to 70 micrograms, from about 3 micrograms to about 60 micrograms, from about 3 micrograms to 50 micrograms, about 3 micrograms to about 35 micrograms, from about 3 micrograms to about 50 micrograms, from about 5 micrograms to about 50 micrograms, from about 5 micrograms to about 45 micrograms, from about 3 micrograms to about 40 micrograms, from about 5 micrograms to about 35 micrograms, about 10 micrograms to about 50 micrograms, about 10 micrograms to about 40 micrograms, about 10 micrograms to about 35 micrograms, about 15 micrograms to about 35 micrograms or from about 15 micrograms to about 35 micrograms of dexmedetomidine or a pharmaceutically acceptable salt thereof Embodiment 12

The pharmaceutical film composition according to any of Embodiments 1 to 11, wherein dexmedetomidine hydrochloride is present in an amount of from about 0.01% to about 50% based on the weight of the film on a dry weight basis, e.g. from about 0.05% to about 30% based on the weight of the film on a dry weight basis, e.g. from about 0.05% to about 20% based on the weight of the film on a dry weight basis.

Embodiment 13

The pharmaceutical film composition according to any of Embodiments 1 to 12, wherein the pharmaceutically acceptable carrier includes, but not limited to, one or more of liquid carriers, flavors, sweeteners, refreshing agents, pH adjusting agents, permeation enhancers, mucoadhesive agents, plasticizers, bulking agents, surfactants, anti-foaming agents, colorants or the like.

Embodiment 14

The pharmaceutical film composition according to any of Embodiments 1 to 13, wherein the film has a thickness of about 20 micrometers to about 1200 micrometers.

Embodiment 15

The pharmaceutical film composition according to any of Embodiments 1 to 14, wherein the film, when placed sublingually, will dissolve in about 10 seconds to about 180 seconds, e.g. about 60 seconds to about 180 seconds.

Embodiment 16

The pharmaceutical film composition according to any of Embodiments 1 to 15, wherein the film is mucoadhesive in nature.

Embodiment 17

The pharmaceutical film composition according to any of Embodiments 1 to 16, wherein the disintegration time of the film composition upon contacting simulated fluids is between about 10 seconds to about 180 seconds, about 15 seconds to about 180 seconds, about 30 seconds to about 180 seconds, about 45 seconds to about 180 seconds, about 60 seconds to about 180 seconds, or about 60 seconds to about 140 seconds; or the disintegration time of the film composition upon contacting simulated fluids is between about 15 seconds to about 180 seconds, about 15 seconds to about 160 seconds, about 25 seconds to about 150 seconds, about 15 seconds to about 140 seconds, about 15 seconds to about 120 seconds, about 40 seconds to about 120 seconds, about 50 seconds to about 120 seconds, for example about 120 seconds.

Embodiment 18

A process for preparing a pharmaceutical film composition comprises the steps of:
(i) preparing a mixture comprising dexmedetomidine or a pharmaceutically acceptable salt thereof, a polymer component(s), and one or more pharmaceutically acceptable carriers including a liquid carrier and optionally one or more other pharmaceutically acceptable carriers;

(ii) dispersing or casting the mixture on a substrate to form a drug-containing polymer matrix; and (iii) drying the drug-containing polymer matrix to remove at least a portion of the liquid carrier to form a monolithic drug-containing matrix film composition.

Embodiment 19

A process for preparing a pharmaceutical film composition comprises the steps of:
(i) preparing a monolithic matrix film composition according to Embodiment 18, except that the composition does not contain any dexmedetomidine or a pharmaceutically acceptable salt thereof (i.e. a "placebo" film composition):
(ii) preparing a second composition comprising dexmedetomidine or a pharmaceutically acceptable salt thereof together with one or more pharmaceutically acceptable carriers including a liquid carrier, and optionally one or more other pharmaceutically acceptable carriers and/or a polymer component;
(iii) depositing the product of step (ii) onto the surface "placebo" film composition of step (i), e.g. as one or more droplets; and
(iv) drying the product of step (iii) to remove at least a portion of the liquid carrier to form a matrix film composition containing drug on the film surface.

Embodiment 20

The process according to Embodiment 19, wherein the second composition comprises a polymer component.

Embodiment 21

A method of treating agitation in a subject in need thereof, the method comprising administering to the subject a therapeutically effective amount of a pharmaceutical film composition according to any of Embodiments 1 to 15.

Embodiment 22

The method according to Embodiment 21, wherein the pharmaceutical film composition is placed in the mouth of the subject under the tongue.

Embodiment 23

The method according to Embodiment 21 or 22, wherein the agitation is associated neurodegenerative diseases selected from the group consisting of Alzheimer's disease, frontotemporal dementia (FTD), dementia, dementia with Lewy bodies (DLB), post-traumatic stress disorder (PTSD), Parkinson's disease, vascular dementia, vascular cognitive impairment, Huntington's disease, multiple sclerosis, Creutzfeldt-Jakob disease, multiple system atrophy, and progressive supranuclear palsy.

Embodiment 24

The method according to Embodiment 21 or 22, wherein the agitation is associated neuropsychiatric conditions selected from the group consisting of schizophrenia, bipolar disorder, bipolar mania, delirium, and depression.

Embodiment 25

The method according to Embodiment 21 or 22, wherein the agitation is associated with conditions such as OPD/IPD procedures (e.g. MRI, CT or CAT scan, lumbar puncture, bone marrow aspiration/biopsy, tooth extraction or other dental procedures).

Embodiment 26

The method according to Embodiment 21 or 22, wherein the agitation is associated with alcohol withdrawal, opioid use disorder, opioid withdrawal and substance abuse withdrawal.

Embodiment 27

The pharmaceutical film composition prepared according to Embodiment 18 or Embodiment 19, wherein said polymer component consisting of at least two different water-soluble polymers.

Embodiment 28

The pharmaceutical film composition according to Embodiment 27, wherein the first water-soluble polymer has a molecular weight from about 5,000 daltons to about 49,000 daltons and one or more second water-soluble polymers each have a molecular weight greater than about 60,000 daltons.

Embodiment 29

The pharmaceutical film composition according to Embodiment 18 or Embodiment 28, wherein the ratio of first water-soluble polymer to second water-soluble polymer(s) (including PEO when present in the film) in the entire film composition is from about 1:10 to 1:30, about 1:15 to about 1:25 or about 1:15 to about 1:20.

Embodiment 30

The pharmaceutical film composition according to Embodiment 19 or Embodiment 28, wherein the ratio of first water-soluble polymer to second water-soluble polymer(s) (including PEO when present in the film) in the polymer matrix composition ("placebo") is from about 1:10 to 1:30, about 1:15 to about 1:25 or about 1:15 to about 1:20.

Embodiment 31

A method of treating agitation associated with opioid withdrawal in a subject in need thereof, the method comprising administering to the subject a therapeutically effective amount of a pharmaceutical film composition comprising an effective amount of dexmedetomidine or a pharmaceutically acceptable salt thereof and an effective amount of opioid antagonist.

Embodiment 32

A method of treating agitation associated with opioid withdrawal in a subject in need thereof, the method comprising administering to the subject a therapeutically effective amount of a pharmaceutical film composition comprising an effective amount of dexmedetomidine or a pharmaceutically acceptable salt thereof and an effective amount of partial agonist.

Embodiment 33

A method of treating agitation associated with post-traumatic stress disorder in a subject in need thereof, the method comprising administering to the subject a therapeutically effective amount of a pharmaceutical film composition comprising an effective amount of dexmedetomidine or a pharmaceutically acceptable salt thereof as adjunct therapeutic to exposure therapy.

Embodiment 34

A method of treating post-traumatic stress disorder in a subject in need thereof, the method comprising administering to the subject a therapeutically effective amount of a pharmaceutical film composition comprising an effective amount of dexmedetomidine or a pharmaceutically acceptable salt thereof as adjunct therapeutic to exposure therapy.

Embodiment 35

A method of treating post-traumatic stress disorder associated with opioid withdrawal in a subject in need thereof, the method comprising administering to the subject a therapeutically effective amount of a pharmaceutical film composition comprising an effective amount of dexmedetomidine or a pharmaceutically acceptable salt thereof.

Embodiment 36

A method of treating traumatic brain injury in a subject in need thereof, the method comprising administering to the subject a pharmaceutical film composition comprising an effective amount of dexmedetomidine or a pharmaceutically acceptable salt thereof.

EXAMPLES

Example 1

Thin Film Formulations
Formulation 1

TABLE 1

Dexmedetomidine hydrochloride dispersed within a polymer matrix film composition:

| Ingredients | Concentration g/100 g | Function |
|---|---|---|
| Dexmedetomidine hydrochloride | 3.60 | Active |
| Hydroxypropyl cellulose (MW = 40,000) | 4.82 | Film former |
| Hydroxypropyl cellulose (MW = 140,000) | 4.82 | Film former |
| Hydroxypropyl cellulose (MW = 370,000) | 28.94 | Film former |
| Polyethylene oxide (MW = 600,000) | 57.84 | Film former & mucoadhesive |
| Purified water* | q.s. | Solvent (or liquid carrier) |

*substantially removed via drying from the final formulation

Process: All the ingredients listed in table 1 were dissolved in water with stirring, cast through a fixed gap onto a release liner substrate to form a film, and subsequently dried in a lab oven at 70° C. for 30 minutes to provide a thin film product.

Formulation 2:

TABLE 2

Dexmedetomidine hydrochloride deposited on the surface of a polymer matrix film composition:

| Film Ingredients | Concentration g/100 g | Function |
|---|---|---|
| Drug-containing composition | | |
| Dexmedetomidine hydrochloride | 0.48 | Active |
| Ethanol* | q.s. | Solvent |
| Polymer matrix composition | | |
| Hydroxypropyl cellulose (MW = 40,000) | 4.98 | Film former |
| Hydroxypropyl cellulose (MW = 140,000) | 4.98 | Film former |
| Hydroxypropyl cellulose (MW = 370,000) | 29.86 | Film former |
| Polyethylene oxide (MW = 600,000) | 59.70 | Film former & mucoadhesive |
| Purified water* | q.s. | Solvent (or liquid carrier) |

*substantially removed via drying from the final formulation

Process: All the polymers of the polymer matrix composition were dissolved in water with stirring, cast through a fixed gap onto a release liner substrate to form a film and subsequently dried in a lab oven at 70° C. for 30 minutes. Separately, dexmedetomidine hydrochloride was dissolved in ethanol on a vortex mixer and then deposited (as droplets) via volumetric pipette onto the film. Deposited drug composition was dried in a lab oven at 70° C. for five minutes to provide the thin film product.

Formulation 3:

TABLE 3

Dexmedetomidine hydrochloride deposited on the surface of a polymer matrix film composition:

| Ingredients | Concentration g/100 g | Function |
|---|---|---|
| Drug-containing composition | | |
| Dexmedetomidine | 0.34 | Active |
| Sodium Chloride | 0.10 | pH neutralizing agent |
| Sodium Hydroxide | 0.65 | pH neutralizing agent |
| Ethanol* | q.s. | Solvent (or liquid carrier) |
| Polymer matrix composition | | |
| Hydroxypropyl cellulose (MW = 40,000) | 4.74 | Film former |
| Hydroxypropyl cellulose (MW = 140,000) | 4.74 | Film former |
| Hydroxypropyl cellulose (MW = 370,000) | 28.44 | Film former |
| Polyethylene oxide (MW = 600,000) | 56.86 | Film former & mucoadhesive |
| Glycine | 3.80 | Alkaline Buffer |
| Sodium Hydroxide | 0.33 | Alkaline Buffer |
| Purified water* | q.s | Solvent (or liquid carrier) |

*substantially removed via drying from the final formulation

Process: All the polymers and alkaline buffers of the polymer matrix composition were dissolved in water with stirring, cast through a fixed gap onto a release liner substrate to form a film and subsequently dried in a lab oven at 70° C. for 30 minutes. Separately, dexmedetomidine hydrochloride was dissolved in ethanol on a vortex mixer, neutralized with excess sodium hydroxide and sodium chloride and then deposited (as droplets) via volumetric pipette onto the film. Deposited drug composition was dried in a lab oven at 70° C. for five minutes to provide the thin film product.

Formulation 4:

TABLE 4

Dexmedetomidine hydrochloride deposited on the surface of a polymer matrix film composition:

| Ingredients | Concentration g/100 g | Function |
|---|---|---|
| Drug-containing composition | | |
| Dexmedetomidine hydrochloride | 0.48 | Active |
| Hydroxypropyl cellulose (MW = 40,000) | 2.08 | Film former |
| Ethanol | q.s. | Solvent (or liquid carrier) |
| Polymer matrix composition | | |
| Hydroxypropyl cellulose (MW = 40,000) | 4.87 | Film former |
| Hydroxypropyl cellulose (MW = 140,000) | 4.87 | Film former |
| Hydroxypropyl cellulose (MW = 370,000) | 29.23 | Film former |
| Polyethylene oxide (MW = 600,000) | 58.47 | Film former & mucoadhesive |
| Purified water | q.s. | Solvent (or liquid carrier) |

Process: All the polymers of the polymer matrix composition were dissolved in water with stirring, cast through a fixed gap onto a release liner substrate to form a film and subsequently dried in a lab oven at 70° C. for 30 minutes. Separately, dexmedetomidine hydrochloride and hydroxypropyl cellulose (MW=40,000) were dissolved in ethanol on a vortex mixer and then deposited (as droplets) via volumetric pipette onto the film. Deposited drug composition was dried in a lab oven at 70° C. for five minutes to provide the thin film product.

Formulation 5:

TABLE 5

Dexmedetomidine hydrochloride deposited on the surface of a polymer matrix film composition:

| Ingredients | Concentration g/100 g | Function |
|---|---|---|
| Drug-containing composition | | |
| Dexmedetomidine hydrochloride | 0.47 | Active |
| Hydroxypropyl cellulose (MW = 40,000) | 0.28 | Film former |
| Hydroxypropyl cellulose (MW = 140,000) | 0.28 | Film former |
| Hydroxypropyl cellulose (MW = 370,000) | 1.54 | Film former |
| Ethanol | q.s. | Solvent (or liquid carrier) |
| Polymer matrix composition | | |
| Hydroxypropyl cellulose (MW = 40,000) | 4.87 | Film former |
| Hydroxypropyl cellulose (MW = 140,000) | 4.87 | Film former |
| Hydroxypropyl cellulose (MW = 370,000) | 29.23 | Film former |
| Polyethylene oxide (MW = 600,000) | 58.46 | Film former & mucoadhesive |
| Purified water | q.s. | Solvent (or liquid carrier) |

Process: All the polymers of the polymer matrix composition were dissolved in water with stirring, cast through a fixed gap onto a release liner substrate to form a film and subsequently dried in a lab oven at 70° C. for 30 minutes. Separately, dexmedetomidine hydrochloride and the hydroxypropyl celluloses of the drug containing composition were dissolved in ethanol on a vortex mixer and then deposited (as droplets) via volumetric pipette onto the film. Deposited drug composition was dried in a lab oven at 70° C. for five minutes to provide the thin film product.

Formulation 6:

TABLE 6

Dexmedetomidine hydrochloride deposited on the surface of a polymer matrix film composition:

| Ingredients | Concentration g/100 g | Function |
|---|---|---|
| *Drug-containing composition* | | |
| Dexmedetomidine hydrochloride | 0.48 | Active |
| Hydroxypropyl cellulose (MW = 40,000) | 0.26 | Film former |
| Hydroxypropyl cellulose (MW = 140,000) | 0.26 | Film former |
| Hydroxypropyl cellulose (MW = 370,000) | 1.57 | Film former |
| Ethanol | q.s. | Solvent (or liquid carrier) |
| *Polymer matrix composition* | | |
| Peppermint Oil | 2.06 | Flavour |
| Sucralose | 0.97 | Sweetener |
| Fast Emerald Green | 0.13 | Colour |
| Hydroxypropyl cellulose (MW = 40,000) | 4.7 | Film former |
| Hydroxypropyl cellulose (MW = 140,000) | 4.7 | Film former |
| Hydroxypropyl cellulose (MW = 370,000) | 28.29 | Film former |
| Polyethylene oxide (MW = 600,000) | 56.58 | Film former & mucoadhesive |
| Purified water | q.s. | Solvent (or liquid carrier) |

Process: All the polymers and other ingredients of the polymer matrix composition were dissolved in water with stirring, cast through a fixed gap onto a release liner substrate to form a film and subsequently dried in a lab oven at 70° C. for 30 minutes. Separately, dexmedetomidine hydrochloride and hydroxypropyl celluloses of the drug containing composition were dissolved in ethanol on a vortex mixer and then deposited (as droplets) via volumetric pipette onto the film. Deposited drug composition was dried in a lab oven at 70° C. for five minutes to provide the thin film product.

Formulation 7:

TABLE 7

Dexmedetomidine hydrochloride deposited on the surface of a polymer matrix film composition:

| Ingredients | Concentration g/100 g | Function |
|---|---|---|
| *Drug-containing composition* | | |
| Dexmedetomidine hydrochloride | 0.48 | Active |
| Hydroxypropyl cellulose (MW = 40,000) | 0.11 | Film former |
| Hydroxypropyl cellulose (MW = 140,000) | 0.11 | Film former |
| Hydroxypropyl cellulose (MW = 370,000) | 0.63 | Film former |
| Polyethylene oxide (MW = 600,000) | 1.25 | Film former |
| Ethanol | q.s. | Solvent (or liquid carrier) |
| Purified water | q.s. | Solvent (or liquid carrier) |
| *Polymer matrix composition* | | |
| Hydroxypropyl cellulose (MW = 40,000) | 4.87 | Film former |
| Hydroxypropyl cellulose (MW = 140,000) | 4.87 | Film former |
| Hydroxypropyl cellulose (MW = 370,000) | 29.23 | Film former |
| Polyethylene oxide (MW = 600,000) | 58.45 | Film former & mucoadhesive |
| Purified water | q.s. | Solvent (or liquid carrier) |

Process: All the polymers of the polymer matrix composition were dissolved in water with stirring, cast through a fixed gap onto a release liner substrate to form a film and subsequently dried in a lab oven at 70° C. for 30 minutes. Separately, dexmedetomidine hydrochloride and polymers of the drug containing composition were dissolved in a mixture of ethanol and water on a vortex mixer and then deposited (as droplets) via volumetric pipette onto the film. Deposited drug composition was dried in a lab oven at 70° C. for five minutes to provide the thin film product.
Formulation 8:

TABLE 8

Dexmedetomidine hydrochloride deposited on the surface of a polymer matrix film composition:

| Ingredients | Concentration g/100 g | Function |
|---|---|---|
| Drug-containing composition | | |
| Dexmedetomidine hydrochloride | 0.49 | Active |
| Butanol | q.s. | Solvent (or liquid carrier) |
| Polymer matrix composition | | |
| Hydroxypropyl cellulose (MW = 40,000) | 4.98 | Film former |
| Hydroxypropyl cellulose (MW = 140,000) | 4.98 | Film former |
| Hydroxypropyl cellulose (MW = 370,000) | 29.85 | Film former |
| Polyethylene oxide (MW = 600,000) | 59.70 | Film former & mucoadhesive |
| Purified water | q.s. | Solvent (or liquid carrier) |

Process: All the polymers of the polymer matrix composition were dissolved in water with stirring, cast through a fixed gap onto a release liner substrate to form a film and subsequently dried in a lab oven at 70° C. for 30 minutes. Separately, dexmedetomidine hydrochloride was dissolved in n-butanol on a vortex mixer and then deposited (as droplets) via volumetric pipette onto the film. Deposited drug composition was dried in a lab oven at 70° C. for five minutes to provide the thin film product.
Formulation 9:

TABLE 9

Dexmedetomidine deposited on the surface of a polymer matrix film composition:

| Ingredients | Concentration g/100 g | Function |
|---|---|---|
| Drug-containing composition | | |
| Dexmedetomidine | 0.41 | Active |
| Sodium Chloride | 0.12 | pH neutralizing agent |
| Hydroxypropyl cellulose (MW = 40,000) | 0.26 | Film former |
| Hydroxypropyl cellulose (MW = 140,000) | 0.26 | Film former |
| Hydroxypropyl cellulose (MW = 370,000) | 1.57 | Film former |
| Ethanol | q.s. | Solvent (or liquid carrier) |
| Polymer matrix composition | | |
| Peppermint Oil | 2.06 | Flavour |
| Sucralose | 0.97 | Sweetener |
| Fast Emerald Green | 0.13 | Colour |
| Hydroxypropyl cellulose (MW = 40,000) | 4.70 | Film former |
| Hydroxypropyl cellulose (MW = 140,000) | 4.70 | Film former |
| Hydroxypropyl cellulose (MW = 370,000) | 28.27 | Film former |
| Polyethylene oxide (MW = 600,000) | 56.55 | Film former & mucoadhesive |
| Purified water | q.s. | Solvent (or liquid carrier) |

Process: All the polymers and other ingredients of the polymer matrix composition were dissolved in water with stirring, cast through a fixed gap onto a release liner substrate to form a film and subsequently dried in a lab oven at 70° C. for 30 minutes. Separately, dexmedetomidine, sodium chloride and the hydroxypropyl celluloses of the drug containing composition was dissolved in ethanol on a vortex mixer and then deposited (as droplets) via volumetric pipette onto the film. Deposited drug composition was dried in a lab oven at 70° C. for five minutes to provide the thin film product.
Formulation 10:

TABLE 10

Dexmedetomidine deposited on the surface of a polymer matrix film composition:

| Ingredients | Concentration g/100 g | Function |
|---|---|---|
| Drug-containing composition | | |
| Dexmedetomidine | 0.34 | Active |
| Sodium Chloride | 0.10 | pH neutralizing agent |
| Hydroxypropyl cellulose (MW = 40,000) | 0.22 | Film former |

TABLE 10-continued

Dexmedetomidine deposited on the surface of a polymer matrix film composition:

| Ingredients | Concentration g/100 g | Function |
|---|---|---|
| Hydroxypropyl cellulose (MW = 140,000) | 0.22 | Film former |
| Hydroxypropyl cellulose (MW = 370,000) | 1.31 | Film former |
| Ethanol | q.s. | Solvent (or liquid carrier) |
| Polymer matrix composition | | |
| Peppermint Oil | 2.07 | Flavour |
| Sucralose | 0.98 | Sweetener |
| Fast Emerald Green | 0.13 | Colour |
| Hydroxypropyl cellulose (MW = 40,000) | 4.53 | Film former |
| Hydroxypropyl cellulose (MW = 140,000) | 4.53 | Film former |
| Hydroxypropyl cellulose (MW = 370,000) | 27.16 | Film former |
| Polyethylene oxide (MW = 600,000) | 54.33 | Film former & mucoadhesive |
| Glycine | 3.76 | Alkaline buffer |
| Sodium hydroxide | 0.32 | pH neutralizing agent |
| Purified water | q.s. | Solvent (or liquid carrier) |

Process: All the polymers and other ingredients of the polymer matrix composition were dissolved in water with stirring, cast through a fixed gap onto a release liner substrate to form a film and subsequently dried in a lab oven at 70° C. for 30 minutes. Separately, dexmedetomidine, sodium chloride and the hydroxypropyl celluloses of the drug containing composition were dissolved in ethanol on a vortex mixer and then deposited (as droplets) via volumetric pipette onto the film. Deposited drug composition was dried in a lab oven at 70° C. for five minutes to provide the thin film product.

Formulation 11:

TABLE 11

Dexmedetomidine hydrochloride deposited on the surface of a polymer matrix film composition:

| Ingredients | Concentration g/100 g | Function |
|---|---|---|
| Drug-containing composition | | |
| Dexmedetomidine hydrochloride | 0.38 | Active |
| Ethanol | q.s. | Solvent (or liquid carrier) |
| Polymer matrix composition | | |
| Hydroxypropyl cellulose (MW = 40,000) | 4.47 | Film former |
| Hydroxypropyl cellulose (MW = 140,000) | 4.47 | Film former |
| Hydroxypropyl cellulose (MW = 370,000) | 26.83 | Film former |
| Polyethylene oxide (MW = 600,000) | 53.61 | Film former & mucoadhesive |
| Sodium Lactate | 6.52 | Acidic Buffer |
| Lactic Acid | 3.72 | Acidic Buffer |
| Purified water | q.s. | Solvent (or liquid carrier) |

Process: All the polymers and acidic buffer system of the polymer matrix composition were dissolved in water with stirring, cast through fixed gap onto a release liner substrate to form a film and subsequently dried in a lab oven at 70° C. for 30 minutes. Separately, dexmedetomidine hydrochloride was dissolved in ethanol on a vortex mixer and then deposited (as droplets) via volumetric pipette onto the film. Deposited drug composition was dried in a lab oven at 70° C. for five minutes to provide the thin film product.

Formulation 12:

TABLE 12

Dexmedetomidine deposited on the surface of a polymer matrix film composition

| Ingredients | Concentration g/100 g (10 µg film) | Concentration g/100 g (20 µg film) | Function |
|---|---|---|---|
| Drug-containing composition | | | |
| Dexmedetomidine hydrochloride | 0.136 | 0.267 | Active agent |
| Hydroxypropyl cellulose, HPC-SSL (MW = 40,000) | 0.301 | 0.593 | Film former |
| Hydroxypropyl cellulose (MW = 140,000) | 0.301 | 0.593 | Film former |
| FD&C Blue #1 Granular | 0.002 | 0.004 | Color |
| Ethyl Alcohol as a solvent | qs | qs | Solvent |
| Polymer matrix composition | | | |
| Hydroxypropyl cellulose (MW = 140,000) | 4.803 | 4.768 | Film former |
| Hydroxypropyl cellulose, HPC-SSL (MW = 40,000) | 4.803 | 4.768 | Film former |
| Hydroxypropyl cellulose (MW = 370,000) | 28.809 | 28.601 | Film former |
| Fast Emerald Green Shade (NO. 06507) | 0.129 | 0.128 | Color |
| Sucralose, USP-NF Grade | 0.993 | 0.985 | Sweetener |
| Peppermint Oil, NF | 2.104 | 2.089 | Flavor |
| Polyethylene oxide (Sentry Polyox WSR 205 LEO NF) (MW = 600,000) | 57.618 | 57.202 | Film former & Mucoadhesive |
| Water as a solvent | qs | qs | Solvent |

(A) Process for the Preparation of Polymer Matrix:
Polymer Mixture:
Polyethylene oxide and fast emerald green shade were mixed in water for at least 180 minutes at about 1400 rpm to about 2000 rpm. Sucralose, hydroxypropyl cellulose (molecular weight 140K), hydroxypropyl cellulose, TIPC-SSL (molecular weight 40K) and hydroxypropyl cellulose (molecular weight 370K) were added and mixed for at least 120 minutes at about 1600 rpm to 2000 rpm. Peppermint Oil was added to water and the resultant dispersion was then added to the polymer mixture and mixed for at least 30 minutes. The resultant mixture was further mixed under vacuum (248 torr) for at least for 30 minutes at a speed of 350 rpm and at temperature of 22.9° C.

Coating Station:
A roll was placed on an unwind stand and the leading edge was thread through guide bars and coating bars. The silicone-coated side of the liner was placed faced up. A gap of 40 millimeters was maintained between the coating bars. The oven set point was adjusted to 70° C. and the final drying temperature was adjusted to 85° C.

Coating/Drying Process:
The polymer mixture was poured onto the liner between the guide bars and the coating bars. The liner was pulled slowly through the coating bar at a constant speed by hand until no liquid was remained on the coating bars. The liner was cut to approximately 12-inch length hand sheets using a safety knife. Each hand sheet was placed on a drying board and was tapped on the corners to prevent curl during drying. The hand sheets were dried in the oven until the moisture content was less than 5% (approximately 30 minutes) and then removed from the drying board. The coating weights were checked against the acceptance criteria, and if met, the hand sheets were then stacked and placed in a 34 inch×40 inch foil bag that was lined with PET release liner.

(B) Process for the Preparation of Deposition Solution:
FDC blue was dissolved in ethyl alcohol for at least 180 minutes. Dexmedetomidine hydrochloride was added to the ethyl alcohol solution with continuous stirring for 10 minutes at about 400 rpm to about 800 rpm. Hydroxypropyl cellulose (40K) and hydroxypropyl cellulose (140K) were added to the mixture, and stirred for at least 30 minutes until all the materials were dissolved.

(C) Process for the Preparation of Micro-Deposited Matrix:
The deposition solution obtained in Step (B) above was filled into a pipette to the required volume (determined according to the specific drug product strength of the final product). An appropriate amount (1.5 microliters=approximately 5 micrograms) of the deposition solution were deposited (e.g. as droplets) onto the polymer matrix obtained in Step (A), and repeated to a total of 10 times (i.e. 10 deposits/droplets) with space between each deposit to prevent merging of the deposits/droplets and allow subsequent cutting of the film into individual drug-containing units. The film was initially die cut in individual units with dimensions of 22 mm×8.8 mm containing a single deposit of the drug-containing composition. The die cut micro-deposited matrixes were then dried in an oven for 70° C. for 10 minutes and further die cut into 10 units with each unit containing a single deposit of the drug-containing composition.

(D) Packaging:
Each defect-free unit was sealed individually into a foil pouch, which was then heat sealed. If the heat seal was acceptable the package was considered as an acceptable unit for commercial use.

Other unit strengths (e.g. 40 µg, 60 µg and 80 µg films) were similarly prepared by varying the concentrations of drug, polymers and colorant within the drug-containing composition. For example, the 40 µg, 60 µg and 80 µg films were prepared from drug-containing compositions containing, respectively, approximately 2×, 3×, and 4× the amounts of drug, polymers and colorant that appear in the 20 µg drug-containing composition described in Table 12 above.

Formulation 13:

TABLE 13

Dexmedetomidine deposited on the surface of a polymer matrix film composition

| Ingredients | Concentration g/100 g | Function |
|---|---|---|
| Drug-containing composition | | |
| Dexmedetomidine HCL | 0.33 | Active |
| Ethanol | q.s. | Solvent (or liquid carrier) |
| Polymer matrix composition | | |
| Hydroxypropyl cellulose (MW = 40,000) | 4.99 | Film former |
| Hydroxypropyl cellulose (MW = 140,000) | 4.99 | Film former |
| Hydroxypropyl cellulose (MW = 370,000) | 29.90 | Film former |
| Polyethylene oxide (MW = 600,000) | 59.79 | Film former & mucoadhesive |
| Purified water | q.s. | Solvent (or liquid carrier) |

Process: All the polymers of the polymer matrix composition were dissolved in water with stirring, cast through a fixed gap onto a release liner substrate to form a film and subsequently dried in a lab oven at 70° C. for 30 minutes. Separately, dexmedetomidine hydrochloride was dissolved in ethanol on a vortex mixer and then deposited (as droplets) via volumetric pipette onto the film. Deposited drug composition was dried in a lab oven at 70° C. for five minutes to provide the thin film product.

Formulation 14:

TABLE 14

Dexmedetomidine deposited on the surface of a polymer matrix film composition

| Ingredients | Concentration g/100 g | Function |
|---|---|---|
| Drug-containing composition | | |
| Dexmedetomidine | 0.34 | Active |
| Sodium Chloride | 0.10 | pH neutralizing agent |
| Hydroxypropyl cellulose (MW = 140,000) | 0.44 | Film former |
| Hydroxypropyl cellulose (MW = 370,000) | 1.31 | Film former |
| Ethanol | q.s. | Solvent (or liquid carrier) |
| Polymer matrix composition | | |
| Peppermint Oil | 2.07 | Flavour |
| Sucralose | 0.98 | Sweetener |
| Fast Emerald Green | 0.13 | Colour |
| Hydroxypropyl cellulose (MW = 40,000) | 4.53 | Film former |
| Hydroxypropyl cellulose (MW = 140,000) | 4.53 | Film former |
| Hydroxypropyl cellulose (MW = 370,000) | 27.16 | Film former |
| Polyethylene oxide (MW = 600,000) | 54.33 | Film former & mucoadhesive |
| Glycine | 3.76 | Alkaline buffer |
| Sodium hydroxide | 0.32 | pH neutralizing agent |
| Purified water | q.s. | Solvent (or liquid carrier) |

Process: All the polymers and other ingredients of the polymer matrix composition are dissolved in water with stirring, cast through a fixed gap onto a release liner substrate to form a film and subsequently dried in a lab oven at 70° C. for 30 minutes. Separately, dexmedetomidine, sodium chloride and the hydroxypropyl celluloses of the drug-containing composition are dissolved in ethanol on a vortex mixer and then deposited (as droplets) via volumetric pipette onto the film. Deposited drug composition is dried in a lab oven at 70° C. for five minutes to provide the thin film product.

Formulation 15:

TABLE 15

Dexmedetomidine deposited on the surface of a polymer matrix film composition

| Ingredients | Concentration g/100 g | Function |
|---|---|---|
| Drug-containing composition | | |
| Dexmedetomidine | 0.34 | Active |
| Sodium chloride | 0.10 | pH neutralizing agent |
| Hydroxypropyl cellulose (MW = 140,000) | 1.75 | Film former |
| Ethanol | q.s. | Solvent (or liquid carrier) |
| Polymer matrix composition | | |
| Peppermint Oil | 2.07 | Flavour |
| Sucralose | 0.98 | Sweetener |
| Fast Emerald Green | 0.13 | Colour |
| Hydroxypropyl cellulose (MW = 40,000) | 4.53 | Film former |
| Hydroxypropyl cellulose (MW = 140,000) | 4.53 | Film former |
| Hydroxypropyl cellulose (MW = 370,000) | 27.16 | Film former |
| Polyethylene oxide (MW = 600,000) | 54.33 | Film former & mucoadhesive |
| Glycine | 3.76 | Alkaline buffer |
| Sodium hydroxide | 0.32 | pH neutralizing agent |
| Purified water | q.s. | Solvent (or liquid carrier) |

Process: All the polymers and other ingredients of the polymer matrix composition are dissolved in water with stirring, cast through a fixed gap onto a release liner substrate to form a film and subsequently dried in a lab oven at 70° C. for 30 minutes. Separately, dexmedetomidine, sodium chloride and hydroxypropyl cellulose (MW=140,000) of the drug containing composition are dissolved in ethanol on a vortex mixer and then deposited (as droplets) via volumetric pipette onto the film. Deposited drug composition is dried in a lab oven at 70° C. for five minutes to provide the thin film product.

Formulation 16:

The formulation was prepared as described in Table 16.

TABLE 16

Dexmedetomidine hydrochloride deposited on the surface of a polymer matrix film composition

| Ingredients | Concentration g/100 g | Function |
|---|---|---|
| Drug-containing composition | | |
| Dexmedetomidine hydrochloride | 0.48 | Active |
| Hydroxypropyl cellulose (MW = 140,000) | 2.09 | Film former |
| Ethanol | q.s. | Solvent (or liquid carrier) |
| Polymer matrix composition | | |
| Peppermint Oil | 2.06 | Flavour |
| Sucralose | 0.97 | Sweetener |
| Fast Emerald Green | 0.13 | Colour |
| Hydroxypropyl cellulose (MW = 40,000) | 4.7 | Film former |
| Hydroxypropyl cellulose (MW = 140,000) | 4.7 | Film former |
| Hydroxypropyl cellulose (MW = 370,000) | 28.29 | Film former |
| Polyethylene oxide (MW = 600,000) | 56.58 | Film former & mucoadhesive |
| Purified water | q.s. | Solvent (or liquid carrier) |

Process: All the polymers and other ingredients of the polymer matrix composition are dissolved in water with stirring, cast through a fixed gap onto a release liner substrate to form a film and subsequently dried in a lab oven at 70° C. for 30 minutes. Separately, dexmedetomidine hydrochloride and hydroxypropyl cellulose of the drug containing composition are dissolved in ethanol on a vortex mixer and then deposited (as droplets) via volumetric pipette onto the film. Deposited drug composition is dried in a lab oven at 70° C. for five minutes to provide the thin film product.

Formulation 17:

TABLE 17

Dexmedetomidine hydrochloride deposited on the surface of a polymer matrix film composition

| Ingredients | Concentration g/100 g | Function |
|---|---|---|
| Drug-containing composition | | |
| Dexmedetomidine hydrochloride | 0.48 | Active |
| Hydroxypropyl cellulose (MW = 140,000) | 0.52 | Film former |
| Hydroxypropyl cellulose (MW = 370,000) | 1.57 | Film former |
| Ethanol | q.s. | Solvent (or liquid carrier) |
| Polymer matrix composition | | |
| Peppermint Oil | 2.06 | Flavour |
| Sucralose | 0.97 | Sweetener |
| Fast Emerald Green | 0.13 | Colour |
| Hydroxypropyl cellulose (MW = 40,000) | 4.7 | Film former |
| Hydroxypropyl cellulose (MW = 140,000) | 4.7 | Film former |
| Hydroxypropyl cellulose (MW = 370,000) | 28.29 | Film former |
| Polyethylene oxide (MW = 600,000) | 56.58 | Film former mucoadhesive |
| Purified water | q.s. | Solvent (or liquid carrier) |

Process: All the polymers and other ingredients of the polymer matrix composition are dissolved in water with stirring, cast through a fixed gap onto a release liner substrate to form a film and subsequently dried in a lab oven at 70° C. for 30 minutes. Separately, dexmedetomidine hydrochloride, and hydroxypropyl celluloses of the drug containing composition are dissolved in ethanol on a vortex mixer and then deposited (as droplets) via volumetric pipette onto the film. Deposited drug composition is dried in a lab oven at 70° C. for five minutes to provide the thin film product.

Formulation 18:

TABLE 18

Dexmedetomidine hydrochloride deposited on the surface of a polymer matrix film composition

| Ingredients | Concentration g/100 g | Function |
|---|---|---|
| Drug-containing composition | | |
| Dexmedetomidine hydrochloride | 0.48 | Active |
| Hydroxypropyl cellulose (MW = 40,000) | 0.26 | Film former |
| Hydroxypropyl cellulose (MW = 140,000) | 0.26 | Film former |
| Hydroxypropyl cellulose (MW = 370,000) | 1.57 | Film former |
| Ethanol | q.s. | Solvent (or liquid carrier) |
| Polymer matrix composition | | |
| Peppermint Oil | 2.06 | Flavour |
| Sucralose | 0.97 | Sweetener |
| Fast Emerald Green | 0.13 | Colour |
| Hydroxypropyl cellulose (MW = 40,000) | 18.845 | Film former |
| Hydroxypropyl cellulose (MW = 140,000) | 18.845 | Film former |
| Polyethylene oxide (MW = 600,000) | 56.58 | Film former & mucoadhesive |
| Purified water | q.s. | Solvent (or liquid carrier) |

Process: All the polymers and other ingredients of the polymer matrix composition are dissolved in water with stirring, cast through a fixed gap onto a release liner substrate to form a film and subsequently dried in a lab oven at 70° C. for 30 minutes. Separately, dexmedetomidine hydrochloride, and the hydroxypropyl celluloses of the drug containing composition are dissolved in ethanol on a vortex mixer and then deposited (as droplets) via volumetric pipette onto the film. Deposited drug composition is dried in a lab oven at 70° C. for five minutes to provide the thin film product.

Formulation 19:

TABLE 19

Dexmedetomidine hydrochloride deposited on the surface of a polymer matrix film composition

| Ingredients | Concentration g/100 g | Function |
|---|---|---|
| Drug-containing composition | | |
| Dexmedetomidine hydrochloride | 0.48 | Active |
| Hydroxypropyl cellulose (MW = 40,000) | 2.09 | Film former |
| Ethanol | q.s. | Solvent (or liquid carrier) |
| Polymer matrix composition | | |
| Peppermint Oil | 2.06 | Flavour |
| Sucralose | 0.97 | Sweetener |
| Fast Emerald Green | 0.13 | Colour |
| Hydroxypropyl cellulose (MW = 40,000) | 18.845 | Film former |
| Hydroxypropyl cellulose (MW = 140,000) | 18.845 | Film former |
| Polyethylene oxide (MW = 600,000) | 56.58 | Film former & mucoadhesive |
| Purified water | q.s. | Solvent (or liquid carrier) |

Process: All the polymers and other ingredients of the polymer matrix composition are dissolved in water with stirring, cast through a fixed gap onto a release liner substrate to form a film and subsequently dried in a lab oven at 70° C. for 30 minutes. Separately, dexmedetomidine hydrochloride, and hydroxypropyl cellulose of the drug containing composition are dissolved in ethanol on a vortex mixer and then deposited (as droplets) via volumetric pipette onto the film. Deposited drug composition is dried in a lab oven at 70° C. for five minutes to provide the thin film product.

Formulation 20:

TABLE 20

Dexmedetomidine hydrochloride deposited on the surface of a polymer matrix film composition

| Ingredients | Concentration g/100 g | Function |
|---|---|---|
| Drug-containing composition | | |
| Dexmedetomidine hydrochloride | 0.48 | Active |
| Hydroxypropyl cellulose (MW = 40,000) | 2.09 | Film former |
| Ethanol | q.s. | Solvent (or liquid carrier) |
| Polymer matrix composition | | |
| Peppermint Oil | 2.06 | Flavour |
| Sucralose | 0.97 | Sweetener |
| Fast Emerald Green | 0.13 | Colour |
| Hydroxypropyl cellulose (MW = 40,000) | 19.27 | Film former |
| Polyethylene oxide (MW = 600,000) | 75.00 | Film former & mucoadhesive |
| Purified water | q.s. | Solvent (or liquid carrier) |

Process: All the polymers and other ingredients of the polymer matrix composition are dissolved in water with stirring, cast through a fixed gap onto a release liner substrate to form a film and subsequently dried in a lab oven at 70° C. for 30 minutes. Separately, dexmedetomidine hydrochloride, and hydroxypropyl cellulose of the drug containing composition are dissolved in ethanol on a vortex mixer and then deposited (as droplets) via volumetric pipette onto the film. Deposited drug composition is dried in a lab oven at 70° C. for five minutes to provide the thin film product.

Formulation 21:

TABLE 21

Dexmedetomidine hydrochloride deposited on the surface of a polymer matrix film composition

| Ingredients | Concentration g/100 g | Function |
|---|---|---|
| Drug-containing composition | | |
| Dexmedetomidine hydrochloride | 0.48 | Active |
| Hydroxypropyl cellulose (MW = 40,000) | 0.26 | Film former |
| Hydroxypropyl cellulose (MW = 140,000) | 0.26 | Film former |
| Hydroxypropyl cellulose (MW = 370,000) | 1.57 | Film former |
| Ethanol | q.s. | Solvent (or liquid carrier) |
| Polymer matrix composition | | |
| Peppermint Oil | 2.06 | Flavour |
| Sucralose | 0.97 | Sweetener |
| Fast Emerald Green | 0.13 | Colour |
| Polyethylene oxide (MW = 600,000) | 94.27 | Film former & mucoadhesive |
| Purified water | q.s. | Solvent (or liquid carrier) |

Process: Polyethylene oxide and other ingredients of the polymer matrix composition are dissolved in water with stirring, cast through a fixed gap onto a release liner substrate to form a film and subsequently dried in a lab oven at 70° C. for 30 minutes. Separately, dexmedetomidine hydrochloride and hydroxypropyl celluloses of the drug containing composition were dissolved in ethanol on a vortex mixer and then deposited (as droplets) via volumetric pipette onto the film. Deposited drug composition was dried in a lab oven at 70° C. for five minutes to provide the thin film product.

Formulation 22:

TABLE 22

Dexmedetomidine hydrochloride deposited on the surface of a polymer matrix film composition

| Ingredients | Concentration g/100 g | Function |
|---|---|---|
| Drug-containing composition | | |
| Dexmedetomidine hydrochloride | 0.48 | Active |
| Hydroxypropyl cellulose (MW = 40,000) | 0.26 | Film former |
| Hydroxypropyl cellulose (MW = 140,000) | 0.26 | Film former |
| Hydroxypropyl cellulose (MW = 370,000) | 1.57 | Film former |
| Ethanol | q.s. | Solvent (or liquid carrier) |
| Polymer matrix composition | | |
| Peppermint Oil | 2.06 | Flavour |
| Sucralose | 0.97 | Sweetener |
| Fast Emerald Green | 0.13 | Colour |
| Hydroxypropyl cellulose (MW = 370,000) | 94.27 | Film former |
| Purified water | q.s. | Solvent (or liquid carrier) |

Process: Hydroxypropyl cellulose and other ingredients of the polymer matrix composition are dissolved in water with stirring, cast through a fixed gap onto a release liner substrate to form a film and subsequently dried in a lab oven at 70° C. for 30 minutes. Separately, dexmedetomidine hydrochloride and hydroxypropyl cellulose of the drug containing composition are dissolved in ethanol on vortex mixer and then deposited (as droplets) via volumetric pipette onto the film. Deposited drug composition is dried in a lab oven at 70° C. for five minutes to provide the thin film product.

Formulation 23:

TABLE 23

Dexmedetomidine hydrochloride deposited on the surface of a polymer matrix film composition

| Ingredients | Concentration g/100 g | Function |
|---|---|---|
| Drug-containing composition | | |
| Dexmedetomidine hydrochloride | 0.48 | Active |
| Hydroxypropyl cellulose (MW = 40,000) | 0.26 | Film former |
| Hydroxypropyl cellulose (MW = 140,000) | 0.26 | Film former |
| Hydroxypropyl cellulose (MW = 370,000) | 1.57 | Film former |
| Ethanol | q.s. | Solvent (or liquid carrier) |

TABLE 23-continued

Dexmedetomidine hydrochloride deposited on the
surface of a polymer matrix film composition

| Ingredients | Concentration g/100 g | Function |
|---|---|---|
| Polymer matrix composition | | |
| Peppermint Oil | 2.06 | Flavour |
| Sucralose | 0.97 | Sweetener |
| Fast Emerald Green | 0.13 | Colour |
| Hydroxypropyl cellulose (MW = 140,000) | 94.27 | Film former |
| Purified water | q.s. | Solvent (or liquid carrier) |

Process: Hydroxypropyl cellulose and other ingredients of the polymer matrix composition are dissolved in water with stirring, cast through a fixed gap onto a release liner substrate to form a film and subsequently dried in a lab oven at 70° C. for 30 minutes. Separately, dexmedetomidine hydrochloride and hydroxypropyl celluloses of the drug containing composition are dissolved in ethanol on a vortex mixer and then deposited (as droplets) via volumetric pipette onto the film. Deposited drug composition is dried in a lab oven at 70° C. for five minutes to provide the thin film product.

Example 2

Ex-Vivo Permeation of Formulations 1 to 13 of Example 1 Compared to PRECEDEX®

Formulations 1 to 13 were evaluated on an oromucosal cell model as a proxy for drug absorption (EpiOral™; MatTek Corp., Ashland, Mass.) tissue to determine the diffusion rates and extent:

ORL-200 24-well plates (MatTek Corp) containing oral cell tissue cultures were utilized within 1 day of receipt and following equilibration overnight in a 5% $CO_2$ chamber set to 37° C. and 95% relative humidity. 300 microliters of TEER-Buffer [DPBS containing Ca2+ and Mg2+ and 3.6 mg/mL glucose] was added to each well within a 24-well plate and placed in the $CO_2$ chamber overnight. The following morning the tissue inserts were removed from the TEER-Buffer and placed into a new 24-well plate containing 300 microlitres of DPBS receiver media. Prior to dosing with Formulations 1 to 13 and Precedex®, TEER was measured on each tissue insert to ensure viability following the equilibration.

Each insert was pre-wetted with 25 microliters DPBS prior to applying Formulations 1 to 13 and Precedex® to the donor side of the tissue insert, followed by an additional 25 microliters of DPBS onto the top of each formulation. Prior to applying Formulations 1 to 13 to the tissue inserts, Formulations 2 to 13 were die-cut to 52.65 mm² and Formulation 1 was die-cut to 13.125 mm². The units were die-cut to deliver the intended dose as specified below.

The 24-well plate containing each tissue insert was returned to the incubator for the specified time and subsequently removed from the incubator following the elapsed time. The tissue inserts were transferred to a fresh 24-well plate containing 300 microliters of receiver media and returned to the incubator for the additional specified time. 300 microliters receiver media from each well of the 24-well plate was transferred to HPLC vials and stored in the refrigerator (1 day) until analyzed via UPLC/MS. This experimental sequence was repeated for all time points.

Results: Table 24 illustrates the assay values and estimated AUCs (nanograms) of Formulations 1 to 13 and Precedex®. Table 24 further illustrates the disintegration time of Formulations 1, 2, 3, 7 and 13. Table 25 elucidates the diffusion of Formulations 1 to 13 and Precedex®, and FIG. 3 presents the diffusion data visually for Formulations 1 to 7, 11 and Precedex®. Each of Formulations 1 to 10 and 12 performed better than Precedex®. For example, the rate and extent of dexmedetomidine permeability through oral cell culture tissue from Formulations 1 to 10 and 12 was in the range of 1.5 to 4.5 times the rate and extent of dexmedetomidine permeability from Precedex®.

TABLE 24

Illustrates the assay values, disintegration time, and estimated AUCs of Formulations 1 to 13 and Precedex ®

| Formulation No. | Assay (micrograms) Average | SD | Disintegration Time (sec) | Mean Normalized flux (ng/cm²) | Estimated AUC (ng) |
|---|---|---|---|---|---|
| 1 | 10.16 | 0.27 | 13 | 46,402 | 10,277 |
| 2 | 6.718 | 0.58 | 59 | 43,491 | 5673 |
| 3 | 8.975 | 0.86 | 83 | 61,954 | 8274 |
| 4 | 6.63 | 1.01 | — | | 5936 |
| 5 | 6.51 | 1.75 | — | | 5886 |
| 6 | 10.58 | NA | — | | 8209 |
| 7 | 6.84 | 1.14 | 64 | Mean flux- 103,319 | 5077 |
| 8 | 11.9 | 37.5 | — | | 10,116 |
| 9 | 9.37 | NA | — | | 9171 |
| 10 | 9.74 | NA | — | | 8356 |
| 12 | Assay of 20 mcg film 20.432 | 1.54 | | Mean Normalized flux of 10 mcg film 46,644 | Estimated AUC (ng) of 10 mcg film 9061 |
| 13 | 2.725 | 1.37 | 35 | 43,113 | 2718 |
| Precedex (100 μg/mL) | — | — | N/A | | 4894 |
| Comparative Formulation 11 | 8.402 | 1.20 | — | | 1924 |

TABLE 25

Elucidates the diffusion of Formulations 1 to 13 (average cumulative amount) and Precedex ® through an oral cell culture membrane:

| | | Time (h) | | | | | |
|---|---|---|---|---|---|---|---|
| | | 0 | 0.08 | 0.25 | 0.5 | 0.75 | 1 |
| Average Cumulative amount (ng) | Formulation 1 (10 μg) | 0 | 1378 | 3355 | 5019 | 6245 | 7137 |
| | Formulation 2 (10 μg) | 0 | 405 | 1402 | 2435 | 3262 | 3890 |

TABLE 25-continued

Elucidates the diffusion of Formulations 1 to 13 (average cumulative amount) and Precedex ® through an oral cell culture membrane:

| | Time (h) | | | | | |
|---|---|---|---|---|---|---|
| | 0 | 0.08 | 0.25 | 0.5 | 0.75 | 1 |
| Formulation 3 (10 µg) | 0 | 132 | 1123 | 2615 | 3916 | 5197 |
| Formulation 4 (10 µg) | 0 | 384 | 1383 | 2481 | 3384 | 4044 |
| Formulation 5 (10 µg) | 0 | 279 | 1196 | 2340 | 3272 | 3971 |
| Formulation 6 (10 µg) | 0 | 721 | 1759 | 3586 | 5197 | 5810 |
| Formulation 7 (10 µg) | 0 | 348 | 1186 | 2120 | 2734 | 3354 |
| Formulation 8 (10 µg) | 0 | 611 | 2122 | 3838 | 5439 | 6690 |
| Formulation 9 (10 µg) | 0 | 801 | 1737 | 3207 | 4976 | 6120 |
| Formulation 10 (10 µg) | 0 | 530 | 1091 | 2364 | 4226 | 5408 |
| Precedex ® (100 µL, 10 µg) | 0 | 159 | 727 | 1353 | 2200 | 2893 |
| Formulation 11 (10 µg) | 0 | 27.9 | 40 | 409 | 698 | 1035 |
| Formulation 12 (10 µg) | 0 | 426.5 | 1968.5 | 3679.7 | 5088.7 | 6210.5 |
| Formulation 13 (10 µg) | 0 | 183.7 | 657.7 | 1087.8 | 1476.8 | 1809 |

Estimated AUC: Estimated area under the flux/time curve from the data using the trapezoidal rule which confers to total drug diffused.

Example 3

Pharmacokinetics in Rabbits (Study 1)
Test Animal Description:
Species: *Oryctolagus cuniculus*
Initial Age: Commensurate with weight
Sex: Male
Breed: New Zealand White
Initial Body Weight: ~1.5-4 kg
Replicates per Treatment: N=5 per dose group, total 30 rabbits (non-crossover)
Washout Interval: Minimum 3 day washout Study design was as follows: Food was withheld from the animals for a minimum of 12 hours prior to study initiation and four hours post-dosing. Prior to dosing, animals were weighed and assigned to experimental groups, stratified according to body weight. Individual doses were calculated based on body weights recorded on the day of dose administration. Animals were anesthetized by isoflurane. Formulations 1, 2, 3, 7 and 13 were administered under the tongue (SL) of the animals. Precedex® was administered via a butterfly needle followed by a 1 mL saline flush or via straight stick in the ear vein. Blood samples were collected pre-dosing, and at 10 minutes, 20 minutes, 30 minutes, 1 hour, 2 hours, 4 hours and 8 hours post-dosing. Blood samples were stabilized and kept cold until analysis. Bioassays were performed using C18RP-HPLC-MS. The concentrations were measured in plasma samples using a standard LC/MS/MS method against calibration curves with a minimum of six points (N=1).

Study design and PK parameters for various formulations are provided in Table 26 and Table 27 respectively:

TABLE 26 depicts the non-crossover study design:

| Group Number | Test Article | Dosing Route | Animals N= | Dose | Dosing Conc. | Dosing Volume | Vehicle |
|---|---|---|---|---|---|---|---|
| 1 | Precedex ® | IV | 5 | 1.5 µg/kg | 4.0 µg/mL | 0.375 mL/kg | 0.9% NaCl |
| 2 | Formulation 1 | SL | 5 | 10 µg | 10 µg | — | — |
| 3 | Formulation 2 | SL | 5 | 10 µg | 10 µg | — | — |
| 4 | Formulation 7 | SL | 5 | 10 µg | 10 µg | — | — |
| 5 | Formulation 3 | SL | 5 | 10 µg | 10 µg | — | — |
| 6 | Formulation 13 | SL | 5 | 10 µg | 10 µg | — | — |

TABLE 27 depicts the summary of Mean Pharmacokinetic Parameters for dexmedetomidine hydrochloride after intravenous and sublingual administration in Male New Zealand White Rabbits with average body weight ranged from 2.96 to 3.34 kg:

| Dexmedetomidine hydrochloride | Group 1 Precedex ® | Group 2 Formulation 1 | Group 3 Formulation 2 | Group 4 Formulation 7 | Group 5 Formulation 3 | Group 6 Formulation 13 |
|---|---|---|---|---|---|---|
| Route | Intravenous | Sublingual | Sublingual | Sublingual | Sublingual | Sublingual |
| Dose | 1.5 µg/kg | 10 µg | 10 µg | 10 µg | 10 µg | 10 µg |
| $C_{max}$ (pg/mL) | 738 | 220 | 112 | 235 | 88.9 | 75.2 |
| $t_{max}$ (hr) | 0.00 | 0.767 | 0.600 | 0.900 | 0.567 | 1.13 |
| $MRT_{last}$ (hr) | 0.325 | 1.14 | 1.16 | 1.46 | 1.51 | 1.06 |
| $AUC_{last}$ (hr · pg/mL) | 161 | 359 | 149 | 426 | 151 | 92.6 |

$C_{max}$: maximum plasma concentration;
$t_{max}$: time of maximum plasma concentration;
$MRT_{last}$: mean residence time, calculated to the last observable time point;
$AUC_{last}$: area under the curve, calculated to the last observable time point;

Result summary: The sublingual film products (Formulations 1, 2 and 7) provided exposure levels of dexmedetomidine hydrochloride in rabbits that are similar to the IV route of administration, when normalized to dose. Based upon mean animal mass at 3.34 kg in Group 1, the IV bolus dose administered was about 5 µg. AUC for the IV product was 161 h·pg·mL in the rabbit study while sublingual film products dosed at twice the strength (10 micrograms) of the IV product gave twice the AUC (range 359-426 h pg·mL). Therefore, the delivery of dexmedetomidine hydrochloride via the films provided exposures equivalent to an IV dose.

Example 4

Pharmacokinetics in Rabbits (Study 2)
Test Animal Description:
Species: *Oryctolagus cuniculus*
Initial Age: Commensurate with weight
Sex: Male
Breed: New Zealand White
Initial Body Weight: ~2.9-3.9 kg
Replicates per Treatment: N=8 per dose group, total 64 rabbits (non-crossover)
Washout Interval: Minimum 7 day washout
Blood Sampling Time Points: Pre-dose, 5, 10, 20, 30 min, 1, 2, 4, and 8 hours post dose Study design was as follows: Animals were anesthetized with isoflurane, prior to dose administration. Dosing formulations were administered sublingually (SL) with the film or Precedex® drops placed in the sublingual space (underneath the tongue of the animal). Micro-deposited films in dose groups were administered sublingually with the letter 'P' facing up (away from the mucosal tissue). Animals in the Precedex® injection dose group were anesthetized via isoflurane and Precedex with 0.9% NaCl was administered via a syringe and 25 gauge needle into the marginal ear vein. The time course began with test article placement (T0). The animals were left anesthetized and in a sternal position with its head propped up for 30 minutes to ensure TA dose does not move (T0-T30). After the dosing period, the sublingual space was not wiped and the animals were recovered (T30).

Blood samples were collected from the rabbits via the ear vessel, jugular vein, or other suitable vessels via direct venipuncture, and then placed into chilled polypropylene tubes containing K2EDTA as an anticoagulant. Samples were maintained chilled throughout processing. Blood samples were centrifuged at 4° C. and 3,000×g for 5 minutes. Plasma was then transferred to a chilled, labeled polypropylene tube, placed on dry ice, and stored in a freezer maintained at −60° C. to −80° C. pending analysis.

Plasma Samples:
Whole blood samples (~2.0 mL) were collected from the rabbits via jugular vein or another suitable vessel at the appropriate time points and placed into tubes containing K2EDTA as the anticoagulant and inverted several times to mix. Blood samples were centrifuged at a temperature of 4° C. at 3000×g for 5 minutes. All samples were maintained chilled throughout processing. The resulting plasma samples were transferred into polypropylene tubes and placed in a freezer set to maintain −60 to −80° C. until shipment to the Sponsor's bioanalytical lab for analysis.

Study design and PK parameters for various formulations are provided in Table 28 and Table 29 respectively.

TABLE 28 depicts the non-crossover study design:

| Test Article | Film Type: | Formulation # | Description |
|---|---|---|---|
| Micro deposited -1 | Micro deposited | Identical to formulation 12 in composition | SL film containing 1.47 µg dexmedetomidine |
| Micro deposited -2 | Micro deposited | Identical to formulation 12 in composition | SL film containing 2.94 µg dexmedetomidine |
| Micro deposited -3 | Micro deposited | Identical to formulation 12 in composition | SL film containing 5.88 µg dexmedetomidine |
| Micro deposited -4 | Micro deposited | Identical to formulation 12 in composition | SL film containing 8.82 µg dexmedetomidine |
| Monolith 1 | Monolith | Identical to formulation 1 in composition | SL film containing 5.88 µg dexmedetomidine |
| Monolith 2 | Monolith | Identical to formulation 1 in composition | SL film containing 8.82 µg dexmedetomidine |

TABLE 28-continued depicts the non-crossover study design:

| Test Article | Film Type: | Formulation # | Description |
|---|---|---|---|
| Precedex (100 µg/mL) | Solution for SL Drops | Reference SL Drops | SL solution containing 100 µg/mL dexmedetomidine |
| Precedex (4 µg/mL) | Solution for IV Injection | Reference Injection | 4 µg/mL dexmedetomidine solution for IV injection |
| Period 2 Results (Minimum 7-day Washout) | | | |
| Precedex (4 µg/mL) | Solution for IV Injection | Reference Injection | 4 µg/mL dexmedetomidine solution for IV injection |
| Precedex (4 µg/mL) | Solution for IV Injection | Reference Injection | 4 µg/mL dexmedetomidine solution for IV injection |
| Precedex (4 µg/mL) | Solution for IV Injection | Reference Injection | 4 µg/mL dexmedetomidine solution for IV injection |

TABLE 29 depicts Arithmetic Mean Pharmacokinetic Results from SL Administration of Dexmedetomidine Containing Films or Precedex ®

| Parameters | Micro-deposited film 1 SL film containing 1.47 µg dexmedetomidine | Micro-deposited film 2 SL film containing 2.94 µg dexmedetomidine | Micro-deposited film 3 SL film containing 5.88 µg dexmedetomidine | Micro-deposited film 4 SL film containing 8.82 µg dexmedetomidine | Monolithic film 1 SL film containing 5.88 µg dexmedetomidine | Monolithic film 2 SL film containing 8.82 µg dexmedetomidine | Precedex SL |
|---|---|---|---|---|---|---|---|
| Dose (µg/kg) | 0.471 | 0.939 | 1.79 | 2.65 | 1.83 | 2.70 | 2.71 |
| $C_{max}$ (ng/mL) | 0.157 | 0.112 | 0.119 | 0.315 | 0.142 | 0.205 | 0.290 |
| $t_{max}$ (h) | 1.06 | 1.56 | 0.833 | 1.25 | 0.667 | 0.688 | 0.396 |
| $AUC_{last}$ (hr · ng/mL) | 0.145 | 0.094 | 0.206 | 0.618 | 0.224 | 0.344 | 0.335 |
| $C_{max}$/Dose | 0.333 | 0.119 | 0.066 | 0.119 | 0.078 | 0.076 | 0.107 |
| $AUC_{last}$/Dose | 0.308 | 0.100 | 0.115 | 0.233 | 0.122 | 0.127 | 0.124 |
| F % | 110% | 52.2% | 70.5% | 83.4% | 63.4% | 45.6% | 44.2% |

[2] F % was calculated using individual animal IV data as a crossover.

Results: The systemic exposure of dexmedetomidine following sublingual dosing showed a numeric trend for higher exposures from increased doses from micro-deposited matrix films 2, 3 and 4 Micro-deposited matrix film 1 showed a greater than dose proportional $C_{max}$ and $AUC_{last}$ compared to Micro-deposited matrix films 2-4. The Monolithic films 1 and 2 showed an approximate dose proportional increase in $C_{max}$ and $AUC_{last}$. The systemic exposure of dexmedetomidine following sublingual dosing showed a numeric trend for higher exposures from increased doses from Micro-deposited matrix films 2, 3 and 4. Micro-deposited matrix films 1 showed a greater than dose proportional $C_{max}$ and $AUC_{last}$ compared to Micro-deposited matrix films 2-4. The Monolithic films 1 and 2 showed an approximate dose proportional increase in $C_{max}$ and $AUC_{last}$. The resulting F % values for the SI films showed higher results as compared to the Precedex SL dosing. Micro-deposited matrix films 1 and 4, which showed a 2.5 and 1.9 fold higher F % compared to the Precedex SL dosing which could be attributed to not have crossover IV data for the animals in these groups.

Example 5

Evaluation of the Films

TABLE 30

Formulation 12 evaluated for various parameters, including stability studies and results

| Parameters | Specification | Formulation 12 | Formulation 12 |
|---|---|---|---|
| Strength (mcg) | | 10 mcg | 20 mcg |
| Appearance | Green rectangular thin film with one blue spot | Pass | Pass |
| Size (mm) | Width: 22 mm ± 1.5 mm Length: 8.8 mm ± 0.5 mm | Width - 22.3 mm Length - 9.2 mm | Width - 22.2 mm Length - 9.1 mm |
| Assay (%) | 90%-110% | 105.3% | 101.0% |
| Uniformity of dosage (%) (Average) | USP<905> Stage 1-10 of 10 specimens AV ≤ 15 Stage 2 (if required)-30 of 30 specimens AV ≤ 25 | Average (10): 105.8% AV: 10 | Average (10): 99.4% AV: 7 |

TABLE 30-continued

Formulation 12 evaluated for various parameters, including stability studies and results

| Parameters | Specification | Formulation 12 | Formulation 12 |
|---|---|---|---|
| Related substances | Hydroxymedetomidine (1-(2,3-Dimethylphenyl)-1-(1H-imidazol-5-yl) ethanol) ≤ 1.0% | ND | ND |
| | N-Benzylhydroxymedetomidine (1-(1-Benzyl-1H-imidazol-5-yl)-1-(2,3-dimethylphenyl)ethanol) ≤ 1.0% | ND | ND |
| | Ethylmedetomidine (5-[1-(2,3-Dimethylphenyl)-ethyl]-1-ethyl-1H-imidazole) ≤ 1.0% | ND | ND |
| | N-Benzylmedetomidine (1-Benzyl-5-[1-(2,3-dimethylphenyl)ethyl]-1H-imidazole) ≤ 1.0% | ND | ND |
| | N-Benzyl vinyl analog (1-Benzyl-5-[1-(2,3-dimethylphenyl)vinyl]-1H-imidazole) ≤ 1.0% | ND | ND |
| | Any Unspecified Degradant ≤ 1.0% | ND | ND |
| | Total Degradant ≤ 5.0% | 0.0% | ND |
| Dissolution | (Q ≥ 80% in 15 minutes) | 104.2% | 102.3% |
| Disintegration time | (USP<701> NMT 3 Minutes) | Pass | Pass |
| Burst strength (g) | — | Average (n = 3): 605.891 g | Average (n = 3): 503.286 g |
| Mucoadhesion (g) (Average peak force) | — | Average peak force (n = 3): 436.011 g | Average peak force (n = 3): 105.937 g |
| Mucoadhesion (g*sec) (Average AUC) | — | Average AUC (n = 3): 21.739 g*sec | Average AUC (n = 3): 4.702 g*sec |
| Water activity | ≤0.75 $A_w$ | Average (n = 3): 0.44 | Average (n = 3): 0.37 |
| Microbial Limits | Total Aerobic Microbial Count < 200 cfu/film | <200 cfu/film (10 film) | <200 cfu/film (10 film) |
| | Total Combined Yeast & molds Count < 20 cfu/film | <20 cfu/film (10 film) | <20 cfu/film (10 film) |
| | *Pseudomona aeruginosa* Negative/10 units | ND | ND |
| | *Staphylococcus aureus* Negative/10 units | ND | ND |

Stability Data:

Formulation 1 (Monolithic film) and Formulation 12 [Micro-deposited matrix film (60 mcg)] were packaged individually in foil pouches. The films were tested for stability by subjecting the packaged films to temperatures of 25° C. and 40° C. After 6 months the films were evaluated with respect to various parameters. The results are provided in Table 31 and Table 32.

TABLE 31 depicts stability data for the micro deposited matrix film (Formulation 12)

| | | Dexmedetomidine 60 mcg sublingual film | | | | | | | |
|---|---|---|---|---|---|---|---|---|---|
| | | Micro-deposited film stored at 25° C./60% RH | | | | Micro-deposited film stored at 40° C./75% RH | | | |
| Parameters | Specification | 0 month | 1 month | 3 months | 6 months | 0 month | 1 month | 3 months | 6 months |
| Appearance | Green rectangular film with one spot | Pass | Pass | Pass | Pass | Pass | Pass | Pass | Pass |

TABLE 31-continued depicts stability data for the micro deposited matrix film (Formulation 12)

Dexmedetomidine 60 mcg sublingual film

| | | Micro-deposited film stored at 25° C./60% RH | | | | Micro-deposited film stored at 40° C./75% RH | | | |
|---|---|---|---|---|---|---|---|---|---|
| Parameters | Specification | 0 month | 1 month | 3 months | 6 months | 0 month | 1 month | 3 months | 6 months |
| Assay | 90%-110% | 100.6.% | 98.2% | 102.3% | 99.4% | 100.6% | 102.2% | 98.8% | 94.3% |
| Related substance | Hydroxy-medetomi-dine ≤ 1% | ND | ND | ND | ND | ND | ND | ND | ND |
| | N-Benzyl-Hydroxy-medetomi-dine ≤ 1% | ND | ND | ND | ND | ND | ND | ND | ND |
| | Ethyl-medetomi-dine ≤ 1% | ND | ND | ND | ND | ND | ND | ND | ND |
| | N-Benzyl-medetomi-dine ≤ 1% | ND | ND | ND | ND | ND | ND | ND | ND |
| | N-Benzyl-vinyl Analog ≤ 1% | ND | ND | ND | ND | ND | ND | ND | ND |
| | Any unspecified degradant ≤ 1% | ND | ND | ND | ND | ND | ND | ND | ND |
| | Total degradant ≤ 5% | 0% | 0% | 0% | 0% | 0% | 0% | 0% | 0% |
| Dissolution | Q ≥ 80% in 15 min | 97.1% | 97.0% | 94.8% | 99.6% | 97.1% | 95.2% | 93.8% | 96.1% |
| Disintegration | USP <701> NMT 3 min | 36-169 sec | 59-122 sec | 24-97 sec | 9-36 sec | 36-169 sec | 20-107 sec | 26-107 sec | 4-31 sec |
| Burst Strength | — | 476.230 g | 526.415 g | 343.996 g | 320.074 g | 476.230 g | 413.866 g | 92.133 g | 57.735 g |
| Mucoadhesion | Peak | 510.173 g | 110.010 g | 84.040 g | 76.815 g | 510.173 g | 198.586 g | 234.896 g | 64.687 g |
| | AUC | 31.307 g*s | 4.839 g*s | 3.583 g*s | 4.024 g*s | 31.307 g*s | 10.158 g*s | 13.046 g*s | 2.424 g*s |
| Water activity | ≤0.75$a_w$ | 0.44 | 0.39 | 0.41 | 0.41 | 0.44 | 0.40 | 0.38 | 0.43 |
| Microbial limits | Total aerobic microbial < 200 cfu/film | Pass | NA | NA | NA | Pass | NA | NA | NA |
| | Total combined Yeasts and Molds < 20 cfu/film | Pass | NA | NA | NA | Pass | NA | NA | NA |
| | *Pseudomonas aeruginosa* Negative/ 10 units | Pass | NA | NA | NA | Pass | NA | NA | NA |
| | *Staphylococcus aureus* Negative/ 10 units | Pass | NA | NA | NA | Pass | NA | NA | NA |

TABLE 32 depicts stability data for the monolithic film (similar to Formulation 1-different in strength)

Dexmedetomidine 60 mcg sublingual film

| | | Monolithic film stored at 25° C./60% RH | | | | Monolithic film stored at 40° C./75% RH | | | |
|---|---|---|---|---|---|---|---|---|---|
| Parameters | Specification | 0 month | 1 month | 2 months | 6 months | 0 month | 1 month | 2 months | 6 months |
| Appearance | | Green rectangular thin film | Green rectangular thin film | Green rectangular thin film | Green rectangular thin film | Green rectangular thin film | Green rectangular thin film | Green rectangular thin film | Green rectangular thin film |
| Assay | | 89.4 | Not done | 88.0 | 85.6 | 89.4 | 77.0 | 71.8 | 71.9 |

TABLE 32-continued depicts stability data for the monolithic film (similar to Formulation 1-different in strength)

| | | Dexmedetomidine 60 mcg sublingual film | | | | | | | |
|---|---|---|---|---|---|---|---|---|---|
| | | Monolithic film stored at 25° C./60% RH | | | | Monolithic film stored at 40° C./75% RH | | | |
| Parameters | Specification | 0 month | 1 month | 2 months | 6 months | 0 month | 1 month | 2 months | 6 months |
| Related substance | | | | | | | | | |
| Hydroxy-medetomidine | ND | Not done | ND | 0.3 | ND | 0.7 | 0.5 | 0.3 | |
| N-Benzyl-hydroxy-medetomidine | ND | Not done | ND | ND | ND | ND | ND | ND | |
| Ethylmedetomidine | ND | Not done | ND | ND | ND | ND | ND | ND | |
| N-Benzyl-medetomidine | ND | Not done | ND | ND | ND | ND | ND | ND | |
| N-Benzyl-vinyl analog | ND | Not done | ND | ND | ND | ND | ND | ND | |
| Unknown A (Vinylmedetomidine) | ND | Not done | ND | ND | ND | ND | 0.2 | 0.8 | |
| Total impurities | 0.0 | Not done | ND | 0.3 | ND | 0.7 | 0.7 | 0.8 | |
| Dissolution at 15 minutes | 87.1 | Not done | ND | 64.7 | 87.1 | 71.1 | NA | 79.4 | |
| Disintegration (sec) | 35.00 | 24.33 | 19.00 | 17.00 | 35.00 | 8.33 | 10.00 | 11.30 | |
| Tensile Strength (g) | 482.27 | 472.37 | 662.84 | 428.79 | 482.27 | 18.3 | 14.22 | 14.46 | |
| Mucoadhesion (g) | 1646.85 | 1004.67 | 1228.72 | 882.54 | 1646.85 | 836.64 | 791.90 | 762.82 | |

Conclusion: Micro-deposited matrix films, as exemplified by Formulation 12, are more stable than monolithic films, as exemplified by Formulation 1, when stored at 25° C. and 40° C. up to 6 months.

Example 6: Phase 1, Randomized, Single-Blind, Placebo-Controlled, Single Ascending Dose Study of the Pharmacokinetics, Safety & Tolerability of Dexmedetomidine Sublingual Film (Formulation 12) in Healthy Adult Volunteers This was a randomized, single-blind, placebo-controlled, single ascending dose pharmacokinetics, safety and tolerability study with 4 dosing groups in healthy adult (18-65 years-old) males and females. The study protocol was reviewed and approved by an institutional review board of site(s). This study was conducted in accordance with the Declaration of Helsinki and ICH— Good Clinical Practices (GCP).

Four (4) doses were evaluated derived from three film strengths of 10 µg, 40 µg, and 60 µg: 10 µg, 20 µg (2×10 µg film), 40 µg, and 60 µg in Cohort 1, 2, 3 and 4 respectively. All eligible participants, who have been previously screened, arrived at the clinical research unit (CRU) a day before for admission and baseline assessment. They were domiciled in the CRU for 4 days (Day −1, 1, 2 and 3) and discharged on Day 4, and were under medical supervision during this time. The pre-dose evaluation of all the participants was done approximately between 07:00 and 09:00 hours, after an overnight fast of at least 8 hours. The participants were given free access to drinking water until at least one hour before dosing. A venous catheter was inserted for allowing sampling for PK. At the beginning of each study session, a single dose of dexmedetomidine sublingual film (Formulation 12) was administered sublingually by an unblinded staff. The dexmedetomidine sublingual film was retained in the sublingual cavity until dissolved. Evaluations were done every 5 minutes for the first 15 minutes and then every 15 minutes to determine the time to dissolution of the film. The ECG, BP and oxygen saturation were monitored as per the schedule. Participants were allowed water as desired at least 1 hour after drug administration. Standard meals were offered at approximately 4, 8, and 12 hours after dexmedetomidine sublingual film dosing. After plasma sampling for 24 hours following dosing of dexmedetomidine sublingual film, the safety and tolerability assessments were continued until the morning of Day 4 (day of discharge), and were repeated again on Day 5, Day 7±1 and Day 14±2. Blood samples were collected immediately prior to dosing (baseline) and 5, 10, 20, 30, 60, 90, 120, 180, 240 min. Additional blood samples were collected at 5, 6, 8, 10, 12 and 24 hours post dose for a total of 16 PK sampling time points.

Number of Participants:

The study evaluated increasing doses of dexmedetomidine sublingual film (Formulation 12) in 4 cohorts of healthy adult participants. In the first two cohorts (Cohort 1 and Cohort 2), twelve (12) new participants were enrolled per cohort, randomized in a ratio of 2:1, i.e. 8 receiving dexmedetomidine sublingual film and 4 receiving Placebo film.

Participants who received active treatment and completed the treatment in Cohort 1, i.e. not discontinued or withdrew, received active treatment in Cohort 3. In addition to the participants who crossed over from Cohort 1 to Cohort 3, six new participants were enrolled in Cohort 3. Similarly, participants who received active treatment and completed the treatment in Cohort 2, i.e. not discontinued or withdrew, received active treatment in Cohort 4. In addition to the participants who crossed over from Cohort 2 to Cohort 4, six new participants were enrolled in Cohort 4.

Participants that dropped out receiving placebo in Cohorts 1 and 2 were replaced by patients to receive placebo when they crossed over, i.e., in the event that placebo participants dropped out, when crossing over from Cohort 1 to Cohort 3 or Cohort 2 to Cohort 4, additional new participants were added to make up the total participants to four (4) in the placebo arms of Cohort 3 and Cohort 4.

Inclusion Criteria:
1. Healthy males and non-pregnant/non-breast-feeding females between 18 and 65 years of age, both inclusive.
2. Participants who were capable of giving written informed consent for the study
3. Participants that had body weight ≥50 kg with body mass index (BMI) in the range of 19-30 kg/m2, both inclusive
4. Participants having physical examination and vital signs judged to be within normal limits by the PI or designee
5. Participants whose clinical laboratory tests (complete blood count, blood chemistry, and urinalysis) were within normal limits or are clinically acceptable to the PI or designee
6. Participants who were sufficiently physically healthy to receive a SL dose strength of dexmedetomidine sublingual film, and tolerate drowsiness, in the opinion of the PI or designee.
7. Participants who were fluent in English and have ability to understand written and verbal protocol-related requirements in English
8. Participants who were willing and able to be confined to the CRU for approximately 4-5 days per dosing cohort and comply with the study schedule and study requirements.
9. Participants that had reliable intravascular access from which to draw blood samples.
10. Male participants, if non-vasectomized, must agree to use a condom with spermicide or abstain from sexual intercourse, during the trial and for 3 months after stopping the medication.
11. Male participant must not donate sperm starting at screening and throughout the study period, and for 90 days after the final study drug administration.
12. For female participants of child-bearing potential, the participant must be willing to practice a clinically accepted method of birth control from at least 30 days prior to the first administration of the study medication, during the study, and for at least 30 days after the last dose of the study medication.
13. For female of non-childbearing potential, the participant was surgically sterile (i.e. has undergone hysterectomy, bilateral oophorectomy, or tubal ligation) or in a menopausal state (at least 1 year without menses), as confirmed by FSH levels.

Exclusion Criteria:
1. The participants with a history of allergic reaction or intolerance to the study drug or related compounds and additives.
2. The participants with a history of major surgery within 4 weeks of screening
3. The participants with a history of significant traumatic brain injury
4. The participants with a history of alcohol or drug dependence by Diagnostic and Statistical Manual of Mental Disorders IV criteria during the 6-month period prior to study entry.
5. The participants with a history of or presence of clinically significant psychiatric illnesses mental retardation, borderline personality disorder, anxiety disorder, or organic brain syndrome
6. The participants with a history of orthostatic hypotension (i.e., a sustained reduction of systolic BP (SBP) of at least 20 mmHg or diastolic BP (DBP) of 10 mmHg, or both, within 3 min of standing or head-up tilt to at least 600 on a tilt table) and high vagal tone
7. The participants who regularly consume large amounts of xanthine-containing substances (i.e., more than 5 cups of coffee or equivalent amounts of xanthine-containing substances per day).
8. The participants who were on maintenance medications that could inhibit or induce the CYP2A6 enzyme and other medications as listed in Appendix 15.1.
9. The participants who had received dexmedetomidine or other alpha-2-agonists within 1 week of the study date.
10. The participants who had clinically significant sleep apnea or chronic obstructive pulmonary disease or history of asthma
11. The participants with suicidal tendency in the judgement of the PI or designee
12. The participants with clinical laboratory abnormalities (including positivity for Hep B, Hep C, HIV) unless treated to remission status.
13. The participants with abnormal vital signs measurement in the judgement of the PI or designee, unless treated to remission status.
14. The participants those were enrolled in another clinical study (e.g., laboratory or clinical evaluation) or have received an investigational drug in the past 30 days (or within 5 half-lives of the investigational drug, if >30 days).
15. The participants that had a resting heart rate of <65 beats per minute or SBP <110 mmHg or >140 mmHg or DBP <70 mmHg or >100 mmHg at screening and pre-dosing. Have evidence of a clinically significant 12 lead ECG abnormality. Subjects that previously failed eligibility criteria at the Screening visit or Day 1 predose due to Exclusion 15 for a resting heart rate <70 beats per minute but not <65 beats per minute may be rescreened.
16. The participants with an aberrant oral/buccal anatomy, inflammation or pathology which in the opinion of the PI, may affect SL drug administration and absorption.
17. The participants with hepatic impairment or who have hepatic dysfunction defined as a history of hepatic dysfunction and an Alanine Aminotransferase (ALT) and Aspartate Aminotransferase (AST) values greater than 2 times normal in the past 6 months prior to study drug administration.
18. The participants who had donated blood within 30 days prior to screening or plasma donation within 7 days prior to screening.
19. The participant who was part of the study staff personnel or family members of the study staff personnel.

Study duration: 39-42 days.

Dosing:
Cohort 1, Cohort 2, Cohort 3 and Cohort 4 were given 10 µg, 20 µg (2×10 µg films), 40 µg and 60 µg dose of dexmedetomidine sublingual films (Formulation 12) and accompanying Placebo respectively. Except for the first dose cohort (10 µg dose), each subsequent dose level was authorized after safety review of the previous dosing cohort. Dosing was done only once to each cohort. Dexmedetomidine sublingual film (having dot) was different from placebo in appearance.

End Points:
1. Area under the curve (AUC0-12, AUC0-24, AUC0-∞) for 0 to 12 hours and 0-24 hours post dosing for Dexmedetomidine plasma concentration, peak plasma Dexmedetomidine concentration (Cmax), time to peak Dexmedetomidine concentration level (Tmax), terminal half-life (t½) of Dexmedetomidine, volume of distribution of Dexmedetomidine and clearance of Dexmedetomidine (CL).

Results:

TABLE 33 summarizes pharmacokinetics parameters of 10 micrograms dexmedetomidine sublingual film in healthy volunteers
10 micrograms dexmedetomidine sublingual film

| Subject ID | Cmax (ng/L) | Tmax (hr) | $t_{1/2}$ (hr) | $AUC_{last}$ (hr*ng/L) | AUC0-INF (hr*ng/L) |
|---|---|---|---|---|---|
| 1001 | 37.94 | 1.5 | 2.06 | 179.19 | 201.32 |
| 1002 | 18.27 | 1.00 | 1.17 | 49.45 | 58.27 |
| 1005 | 33.28 | 2.00 | 1.86 | 116.63 | 140.07 |
| 1007 | 35.74 | 2.00 | 2.95 | 142.22 | 168.59 |
| 1009 | 24.15 | 3.02 | 2.70 | 102.76 | 147.74 |
| 1011 | 30.87 | 1.00 | 2.75 | 114.35 | 138.82 |
| 1012 | 24.53 | 1.50 | 2.58 | 98.28 | 132.11 |
| 1016 | 35.19 | 2.00 | 1.24 | 119.28 | 129.17 |
| N | 8 | 8 | 8 | 8 | 8 |
| Mean | 29.996 | 1.752 | 2.163 | 115.271 | 139.512 |
| SD | 6.930 | 0.659 | 0.693 | 37.049 | 40.525 |
| CV % | 23.1 | 37.6 | 32.0 | 32.1 | 29.0 |
| Min | 18.27 | 1.00 | 1.17 | 49.45 | 58.27 |
| Median | 32.08 | 1.75 | 2.32 | 115.49 | 139.45 |
| Max | 37.94 | 3.02 | 2.95 | 179.19 | 201.32 |
| Geometric Mean | 29.214 | 1.648 | 2.051 | 109.219 | 132.838 |
| Geometric CV % | 25.79 | 39.08 | 37.61 | 38.59 | 37.6 |

TABLE 34 summarizes pharmacokinetics parameters of 20 micrograms dexmedetomidine sublingual film in healthy volunteers
20 micrograms dexmedetomidine sublingual film

| Subject ID | Cmax (ng/L) | Tmax (hr) | $t_{1/2}$ (hr) | $AUC_{last}$ (hr*ng/L) | AUC0-INF (hr*ng/L) |
|---|---|---|---|---|---|
| 2001 | 0.00 | | | 0.00 | 0.00 |
| 2003 | 83.08 | 1.00 | 2.2 | 359.59 | 389.48 |
| 2004 | 65.17 | 2.00 | 1.72 | 259.5 | 279.49 |
| 2007 | 84.90 | 1.50 | 1.60 | 401.79 | 416.92 |
| 2011 | 70.76 | 2.00 | 1.85 | 309.75 | 337.01 |
| 2013 | 85.92 | 1.00 | 1.85 | 307.97 | 330.48 |
| 2016 | 42.34 | 3.00 | 1.97 | 198.79 | 225.81 |
| 2106 | 66.75 | 1.50 | 1.57 | 283.34 | 301.60 |
| N | 8 | 7 | 7 | 8 | 8 |
| Mean | 62.365 | 1.714 | 1.824 | 265.092 | 285.099 |
| SD | 28.982 | 0.699 | 0.221 | 123.337 | 129.906 |
| CV % | 46.5 | 40.8 | 12.1 | 46.5 | 45.6 |
| Min | 0.00 | 1.00 | 1.57 | 0.00 | 0.00 |
| Median | 68.76 | 1.50 | 1.85 | 295.66 | 316.04 |
| Max | 85.92 | 3.00 | 2.20 | 401.79 | 416.92 |
| Geometric Mean | | 1.601 | 1.813 | | |
| Geometric CV % | | 41.30 | 11.95 | | |

TABLE 35 summarizes pharmacokinetics parameters of 40 micrograms dexmedetomidine sublingual film in healthy volunteers
40 micrograms dexmedetomidine sublingual film

| Subject ID | Cmax (ng/L) | Tmax (hr) | $t_{1/2}$ | $AUC_{last}$ (hr*ng/L) | AUC0-INF (hr*ng/L) |
|---|---|---|---|---|---|
| 3011 | 140.25 | 1.00 | 1.78 | 685.15 | 709.61 |
| 3012 | 78.69 | 2.00 | 2.00 | 427.97 | 461.18 |
| 3013 | 97.01 | 1.07 | 1.76 | 292.84 | 310.29 |
| 3023 | 126.60 | 1.00 | 1.86 | 493.89 | 508.98 |
| 3026 | 135.02 | 1.50 | 1.38 | 482.44 | 499.41 |
| 3032 | 78.06 | 2.00 | 3.38 | 378.67 | 439.85 |
| 3114 | 167.99 | 1.00 | 2.05 | 777.66 | 806.08 |
| 3131 | 123.52 | 2.02 | 2.42 | 600.88 | 627.60 |
| 4001 | 109.62 | 1.00 | 1.82 | 419.51 | 446.40 |
| 4022 | 204.03 | 1.00 | 1.82 | 664.47 | 704.50 |
| 4026 | 123.68 | 2.00 | 1.83 | 507.83 | 534.00 |
| 4130 | 143.95 | 2.00 | 1.97 | 772.97 | 798.78 |
| N | 12 | 12 | 12 | 12 | 12 |
| Mean | 127.368 | 1.465 | 2.007 | 542.024 | 570.557 |
| SD | 35.794 | 0.495 | 0.496 | 157.144 | 156.810 |
| CV % | 28.1 | 33.8 | 24.7 | 29.0 | 27.5 |
| Min | 78.06 | 1.00 | 1.38 | 292.84 | 310.29 |
| Median | 125.14 | 1.28 | 1.85 | 500.86 | 521.49 |
| Max | 204.03 | 2.02 | 3.38 | 777.66 | 806.08 |
| Geometric Mean | 122.839 | 1.389 | 1.961 | 520.580 | 550.254 |
| Geometric CV % | 28.87 | 35.22 | 21.81 | 30.84 | 29.15 |

TABLE 36

Evaluation of RASS Score in the First 2 Hours - Pharmacodynamics Population

| Parameters | 10 mcg | 20 mcg | 40 mcg | Placebo |
|---|---|---|---|---|
| Evaluable patients per RASS | 8 | 8 | 12 | 14 |
| Number of patients who have reached at least RASS of −1 at any time in the first 2 hours | 2 | 4 | 4 | 3 |
| Number of patients who have reached a RASS of −2 at any time in the first 2 hours | 1 | 0 | 0 | 1 |

Results: The data given in the tables 33 to 35 reflects the dose proportional pharmacokinetics. This data clearly shows that pharmacodynamics effects lasts for 4 to 6 hours which is consistent with the optimal treatment window. Dexmedetomidine plasma concentrations increase rapidly following placement of the film formulation and achieve plasma exposures to produce the pharmacodynamic effect. The half-life of dexmedetomidine sublingual film Formulation 12 is comparable to IV dexmedetomidine. FIG. 4 reflects the mean dexmedetomidine plasma log concentration vs. time for 10, 20 and 40 mcg of dexmedetomidine sublingual film (semi-log scale) and clearly demonstrates that 70-80% of the mean concentrations were achieved before 1 hour of dexmedetomidine film administration. Further data revealed that dexmedetomidine sublingual thin film (Formulation 12) was safe and well tolerated with no serious adverse events. All adverse events were transient and mild (below grade 2) except moderate headache (2 in placebo group), moderate systolic/diastolic decrease (1 in placebo), and moderate dizziness (2 subjects in 40 µg group with orthostatic changes). Only drowsiness and dizziness were seen at rates greater than 1-2 subjects per group, thus there is no clear sedative effect. vs. placebo. The most common adverse event seen was drowsiness, observed at rates similar to placebo. Lower rates of dizziness were reported in all groups, and was greater than placebo only for 40 µg group. The study demonstrated that mean cardiovascular changes were not clinically meaningful and the maximum tolerated dose as not reached. The data is further depicted in FIGS. 5 to 11.

Example 7: A Phase Ib Multicenter, Randomized, Double-Blind, Placebo-Controlled, Multiple Ascending Dose Study to Determine Efficacy, Pharmacokinetics and Safety of Dexmedetomidine Sublingual Film in Agitation Associated with Schizophrenia Adaptive evaluation of escalating dose regimens of 20 μg, 60 μg and 120 μg were performed for the first stage, with an option to test a different dose should a safety or tolerability signal be observed. Male and female adults with acute agitation associated with schizophrenia, schizoaffective disorder, or schizophreniform disorder were enrolled in each cohort. Investigators chose to repeat the 20 μg dose 1 hour after initial administration.

Arms and Interventions (Table 37)

| Arms | Intervention |
| --- | --- |
| Placebo Comparator: Placebo Sublingual Film with no active drug; single administration | Drug: Placebo film Placebo film for dexmedetomidine hydrochloride |
| Experimental: 20 micrograms Sublingual Film containing 20 micrograms dexmedetomidine; single administration with repeat dose after 1 hour | Drug: Sublingual film containing dexmedetomidine hydrochloride Administration: Sublingual film containing dexmedetomidine for the treatment of agitation associated with Schizophrenia |
| Experimental: 60 micrograms Sublingual Film containing 60 micrograms dexmedetomidine; single administration | Drug: Sublingual film containing dexmedetomidine hydrochloride. Administration: Sublingual film containing dexmedetomidine for the treatment of agitation associated with Schizophrenia |
| Experimental: 120 micrograms 2 Sublingual Films, each containing 60 micrograms dexmedetomidine; single administration of 2 films | Drug: Sublingual film containing dexmedetomidine hydrochloride. Administration: Sublingual film containing dexmedetomidine for the treatment of agitation associated with Schizophrenia |

Blinded periodic safety data reviews were undertaken on an ongoing basis to review all subjects assigned, dosed and as data became available. Dose escalation was allowed unless a safety or tolerability issue became evident upon periodic regular safety review. Each site was assigned a small number of each dose cohort in an escalating although blinded fashion such that a given cohort was balanced between sites to account for subject-site and inter-rater variability. Patients at a site were assigned to the lowest dose cohort with subsequent patients assigned to increasing doses. This sequential escalating adaptive enrollment ensures subject safety; the lowest dose cohort completes accrual first, higher dose cohorts complete last. Should a subject not respond, the investigator might repeat the dose such that the subject receives a second administration (and no further) of the same randomized dose thereby testing the safety/efficacy of receiving two doses separated by 1 hour which approximates dosing before initiating the next dose level cohort. Sequential accrual of subjects in the high dose cohort enables more rapid discontinuation of dosing, exposing only a minimum number of subjects, should dose-limiting safety or tolerability be observed. Further, based upon blinded analyses integrating PK, exposure and the safety/tolerability of all subjects and doses, the dose regimen may be altered (e.g. repeated dosing may be discontinued or allowed only after an elapsed time), or different dose may be selected to test the hypothesis that a (typically lower) dose regimen is better tolerated.

Eligible subjects were randomized to dexmedetomidine sublingual film (Formulation 12) or Placebo. At the beginning of each study session, a single dose of dexmedetomidine sublingual film (Formulation 12) was self-administered sublingually by the patient, after training with a placebo film and under the supervision of an unblinded staff who had not participated in evaluation of safety or efficacy.

Dexmedetomidine sublingual film (Formulation 12) was retained in the sublingual cavity until dissolved. Participants were evaluated for local irritation around the area where the film was placed. Efficacy and safety assessments were conducted periodically before and after dosing. If reduction in PEC is less than or equal to 40% one hour after the first administration, the investigator may request a second dose of dexmedetomidine sublingual film be administered (of the same randomized dose) with an additional PEC assessment completed at 1.5 hours post-dose. Should the patient's situation warrant it, standard of care treatment may be initiated, e.g. after the 4 hours assessments are completed.

Stage 1: In each cohort twenty-seven (27) new participants were enrolled, randomized 2:1 Dexmedetomidine sublingual film: Placebo film, i.e. 18 received dexmedetomidine sublingual film and 9 received placebo film. Three doses were initially planned (total of 81 subjects). A different or additional dose may be tested based on ongoing safety reviews. At the conclusion of Stage 1, two doses that describe a safe and effective range (High and Low) will selected based upon blinded review of the overall clinical safety, tolerability, adverse effects and PK observed during dosing.

Stage 2: In order to more accurately estimate the range of safety tolerability and calming effects observed upon exposing greater numbers of subjects, an additional 120 subjects are enrolled in a double blind placebo controlled parallel group sequential 3-arm design testing each of two identified effective doses or placebo (randomized 1:1:1 High:Low: placebo with 40 subjects per arm; total 120 subjects in Stage 2; Study total of approximately 201 subjects).

Vital Signs and ECG with rhythm strip are measured as per schedule of assessments, prior to any PK assessments. Participants are allowed water as desired 30 minutes after completion of dosing. Standard meals may be offered beginning 1 hour after dexmedetomidine sublingual film dosing. Safety and tolerability assessments are continued until the morning of Day 3 (day of discharge) and will be repeated again on Day 7(+2).

Approximately 4 mL of venous blood (to obtain a minimum of 1.2 mL plasma) will be taken into K2-EDTA tubes at set time intervals for the determination of plasma concentrations of study drug (or Placebo). The PK plasma samples should be collected within 5 minutes of the scheduled sampling time on Day 1. Blood samples will be collected per Table 3-1 Schedule of Events.

Number of subjects (planned): An estimated 201 subjects (81 in stage 1 and 120 in stage 2) are enrolled at approximately 12-20 study sites in the United States.

Diagnosis and Main Criteria for Eligibility:

Inclusion Criteria:

1. Male and female patients between the ages of 18 to 65 years, inclusive.
2. Patients who have met DSM-5 criteria for schizophrenia, schizoaffective, or schizophreniform disorder.
3. Patients who are judged to be clinically agitated at Baseline with a total score of ≥14 on the 5 items (poor impulse control, tension, hostility, uncooperativeness, and excitement) comprising the PANSS Excited Component (PEC).
4. Patients who have a score of ≥4 on at least 1 of the 5 items on the PEC.
5. Patients who read, understand and provide written informed consent.
6. Patients who are in good general health prior to study participation as determined by a detailed medical history, physical examination, 12-lead ECG with rhythm strip, blood chemistry profile, hematology, urinalysis and in the opinion of the Principal Investigator.
7. Female participants, if of child-bearing potential and sexually active, and male participants, if sexually active with a partner of child-bearing potential, who agree to use a medically acceptable and effective birth control method throughout the study and for one week following the end of the study. Medically acceptable methods of contraception that may be used by the participant and/or his/her partner include abstinence, birth control pills or patches, diaphragm with spermicide, intrauterine device (IUD), condom with foam or spermicide, vaginal spermicidal suppository, surgical sterilization and progestin implant or injection. Prohibited methods include: the rhythm method, withdrawal, condoms alone, or diaphragm alone.

Exclusion Criteria:
1. Patients with agitation caused by acute intoxication, including positive identification of alcohol by breathalyzer or non-prescription drugs (with the exception of THC) during urine screening.
2. Patients treated within 4 hours prior to study drug administration with benzodiazepines, other hypnotics or oral or short-acting intramuscular antipsychotics.
3. Treatment with alpha-1 noradrenergic blockers (terazosin, doxazosin, tamsulosin, and alfuzosin, and prazocin) or other prohibited medications.
4. Patients with significant risk of suicide or homicide per the investigator's assessment, or any suicidal behaviour in last 6 months prior to screening.
5. Female patients who have a positive pregnancy test at screening or are breastfeeding.
6. Patients who have hydrocephalus, seizure disorder, or history of significant head trauma, stroke, transient ischemic attack, subarachnoid bleeding, brain tumor, encephalopathy, meningitis, Parkinson's disease or focal neurological findings.
7. History of syncope or other syncopal attacks, current evidence of hypovolemia, orthostatic hypotension, a screening heart rate of <55 beats per minutes or systolic blood pressure <110 mmHg or diastolic BP<70 mmHg.
8. Patients with laboratory or ECG abnormalities considered clinically significant by the investigator or qualified designee [Advanced heart block (second-degree or above atrioventricular block without pacemaker), diagnosis of Sick sinus syndrome] that would have clinical implications for the patient's participation in the study.
9. Patients with serious or unstable medical illnesses. These include current hepatic (moderate severe hepatic impairment), renal, gastroenterologic, respiratory, cardiovascular (including ischemic heart disease, congestive heart failure), endocrinologic, or hematologic disease.
10. Patients who have received an investigational drug within 30 days prior to the current agitation episode.
11. Patients who are unable to use the sublingual film or considered by the investigator, for any reason, to be an unsuitable candidate for receiving dexmedetomidine; e.g. patients with a history of allergic reactions to dexmedetomidine.

Test Product, Dose, and Mode of Administration: Dexmedetomidine sublingual film (Formulation 12) is tested in a small, solid-dose film formulation, approximately 193.6 mm$^2$ in area and 0.7 mm thick, designed to completely dissolve in the SL space within 2-3 minutes.

Reference therapy, dosage and mode of Administration: Matching placebo films to be taken sublingually as described above.

Duration of Treatment: 1 day
Criteria for Evaluation

Efficacy assessment: Assessment of drug effects on acute agitation done by the Positive and Negative Syndrome Scale—Excited Component (PEC). The PEC comprises 5 items associated with agitation: poor impulse control, tension, hostility, uncooperativeness, and excitement; each scored 1 (minimum) to 7 (maximum). The PEC, the sum of these 5 subscales, thus ranges from 5 to 35.

Overall agitation and sedation will be evaluated with the Agitation-Calmness Evaluation Scale (ACES), where 1 indicates marked agitation; 2—moderate agitation; 3—mild agitation; 4—normal behavior; 5—mild calmness; 6—moderate calmness; 7—marked calmness; 8—deep sleep; and 9—unarousable. The change in agitation in response to treatment will also be measured by the Clinical Global Impressions—Improvement (CGI-I). CGI-I scores range from 1 to 7: 0=not assessed (missing), 1=very much improved, 2=much improved, 3=minimally improved, 4=no change, 5=minimally worse, 6=much worse, 7=very much worse.

Safety and tolerability assessments: AEs, clinical laboratory tests, ECG with rhythm strip, and vital signs are monitored for tolerability assessment. All observed and volunteered AEs are recorded. The relationship of AEs to the study drugs are graded as not related, unlikely/remotely related, possibly related, probably related or definitely related by the investigators. Vital signs including systolic blood pressure (SBP), diastolic blood pressure (DBP), and heart rate are measured prior to the PK blood samples. The application site of the SL preparation (buccal mucosa) is inspected for any signs of local irritation.

Additional Assessments:
Demographic Data
Medical History
Prior and Concomitant Medication
Physical Examination
Pregnancy Efficacy Analyses: The primary efficacy endpoint for Stage 1 is the proportion of subjects at each dose that achieve a 40% reduction in PEC at 2 hr. The primary efficacy endpoint for Stage 2 is the absolute change from baseline in the PEC total score at 2 hr.

Sample Size Determination: The study is not powered for detecting statistically significant differences in efficacy parameters. However, cohorts of up to 27 subjects (2:1 ratio of dexmedetomidine sublingual film:placebo) are sufficient to characterize the safety, tolerability and PK profile in Stage 1. In Stage 2, cohorts of 40 subjects are enrolled (40 on high dexmedetomidine sublingual film dose, 40 on low dexmedetomidine sublingual film dose, 40 on placebo).

Results of Stage 1

TABLE 38

Summary statistics of PK parameter estimates

| Cohort | Dose (ug) | Redose | Statistics | Tmax (hr) | Cmax (ng/L) | t½ (hr) | AUClast (hr*ng/L) | AUCINF_obs (hr*ng/L) |
|---|---|---|---|---|---|---|---|---|
| 1 | 20 | No | N | 10 | 10 | 9 | 10 | 9 |
| | | | Mean | 1.895 | 39.898 | 3.313 | 171.639 | 246.444 |
| | | | SD | 0.813 | 15.019 | 1.021 | 57.654 | 63.994 |
| | | | CV % | 42.9 | 37.6 | 30.8 | 33.6 | 26.0 |
| | | | Min | 1.00 | 14.07 | 2.12 | 57.43 | 145.57 |
| | | | Median | 1.74 | 37.02 | 3.17 | 180.09 | 241.74 |
| | | | Max | 4.02 | 69.05 | 5.36 | 264.45 | 332.10 |
| | | | Geometric Mean | 1.778 | 37.157 | 3.183 | 160.056 | 238.688 |
| | | | Geometric CV % | 36.99 | 43.89 | 30.51 | 45.41 | 27.86 |
| 1 | 20 | Yes | N | 8 | 8 | 7 | 8 | 7 |
| | | | Mean | 2.935 | 96.589 | 2.946 | 586.103 | 499.866 |
| | | | SD | 2.077 | 36.954 | 0.857 | 556.166 | 226.187 |
| | | | CV % | 70.8 | 38.3 | 29.1 | 94.9 | 45.2 |
| | | | Min | 1.83 | 49.87 | 1.81 | 230.06 | 294.47 |
| | | | Median | 2.31 | 104.54 | 3.01 | 444.23 | 520.36 |
| | | | Max | 8.03 | 138.69 | 4.02 | 1912.52 | 939.05 |
| | | | Geometric Mean | 2.578 | 89.711 | 2.833 | 453.552 | 461.828 |
| | | | Geometric CV % | 50.30 | 44.50 | 31.46 | 78.77 | 44.05 |
| 2 | 60 | No | N | 18 | 18 | 17 | 18 | 17 |
| | | | Mean | 1.528 | 139.589 | 2.861 | 681.542 | 792.552 |
| | | | SD | 0.689 | 47.223 | 1.381 | 482.593 | 525.000 |
| | | | CV % | 45.1 | 33.8 | 48.3 | 70.8 | 66.2 |
| | | | Min | 0.98 | 73.42 | 1.48 | 265.85 | 293.67 |
| | | | Median | 1.50 | 131.78 | 2.36 | 503.20 | 616.68 |
| | | | Max | 3.95 | 253.14 | 6.98 | 2072.02 | 2195.38 |
| | | | Geometric Mean | 1.429 | 132.558 | 2.640 | 576.084 | 673.986 |
| | | | Geometric CV % | 36.00 | 33.88 | 40.27 | 60.19 | 60.92 |

TABLE 39

Individual and summary statistics of PK parameter estimates of dexmedetomidine in plasma

| Cohort | Dose (ug) | Redose | Subject ID | Tmax (hr) | Cmax (ng/L) | t½ (hr) | AUClast (hr*ng/L) | AUCINF_obs (hr*ng/L) |
|---|---|---|---|---|---|---|---|---|
| 1 | 20 | No | 01-001 | 1.50 | 35.54 | 4.10 | 224.01 | 326.88 |
| | | | 01-002 | 1.50 | 38.55 | 3.68 | 182.58 | 241.74 |
| | | | 01-010 | 1.00 | 59.82 | 2.12 | 104.40 | 145.57 |
| | | | 01-026 | 4.02 | 14.07 | | 57.43 | |
| | | | 07-015 | 1.53 | 33.41 | 5.36 | 177.60 | 299.81 |
| | | | 07-030 | 2.00 | 34.31 | 2.29 | 176.11 | 203.81 |
| | | | 10-027 | 2.00 | 35.38 | 3.64 | 184.37 | 255.41 |
| | | | 23-016 | 1.48 | 69.05 | 2.95 | 264.45 | 332.10 |
| | | | 23-018 | 1.97 | 40.37 | 3.17 | 154.62 | 186.40 |
| | | | 23-020 | 1.95 | 38.49 | 2.51 | 190.81 | 226.26 |
| | | | N | 10 | 10 | 9 | 10 | 9 |
| | | | Mean | 1.895 | 39.898 | 3.313 | 171.639 | 246.444 |
| | | | SD | 0.813 | 15.019 | 1.021 | 57.654 | 63.994 |
| | | | CV % | 42.9 | 37.6 | 30.8 | 33.6 | 26.0 |
| | | | Min | 1.00 | 14.07 | 2.12 | 57.43 | 145.57 |
| | | | Median | 1.74 | 37.02 | 3.17 | 180.09 | 241.74 |
| | | | Max | 4.02 | 69.05 | 5.36 | 264.45 | 332.10 |
| | | | Geometric Mean | 1.778 | 37.157 | 3.183 | 160.056 | 238.688 |
| | | | Geometric CV % | 36.99 | 43.89 | 30.51 | 45.41 | 27.86 |
| 1 | 20 | Yes | 01-009 | 2.00 | 130.44 | 3.94 | 662.46 | 939.05 |
| | | | 01-013 | 2.00 | 122.23 | 2.73 | 486.82 | 563.33 |
| | | | 05-007 | 2.50 | 49.87 | 4.02 | 230.06 | 334.28 |
| | | | 05-008 | 2.12 | 66.64 | 2.00 | 272.47 | 304.52 |
| | | | 05-021 | 2.50 | 86.86 | 3.10 | 410.74 | 543.04 |
| | | | 05-023 | 2.50 | 52.29 | 3.01 | 236.04 | 294.47 |
| | | | 05-024 | 8.03 | 138.69 | | 1912.52 | |
| | | | 07-028 | 1.83 | 125.70 | 1.81 | 477.73 | 520.36 |

TABLE 39-continued

Individual and summary statistics of PK parameter estimates of dexmedetomidine in plasma

| Cohort | Dose (ug) | Redose | Subject ID | Tmax (hr) | Cmax (ng/L) | t½ (hr) | AUClast (hr*ng/L) | AUCINF_obs (hr*ng/L) |
|---|---|---|---|---|---|---|---|---|
| | | | N | 8 | 8 | 7 | 8 | 7 |
| | | | Mean | 2.935 | 96.589 | 2.946 | 586.103 | 499.866 |
| | | | SD | 2.077 | 36.954 | 0.857 | 556.166 | 226.187 |
| | | | CV % | 70.8 | 38.3 | 29.1 | 94.9 | 45.2 |
| | | | Min | 1.83 | 49.87 | 1.81 | 230.06 | 294.47 |
| | | | Median | 2.31 | 104.54 | 3.01 | 444.23 | 520.36 |
| | | | Max | 8.03 | 138.69 | 4.02 | 1912.52 | 939.05 |
| | | | Geometric Mean | 2.578 | 89.711 | 2.833 | 453.552 | 461.828 |
| | | | Geometric CV % | 50.30 | 44.50 | 31.46 | 78.77 | 44.05 |
| 2 | 60 | No | 01-044 | 1.00 | 93.67 | 3.10 | 442.23 | 558.81 |
| | | | 01-047 | 1.00 | 73.42 | 2.23 | 265.85 | 293.67 |
| | | | 01-055 | 1.50 | 113.35 | 2.87 | 474.46 | 562.60 |
| | | | 01-056 | 1.50 | 154.79 | 1.48 | 413.53 | 428.64 |
| | | | 03-036 | 1.55 | 83.52 | 1.62 | 347.11 | 369.07 |
| | | | 05-050 | 1.00 | 121.52 | 1.86 | 352.24 | 377.98 |
| | | | 05-052 | 1.45 | 105.84 | 2.36 | 330.30 | 369.14 |
| | | | 06-033 | 1.45 | 253.14 | 2.27 | 737.87 | 834.44 |
| | | | 06-034 | 1.53 | 206.42 | 2.35 | 887.27 | 1007.71 |
| | | | 06-041 | 2.07 | 144.27 | 6.98 | 1714.29 | 1882.10 |
| | | | 06-043 | 1.02 | 186.40 | 2.53 | 748.96 | 877.63 |
| | | | 07-048 | 0.98 | 201.12 | 2.91 | 874.85 | 1064.08 |
| | | | 08-046 | 2.00 | 93.22 | | 346.61 | |
| | | | 09-042 | 3.95 | 146.17 | 5.43 | 2072.02 | 2195.38 |
| | | | 10-032 | 1.50 | 136.25 | 3.40 | 650.22 | 807.14 |
| | | | 10-035 | 1.50 | 127.27 | 2.78 | 519.54 | 616.68 |
| | | | 10-039 | 1.00 | 144.93 | 2.27 | 603.55 | 691.00 |
| | | | 10-045 | 1.50 | 127.30 | 2.19 | 486.85 | 537.29 |
| | | | N | 18 | 18 | 17 | 18 | 17 |
| | | | Mean | 1.528 | 139.589 | 2.861 | 681.542 | 792.552 |
| | | | SD | 0.689 | 47.223 | 1.381 | 482.593 | 525.000 |
| | | | CV % | 45.1 | 33.8 | 48.3 | 70.8 | 66.2 |
| | | | Min | 0.98 | 73.42 | 1.48 | 265.85 | 293.67 |
| | | | Median | 1.50 | 131.78 | 2.36 | 503.20 | 616.68 |
| | | | Max | 3.95 | 253.14 | 6.98 | 2072.02 | 2195.38 |
| | | | Geometric Mean | 1.429 | 132.558 | 2.640 | 576.084 | 673.986 |
| | | | Geometric CV % | 36.00 | 33.88 | 40.27 | 60.19 | 60.92 |

Tables 38 and 39 and FIGS. 17 and 18 illustrate that the median Tmax ranges from 1.5-2.3 hours for different dose levels. Further, exposure is increasing with increasing dose from 20 to 60 mcg in a proportional manner. The redosing of 20 mcg after 1 hr in Cohort 1 led to 2.5-fold increase in the geometric mean of Cmax and in AUC.

FIGS. 19 and 20 show that in Cohort 3, a 120 mcg dose resulted in a significant decrease in the PEC Score, compared with pooled placebo group. Notably, the decrease in PEC Score in 120 mcg is differentiated from the pooled placebo group at 0.5 hr and is maintained throughout the course of the measurement (6 hr).

Example 8: Clinical Study of the Efficacy (Sedation and Anti-Agitation), Pharmacokinetics and Safety of Dexmedetomidine Infused Intravenously in Subjects Suffering from Schizophrenia A Key Objective of the study was to determine the optimal intravenous (IV) dose of dexmedetomidine hydrochloride in the target population in terms of efficacy and safety to achieve arousable sedation (RASS of −1) which can be reversed by verbal stimulation. When this goal was achieved in each participant, the IV infusion of dexmedetomidine hydrochloride ceased. Another Key Objective of the study was to determine the reduction in the level of agitation, as determined by their PEC score, at the doses to achieve a RASS of −1.

In addition, the following Secondary Objectives were:
Determine how rapidly the drug can be administered up to the total dose needed to achieve RASS −1.
Determine how long the calming effect persists after discontinuation of study drug administration.
Determine whether any adverse effects on blood pressure, heart rate, or respiratory drive occurs before or coincident with the achievement of Primary Objective. Stopping rules for blood pressure and heart rate, indicating a clinically significant event, are:
drop in systolic BP<90 mm of Hg.
drop in diastolic BP<60 mm of Hg
drop below 50 beats per minute Participants were provide written informed consent before any study related procedures were performed. All participants were screened for inclusion and exclusion criteria. The participants were admitted to the site at screening (Day −1), the day before the infusion. Baseline assessments were performed on Day −1, as well as on the day of infusion (Day 1). The participants were on Day 1 prepared for the infusion, infused for up to 3 hours and monitored for resolution of sedation and any decreases in blood pressure or heart rate which met stopping criteria. The participants were not discharged from the research unit until three hours after resolution of any reduction in the level of arousal (e.g., RASS −1) and/or resolution of any decrease in blood pressure or heart rate meeting stopping criteria. The Principal Investigator had discretion to keep the participant overnight at the site the evening of Day 1 for extended monitoring and then discharge home the participant on Day 2 if the Principal Investigator or designee determined that the participant has returned to their baseline state.

The study population included 14 participants, 10 active and 4 placebo. Patients 5, 7, 8 and 9 received placebo. Patients 1, 2, 3, 4, 11, 12, 14, 16, 17, 18 were infused with intravenous dexmedetomidine hydrochloride, starting at a rate of 0.2 mcg/kg/hr, and rising by 0.1 mcg/kg/hr every 30 minutes until stopping criteria were reached up or to a maximum duration of 3 hours. Participants randomized to placebo received a matching intravenous infusion of placebo solution.

TABLE 40

Study Treatments

| Treatment | Formulation | Frequency |
|---|---|---|
| Dexmedetomidine hydrochloride | Precedex ® | Continuous infusion, increment every 30 minutes |
| Placebo | Normal Saline | Continuous infusion |

Once the participant was drowsy (RASS −1), the infusion was stopped. The maximum total dose administered was 1.6 mcg/kg/hr, when either the desired level of sedation was achieved or the maximum allowable decrease in either systolic or diastolic blood pressure or heart rate occurred.

The participants were continuously monitored during the study by the site personnel, including monitoring blood pressure and heart rate. Intermittent electrocardiograms were taken from the start of the infusion through resolution of the sedation and/or any adverse effects on blood pressure or heart rate.

Whenever the above stopping criteria was met, the site stopped the infusion and the site continued to monitor the participant's vital signs every 15 minutes until the participant has reached their baseline parameters or in the judgment of the principal investigator the participant has reached a stable and acceptable level of blood pressure and heart rate. Return to baseline parameters is defined as BP falling within 15 mm of Hg of baseline reading prior to drug administration or HR falling within 10 beats per minute of baseline reading prior to drug administration.

In the event the investigator deemed the fall in blood pressure or heart rate to be clinically significant, suitable remedial drugs could be administered in addition to termination of the dexmedetomidine hydrochloride infusion, based on investigator's judgement.

Adverse events (AEs), including serious adverse events (SAEs), were assessed, recorded, and reported in accordance with FDA guidance. Should any SAE occur, the study would be stopped until a cause for the SAE was determined.

Efficacy Assessment:

(1) Richmond Agitation Sedation Scale (RASS): The desired endpoint was how rapidly drowsiness (RASS −1) could be achieved without causing changes in heart rate or blood pressure greater than that specified by the protocol. The study also monitored how long the participant remained at that level of sedation; sedation was considered resolved when the participant was awake and spontaneously responding.

(2) PANSS: Change from baseline for mildly agitated patients (3) Clinical Global Impression of Improvement (CGI-I) (National Institute of Mental Health 1976) ranging from 1 (very much improved) to 7 (very much worse) compared with baseline. Each participant was rated, based on the severity of agitation, at 15 and 30 minutes for every dose infusion, at the endpoint, and at the time the participant returned to baseline (in terms of level of arousal). CGI-I focused on the severity of agitation rather than the severity of the illness.

(4) After the infusion was stopped, the participants were judged for the suitability for discharge by the principal investigator or designee as witnessed by a return to their baseline level of alertness and awareness with no impairment in balance, gait, and reaction time as determined by the principal investigator or designee.

Results (A) Efficacy Study

RASS (Richmond Agitation-Sedation Scale)

9 out of 10 patients in the treatment arm (subjects 1-3, 11, 12, 14, and 16-18) achieved a RASS score of at least −1, while no patients in the placebo arm (subjects 5, and 7-9) experienced meaningful sedation (see FIG. 12 and Table 41).

TABLE 41

Depicts the RASS score of Schizophrenia patients receiving infusion of dexmedetomidine hydrochloride and normalsaline

| Infusion (minutes) | RASS values after infusion start Patient No. | | | | | | | | | | | | | |
|---|---|---|---|---|---|---|---|---|---|---|---|---|---|---|
| | 1 T | 2 T | 3 T | 4 T | 5 P | 7 P | 8 P | 9 P | 11 T | 12 T | 14 T | 16 T | 17 T | 18 T |
| 0 | 1 | 3 | 1 | 1 | 1 | 1 | 1 | 1 | 1 | 1 | 1 | 1 | 1 | 0 |
| 15 | −2 | | | | | | | | | | | | | −1 |
| 30 | | 0 | 0 | 0 | 1 | 1 | 1 | 1 | 0 | 0 | 0 | 0 | 0 | |
| 45 | | | 0 | | | | | | | | | | −1 | |
| 60 | | 0 | −1 | 0 | 1 | 1 | 0 | 1 | 0 | 0 | 0 | 0 | | |
| 75 | | −1 | | | | | | | | −1 | | −1 | −1 | |
| 90 | | | | 0 | 1 | 0 | 0 | 1 | | 0 | | | | |
| 105 | | | | | | | | | | | | | | |
| 120 | | | | 0 | 0 | 0 | 0 | 1 | | −1 | | | | |
| 135 | | | | 0 | | | | | | | | | | |
| 150 | | | | | 0 | 0 | 0 | 1 | | | | | | |
| 165 | | | | | | | | | | | | | | |
| 180 | | | | | 0 | 0 | 0 | 1 | | | | | | |

T—treatment arm;
P—placebo arm

PEC (PANSS Excitement Component)

9 out of 10 patients in the treatment arm (subjects 1-4, 11, 12, 146 an 17) had agitation reduced to a minimum (as measured by PEC score of or below) (see Table 42 and FIG. 13).

TABLE 42

Depicts the PEC data of schizophrenia patients receiving infusion of dexmedetomidine and normal saline PEC values after infusion start Patient No.

| Time (Mins) | 1 T | 2 T | 3 T | 4 T | 5 P | 7 P | 8 P | 9 P | 11 T | 12 T | 14 T | 16 T | 17 T | 18 T |
|---|---|---|---|---|---|---|---|---|---|---|---|---|---|---|
| 0 | 9 | 16 | 12 | 9 | 11 | 12 | 9 | 13 | 13 | 13 | 10 | 10 | 10 | |
| 15 | 5 | 13 | 12 | 9 | 10 | 12 | 9 | 13 | 13 | 13 | 9 | 9 | 8 | |
| 30 | | 12 | 10 | 8 | 9 | 9 | 8 | 12 | 11 | 13 | 6 | 6 | 7 | |
| 45 | | 11 | 7 | 8 | 9 | 8 | 8 | 12 | 9 | 10 | 6 | 6 | 5 | |
| 60 | | 9 | 6 | 7 | 8 | 8 | 8 | 13 | 9 | 10 | 5 | 7 | | |
| 75 | | 7 | | 7 | 8 | 8 | 7 | 11 | 7 | 8 | 5 | 5 | | |
| 90 | | | | 7 | 7 | 9 | 7 | 11 | | 6 | | | | |
| 105 | | | | 7 | 8 | 8 | 7 | 10 | | 5 | | | | |
| 120 | | | | 7 | 8 | 8 | 7 | 10 | | | | | | |
| 135 | | | | 7 | 8 | 7 | 7 | 9 | | | | | | |
| 150 | | | | | 8 | 7 | 7 | 9 | | | | | | |
| 165 | | | | | 8 | 8 | 7 | 9 | | | | | | |
| 180 | | | | | 8 | 8 | 7 | 10 | | | | | | |

T—treatment arm;
P—placebo arm (B) Pharmacokinetic Study: (PK Study)

The level of dexmedetomidine in the plasma of patients was also measured over the time of infusion. The results are tabulated in Table 43. The maximum dexmedetomidine concentrations in schizophrenic patients ($C_{max}$) ranged from about 22.45 μg/ml to about 406.3 μg/ml. Time to reach $C_{max}$ ranged from about 15 minutes to about 105 minutes. Mean infusion rate is 0.36 mcg/kg/hr with the maximum rate ranging from about 0.2 mcg/kg/hr to about 0.6 mcg/kg/hr (see FIGS. 14 and 16).

TABLE 43 depicts the plasma concentrations (pg/mL) of schizophrenia patients at different timepoints during the infusion of dexmedetomidine hydrochloride and normal saline Plasma level concentration (picogram/ml)

| Time (Mins) | 1 T | 2 T | 3 T | 4 T | 5 P | 7 P | 8 P | 9 P | 11 T | 12 T | 14 T | 16 T | 17 T | 18 T |
|---|---|---|---|---|---|---|---|---|---|---|---|---|---|---|
| 0 | BLQ | BLQ | | BLQ | BLQ | BLQ | BLQ | BLQ | BLQ | BLQ | BLQ | BLQ | BLQ | BLQ |
| 15 | 22.45 | | | BLQ | BLQ | BLQ | BLQ | BLQ | 41.0 | BLQ | BLQ | 2.56 | 15.87 | 48.36 |
| 30 | 14.72 | BLQ | BLQ | BLQ | BLQ | BLQ | BLQ | BLQ | 62.91 | 44.87 | 52.66 | 15.59 | BLQ | 54.53 |
| 45 | | | | BLQ | BLQ | BLQ | BLQ | BLQ | 124.07 | 50.51 | 46.53 | 41.17 | 39.93 | |
| 60 | | | | | BLQ | BLQ | BLQ | BLQ | 150.47 | 108.6 | 406.3 | 67.88 | | |
| 75 | | | | | BLQ | BLQ | BLQ | BLQ | | 158.54 | | 72.26 | | |
| 90 | | | | 44.3 | BLQ | BLQ | BLQ | BLQ | | 237.83 | | | | |
| 105 | | | | | BLQ | BLQ | BLQ | BLQ | | 267.3 | | | | |
| 120 | | | | | BLQ | BLQ | BLQ | BLQ | | | | | | |
| 135 | | | | | BLQ | BLQ | BLQ | BLQ | | | | | | |
| 150 | | | | | BLQ | BLQ | BLQ | BLQ | | | | | | |
| 165 | | | | | BLQ | BLQ | BLQ | BLQ | | | | | | |
| 180 | | | | | BLQ | BLQ | BLQ | BLQ | | | | | | |
| Total duration of infusion (Mins) | 19 | 75 | 60 | 149 | 180 | 180 | 180 | 179 | 68 | 103 | 64 | 66 | 36 | 30 |

*BLQ—below limit of quantification
T—treatment;
P—placebo

Discussion:

The administration of dexmedetomidine hydrochloride by the IV route produced a >=50% reduction in PEC score in a total of 7 of 10 subjects, with one subject (Patient 1) responding at a Cmax of 22 pg/mL. 5 of 10 subjects (Patients 1, 2, 3, 16 and 17) exhibited a 40% reduction in PEC score at a Cmax of =<72 pg/mL. The good response rates at these plasma exposure levels indicates that sublingual dexmedetomidine hydrochloride administration at similar or higher Cmax exposure levels will achieve good anti-agitation effects. As demonstrated in Example 6 above, sublingual dexmedetomidine hydrochloride administered to healthy volunteers produced good plasma exposure levels at doses of 10, 20 and 40 micrograms, indicating that such doses would be suitable for obtaining good anti-agitation effects (e.g. as measured by a reduction in PEC score) in agitated subjects, including subjects with schizophrenia, without also producing clinically meaningful detrimental effects on blood pressure and/or heart rate.

The invention claimed is:

1. A self-supporting, dissolvable, film, comprising:
  (i) dexmedetomidine or a pharmaceutically acceptable salt thereof;
  (ii) one or more first water-soluble hydroxypropyl cellulose polymers having a molecular weight of about 40,000 daltons;
  (iii) one or more second water-soluble hydroxypropyl cellulose polymers having a molecular weight of about 140,000 daltons;
  (iv) one or more third water-soluble hydroxypropyl cellulose polymers having a molecular weight of about 370,000 daltons; and
  (v) one or more pharmaceutically acceptable carriers;
    wherein the first water-soluble hydroxypropyl cellulose polymer having a molecular weight of about 40,000 daltons is present at about 3% to about 8% w/w of the total film weight
    wherein the second water-soluble hydroxypropyl cellulose polymer having a molecular weight of about 140,000 daltons is present at about 3% to about 8% w/w of the total film weight
    wherein the third water-soluble hydroxypropyl cellulose polymer having a molecular weight of about 370,000 daltons is present at about 20% to about 40% w/w of the total film weight
    wherein the dexmedetomidine or a pharmaceutically acceptable salt thereof is present at about 0.05% to about 3% weight/weight (w/w) of the total film weight, and
    wherein the dexmedetomidine or a pharmaceutically acceptable salt thereof is substantially uniformly distributed throughout the film.

2. The film of claim 1, wherein the pharmaceutically acceptable carriers are selected from the group consisting of: liquid carriers, flavors, sweeteners, refreshing agents, pH adjusting agents, permeation enhancers, plasticizers, bulking agents, surfactants, anti-foaming agents, and colorants.

3. The film of claim 1, wherein the dexmedetomidine or a pharmaceutically acceptable salt thereof is present in a dose of about 0.5 micrograms to about 200 micrograms.

4. The film of claim 1, wherein the dexmedetomidine or a pharmaceutically acceptable salt thereof is present in a dose of about 120 micrograms.

5. The film of claim 1, further comprising a water-soluble polyethylene oxide polymer having a molecular weight of about 600,000 daltons, wherein said water-soluble polyethylene oxide polymer having a molecular weight of about 600,000 daltons is present at about 50% to about 60% w/w of the total film weight.

6. The film of claim 1, wherein the dexmedetomidine or a pharmaceutically acceptable salt thereof is present in a dose of about 30 micrograms.

7. The film of claim 1, wherein the dexmedetomidine or a pharmaceutically acceptable salt thereof is present in a dose of about 60 micrograms.

8. The film of claim 1, wherein the dexmedetomidine or a pharmaceutically acceptable salt thereof is present in a dose of about 90 micrograms.

* * * * *